United States Patent
Shalitin et al.

(10) Patent No.: US 11,111,491 B2
(45) Date of Patent: Sep. 7, 2021

(54) METHODS FOR IMPROVING TRAITS IN PLANTS

(71) Applicant: PLANTARCBIO LTD., Raanana (IL)

(72) Inventors: Dror Shalitin, Raanana (IL); Noam Grimberg, Raanana (IL); Arava Shatil Cohen, Raanana (IL)

(73) Assignee: PLANTARCBIO LTD., Raanana (IL)

( * ) Notice: Subject to any disclaimer, the term of this patent is extended or adjusted under 35 U.S.C. 154(b) by 107 days.

(21) Appl. No.: 16/496,445

(22) PCT Filed: Mar. 27, 2018

(86) PCT No.: PCT/IL2018/050349
§ 371 (c)(1),
(2) Date: Sep. 22, 2019

(87) PCT Pub. No.: WO2018/178975
PCT Pub. Date: Oct. 4, 2018

(65) Prior Publication Data
US 2020/0115704 A1    Apr. 16, 2020

Related U.S. Application Data

(60) Provisional application No. 62/644,600, filed on Mar. 19, 2018, provisional application No. 62/477,517, filed on Mar. 28, 2017.

(51) Int. Cl.
*C12N 15/82* (2006.01)
*C12N 15/10* (2006.01)

(52) U.S. Cl.
CPC ..... *C12N 15/1075* (2013.01); *C12N 15/8273* (2013.01)

(58) Field of Classification Search
None
See application file for complete search history.

(56) References Cited

U.S. PATENT DOCUMENTS

| | | | |
|---|---|---|---|
| 6,030,779 A | 2/2000 | Short | |
| 6,368,798 B1 | 4/2002 | Short | |
| 6,972,183 B1 | 12/2005 | Lafferty et al. | |
| 2002/0150949 A1 | 10/2002 | Short et al. | |
| 2010/0012051 A1 | 1/2010 | Born | |
| 2011/0088126 A1* | 4/2011 | Chang | C07K 14/415 800/298 |
| 2012/0131696 A1 | 5/2012 | Sharon et al. | |

FOREIGN PATENT DOCUMENTS

| | | |
|---|---|---|
| EP | 1025262 | 8/2000 |
| WO | 2008027591 A2 | 3/2008 |
| WO | 2016095124 A1 | 6/2016 |

OTHER PUBLICATIONS

Qin et al 2016 (Plant Cell Tiss Organ Cult 125: p. 471-478) (Year: 2016).*
Im et al 2009 (Plant Physiology 151: p. 893-904) (Year: 2009).*
Janbon et al 2014 (Genbank AFR94946) (Year: 2014).*
Gabor et al (2004) Quantifying the acccessibility of the metagenome by random expression cloning techniques, Environ Microbiol 6, 879-886.
Culligan et al (2014) Metagenomics and novel gene discovery: promise and potential for novel therapeutics, Virulence 5, 399-412.
Venter et al (2004) Environmental genome shotgun sequencing of the Sargasso Sea, Science, 304, 66-74.
Farooq et al (2009) Plant drought stress: effects, mechanisms and management, Agron. Sustain. Dev. 29, 185-212.
Carillo et al (2011) Salinity stress and salt tolerance, abiotic stress in plants—mechanisms and adaptations. In: Arun Shanker, editor Tech, DOI: 10.5772/22331.
Yang T-T et al (1996) Optimized codon usage and chromophore mutations provide enhanced sensitivity with the green fluorescent protein. Nucleic Acids Res 24:4592-4593.
Hema et al (2014) Stable Expression of mtlD Gene Imparts Multiple Stress Tolerance in Finger Millet. PLoS ONE 9(6): e99110.
Karaba et al (2007) Improvement of water use efficiency in rice by expression of HARDY, an *Arabidopsis* drought and salt tolerance gene, Proc Natl Acad Sci USA, 104:5270-5275.
Dao et al (1997) The *Arabidopsis* NPR1 gene that controls systemic acquired resistance encodes a novel protein containing ankyrin repeats, Cell 88(1), 57-63.
Lever et al (2015) A modular method for the extraction of DNA and RNA, and the separation of DNA pools from diverse environmental sample types, Frontiers in Microbiology, 6, 476.
Wujuan et al (2001) Determination of nucleic acids with crystal violet by a resonance light-scattering technique, Analyst, 126(4), 513-517.
Jayakannan et al (2015) The NPR1-dependent salicylic acid signalling pathway is pivotal for enhanced salt and oxidative stress tolerance in *Arabidopsis*, Journal of Experimental Botany, 66(7), 1865-1875.
Nonami H. (1998) Plant water relations and control of cell elongation at low water potentials, J. Plant Res. 111, 373-382.
Parida et al (2005) Salt tolerance and salinity effects on plants: a review, Ecotoxiocology and Environmental Safety, 60(3), 324-349.

(Continued)

*Primary Examiner* — Matthew R Keogh
(74) *Attorney, Agent, or Firm* — The Roy Gross Law Firm, LLC; Roy Gross

(57) ABSTRACT

The present invention discloses a method for screening for and identifying a desirable plant improving trait, said method comprises steps of: (a) obtaining genetic material from a sampling of a predefined source and (b) constructing an expression library from said genetic material. The aforementioned method further comprises steps of: (c) producing plants transformed with said expression library at a transformation efficiency of at least 0.05%-30%, representing at least $10^2$-$10^{10}$ transgenes; (d) screening for transformed plants expressing said desirable trait; and (e) identifying said transgene of said transformed plants expressing said desirable trait.

4 Claims, 13 Drawing Sheets

Specification includes a Sequence Listing.

(56) References Cited

OTHER PUBLICATIONS

Gaj et al (2013) ZFN, TALEN and CRISPR/Cas-based methods for genome engineering, Trends in Biotechnology, 31 (7), 397-405.
Christoph Weiste et al (2007) In planta ORFeome analysis by large-scale over-expression of GATEWAY-compatible cDNA clones: screening of ERF transcription factors involved in abiotic stress defense: Functional analysis of the *Arabidopsis* transcription factor ORFeome, The Plant Journal, vol. 52, No. 2 pp. 382-390.
Wan-Song et al (2017) Construction of a Plant Transformation-ready Expression cDNA Library for Thellungiella halophila Using Recombination Cloning, Journal of Integrative Plant Biology, pp. 1313-1319.

\* cited by examiner

METHODS FOR IMPROVING TRAITS IN PLANTS

RELATED APPLICATIONS

This application is a National Phase of PCT Patent Application No. PCT/IL2018/050349 having International filing date of Mar. 27, 2018, which claims the benefit of priority of U.S. Provisional Application Nos. 62/477,517 and 62/644,600, filed on Mar. 28, 2017 and Mar. 19, 2018, respectively. The contents of the above applications are all incorporated by reference as if fully set forth herein in their entirety.

SEQUENCE LISTING

The instant application contains a Sequence Listing which has been submitted electronically in ASCII txt. format and is hereby incorporated by reference in its entirety. Said ASCII copy, is named seq.listing 1754-P-01-PCT_ST25 and is 491 KB in size.

FIELD OF THE INVENTION

The present invention generally relates to the field of improving traits in plants. More particularly, the present invention relates to improving traits in plants by transformation of expression libraries from predefined sources into plants and screening for desirable traits.

BACKGROUND OF THE INVENTION

The world population is estimated to be 9.2 billion in 2050. To sufficiently feed this population, the total food production will have to increase by 60%-70%. Climate models predict that warmer temperatures and increases in the frequency and duration of drought during the present century will have negative impact on agricultural productivity. For example, maize production in Africa could be at risk of significant yield losses as researchers predict that each degree-day that the crop spends above 30° C. reduces yields by 1% if the plants receive sufficient water. These predictions are similar to those reported for maize yield in the United States. It has been further shown that maize yields in Africa decreased by 1.7% for each degree-day the crop spent at temperatures of over 30° C. under drought. Wheat production in Russia decreased by almost one-third in 2010, largely due to the summer heat wave. Similarly, wheat production declined significantly in China and India in 2010, largely due to drought and sudden rise in temperature respectively, thereby causing forced maturity. These new global challenges require a more complex integrated agriculture.

In addition global warming leads to the concurrence of a number of abiotic and biotic stresses, thus affecting agricultural productivity. Occurrence of abiotic stresses can alter plant-pest interactions by enhancing host plant susceptibility to pathogenic organisms, insects, and by reducing competitive ability with weeds. On the contrary, some pests may alter plant response to abiotic stress factors.

Biotic stress factors are caused by pathogens, insects, pests, weeds, or intraspecific competition for resources. The ability of biotic stress factors to cause yield or quality loss depends on the environment and thus may vary from region to region or from one agroecology to another. For example, in Australia, barley foliar diseases are some of the major biotic stress factors causing substantial yield and quality losses. Although it is known that some plant species have resistance to various diseases, they are hard or even impossible to breed in conventional methods.

The challenge is to create crops that are resistance to biotic stress factors and are flexible and adaptable to diverse environments and populations. There are currently two major acceptable ways to adapt crops to new environments: developing new crops through conventional breeding (long-term endeavor starting with domestication) and introducing target traits into existing crops through plant breeding, which includes genetic engineering. To maintain productivity in the face of increased climatic variability, both the population and the plant cultivars will need to be continually developed to withstand "new" climate extremes and other stresses such as diseases, pathogens, insects, pests etc. In addition there is a constant need to find new herbicide tolerance or resistant genes for new chemicals and new herbicides mode of action.

Genetic engineering has the potential to address some of the most challenging biotic and abiotic constraints faced by farmers, which are not easily addressed through conventional plant breeding alone.

Advantageous outcomes of these genetic modifications include increased food production, reliability, and yields; enhanced taste and nutritional value; and decreased losses due to various biotic and abiotic stresses, such as fungal and bacterial pathogens. These objectives continue to motivate modern breeders and food scientists, who are seeking for newer genetic modification methods for identifying, selecting, and analyzing individual organisms that possess genetically enhanced features.

The option to transform plants with foreign genes and/or genes from the same specie or genus, that are hard or impossible to breed, overcomes species barriers, making it possible to exploit powerful 'super-traits' that are not attainable through traditional methods. However, the molecular interactions and outcomes of introduced trans-genes and endogenous genes are not predictable.

When genes coding for certain traits are transferred, typically from one plant species to another, the desired traits are not always expressed unless the environment interacts with the genes in the anticipated way triggering the desired response, which depends on the regulating sequences inserted with the gene. This means that new transgenic cultivars, developed under laboratory conditions in a controlled climate, have to be tested under field conditions, as in more traditional breeding methods, so currently there is little difference in the speed with which either method will result in the release of new cultivars.

The knowledge gained from basic plant research will underpin future crop improvements, but effective mechanisms for the rapid and effective translation of research discoveries into public good agriculture remain to be developed.

U.S. Pat. Nos. 6,030,779 and 6,368,798 disclose a process for identifying clones having a specified enzyme activity by selectively isolating target nucleic acid from genomic DNA population, by use of polynucleotide probe identifying the nucleic acid sequence encoding an enzyme having the specified enzyme activity; and transforming a host with the isolated target nucleic acid to produce a library of clones which are screened for the specified enzyme activity.

U.S. Pat. No. 6,972,183 discloses a process for screening an expression library to identify clones expressing enzymes having a desired activity. The process involves generating from genomic DNA samples of one or more microorganisms an expression library comprising a plurality of recombinant cell clones, and then introducing into capillaries in a capillary array a substrate and a subset of the clones. Interaction of the substrate and a clone expressing an enzyme having the desired activity produces an optically detectable signal, which can then be spatially detected to identify capillaries containing clones producing such a signal. The signal-producing clones can then be recovered from the identified capillaries.

EP patent application 1025262 and US patent application 20020150949 teach a process for identifying clones having a specified activity of interest, by (i) generating expression libraries derived from nucleic acid directly isolated from the environment; (ii) exposing said libraries to a particular substrate or substrates of interest; and (iii) screening said exposed libraries utilizing a fluorescence activated cell sorter to identify clones which react with the substrate or substrates.

US patent application 20100152051 relates to a method for the identification and/or characterization of clones conferring a desired biological property from an expression library. The method comprises the step of screening for the expression of at least one (poly)peptide, such as a tag expressed as a fusion protein, together with a recombinant insert of a clone of said expression library. Said (poly)peptide may be fused N-terminally or C-terminally to said insert. The method further comprises the steps of contacting a ligand specifically interacting with the (poly)peptide expressed by the insert of a clone conferring said desired biological property.

All the above methods are based upon screening a DNA library (produced from microorganisms or environmental sample) for a specific sequence or biochemical activity via interaction with a predetermined probe. In addition, the screening and selection for a clone having the predetermined sequence or activity is performed prior to transformation into plant cells and could be expressed in plant cells (tissue cultures) but not in whole plants. Thus by the up-to-date used methods, only the preselected clone is expressed in plants and the expression and effect of the selected sequence in plants is unpredictable. In addition, in the methods described above, one can screen only for known activities based on prior knowledge. Thus, these methods are limited under the scope of known enzyme activities and enzyme families and prior known function.

In view of the above, there is a long felt need for efficient methods for screening and identifying unknown sequences conferring desirable plant improving traits.

SUMMARY OF THE INVENTION

It is therefore one object of the present invention to disclose a method for screening for and identifying a desirable plant improving trait, the method comprises steps of: (a) obtaining genetic material from a sampling of a predefined source; (b) constructing an expression library from said genetic material; wherein said method further comprises steps of: (c) producing plants transformed with said expression library at a transformation efficiency of at least 0.05%-30%, representing at least $10^2$-$10^{10}$ transgenes; (d) screening for transformed plants expressing said desirable trait; and (e) identifying said transgene of said transformed plants expressing said desirable trait.

It is a further object of the present invention to disclose the method as defined above, further comprising a step of editing a target gene in a desirable crop plant according to genetic information obtained from said transgene.

It is a further object of the present invention to disclose the method as defined in any of the above, wherein said editing of said target gene is performed using any genome editing system or method including systems using engineered nucleases selected from the group consisting of: meganucleases, zinc finger nucleases (ZFNs), transcription activator-like effector-based nucleases (TALEN), clustered regularly interspaced short palindromic repeats (CRISPR) system and any combination thereof.

It is a further object of the present invention to disclose the method as defined in any of the above, wherein said predefined source comprises plant, microbial, fungal or other organisms or parts thereof of an environmental niche.

It is a further object of the present invention to disclose the method as defined in any of the above, wherein said screening step comprises measurements of said transformed plants as compared to control plants, said measurements are selected from the group consisting of: turgor pressure measurements, plant death, leaf area, plant shoots fresh weight, leaf number, branch fresh weight, main branch length, flowers yield, pods or fruits yield, chlorosis, damage to leaves, state or performance of plants and any combination thereof.

It is a further object of the present invention to disclose the method as defined in any of the above, wherein said control plant is a plant of the same genus as said transgenic plant and lacking said transgene or a plant of the same genus as said transgenic plant, lacking said transgene and transformed with a known gene conferring said plant improving trait.

It is a further object of the present invention to disclose the method as defined in any of the above, wherein said step (a) further comprises steps of enriching said genetic material by growth on rich media or on selective media.

It is a further object of the present invention to disclose the method as defined in any of the above, wherein said step (a) further comprises steps of enhancing expression of said desirable trait by culturing said genetic material on selective media for said desirable trait.

It is a further object of the present invention to disclose the method as defined in any of the above, wherein said step (b) comprises steps of producing prokaryotic cDNA library or eukaryotic cDNA library or both.

It is a further object of the present invention to disclose the method as defined in any of the above, wherein said step (b) further comprises steps of cloning said cDNA library into at least one binary vector.

It is a further object of the present invention to disclose the method as defined in any of the above, wherein said binary vector comprises a constitutive promoter or a stress induced promoter.

It is a further object of the present invention to disclose the method as defined in any of the above, wherein said binary vector comprises bacterial selection marker and plant transformation selection marker.

It is a further object of the present invention to disclose the method as defined in any of the above, further comprises steps of transforming said cloned binary vectors into host cells.

It is a further object of the present invention to disclose the method as defined in any of the above further comprises steps of transforming said cloned binary vectors into *Agrobacterium tumefaciens*.

It is a further object of the present invention to disclose the method as defined in any of the above further comprises steps of introducing said transformed *Agrobacterium tumefaciens* into at least one of: whole plant, plant tissue and plant cell.

It is a further object of the present invention to disclose the method as defined in any of the above, comprises steps of introducing said transformed *Agrobacterium tumefaciens* by spraying said plants with an inoculum comprising transformed *Agrobacterium*.

It is a further object of the present invention to disclose the method as defined in any of the above, wherein said step (d) comprises growing said transformed plants under conditions selective for said desirable trait.

It is a further object of the present invention to disclose the method as defined in any of the above, further comprises steps of: (f) collecting T1 seeds from said transformed plants of step (d); (g) determining seed library transformation efficiency of said T1 seeds; (h) sowing said T1 seeds of step (e) under selective conditions allowing screening and selection of transformed plants expressing said desirable trait; (i) testing said selected plants expressing said desirable trait of step (g) for presence of said transgene; and (j) isolating and sequencing said transgene of said selected transformed plants positively tested for said transgene of step (h).

It is a further object of the present invention to disclose the method as defined in any of the above, further comprises steps of (k) collecting T2 seeds from said plants of (h), which are found positive for presence of said transgene; (l) growing plants of said T2 seeds under selective conditions allowing screening and selection of transformed plants expressing said desirable trait as compared to control plants transformed with known genes conferring said desirable trait; and (m) optionally, isolating and sequencing said transgene of said selected plants of step (j).

It is a further object of the present invention to disclose the method as defined in any of the above, comprises steps of (a) recloning and sequencing said isolated transgene of step (i) and/or (l); (b) transforming said recloned transgene into plants; (c) screening said transformed plants of step (b) for selection of transformed plants expressing said desirable trait; (d) isolating said transgene from said selected plants of step (c); and (e) optionally, repeating steps (a) to (d).

It is a further object of the present invention to disclose the method as defined in any of the above, wherein said environmental niche comprises ecological niche, populations, habitats, gene pools, prokaryotic culture, eukaryotic culture and any combination thereof.

It is a further object of the present invention to disclose the method as defined in any of the above, wherein said environmental niche comprises microbiome, microbiota, microbial culture, plant, yeast, algae, nematode or any other organism or combinations thereof.

It is a further object of the present invention to disclose the method as defined in any of the above, wherein said environmental niche comprises predefined biotic factors, abiotic factors and a combination thereof.

It is a further object of the present invention to disclose the method as defined in any of the above, wherein said sampling comprises soil sample, water sample, organic matter sample and any combination thereof.

It is a further object of the present invention to disclose the method as defined in any of the above, wherein said desirable trait is selected from the group consisting of resistance or tolerance to at least one biotic stress, resistance or tolerance to at least one abiotic stress, improved yield, improved biomass, improved food qualities and values, improved grain yield, herbicide or chemical resistance or tolerance and any combination thereof.

It is a further object of the present invention to disclose the method as defined in any of the above, wherein said abiotic stress is selected from the group consisting of: drought, salinity, heat, cold, fertilizer uptake, fertilizer usage efficiency and any combination thereof.

It is a further object of the present invention to disclose the method as defined in any of the above, wherein said biotic stress is selected from the group consisting of: plant diseases, pathogens, bacteria, viruses, fungi, parasites, beneficial and harmful insects, weeds, and cultivated or native plants or any combination thereof.

It is a further object of the present invention to disclose the method as defined in any of the above, wherein said step (a) comprises steps of extracting RNA from said sampling of said predefined environmental niche.

It is a further object of the present invention to disclose the method as defined in any of the above, wherein said RNA extraction is performed according to standard commercial kits or according to any other protocol for extraction of RNA from environmental sampling.

It is a further object of the present invention to disclose the method as defined in any of the above, wherein said protocol for extraction of RNA from environmental sampling comprises steps of: (a) obtaining a soil sample; (b) mixing said soil sample with an extraction buffer comprising 500 mM phosphate buffer pH 8 and 5% w/v cetyltrimethylammonium bromide (CTAB) with phenol (pH 8)/chloroform/IAA ratio of 25:24:1; (c) subjecting said mixture of step (b) to 15 min shaking at 37° C. or to a bead beater for 1 min; (d) centrifuging said mixture of step (c) at 2,500 g for about 10 minutes at room temperature to obtain an aqueous phase; (e) transferring said aqueous phase into a new tube; (f) adding to said aqueous phase within said tube of step (e) an equal amount of iso-propanol supplemented with 20 mg/ml crystal violet solution to obtain violate stained solution; (g) mixing said solution by inverting said tube of step (f) and then incubating said tube for about 30 minutes at room temperature; (h) centrifuging said tube of step (g) at 2,500 g for about 30 minutes at room temperature to obtain a violet stained layer; (i) transferring said violate stained layer into a new tube and centrifuging said tube for about 5 min at maximal speed to obtain pellet and supernatant; (j) washing said pellet with 80% v/v ice cold ethanol and centrifuging for additional 5 min to obtain pellet and supernatant; (k) removing said supernatant of step (j) and allowing said pellet to dry; and (l) suspending said dried pellet in water in a ratio of 100 µl water to 2 gr of soil of step (a).

It is a further object of the present invention to disclose a plant comprising said transgene identified by the method as defined in any of the above.

It is a further object of the present invention to disclose the plant as defined above, wherein said plant has at least one plant improving trait as compared to a plant of the same genus lacking said transgene.

It is a further object of the present invention to disclose a polynucleotide sequence obtainable by the method as defined in any of the above.

It is a further object of the present invention to disclose the polynucleotide as defined in any of the above, wherein said polynucleotide comprises a nucleotide sequence corresponding to the sequence as set forth in a polynucleotide sequence selected from the group consisting of SEQ ID NOs:1-148 and any combination thereof.

It is a further object of the present invention to disclose a polynucleotide sequence having at least 80% sequence similarity to the polynucleotide sequence as defined in any of the above.

It is a further object of the present invention to disclose a polypeptide sequence obtainable by the method as defined in any of the above.

It is a further object of the present invention to disclose the polypeptide sequence as defined in any of the above, wherein said polypeptide comprises an amino acid sequence corresponding to the sequence as set forth in a polypeptide sequence selected from the group consisting of SEQ ID NOs: 149-321 and any combination thereof.

It is a further object of the present invention to disclose a polypeptide sequence having at least 60% sequence similarity to the polypeptide sequence as defined in any of the above.

It is a further object of the present invention to disclose the use of the method as defined in any of the above for identifying genes conferring plant improving traits selected from the group consisting of resistance or tolerance to abiotic stress, resistance or tolerance to biotic stress, improved yield, improved biomass, improved food qualities and values, improved grain yield, herbicide or chemical resistance or tolerance and any combination thereof.

It is a further object of the present invention to disclose the use as defined in any of the above, wherein said abiotic stress is selected from the group consisting of: drought, salinity, heat, cold, fertilize utilization and any combination thereof.

It is a further object of the present invention to disclose the use as defined in any of the above, wherein said biotic stress is selected from the group consisting of: plant diseases, pathogens, bacteria, viruses, fungi, parasites, beneficial and harmful insects, weeds, and cultivated or native plants or any combination thereof.

It is a further object of the present invention to disclose a method for screening for and identifying a drought or salinity resistance or tolerance improving trait in plants, said method comprises steps of: (a) obtaining genetic material derived from a low moisture or a high salinity source sample; (b) constructing expression library from said genetic material; wherein said method further comprises steps of: (c) producing plants transformed with said expression library at a transformation efficiency of at least 0.5%-30% representing at least $10^2$-$10^{10}$ transgenes; (d) screening for transformed plants resistant or tolerant to predetermined drought or salinity conditions; and (e) identifying said transgene of said drought or salinity resistant or tolerant transformed plants of step (d).

It is a further object of the present invention to disclose the method as defined in any of the above, further comprising a step of editing a target gene in a desirable crop plant according to genetic information obtained from said transgene.

It is a further object of the present invention to disclose the method as defined in any of the above, wherein said editing of said target gene is performed using any genome editing system or method including systems using engineered nucleases selected from the group consisting of: meganucleases, zinc finger nucleases (ZFNs), transcription activator-like effector-based nucleases (TALEN), clustered regularly interspaced short palindromic repeats (CRISPR) system and any combination thereof.

It is a further object of the present invention to disclose the method as defined in any of the above, wherein said predefined source comprises plant, microbial, fungal or other organisms or parts thereof of an environmental niche.

It is a further object of the present invention to disclose the method as defined in any of the above, wherein said screening step comprises measurements of said transformed plants as compared to control plants, said measurements are selected from the group consisting of: turgor pressure measurements, plant death, leaf area, plant shoots fresh weight, leaf number, branch fresh weight, main branch length, flowers yield, pods or fruits yield, chlorosis, damage to leaves, state or performance of plants and any combination thereof.

It is a further object of the present invention to disclose the method as defined in any of the above, wherein said control plant is a plant of the same genus as said transgenic plant and lacking said transgene or a plant of the same genus as said transgenic plant, lacking said transgene and transformed with a known gene conferring said plant improving trait.

It is a further object of the present invention to disclose the method as defined in any of the above, wherein said step (b) further comprises steps of cloning said expression library into at least one binary vector.

It is a further object of the present invention to disclose the method as defined in any of the above, further comprises steps of: (f) collecting T1 seeds from said transformed plants of step (c); (g) sowing said T1 seeds in soil selective for transformed plants, with water content of about 100% capacity; (h) growing plants of said T1 seeds in drought or salinity conditions and/or without irrigation until most of the plants die, to produce transformed plants surviving said drought or salinity conditions; (i) growing said drought or salinity surviving transformed plants to produce T2 seeds; (j) screening said drought or salinity surviving transformed plants of step (i) for presence of a transgene; and (k) isolating and sequencing said transgene from positively screened plants of step (j).

It is a further object of the present invention to disclose the method as defined in any of the above, further comprises steps of (l) collecting T2 seeds from each of said transgene-containing positively screened drought or salinity surviving transformed plants of step (j); (m) growing T2 plants from each of said transgene-containing T2 seeds of step (l) under predetermined drought or salinity conditions as compared to control plants of the same genus and lacking said transgene or transformed with known genes conferring drought or salinity tolerance or drought or salinity resistance; (n) performing drought tolerance or resistance screening measurements for each of said transgene-containing T2 plants as compared to said control plants, said measurements are selected from the group consisting of: turgor pressure measurements, plant death, leaf area, fresh weight, leaf number, branch fresh weight, main branch length, flowers and pods production, Chlorosis and damage to leaves, state or performance of plants and any combination thereof; (o) isolating the transgene from said screened dough or salinity resistance performing T2 plants of step (n); (p) optionally, recloning said transgene into a binary vector; (q) optionally, transforming said cloned binary vector into plants and growing said transformed plants under predetermined drought or salinity conditions; and (r) optionally, repeating steps (l) to (q).

It is a further object of the present invention to disclose the method as defined in any of the above, wherein said step of growing T2 plants comprises steps of: (a) sowing said T2 seeds in soil selective for transformed plants, with water content of about 100% capacity; and (b) irrigating said plants when water content in the soil reaches about 5-10%.

It is a further object of the present invention to disclose the method as defined in any of the above, wherein said predetermined drought or salinity conditions are selected from the group consisting of low moisture, high salinity, dry soil and heat.

It is a further object of the present invention to disclose a polynucleotide sequence obtainable by the method as defined in any of the above.

It is a further object of the present invention to disclose the polynucleotide as defined in any of the above, wherein said polynucleotide comprises a nucleotide sequence corresponding to the sequence as set forth in a polynucleotide sequence selected from the group consisting of SEQ ID NOs:1 to SEQ ID NO:148 and any combination thereof.

It is a further object of the present invention to disclose a polynucleotide sequence having at least 80% sequence similarity to the polynucleotide sequence as defined in any of the above.

It is a further object of the present invention to disclose a polypeptide sequence obtainable by the method as defined in any of the above.

It is a further object of the present invention to disclose the polypeptide sequence as defined in any of the above comprises an amino acid sequence corresponding to the sequence as set forth as set forth in polypeptide sequence selected from the group consisting of SEQ. ID Nos: 149-321 and any combination thereof.

It is a further object of the present invention to disclose a polypeptide sequence having at least 60% sequence similarity with the polypeptide sequence as defined in any of the above.

It is a further object of the present invention to disclose a method for extracting RNA from a soil sample comprising steps of: (a) obtaining a soil sample; (b) mixing said soil sample with an extraction buffer comprising 500 mM phosphate buffer pH 8 and 5% w/v cetyltrimethylammonium bromide (CTAB) with phenol (pH 8)/chloroform/IAA ratio of 25:24:1; (c) subjecting said mixture of step (b) to 15 min shaking at 37° C. or to a bead beater for 1 min; (d) centrifuging said mixture of step (c) at 2,500 g for about 10 minutes at room temperature to obtain an aqueous phase; (e) transferring said aqueous phase into a new tube; (f) adding to said aqueous phase within said tube of step (e) an equal amount of iso-propanol supplemented with 20 mg/ml crystal violet solution to obtain violate stained solution; (g) mixing said solution by inverting said tube of step (f) and then incubating said tube for about 30 minutes at room temperature; (h) centrifuging said tube of step (g) at 2,500 g for about 30 minutes at room temperature to obtain a violet stained layer; (i) transferring said violate stained layer into a new tube and centrifuging said tube for about 5 min at maximal speed to obtain pellet and supernatant; (j) washing said pellet with 80% v/v ice cold ethanol and centrifuging for additional 5 min to obtain pellet and supernatant; (k) removing said supernatant of step (j) and allowing said pellet to dry; and (l) suspending said dried pellet in water in a ratio of 100 μl water to 2 gr of soil of step (a).

It is a further object of the present invention to disclose a method for screening for and identifying a desirable plant improving trait, said method comprises steps of: (a) obtaining a sampling of a predefined source; (b) extracting RNA from said sampling according to the method of claim 60; (c) constructing an expression library from said RNA of step (b); wherein said method further comprises steps of: (d) producing plants transformed with said expression library at an efficiency of at least 0.05%-30% representing at least $10^2$-$10^{10}$ transgenes; (e) screening for transformed plants expressing said desirable trait; and (f) identifying said transgene of said transformed plants expressing said desirable trait.

It is a further object of the present invention to disclose the method as defined in any of the above, further comprising a step of editing a target gene in a desirable crop plant according to genetic information obtained from said transgene.

It is a further object of the present invention to disclose the method as defined in any of the above, wherein said editing of said target gene is performed using any genome editing system or method including systems using engineered nucleases selected from the group consisting of: meganucleases, zinc finger nucleases (ZFNs), transcription activator-like effector-based nucleases (TALEN), clustered regularly interspaced short palindromic repeats (CRISPR) system and any combination thereof.

It is a further object of the present invention to disclose the method as defined in any of the above, wherein said predefined source comprises plant, microbial, fungal or other organisms or parts thereof of an environmental niche.

It is a further object of the present invention to disclose the method as defined in any of the above, wherein said screening step comprises measurements of said transformed plants as compared to control plants, said measurements are selected from the group consisting of: turgor pressure measurements, plant death, leaf area, plant shoots fresh weight, leaf number, branch fresh weight, main branch length, flowers yield, pods or fruits yield, chlorosis, damage to leaves, state or performance of plants and any combination thereof.

It is a further object of the present invention to disclose the method as defined in any of the above, wherein said control plant is a plant of the same genus as said transgenic plant and lacking said transgene or a plant of the same genus as said transgenic plant, lacking said transgene and transformed with a known gene conferring said plant improving trait.

It is a further object of the present invention to disclose an isolated polynucleotide having at least 80% sequence similarity to a nucleotide sequence selected from the group consisting of SEQ ID NOs:1 to SEQ ID NO:148 and any combination thereof.

It is a further object of the present invention to disclose an isolated polypeptide having at least 60% sequence similarity to an amino acid sequence selected from the group consisting of SEQ. ID Nos: 149-321 and any combination thereof.

BRIEF DESCRIPTION OF THE DRAWINGS

In order to understand the invention and to see how it may be implemented in practice, several embodiments will now be described, by way of non-limiting example only, with reference to the accompanying drawing, in which:

FIG. 1A illustrates the pPA-35H vector, which has a constitutive CaMV 35S promoter. FIGS. 1B-D present vectors containing stress induced promoters of *Arabidopsis thaliana*: pPA-CH with CBF3 promoter (FIG. 1B), pPA-EH with Erd10 promoter (FIG. 1C) and pPA-KH with Kin1 promoter (FIG. 1D);

DETAILED DESCRIPTION OF THE PREFERRED EMBODIMENTS

Figure 1A:
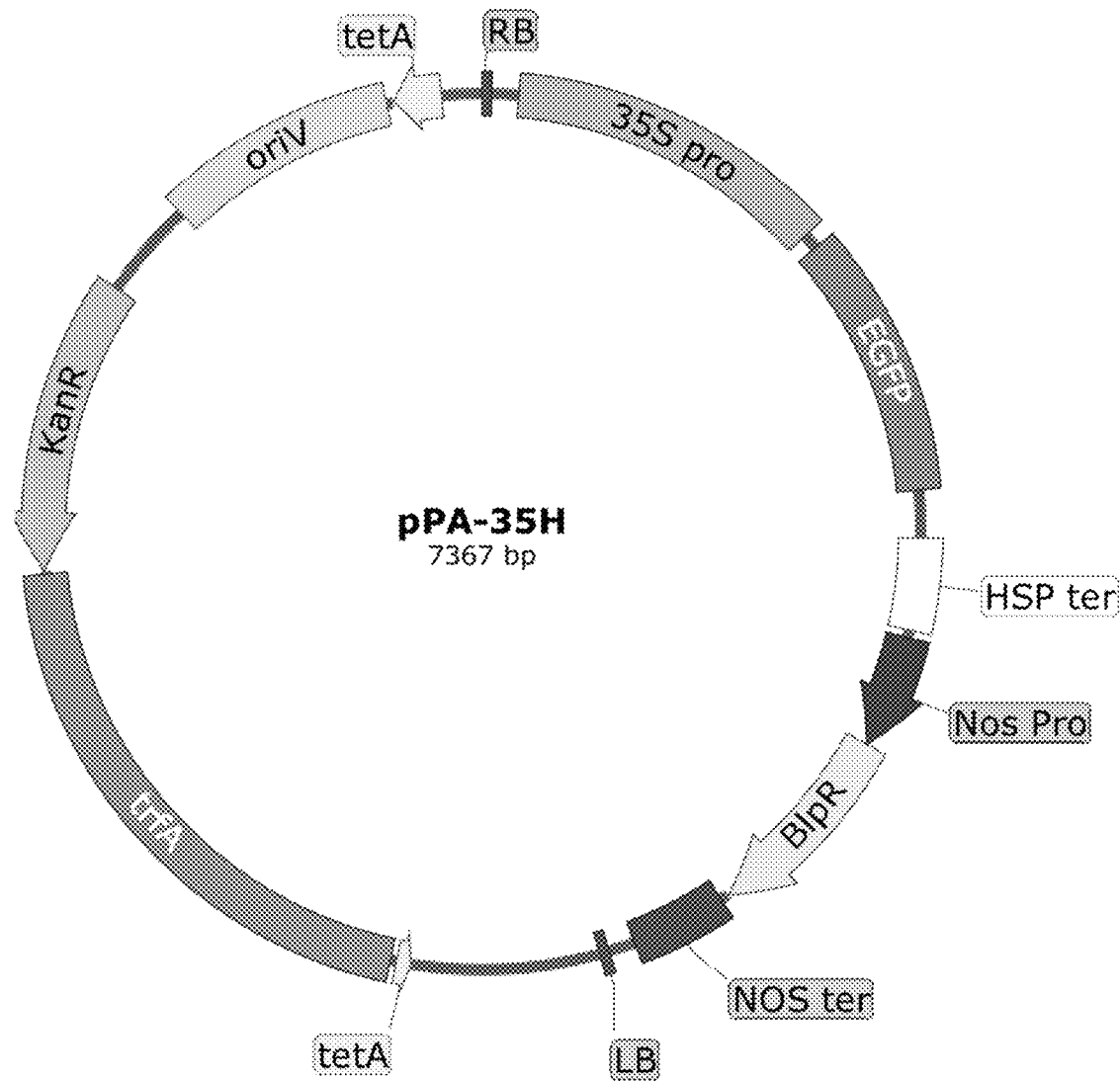
FIGS. 1A-D present schematic illustrations of binary vectors used for insertion of amplified cDNA clones between the promoter(s) (35S, CBF3, Erd10 and Kin1) and the HSP terminator.

The following description is provided, alongside all chapters of the present invention, so that to enable any person skilled in the art to make use of the invention and sets forth the best modes contemplated by the inventor of carrying out this invention. Various modifications, however, will remain apparent to those skilled in the art, since the generic principles of the present invention have been defined specifically to provide means and methods for screening and identifying a desirable plant improving trait.

It is known that some plant species have resistance to various diseases. However, such species are usually hard or impossible to breed in conventional techniques and methods.

The present invention provides a method and platform to discover and identify genes from plants that have unique and valuable features, such as disease resistance, abiotic stress resistance or tolerance, food improving qualities (e.g. improved oils, protein content, amino acids, vitamins etc.) and then to insert or express them in desired crops through gene editing, or other transformation technique.

It is therefore within the scope of the present invention to introduce target traits into existing crops through plant breeding, which includes genetic engineering and gene (genome) editing.

The present invention provides a novel method for screening and identifying a desirable plant improving trait. The method comprises steps of: (a) obtaining genetic material from a sampling of a predefined environmental niche or genetic material extracted from other sources such as plants from the same or other genus; and (b) constructing an expression library from said genetic material. According to core aspects, the present invention further comprises steps of: (c) producing plants transformed with said expression library at an efficiency of at least 0.05%-30% representing at least $10^2$-$10^{10}$ transgenes; (d) screening for transformed plants expressing said desirable trait; and (e) identifying said transgene of said transformed plants expressing said desirable trait.

The present invention provides for the first time a method for screening for and selecting unknown sequences derived from predefined sources (e.g. ecological niches and/or plants) which confer improved traits in valuable crop plants. The current method is effective and advantageous upon common and conventional screening methods by the following aspects:

1. An expression library is prepared from genetic material or genetic pool (i.e. RNA) originating from predefined sources, such as extreme environment, plant material and other. In this way, only genes which are expressed in the preselected environmental conditions are used for the screening procedure in plants.

2. The entire expression library is transformed into plants at an efficiency of 0.05%-30% and representation of at least $10^2$-$10^{10}$ unique transgenes.

3. In the method of the present invention, the screening of the expressed library for the desirable phenotype is performed at the target organism, which is the plant. In this way there is no preselection and new and unique genes for the desired phenotype, which are expressible in plants, are revealed.

In the conventional methods, the first step is selecting genes for a predefined trait in a source genetic material, e.g. by probing a DNA library with known sequences in prokaryotic- or eukaryotic cells, and only then the preselected gene is expressed in plants. The outcome of such a conventional method is limited and has the following drawbacks:

1. The screening is performed in a host cell/organism which is not the target organism (usually in prokaryotic or unicellular organism).

2. The screening is limited since it is performed with known sequences or probes or activity. It was shown that functional screening methods require detectable levels of enzyme activity that cannot be always achieved, for example, only about 40% of the enzymatic activities are likely to be detected in E. coli-based expression systems (Gabor et al., 2004). In addition, it is herein pointed out that despite the advanced sequencing techniques available, ~35-60% of the total protein-coding genes display high similarities to "hypothetical proteins", "predicted proteins" or "protein of unknown function" (Culligan, et al., 2014; Venter, et al., 2004).

3. Only the preselected clone is transformed into plants.

4. The expression and effect of a preselected clone in the target plant is unpredictable.

For the aforementioned reasons the novel method of the present invention of screening plants transformed with an expression library for a desirable phenotype is advantageous.

It is herein acknowledged that drought and salinity are considered as two abiotic stresses that have major effects on plant growth and development.

With respect to drought, it is considered the most devastating environmental stress, which decreases crop growth and productivity. Drought severely affects plant growth and development with substantial reductions in growth rate and biomass accumulation. The main consequences of drought in plants are reduced rate of cell division and expansion, leaf size, stem elongation and root proliferation, and disturbed stomatal oscillations, and water use efficiency (WUE) (Farooq et al. 2009). This phenomenon involves genetic, physiological, and environmental events and their complex interactions. The rate and amount of plant growth depend on these events, which are affected by water deficit. Cell growth is one of the most drought-sensitive physiological processes due to the reduction in turgor pressure and water availability (Taiz and Zeiger, 2006). Under water deficiencies, cell elongation of higher plants can be inhibited by interruption of water flow from the xylem to the surrounding elongating cells. Impaired mitosis, reduced cell elongation and expansion result in reduced plant height, leaf area and crop growth (Nonami, 1998).

Salinity is also considered one of the major severe abiotic factors affecting crop growth and productivity. During salt stress, all major processes such as photosynthesis, protein synthesis and energy and lipid metabolism are affected (Parida & Das, 2005). During initial exposure to salinity, plants experience water stress, which in turn reduces leaf expansion. The osmotic effects of salinity stress can be observed immediately after salt application and are believed to continue for the duration of exposure, resulting in inhibited cell expansion and cell division, as well as stomatal closure. During long-term exposure to salinity, plants experience ionic stress, which can lead to premature senescence of adult leaves, and thus a reduction in the photosynthetic area available to support continued growth. In fact, excess sodium and more importantly chloride has the potential to negatively affect plant enzymes, resulting in reduced energy production and other physiological changes. It is further acknowledged that ionic stress results in premature senescence of older leaves and in toxicity symptoms (chlorosis, necrosis) in mature leaves. Without wishing to be bound by theory, the high sodium ions affect plants by disrupting protein synthesis and interfering with enzyme activity (Carillo et al., 2011).

The present invention provides a method for efficiently screening for novel genes conferring resistance or improved tolerance to drought and/or salinity in plants and especially in valuable crops.

The method of the present invention overcomes the above drawbacks by using expressed genetic material (such as RNA or mRNA) that represent the genes that are being expressed in selected organisms, e.g. as a result of environmental conditions (such as drought or high salt), and producing a cDNA library that represents the 'Meta-Expression' or metatranscriptome status of a certain biological niche or other genetic source. The entire cDNA library is then transformed into plants and expressed and screened for the desirable phenotype in the plants.

A core aspect of the present invention is that an expression library is produced from various sources (including plants) and environments. The expression library is transformed into plants, which is the target organism in order to improve its traits or functions. The plant expression library is then screened for the desirable trait, such as salt or drought resistance or tolerance, improved biomass and yield production, biotic stresses (diseases and pathogens) resistance or tolerance, improved nutritional value or improved fertilizers utilization.

It is herein acknowledged that the environments (such as soils) in which plants grow are inhabited by microbial communities, e.g. one gram of soil contains about $10^7$-$10^9$ microbial cells (estimates of the number of species of bacteria per gram of soil vary between 2000 and 8.3 million, https://www.ncbi.nlm.nih.gov/pmc/articles/PMC2970868/) which comprise about one gigabase of sequence information, or more. The microbial communities which inhabit environments in which plants grow (such as soils) are complex and remain poorly understood despite their economic importance. Such microbial consortia provide the ecosystem necessary for plant growth, including fixing atmospheric nitrogen, nutrient cycling, disease suppression, and sequester iron and other metals.

It is within the scope of the present invention to use functional metagenomics and metatrascriptomics approaches to explore new genes which confer improved traits to plants.

Reference is now made to metagenomics approaches, employed by the present invention according to some aspects. Metagenomics is the study of genetic material derived from environmental samples. It generally refers to as environmental genomics, eco-genomics or community genomics. While traditional microbiology and microbial genome sequencing and genomics rely upon cultivated clonal cultures, environmental gene sequencing cloned specific genes to produce a profile of diversity in a natural sample. In some aspects, metagenomics uses the study of the genomes in a microbial community to constitute the first step to studying the microbiome. Its main purpose is to infer the taxonomic profile of a microbial community. The whole-metagenome sequencing (WMS) provides data on the functional profile of a microbial community. Such work revealed that the vast majority of microbial biodiversity had been missed by cultivation-based methods. In fact it is estimated that over 99% of all microorganisms in almost every environment on earth cannot be cultivated in the laboratory.

Metagenomics is herein also refers to metatranscriptomics, which studies and correlates the transcriptomes of a group of interacting organisms or species. Metatranscriptomics involves sequencing the complete (meta)transcriptome of the microbial community. In some aspects, metatranscriptomics informs the genes that are expressed by the community as a whole. With the use of functional annotations of expressed genes, it is possible to infer the functional profile of a community under specific conditions, which are usually dependent on the status of the host. While metagenomics provides data on the composition of a microbial community under different conditions, metatrascriptomics provides data on the genes that are collectively expressed under different conditions. Metatranscriptomics involves profiling of community-wide gene expression (RNA-seq). In specific aspects, metatranscriptomics describes the genes that are expressed in a specific microbial environment. Thus, metatranscriptomics is the study of the function and activity of the complete set of transcripts (RNA-seq) from environmental samples.

It is noted that gene expression is log-like distributed, for example, top 100 genes of highest expression can cover up to 30% of all transcripts. Even a single gene can cover up to 10%. Thus, a very high sequencing depth is required to see also lower expressed genes.

By using methods such as "shotgun" or PCR directed sequencing, largely unbiased samples of the genes from the members of sampled communities can be obtained. It is herein acknowledged that metagenomics approaches provide a powerful tool for utilizing microbial ecology to improve traits in plants, for example, biological mechanisms that can be harnessed for agriculture and improved plant traits.

As used herein, the term "about" denotes ±25% of the defined amount or measure or value.

As used herein the term "similar" denotes a correspondence or resemblance range of about ±20%, particularly ±15%, more particularly about ±10% and even more particularly about ±5%.

As used herein the term "average" refers to the mean value as obtained by measuring a predetermined parameter in each plant of a certain plant population and calculating the mean value according to the number of plants in said population.

As used in this specification and the appended claims, the singular forms "a", "an", and "the" include plural referents unless the context clearly dictates otherwise. Thus, for example, reference to "a plant" includes one or more plants, reference to "a trait" includes one or more traits and reference to "a cell" includes mixtures of cells, tissues, and the like.

A "plant" as used herein refers to any plant at any stage of development, including a plant seed.

The term "plant" includes the whole plant or any parts or derivatives thereof, such as plant cells, plant protoplasts, plant cell tissue culture from which plants can be regenerated, plant callus or calli, meristematic cells, microspores, embryos, immature embryos, pollen, ovules, anthers, fruit, flowers, leaves, cotyledons, pistil, seeds, seed coat, roots, root tips and the like.

The term "plant cell" used herein refers to a structural and physiological unit of a plant, comprising a protoplast and a cell wall. The plant cell may be in a form of an isolated single cell or a cultured cell, or as a part of higher organized unit such as, for example, plant tissue, a plant organ, or a whole plant.

The term "plant cell culture" or "tissue culture" as used herein means cultures of plant units such as, for example, protoplasts, regenerable cells, cell culture, cells, cells in plant tissues, pollen, pollen tubes, ovules, embryo sacs, zygotes and embryos at various stages of development, leaves, roots, root tips, anthers, meristematic cells, microspores, flowers, cotyledons, pistil, fruit, seeds, seed coat or any combination thereof.

The term "plant material" or "plant part" used herein refers to leaves, stems, roots, root tips, flowers or flower parts, fruits, pollen, egg cells, zygotes, seeds, seed coat, cuttings, cell or tissue cultures, or any other part or product of a plant or any combination thereof.

A "plant organ" as used herein means a distinct and visibly structured and differentiated part of a plant such as a root, stem, leaf, flower, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture, protoplasts, meristematic cells, calli and any group of plant cells organized into structural and/or functional units. The use of this term in conjunction with, or in the absence of, any specific type of plant tissue as listed above or otherwise embraced by this definition is not intended to be exclusive of any other type of plant tissue.

As used herein, the term "trait" refers to a characteristic or phenotype, particularly, to a plant improving characteristic or phenotype. A phenotypic trait may refer to the appearance or other detectable characteristic of an individual, resulting from the interaction of its genome, proteome and/or metabolome with the environment. For example, in the context of the present invention a plant improving trait or a desirable plant improving trait relates to resistance or tolerance to at least one biotic stress, resistance or tolerance to at least one abiotic stress, improved yield or biomass, improved grain yield, improved fertilizer uptake and usage efficiency and any combination thereof.

A trait may be inherited in a dominant or recessive manner, or in a partial or incomplete-dominant manner. A trait may be monogenic (i.e. determined by a single locus) or polygenic (i.e. determined by more than one locus) or may also result from the interaction of one or more genes with the environment. A dominant trait results in a complete phenotypic manifestation at heterozygous or homozygous state; conventionally, a recessive trait manifests itself only when present at homozygous state.

The term "phenotype" is understood within the scope of the present invention to refer to a distinguishable characteristic(s) of a genetically controlled trait.

As used herein, the phrase "phenotypic trait" refers to the appearance or other detectable characteristic of an individual, resulting from the interaction of its genome, proteome and/or metabolome with the environment.

It is within the scope of the current invention that "stress" may be defined as any external factor that has a negative influence on plant growth, function and/or reproduction The term "abiotic stress" is herein generally defined as the negative impact of non-living factors on the plant in a specific environment. The non-living variable must influence the environment beyond its normal range of variation to adversely affect the plant or plant population performance or physiology in a significant way. Non limiting examples of abiotic stress factors, or stressors, or environmental factors may encompass factors such as sunlight, wind, temperature (cold, heat), salinity, over watering (flooding), drought and factors such as fertilizer uptake and fertilizer usage efficiency and any combination thereof. Abiotic stress resistance or tolerance may enhance the growth and productivity of plants and specifically crops. It has been shown that abiotic stressors are most harmful and may result in synergistic effects when they occur together, in combinations of abiotic stress factors.

The term "drought" refers hereinafter to a physical phenomenon generally caused by an extended period of below average precipitation or irrigation. For example, not enough or low moisture (at the soil or at the air), water supply shortages, dry soil, moisture regimes, high salinity, heat and any combination thereof. Dry conditions may develop for different reasons. It can have a substantial impact on the ecosystem and agriculture, e.g. reduction in yield and crop damage.

Many organisms have drought tolerance physiological and genetic adaptations.

"Biotic stress" is herein defined as stress that occurs as a result of damage done to plants by other living organisms, such as bacteria, viruses, fungi, whitefly, thrips, spidermites, nematodes, parasites, beneficial and harmful insects, weeds, and cultivated or native plants. The types of biotic stresses imposed on a plant may be depended on both geography and climate and on the host plant and its ability to resist particular stresses.

As used herein, the phrase "resistance" refers to the ability of a plant to restrict the growth and development of a specified pathogen and/or the damage caused to the plant when compared to susceptible plants under similar environmental conditions. Resistant plants may exhibit some disease symptoms or damage under pathogen or pest pressure or under abiotic stress condition.

It is further within the scope of the present invention that resistance means that a plant completely immunizes itself from a particular stress, for example to a biotrophic pathogen infection. According to specific embodiments of the invention, by transformation of an expression library to a host plant, the transformed host acquires a resistance gene which prevents the proliferation of the pathogen and/or confers resistance to a particular abiotic stress (e.g. drought).

According to some aspects, resistance is an absolute term where the plant completely immunizes itself to a particular stress. It should be noted that this does not mean that tolerance cannot be obtained in case of biotic or abiotic stress.

The term "tolerance" refers hereinafter to the characteristic of a plant that allows a plant to avoid, tolerate or recover from biotic or abiotic stressors, under conditions that would typically cause a greater amount of injury to other plants of the same species. These inheritable characteristics influence the degree of damage caused to the plant. In terms of agricultural production tolerance means that the plant can be under stress (diseased/infected/or physiologically challenged) but the extent of loss does not exceed the economic threshold level (an extent of loss which do not hamper the economic potential of the produce). According to further aspects of the present invention, tolerance is a relative term. Examples of tolerance can be found in case of plant pathogens and all abiotic stresses, especially in the case of complex traits that are governed by multiple factors.

In general, 'resistance' and 'tolerance' are the terms used to denote the ability of the plant to manage the stress, be it biotic or abiotic.

The term "transformation" used herein refers to genetic alteration or modification induced by the introduction of exogenous DNA into a cell. This includes both integration of the exogenous DNA into the host genome, and/or introduction of plasmid DNA containing the exogenous DNA into the plant cell. Such a transformation process results in the uptake, incorporation and expression of exogenous genetic material (exogenous DNA, for examples expression library prepared from ecological niche sampling). Plant transformation may refer to the introduction of exogenous genes into plant cells, tissues or organs, employing direct or indirect means developed by molecular and cellular biology.

The term "environmental niche" or "ecological niche" generally refers to the behavior of a species living under specific environmental conditions. It includes the microbes, fungi, plants or other organisms that inhabit a given environmental location (extremophiles). The ecological niche describes how an organism or population responds to the distribution of resources and competitors and how it in turn alters those same factors. The type and number of variables comprising the dimensions of an environmental niche vary from one species to another and the relative importance of particular environmental variables for a species may vary according to the geographic abiotic and biotic contexts.

According to other aspects, the term "environmental niche" or "ecological niche" describes the relational position of a species or population in an ecosystem. More specifically, it describes how a population responds to the abundance of its resources and competitors and how it affects those same factors. The abiotic or physical environment is also part of the niche because it influences how populations affect, and are affected by, resources and competition. The description of a niche may include descriptions of the organism's life history, habitat, and place in the food chain. In context of the present invention "environmental niche" or "ecological niche" can be defined according to biotic factors or abiotic factors such as high salinity, drought conditions, elevated heat, cold conditions, pH or any other extreme environmental conditions.

It is within the scope of the current invention that the genetic material is derived from a sampling of a predefined environmental niche, including from soil, water, plant biomass, microorganisms, yeast, algae, nematode, etc.

The term "microbiome" or "microbiota" as used herein refers to an ecological community of commensal, symbiotic and pathogenic microorganisms found in and on all multicellular organisms from plants to animals. A microbiota includes bacteria, archaea, protists, fungi and viruses. Microbiota has been found to be crucial for immunologic, hormonal and metabolic homeostasis of their host. The synonymous term microbiome describes either the collective genomes of the microorganisms that reside in an environmental niche or the microorganisms themselves. The microbiome and host emerged during evolution as a synergistic unit from epigenetics and genomic characteristics, sometimes collectively referred to as a holobiont.

The term "genetic material" or "genetic pool" refers hereinafter to sum of a population's genetic material at a given time. It includes all genes and combinations of genes (sum of the alleles) in the population.

The term "isolated" as used hereinafter means that material is removed from its original environment (e.g., the natural environment if it is naturally occurring). For example, a naturally-occurring polynucleotide or polypeptide which is separated from some or all of the coexisting materials in the natural system is isolated.

The nucleic acid isolated or derived from microorganisms or any organism can preferably be inserted into a vector or a plasmid. Such vectors or plasmids are preferably those containing expression regulatory sequences, including promoters, enhancers and the like suitable for expression in plants. Particularly preferred plasmids and methods for introduction and transformation into them are described in detail in the protocol set forth herein.

The term "expression library" as used hereinafter refers to a collection of vectors or viruses (such as plant viruses used as virus-vectors) or plasmids or phages containing a representative sample of cDNA or genomic fragments that are constructed in such a way that they will be transcribed and or translated by the host organism (in the context of the present invention, plants). The technique uses expression vectors to generate a library of clones, with each clone transcribing one RNA and or expressing one protein. This expression library is then screened for the property of interest and clones of interest recovered for further analysis. One and non-limiting example would be using an expression library to isolate genes that could confer resistance or tolerance to drought.

It is within the scope of the present invention that the expression library (usually derived from microbial genetic material) can be constructed in a binary vector (or transfer DNA (T-DNA) binary system or a shuttle vector) able to replicate in multiple hosts (e.g. *E. coli* and *Agrobacterium tumefaciens*) to produce genetically modified plants. These are artificial vectors that have been created from the naturally occurring Ti plasmid found in *Agrobacterium tumefaciens*. In some aspects, the expression libraries are transferred from *Agrobacterium tumefaciens* to plants.

The term "editing" or "gene editing" or "genome editing" refers hereinafter to any conventional or known genome editing system or method including systems using engineered nucleases selected from the group consisting of: meganucleases, zinc finger nucleases (ZFNs), transcription activator-like effector-based nucleases (TALEN), clustered regularly interspaced short palindromic repeats (CRISPR) system and any combination thereof. In the context of the present invention, the aforementioned gene editing techniques are used to edit a target gene in a desirable crop according to the information obtained from the transgene identified by the method of the present invention.

The term "corresponding to the sequence" refers hereinafter to sequence homology or sequence similarity. These terms relate to two or more nucleic acid or protein sequences, that are the same or have a specified percentage of amino acid residues or nucleotides that are the same, when compared and aligned for maximum correspondence, as measured using one of the available sequence comparison algorithms or by visual inspection.

According to further aspects of the invention, the term "corresponding to the nucleotide sequence" refers to variants, homologues and fragments of the indicated nucleotide sequence which possess or perform the same biological function or correlates with the same phenotypic characteristic of the indicated nucleotide sequence.

Another indication that two nucleic acid sequences are substantially similar or that a sequence is "corresponding to the nucleotide sequence" is that the two molecules hybridize to each other under stringent conditions. High stringency conditions, such as high hybridization temperature and low salt in hybridization buffers, permits only hybridization between nucleic acid sequences that are highly similar, whereas low stringency conditions, such as lower temperature and high salt, allows hybridization when the sequences are less similar.

The term "similarity" or "sequence similarity" refers hereinafter to the degree of resemblance between two sequences when they are compared. This is dependent on their identity and it shows the extent to which residues are aligned. Sequence similarity refers to an optimal matching problem (i.e. for sequence alignments). The optimal matching algorithm finds the minimal number of edit operations (inserts, deletes, and substitutions) in order to align one sequence to another sequence. Sequence similarity searches can identify "homologous" proteins or genes by detecting excess similarity, meaning, statistically significant similarity that reflects common ancestry.

It is within the scope of the current invention that similarity searching is an effective and reliable strategy or tool for identifying homologs (i.e. sequences that share a common evolutionary ancestor). Non limiting examples of similarity searching programs, include BLAST (e.g. Altschul et al. 1997); units 3.3 and 3.4), PSI-BLAST (e.g. Altschul et al., 1997), SSEARCH (e.g. Smith and Waterman, 1981); Pearson, 1991, unit 3.10), FASTA (e.g. Pearson and Lipman, 1988, unit 3.9) and the HMMER3 (e.g. Johnson et al., 2010). Such programs produce accurate statistical estimates, and can ensure that protein or nucleic acid sequences that share significant similarity also may have similar structures. Similarity searching is effective and reliable because sequences that share significant similarity can be inferred to be homologous; namely sharing a common ancestor.

Similarity is understood within the scope of the present invention to refer to a sequence similarity of at least 60%, particularly a similarity of at least 70%, preferably more than 80% and still more preferably more than 90%. The term "substantially similar" refers to a nucleic acid, which is at least 50% identical in sequence to the reference when the entire ORF (open reading frame) is compared, where the sequence similarity is preferably at least 70%, more preferably at least 80%, still more preferably at least 85%, especially more than about 90%, most preferably 95% or greater, particularly 98% or greater.

In some embodiments of the invention, such substantially similar sequences refer to polynucleotide or amino acid sequences that share at least about 60% similarity, preferably at least about 80% similarity, alternatively, about 90%, 95%, 96%, 97%, 98% or 99% similarity to the indicated polynucleotide or amino acid sequence/s.

The present invention encompasses nucleotide sequences having at least 60% similarity, preferably 70%, more preferably 80%, even more preferable 90% and especially more preferable 95% similarity to polynucleotide sequences identified by the method of the present invention or to a reference sequence.

The present invention further encompasses amino acid sequences having at least 60% similarity, preferably 70%, more preferably 80%, even more preferable 90% and especially more preferable 95% similarity to polypeptide sequences identified by the method of the present invention or to a reference sequence.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene or protein sequence.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

The term "identity" or "sequence identity" further refers hereinafter to the amount of characters which match exactly between two different sequences. Hereby, gaps are not counted and the measurement is relational to the shorter of the two sequences.

In other words, if two sequences, which are to be compared with each other, differ in length, sequence identity preferably relates to the percentage of the nucleotide residues of the shorter sequence, which are identical with the nucleotide residues of the longer sequence. As used herein, the percent of identity between two sequences is a function of the number of identical positions shared by the sequences, taking into account the number of gaps, and the length of each gap, which needs to be introduced for optimal alignment of the two sequences. The comparison of sequences and determination of identity percent between two sequences can be accomplished using a mathematical algorithm as known in the relevant art.

It is further within the scope that the terms "similarity" and "identity" additionally refer to local homology, identifying domains that are homologous or similar (in nucleotide and/or amino acid sequence). It is acknowledged that bioinformatics tools such as BLAST, SSEARCH, FASTA, and HMMER calculate local sequence alignments which identify the most similar region between two sequences. For domains that are found in different sequence contexts in different proteins, the alignment should be limited to the homologous domain, since the domain homology is providing the sequence similarity captured in the score. According to some aspects the term similarity or identity further includes a sequence motif, which is a nucleotide or amino-acid sequence pattern that is widespread and has, or is conjectured to have, a biological significance. Proteins may have a sequence motif and/or a structural motif, a motif formed by the three-dimensional arrangement of amino acids which may not be adjacent.

According to further embodiments, protein or polynucleotide sequences with specific location or domain sequence similarity are identified by the method of the present invention. When comparing residues with no conservation the low similarity is meaningless thus lower overall similarity sequences with high conservation in conserved region will be still considered as similar in a given range, for example of >60% (i.e. sequences showing low similarity of ~37% to the nearest homolog but possess all the conserved substrate binding residues of a specific protein family) that can be found in hmm-based search algorithms such as HMMER3.

The term "Conserved Domain Database (CDD)" refers to a collection of sequence alignments and profiles representing protein domains. It also includes alignments of the domains to known 3-dimensional protein structures in the database (i.e. Molecular Modeling Database (MMDB).

In some embodiments of the invention, such substantially identical sequences refer to polynucleotide or amino acid sequences that share at least about 60% identity, preferably at least about 80% identity, alternatively, about 90%, 95%, 96%, 97%, 98% or 99% identity to the indicated polynucleotide or amino acid sequence/s.

Polypeptides within the scope of the present invention are at least 50% identical to the protein identified by the method of the present invention; or at least 55% identical, or at least 60% identical, or at least 65% identical, or at least 70% identical, or at least 75% identical, or at least 80% identical, or at least 85% identical or at least 90% identical or at least 95% identical to the protein identified by the method of the present invention or to a reference sequence.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. J. Mol. Biol. 48:443).

The term "homolog" as used herein, refers to a DNA or amino acid sequence having a degree of sequence similarity in terms of shared amino acid or nucleotide sequences. There may be partial similarity or complete similarity (i.e., identity). For protein sequences, amino acid similarity matrices may be used as are known in different bioinformatics programs (e.g. BLAST, FASTA, Bestfit program-Wisconsin Sequence Analysis Package, Version 8 for Unix, Genetics Computer Group, University Research Park, 575 Science Drive Madison, Wis. 53711, Smith Waterman). Different results may be obtained when performing a particular search with a different matrix. Degrees of similarity for nucleotide sequences are based upon identity matches with penalties made for gaps or insertions required to optimize the alignment, as is well known in the art (e.g. Altschul S. F. et al., 1990, J Mol Biol 215(3):403-10; Altschul S. F. et al., 1997, Nucleic Acids Res. 25:3389-3402). Guidance in determining which amino acid residues may be substituted, inserted, or deleted without abolishing biological or activity may be found using computer programs well known in the art, for example, DNASTAR software.

The term "polymorphism" is understood within the scope of the invention to refer to the presence in a population of two or more different forms of a gene, genetic marker, or inherited trait or a gene product obtainable, for example, through alternative splicing, DNA methylation, etc.

The present invention encompasses "High-throughput screening" or "HTS" technique, which herein refers to a method to rapidly identify genes that modulate a particular biomolecular pathway or function. It includes metatranscriptomic and metagenomic gene expression.

The present invention outlines a procedure for producing expression libraries from genetic material isolated from ecological niches, which expression libraries can be transformed into the target plant for screening for a desirable trait such as tolerance or resistance to biotic or abiotic stress and improving yield or biomass production.

According to one embodiment, the present invention provides a method for screening for and identifying a desirable plant improving trait, the method comprises steps of: (a) obtaining genetic material from a sampling of a predefined environmental niche; and (b) constructing an expression library from the genetic material. According to core embodiments, the present invention further comprises steps of: (c) producing plants transformed with the expression library at an efficiency of at least 0.05%-30%, representing at least $10^2$-$10^{10}$ transgenes, thus creating the expressed library within the plants or seeds; (d) screening for transformed plants expressing the desirable trait; and (e) identifying the transgene of the transformed plants expressing the desirable trait.

It is further within the scope to disclose the method as defined in any of the above, wherein the step (a) further comprises steps of enriching the genetic material by growth on rich media or on selective media.

It is further within the scope to disclose the method as defined in any of the above, wherein the step (a) further comprises steps of enhancing expression of the desirable trait by culturing the genetic material on selective media for the desirable trait.

It is further within the scope to disclose the method as defined in any of the above, wherein the step (b) comprises steps of producing prokaryotic cDNA library or eukaryotic cDNA library or both.

It is further within the scope to disclose the method as defined in any of the above, wherein the step (b) further comprises steps of cloning the cDNA library into at least one binary vector.

It is further within the scope to disclose the method as defined in any of the above, wherein the binary vector comprises a constitutive promoter or a stress induced promoter.

It is further within the scope to disclose the method as defined in any of the above, wherein the binary vector comprises bacterial selection marker and plant transformation selection marker.

It is further within the scope to disclose the method as defined in any of the above, wherein the bacterial selection marker is Kanamycin resistance, or any other antibiotic resistance conferring gene, and the plant transformation selection marker is bar gene, conferring resistance to phosphinothricin containing herbicide (e.g. Basta herbicide).

Reference is now made to Glufosinate (also known as phosphinothricin and often an ammonium salt) is a naturally occurring broad-spectrum systemic herbicide produced by several species of Streptomyces soil bacteria. Glufosinate is a broad-spectrum herbicide that is used to control weeds. It is sold in formulations under brands including Basta, Rely, Finale, Challenge and Liberty. The bar gene confers resistance to the herbicide Basta (containing phosphinothricin).

It is further within the scope to disclose the method as defined in any of the above, further comprises steps of transforming the cloned binary vectors into host cells.

It is further within the scope to disclose the method as defined in any of the above, further comprises steps of transforming the cloned binary vectors into *Agrobacterium tumefaciens*.

It is further within the scope to disclose the method as defined in any of the above further comprises steps of introducing the transformed *Agrobacterium tumefaciens* into at least one of: whole plant, plant tissue and plant cell.

It is further within the scope to disclose the method as defined in any of the above, comprises steps of introducing the transformed *Agrobacterium tumefaciens* by spraying the plants with an inoculum comprising transformed *Agrobacterium*.

It is further within the scope to disclose the method as defined in any of the above, wherein the step (d) comprises growing the transformed plants under conditions selective for the desirable trait.

It is further within the scope to disclose the method as defined in any of the above, further comprises steps of:
f. collecting T1 seeds from the transformed plants of step (d);
g. determining seed library efficiency of the T1 seeds by calculating ratio of phosphinothricin resistant plants to total number of plants;
h. sowing the T1 seeds of step (e) under selective conditions allowing screening and selection of transformed plants expressing the desirable trait;
i. testing the selected plants expressing the desirable trait of step (g) for presence of the transgene; and
j. isolating and sequencing the transgene of the selected transformed plants positively tested for the transgene of step (h).

It is further within the scope to disclose the method as defined in any of the above, further comprises steps of
k. collecting T2 seeds from the plants of (h), which are found positive for presence of the transgene;
l. growing plants of the T2 seeds under selective conditions allowing screening and selection of transformed plants expressing the desirable trait as compared to control plants transformed with known genes conferring the desirable trait; and
m. optionally, isolating and sequencing the transgene of the selected plants of step (j).

It is further within the scope to disclose the method as defined in any of the above, comprises steps of
a. recloning and sequencing the isolated transgene of step (i) and/or (l);
b. transforming the recloned transgene into plants;
c. screening the transformed plants of step (b) for selection of transformed plants expressing the desirable trait;
d. isolating the transgene from the selected plants of step (c); and
e. optionally, repeating steps (a) to (d).

It is further within the scope to disclose the method as defined in any of the above, wherein the environmental niche comprises samples derived from ecological niches, sources, populations, habitats, gene pools, prokaryotic culture, eukaryotic culture and any combination thereof.

It is further within the scope to disclose the method as defined in any of the above, wherein the environmental niche sampling comprises microbiome, microbiota or microbial culture, plant, yeast, algae, nematode or any other organism or combinations thereof.

It is further within the scope to disclose the method as defined in any of the above, wherein the environmental niche is defined according to biotic factors, abiotic factors and a combination thereof.

It is further within the scope to disclose the method as defined in any of the above, wherein the environmental niche sampling comprises soil sample, water sample, organic matter sample, any living organisms (such as plant, yeast, bacteria, microorganism, algae, nematode) and any combination thereof.

It is further within the scope to disclose the method as defined in any of the above, wherein the desirable trait is selected from the group consisting of resistance or tolerance to at least one biotic stress, resistance or tolerance to at least one abiotic stress, improved yield or biomass, improved grain yield, improved fertilizer uptake and improved usage efficiency and a combination thereof.

It is further within the scope to disclose the method as defined in any of the above, wherein the abiotic stress is selected from the group consisting of: drought, salinity, heat, cold, fertilizer uptake, fertilizer utilization efficiency and any combination thereof.

It is further within the scope to disclose the method as defined in any of the above, wherein the biotic stress is selected from the group consisting of: pathogens, bacteria, viruses, fungi, parasites, beneficial and harmful insects, weeds, and cultivated or native plants or any combination thereof.

It is further within the scope to disclose the method as defined in any of the above, wherein the method comprises steps of extracting RNA from the sampling of the predefined environmental niche.

It is further within the scope to disclose the method as defined in any of the above, wherein the RNA extraction is performed according to standard commercial kits or according to any other protocol for extraction of RNA from environmental sampling.

It is further within the scope to disclose the method as defined in any of the above, wherein the protocol for extraction of RNA from environmental sampling comprises steps of:
a. obtaining a soil sample;
b. mixing the soil sample with an extraction buffer comprising 500 mM phosphate buffer pH 8 and 5% w/v cetyltrimethylammonium bromide (CTAB) with phenol (pH 8)/chloroform/IAA ratio of 25:24:1;

c. subjecting the mixture of step (b) to 15 min shaking at 37° C. or to a bead beater for 1 min;
d. centrifuging the mixture of step (c) at 2,500 g for about 10 minutes at room temperature to obtain an aqueous phase;
e. transferring the aqueous phase into a new tube;
f. adding to the aqueous phase within the tube of step (e) an equal amount of iso-propanol supplemented with 20 mg/ml crystal violet solution to obtain violate stained solution;
g. mixing the solution by inverting said tube of step (f) and then incubating the tube for about 30 minutes at room temperature;
h. centrifuging the tube of step (g) at 2,500 g for about 30 minutes at room temperature to obtain a violet stained layer;
i. transferring the violate stained layer into a new tube and centrifuging the tube for about 5 min at maximal speed to obtain pellet and supernatant;
j. washing the pellet with 80% v/v ice cold ethanol and centrifuging for additional 5 min to obtain pellet and supernatant;
k. removing the supernatant of step (j) and allowing the pellet to dry; and
l. suspending the dried pellet in water in a ratio of 100 μl water to 2 gr of soil of step (a).

It is further within the scope to disclose polynucleotide sequences obtainable by the method as defined above.

It is further within the scope to disclose the polynucleotide as defined above, wherein the polynucleotide comprises a nucleotide sequence corresponding to the sequence as set forth in a polynucleotide sequence selected from the group consisting of SEQ ID NOs:1-148 and any combination thereof.

It is further within the scope to disclose a polynucleotide sequence having at least 80%, 85%, 90% or 95% sequence similarity to a polynucleotide sequence obtainable by the method as defined above.

It is further within the scope to disclose a polypeptide sequence obtainable by the method as defined above.

It is further within the scope to disclose the polypeptide sequence as defined above, wherein the polypeptide comprises an amino acid sequence corresponding to the sequence as set forth in a polypeptide sequence selected from the group consisting of SEQ ID NOs: 149-321 and any combination thereof.

It is further within the scope to disclose an amino acid sequence having at least 60%, 70%, 80% or 90% sequence similarity to an amino acid sequence obtainable by the method as defined above.

It is further within the scope to disclose the use of the method as defined above for identifying genes conferring resistance or tolerance to abiotic or biotic stress.

It is further within the scope to disclose the use of the method as defined above for identifying genes conferring improved yield and biomass, i.e. improved grain yield, in plants, for example by enhancing growth, with or without exposure to stress conditions.

It is further within the scope to disclose the use of the method as defined above for identifying genes conferring improved yield.

It is further within the scope to disclose the use as defined in any of the above, wherein the abiotic stress is selected from the group consisting of: drought, salinity, heat, cold, fertilizer utilization, fertilizer uptake and any combination thereof.

It is further within the scope to disclose the use as defined in any of the above, wherein the biotic stress is selected from the group consisting of: pathogens, bacteria, viruses, fungi, parasites, beneficial and harmful insects, weeds, and cultivated or native plants or any combination thereof.

It is further within the scope to disclose a method for screening for and identifying a drought resistance or tolerance improving trait in plants, the method comprises steps of: (a) obtaining genetic material derived from a low moisture or a high salinity environmental niche sample; and (b) constructing expression library from the genetic material. According to core embodiments, the method further comprises steps of: (c) producing plants transformed with the expression library at an efficiency of at least 0.05%-30%, representing at least $10^2$-$10^{10}$ transgenes; (d) screening for transformed plants surviving predetermined drought conditions; and (e) identifying the transgene of the drought surviving transformed plants of step (d).

It is further within the scope to disclose the method as defined above, wherein the step (b) further comprises steps of cloning the expression library into at least one binary vector.

It is further within the scope to disclose the method as defined in any of the above, further comprises steps of:
f. collecting T1 seeds from the transformed plants of step (c);
g. sowing the T1 seeds in soil selective for transformed plants, with water content of about 100% capacity;
h. growing plants of the T1 seeds in drought condition and/or without irrigation until most of the plants die, to produce transformed plants surviving the drought conditions;
i. growing the drought surviving transformed plants to produce T2 seeds;
j. screening the drought surviving transformed plants of step (i) for presence of a transgene;
k. isolating and sequencing the transgene from positively screened plants of step (j);

It is further within the scope to disclose the method as defined in any of the above, further comprises steps of
l. collecting T2 seeds from each of the transgene-containing positively screened drought surviving transformed plants of step (j);
m. growing T2 plants from each of the transgene-containing T2 seeds of step (l) under predetermined drought conditions as compared to control plants transformed with known genes conferring drought tolerance or drought resistance;
n. performing drought tolerance or resistance screen measurements for each of the transgene-containing T2 plants as compared to the control plants selected from the group consisting of: turgor measurements, number of plants death, state of plants and any combination thereof;
o. isolating the transgene from the screened drought resistance performing T2 plants of step (n);
p. optionally, recloning the transgene into a binary vector;
q. optionally, transforming the cloned binary vector into plants and growing the transformed plants under predetermined drought conditions; and
r. optionally, repeating steps (l) to (q).

It is further within the scope to disclose the method as defined in any of the above, wherein the step of growing T2 plants comprises steps of: (a) sowing the T2 seeds in soil selective for transformed plants, with water content of about 100% capacity; and (b) irrigating the plants when water content in the soil reaches about 5-10%.

It is further within the scope to disclose the method as defined in any of the above, wherein the predetermined drought conditions are selected from the group consisting of low moisture, high salinity, dry soil and heat.

It is further within the scope to disclose polynucleotide sequences obtainable by the method as defined in any of the above.

It is further within the scope to disclose the polynucleotide as defined above, wherein the polynucleotide comprises a nucleotide sequence corresponding to the sequence as set forth in a polynucleotide sequence selected from the group consisting of SEQ ID NOs:1 to SEQ ID NO:148 and any combination thereof.

It is further within the scope to disclose polynucleotide sequences having at least 80%, 85%, 90% or 95% sequence similarity to polynucleotide sequences obtainable by the method as defined in any of the above.

It is further within the scope to disclose a polypeptide sequence obtainable by the method as defined in any of the above.

It is further within the scope to disclose the polypeptide sequence as defined above, wherein the polypeptide sequence comprises an amino acid sequence corresponding to the sequence as set forth in polypeptide sequence selected from the group consisting of SEQ. ID Nos: 149-321 and any combination thereof.

It is further within the scope to disclose polypeptide sequences having at least 60%, 70%, 80% or 90% sequence similarity to amino acid sequences obtainable by the method as defined in any of the above.

It is further within the scope of the present invention to disclose a method for extracting RNA from a soil sample comprising steps of:
  m. obtaining a soil sample;
  n. mixing said soil sample with an extraction buffer comprising 500 mM phosphate buffer pH 8 and 5% w/v cetyltrimethylammonium bromide (CTAB) with phenol (pH 8)/chloroform/IAA ratios of 25:24:1;
  o. subjecting said mixture of step (b) to about 15 min shake at 37° C. or to a bead beater for 1 min;
  p. centrifuging said mixture of step (c) at 2,500 g for about 10 minutes at room temperature to obtain an aqueous phase;
  q. transferring said aqueous phase into a new tube;
  r. adding to said aqueous phase within said tube of step (e) an equal amount of iso-propanol supplemented with 20 mg/ml crystal violet solution to obtain violate stained solution;
  s. mixing said solution by inverting said tube of step (f) and then incubating said tube for about 30 minutes at room temperature;
  t. centrifuging said tube of step (g) at 2,500 g for about 30 minutes at room temperature to obtain a violet stained layer;
  u. transferring said violate stained layer of step (h) into a new tube and centrifuging said tube for about 5 min at maximal speed to obtain pellet and supernatant;
  v. washing said pellet with 80% v/v ice cold ethanol and centrifuging for about additional 5 min to obtain pellet and supernatant;
  w. removing said supernatant of step (j) and the pellet is left to dry; and
  x. suspending said dried pellet in water in a ratio of 100 µl water to 2 gr of soil of step (a).

It is further within the scope of the present invention to disclose a method for screening for and identifying a desirable plant improving trait, said method comprises steps of:
  y. obtaining a sampling of a predefined environmental niche;
  z. extracting RNA from the sampling according to the method for extracting RNA from a soil sample as defined above;
  aa. constructing an expression library from the RNA of step (b);

The method further comprises steps of:
  bb. producing plants transformed with the expression library at an efficiency of at least 0.05%-30% representing at least $10^2$-$10^{10}$ transgenes;
  cc. screening for transformed plants expressing the desirable trait; and
  dd. identifying the transgene of the transformed plants expressing the desirable trait.

It is further within the scope of the present invention to disclose an isolated polynucleotide having a nucleotide sequence corresponding to the sequence as set forth in a polynucleotide sequence selected from the group consisting of SEQ ID NOs:1 to SEQ ID NO:148 and any combination thereof.

It is further within the scope of the present invention to disclose an isolated polypeptide having an amino acid sequence corresponding to the sequence as set forth in polypeptide sequence selected from the group consisting of SEQ. ID Nos: 149-321 and any combination thereof.

In order to understand the invention and to see how it may be implemented in practice, a plurality of preferred embodiments will now be described, by way of non-limiting example only, with reference to the following examples.

Example 1

A Process for Improving Traits in Plants by Transformation of Expression Libraries from Ecological Niches into Plants and Screening for Desired Traits 1. Sample Collection and Processing In the first step, genetic pools of a varied environmental samples and sources such as soil, water or organic matter from different habitats have been isolated. The source is selected according to the specific desired target traits. For example, when screening for drought or salinity resistant gene, a dry land such as desert land or a high salinity land or other enforcement will be used, but not necessarily.

The microbiome found in each sample may optionally be enriched by growth on rich media or selectively grown with antibiotics. To enhance expression of potentially desired genes, the culture is grown in stress conditions or media resembling, associated with or affecting the target trait, such as salt or PEG rich media for drought or salinity resistance trait.

Sample enrichment is carried on rich growth media (e.g. YPD) for several days at 28° C.-37° C. in shaker incubator. If eukaryotic libraries are prepared, anti-bacterial antibiotics such as Penicillin-Streptomycin and Spectinomycin are added.

To induce stress resistant genes, the sample is grown under any desired environmental stress conditions. For example, to induce drought resistance genes, the sample is grown under high osmotic stress by adding PEG to the growth media (10%-30% w/v). High salt concentration media such as NaCl (5%-10% w/v) was used to induce high salinity stress. In addition, the samples are exposed to different nitrogen concentration (from 0-100 mM $KNO_3$ in water supplemented with 6 mM KH$_2$PO$_4$ and micro elements, see Table 1, http://www.gatfertilizers.com/properties-of-solid-and-liquid-fertilizers/as recommended by the manufacturer), extreme temperatures (50-60° C.) and any environmental stress desired.

TABLE 1

| Element | Percentage | gr/Lt |
|---|---|---|
| Iron | 1.09 | 12.20 |
| Manganese | 0.48 | 5.47 |
| Zinc | 0.15 | 1.75 |
| Copper | 0.05 | 0.55 |
| Molybdenum | 0.02 | 0.16 |
| Boron | 0.20 | 2.00 |

2. RNA Extraction

Total RNA extraction has been performed according to standard commercial kits such as RNeasy PowerSoil Total RNA Kit (Qiagen) and Quick-RNA (Zymo research). In addition, a unique protocol is used for extraction of RNA from soil samples, as follows:

In a 7 ml tube, 2 g of soil is disrupted with extraction buffer (500 mM Phosphate buffer pH 8 and 5% w/v CTAB with Phenol (pH 8), chloroform, IAA (25:24:1)). The tube is subjected to 15 min shaking at 37° C. or to a bead beater for 1 min. The tube is then centrifuged at 2,500 g for 10 minutes at room temperature. The aqueous phase is transferred into a new tube and an equal amount of iso-propanol supplemented with 5 ul of crystal violate solution (20 mg/ml) is added. The tubes are mixed by inverting and left to stand for 30 minutes at room temperature, then centrifuged at 2,500 g for 30 minutes at room temperature. The violate stained layer is transferred into a new 1.5 ml tube and centrifuged for 5 min at maximal speed. The pellet is washed with 500 µl of 80% v/v ice cold ethanol and centrifuged for additional 5 min. After centrifugation, the liquid is removed, and the pellet is left to dry. The dry pellet is suspended in 100 µl water.

3. Construction of cDNA Libraries 3.1. Eukaryotic cDNA Libraries

Figure 1B:
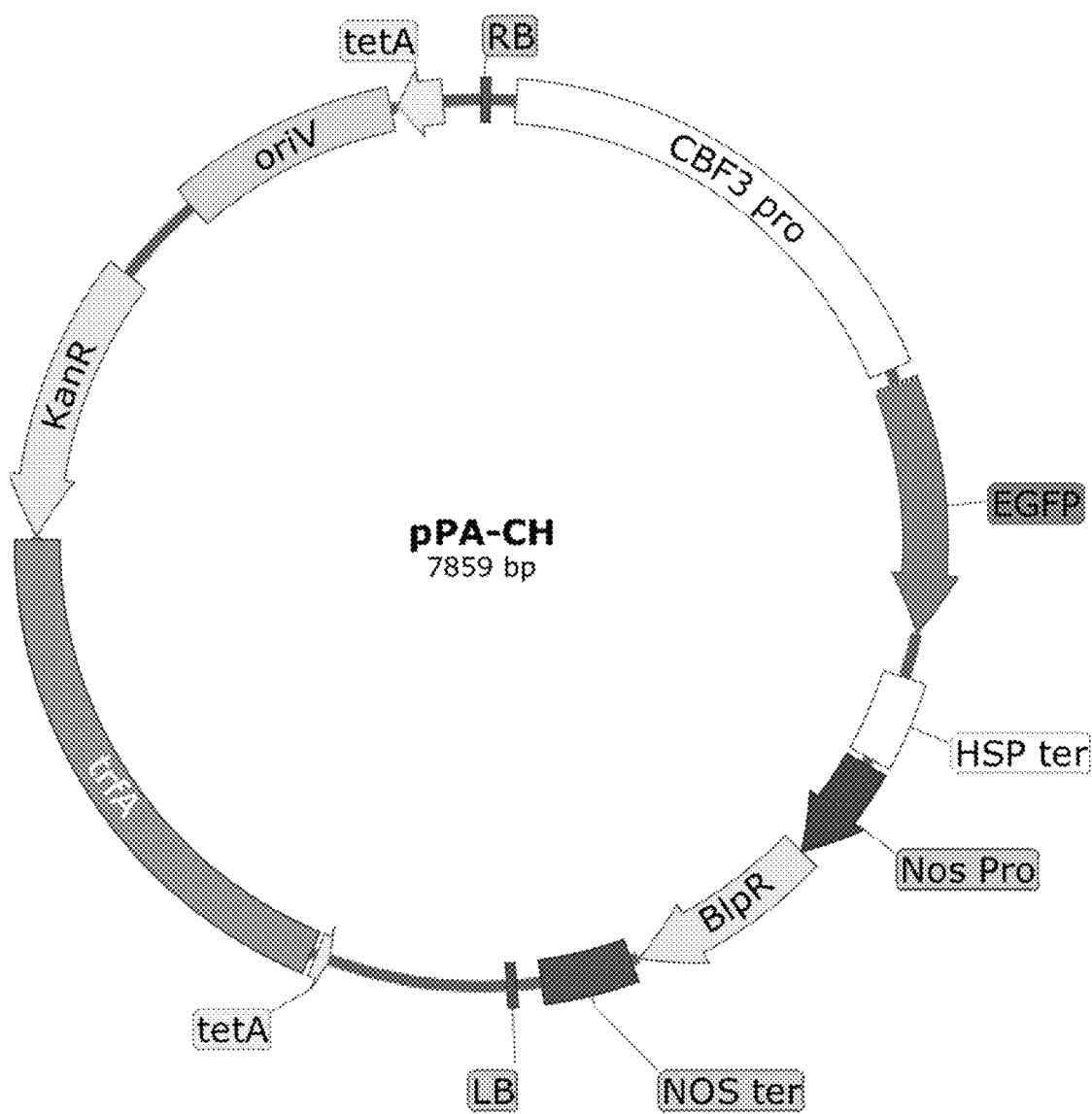
Figure 1C:
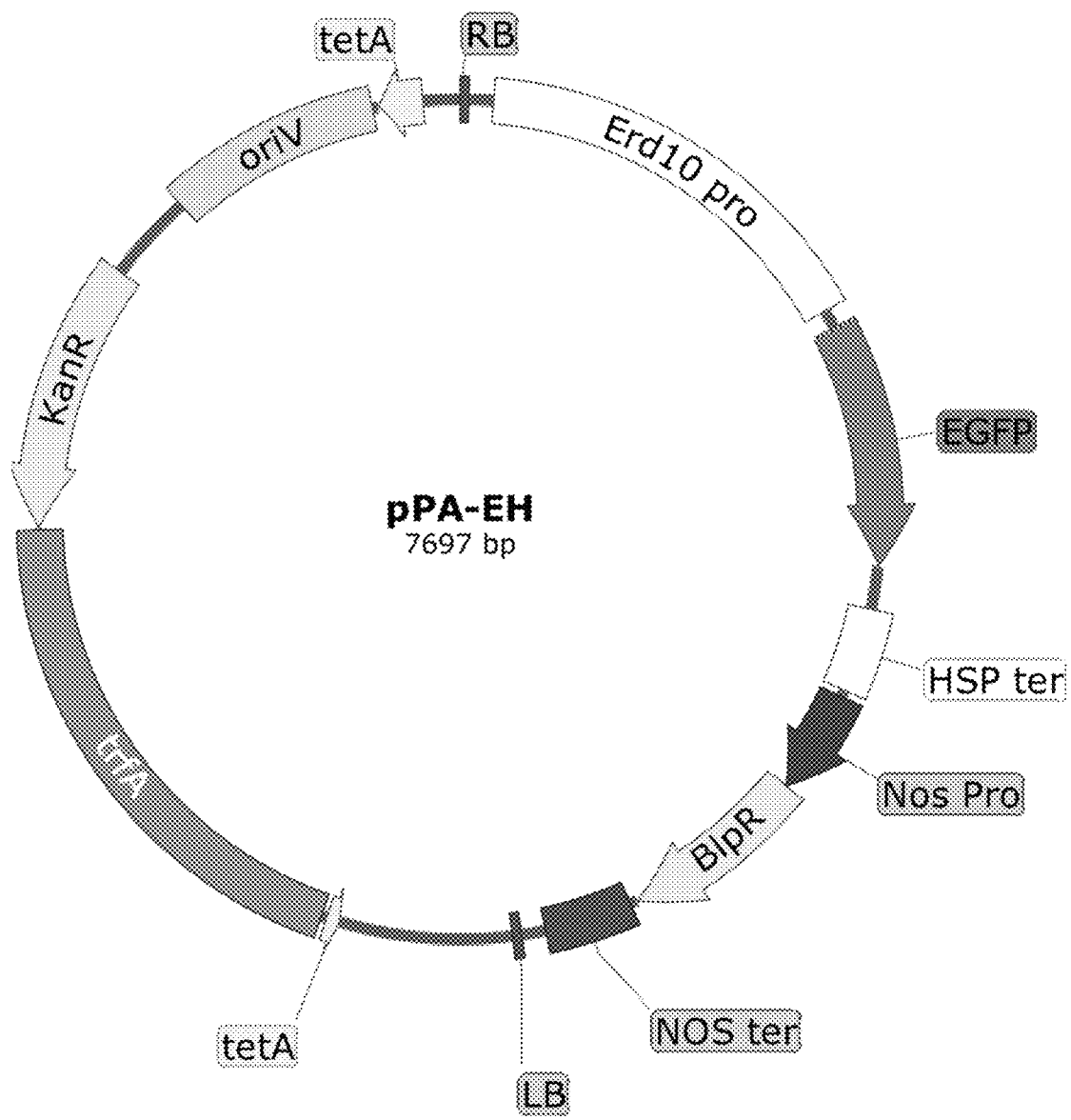
Figure 1D:
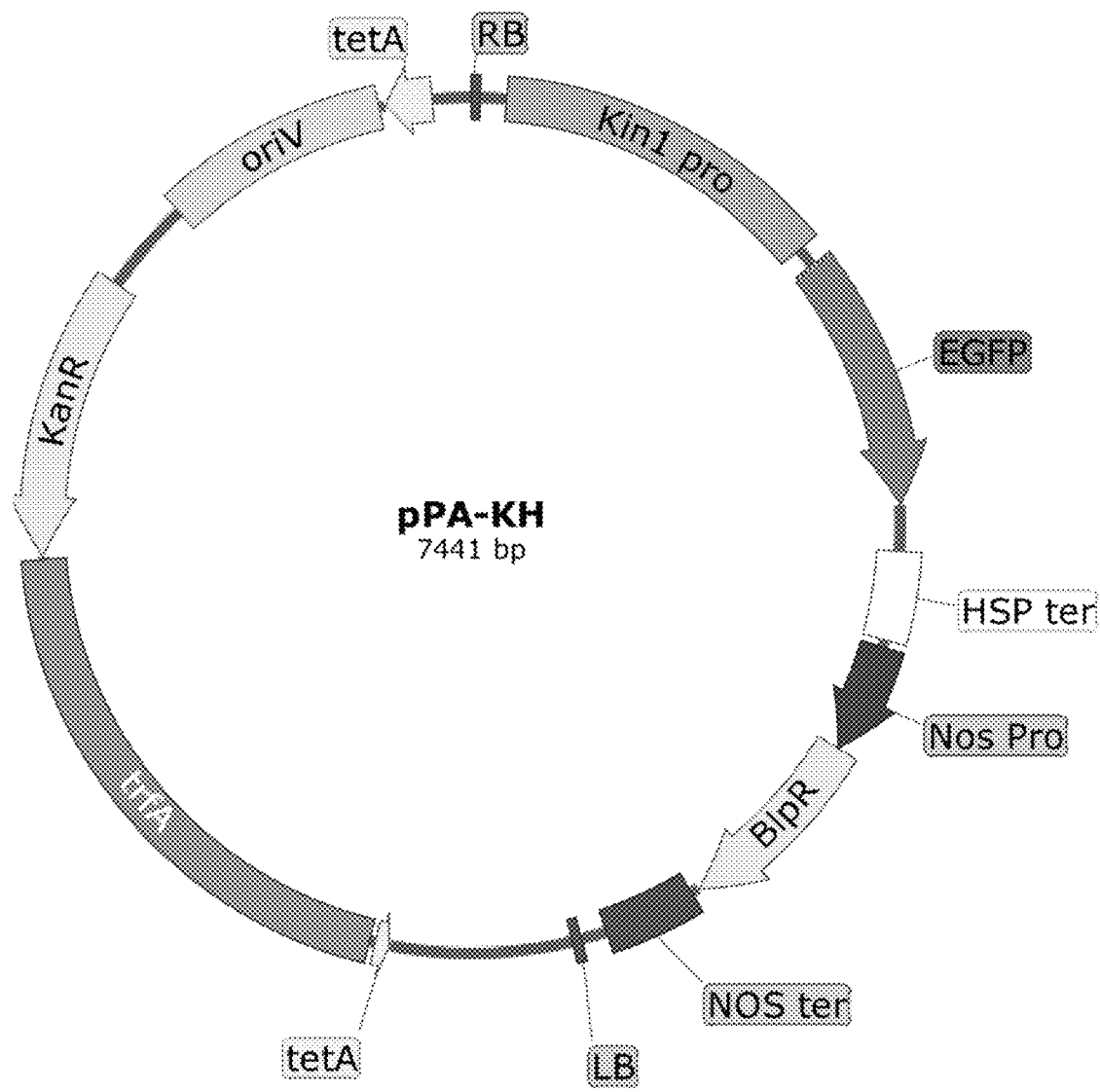
Figure 2:
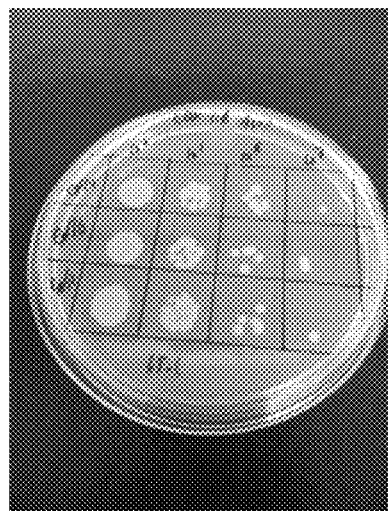
FIG. 2 presents a photographic illustration of *Agrobacterium* library counting for 3 different libraries on LB petri dishes.

Eukaryotic cDNA libraries from total-RNA and mRNA are constructed based on template switching-reverse transcription of poly-A mRNA (SMART) or oligo-capping rapid amplification of cDNA ends (5'-RACE) methods. The reverse transcription of poly-A mRNA primers used are 5'-ATTCTAGAGCGATCGCA-CATGTTTTTTTTTTTTTTTTTTTTTTTTTTTTTTVN-3' (referred to as SEQ. ID NO:321) and 5'-AAGCAGTGGTATCAACGCAGAGTGGCGCGCCr-GrGG-3' (referred to as SEQ. ID NO:322). The oligo-capping rapid amplification of cDNA ends primers used are 5'-ATTCTAGAGCGATCGCA-CATGTTTTTTTTTTTTTTTTTTTTTTTTTTTTTTVN-3' (referred to as SEQ. ID NO:321) and 5'-InvddT (5' Inverted Dideoxy-T)-r (AAGCAGUGGUAU-CAACGCAGAGUGGCGCGCCG)-3' (referred to as SEQ. ID NO: 323). The amplified cDNA is inserted into binary vectors (see FIGS. 1-4) between the promoter(s) (35S, KIN1, erd10 and/or CBF3) and the HSP or NOS terminator. FIG. 1A illustrates the pPA-35H vector, which has a constitutive CaMV 35S promoter with the GFP gene cloned between the promoter and terminator as an example. FIGS. 1B-D present vectors containing stress induced promoters from *Arabidopsis thaliana*: pPA-CH vector with CBF3 promoter having a nucleotide sequence as set forth in SEQ. ID NO: 330 (FIG. 1B), pPA-EH with Erd10 promoter having a nucleotide sequence as set forth in SEQ. ID NO: 331 (FIG. 1C) and pPA-KH with Kin1 promoter having a nucleotide sequence as set forth in SEQ. ID NO: 332 (FIG. 1D) with the GFP gene cloned between the promoter and terminator as an example (Plant Physiol. 1997 October; 115(2): 327-334, Plant Journal (2004) 38, 982-993 incorporated herein by reference).

Figure 5:
FIG. 5 presents a photographic illustration of T2 and T3 controlled experiments in the greenhouse.

These vectors contain Kanamycin as a bacterial selection and the bar gene as a transgenic plant selection conferring resistance to the phosphinothricin herbicide. At least one of the non-limiting examples of Gibson assembly, Restriction-ligation, Restriction free or In-Fusion methods is used and then ligation products are transformed to *E. coli* competent cells to grow under kanamycin selection. The library size is estimated by live count of transformed bacteria sown on LB petri dishes (usually 10^5-10^7) (FIG. 5). Vectors of the cDNA library are purified from *E. coli* bacteria with standard mini-prep kits and transformed to electrocompetent *Agrobacterium tumefaciens* GV3101 cells. The transformed *Agrobacterium* are grown on LB media under kanamycin and rifampicin selection (50 µg/ml each) over night at 28° C., (250 ml per 1 m$^2$ of target plant growth area). The growth arrested on ice for at list 30 min and then centrifuged for 10 min at 8000 rpm at 4° C. The pelleted *Agrobacterium* are suspended in suspension buffer (5% sucrose and 0.03% L-77 Silwet, Momentive, US).

3.2. Prokaryotes cDNA Libraries

Prokaryotes cDNA libraries from total RNA are constructed based on standard 5' and 3' RNA modifications with ScriptSeq™ Complete Kit (epicenter). Primers used are 5'-ATTCTAGAGCGATCGCA-CATGTTTTTTTTTTTTTTTTTTTTTTTTTTTTTTVN-3' (referred to as SEQ. ID NO:321) and 5'-InvddT (5' Inverted Dideoxy-T)-r(AAGCAGUGGUAU-CAACGCAGAGUGGCGCGCCG)-3' (referred to as SEQ. ID NO:324). The amplified cDNA inserted into carrier vectors barring Kanamycin and phosphinothricin resistance and then transformed to *E. coli* competent cells to grow under kanamycin selection (50 µg/ml). The library size is estimated by live count of transformed hosts (usually 10^5-10^7). Vectors of the cDNA library are purified from host cells with standard mini-prep kit (50 µl) and transformed to electrocompetent *Agrobacterium* GV3103 cells (100 µl). The transformed *Agrobacterium* are grown on LB media under kanamycin and rifampicin selection (50 µg/ml) over night at 28° C. (100 ml per 1 m$^2$ of target plant growth area). The growth is arrested on ice for at list 30 min and then centrifuged for 5 min at 8000 rpm at 4° C. The pelleted *Agrobacterium* are suspended in suspension buffer (5% sucrose and 0.03% L-77 Silwet).

4. Growing and Transformation of Plants 4.1. Arabidopsis Plants

Plants are grown in controlled greenhouses as a preparation for transformation. Plants are grown in soil composed of 75% peat, 25% perlite and are being irrigated routinely with water supplemented with fertilizer (e.g. Shefer 5.3.8, ICL Israel) according to manufacturer instructions, as needed. Plants start flowering after 3-4 weeks and then they are ready for transformation. Transformed *Agrobacterium* with expression libraries are grown as mentioned above and suspended in suspension buffer (5% sucrose and 0.03% L-77 Silwet) and are sprayed by 2 liter sprayers (e.g. Solo, Germany) on the flowers. After 5-6 weeks of continued growth when plants become dry, seeds are collected and kept in a cool dry place for 2 weeks or until used.

4.2. Tobacco Plants

Figure 3A:
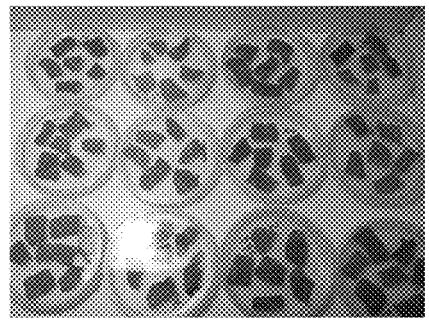
FIG. 3 presents a photographic illustration of tobacco tissue culture transformed with a library, 7 days after transformation (FIG. 3A), 40 days after transformation (FIG. 3B) and 6-8 weeks after transformation (FIG. 3C)
Figure 3B:
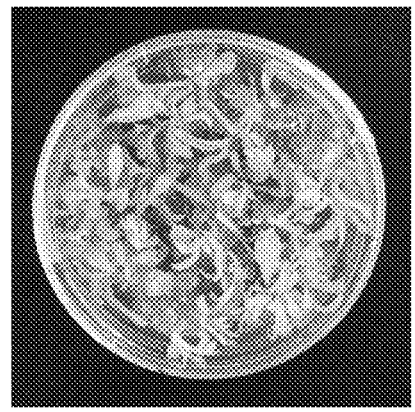
Figure 3C:

Tobacco leaves are cut into 1-2 cm² pieces and sterilized by 70% ethanol followed by 0.3% bleach treatments for 5 minutes. Leaf pieces are mixed with libraries transformed *Agrobacterium* (or with a any identified gene of SEQ ID 1-148 from Table 4), suspended in liquid Regeneration Medium (RM) supplemented with MS including Gamborg B5 vitamins, 3% sucrose, 2 mg/L BAP (6-Benzylaminopurine) and 0.2 mg/L NAA (Naphthalene acetic acid) (e.g. Duchefa, Netherland) for 30 minutes. Bacteria are than washed and leaf pieces are placed on RM plant-agar plates for one day in the dark. Leaf pieces are transferred to new selection RM plant-agar plates supplemented with 300 µg/ml of timentin antibiotic to kill the *Agrobacterium* and 1.5 µg/ml phosphoinotricin (e.g. Duchefa, Netherland) for selection of transgenic plants. FIG. 3A-B present a photographic illustration of tobacco tissue culture transformed with a library, 7 days after transformation (FIG. 3A) and 40 days after transformation (FIG. 3B). After 6-8 weeks, plantlets start to appear and are transferred to new vessels containing the same selection RM plant-agar, but BAP is excluded (see FIG. 3C). After rooting, plants are transferred to soil in the greenhouse.

Example 2

A Process for Identifying Drought Resistance Traits in Plants

A. Screening for Drought and/or Salinity Resistant Plants/Genes

Figure 4:
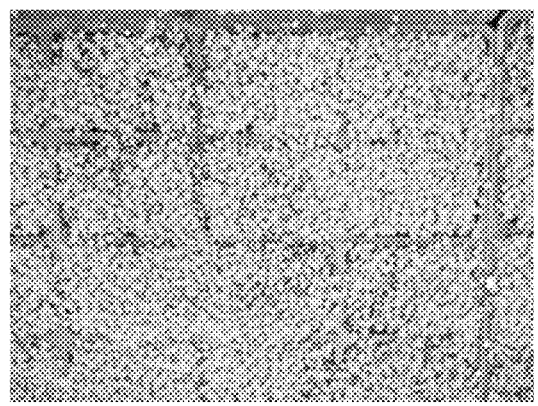
FIG. 4 presents a photographic illustration demonstrating selection for phosphinothricin resistance of 10 days old Arabidopsis expressing library seedlings. The green plants are resistant to phosphinothricin while small yellow plants are absent of the transgene and therefore susceptible.

Arabidopsis T1 seeds harboring the desired expression library are being used for the screen. At the first stage, the transformation efficiency is defined for a specific seed library. 1 ml of seeds (~50,000 seeds) is being sowed on soil irrigated with water supplemented with Basta (e.g. Bayer, Germany) according to manufacturer instructions. Seven days post sowing, the number of phosphinothricin resistant plants is counted and compared with phosphinothricin susceptible plants (FIG. 4). As demonstrated in FIG. 4, the bigger plants are resistant to phosphinothricin while small plants are absent of the transgene and therefore susceptible and will die. The seed library efficiency is represented by the ratio of the number of resistant plants to the number of total plants.

The library is then sowed according to the desired number of plants intended to be represented in the specific experiment and which represents best the library size. For example, if an expression library consists of $5 \times 10^4$ genes, and the transformation efficiency is 1%, >5 million seeds should be sowed. In this case, in ~20 m² of soil, 50,000 Basta resistant plants will be grown for the experiment.

Soil is irrigated once, when seeds are sown, with water supplemented with phosphinothricin and fertilizer (e.g. Shefer 5.3.8, ICL Israel) according to manufacturer instructions, and soil water content reaches 100% capacity. Plants are grown in air-conditioned controlled greenhouses, and soil is not irrigated until most of the plants die from lack of water. Surviving plants, ~0.1% of initial phosphinothricin resistant plants, are being rescued by irrigation until they produce seeds which are being collected for T2 experiments. During their growth, the surviving plants are tested for their transgene, by gDNA extraction from one of their leaves and PCR using primers for the gene specific promoters (CaMV 35S, CBF3, Erd10 and Kin1) and terminators (NOS, HSP) (see Table 2). PCR products are being sequenced and the resulted sequence is blasted versus sequence databases such as NCBI, both for DNA comparisons (i.e. BLASTn) and for amino acid sequence comparisons (i.e. BLASTx).

Reference is now made to Table 2 presenting SEQ ID NOs of primer and promoter sequences used in the present invention:

TABLE 2

| SEQ ID NOs of primer sequences | |
|---|---|
| SEQ ID NO. | Description |
| SEQ ID NO: 321 | Reverse primer for transcription of poly-A mRNA |
| SEQ ID NO: 322 | Forward primer for transcription of poly-A mRNA |
| SEQ ID NO: 323 | Forward primer for oligo-capping amplification of cDNA ends |
| SEQ ID NO: 324 | Forward primer for amplification of prokaryote cDNA library (e.g. derived from total RNA) |
| SEQ ID NO: 325 | Forward primer for CaMV 35S promoter |
| SEQ ID NO: 326 | Forward primer for CBF3 promoter |
| SEQ ID NO: 327 | Forward primer for Erd10 promoter |
| SEQ ID NO: 328 | Forward primer for Kin1 promoter |
| SEQ ID NO: 329 | Reverse primer for NOS/HSP terminator |
| SEQ ID NO: 330 | CBF3 promoter |
| SEQ ID NO: 331 | Erd10 promoter |
| SEQ ID NO: 332 | Kin1 promoter |

B. Subsequent Generations ($T_2$, $T_3$) Experiments

Seeds collected from drought surviving plants are being tested again in further experiments including repeats and controls to test their resistance/tolerance to drought (see FIG. 5).

Several genes were chosen to serve as controls in the drought experiments:
1) EGFP—jellyfish green fluorescent protein, cloned under the control of the various used promoters and HSP terminator (see vector maps of FIGS. 1A-D), is being served as a negative control for drought, since it was not been shown to be associated with improving plants resistance to drought (Yang T-T, et al., 1996).
2) mtlD—mannitol-1-phosphate dehydrogenase from *Escherichia coli*, cloned under the control of the various used promoters and HSP terminator (see vector maps of FIGS. 1A-D), is being served as a positive control since it was shown to be associated with improving plants resistance to drought and salt (Hema R. et al., 2014).
3) HRD—The HARDY gene from *Arabidopsis thaliana* cloned under the control of the various used promoters and HSP terminator (see vector maps of FIGS. 1A-D), is being served as a positive control since was shown to be associated with improving plants resistance to drought and salt (Karaba A, et al., 2007).

Plants identified as expressing unique genes in the screen experiments, including all controls, are sown in trays 38×28 cm with 16 plastic inserts in each tray (e.g. Desch Plantpak, Netherland), filled with soil supplemented with fertilizer and phosphinothricin as above. In each insert several seeds are sown and after 10 days a single phosphinothricin resistant plant is being kept for further experiments. Each experiment contains 20-40 repeats of each plant, representing the expressed unique genes, which are spread in random on the greenhouse tables. Irrigation of the soil is similar to the screen experiment; it is done when the seeds are sown, except when soil is completely dry and reaches weight lower then initial weight of soil before irrigation (~5%-10% of water content), then plants are irrigated again to check revival performance.

Figure 6:
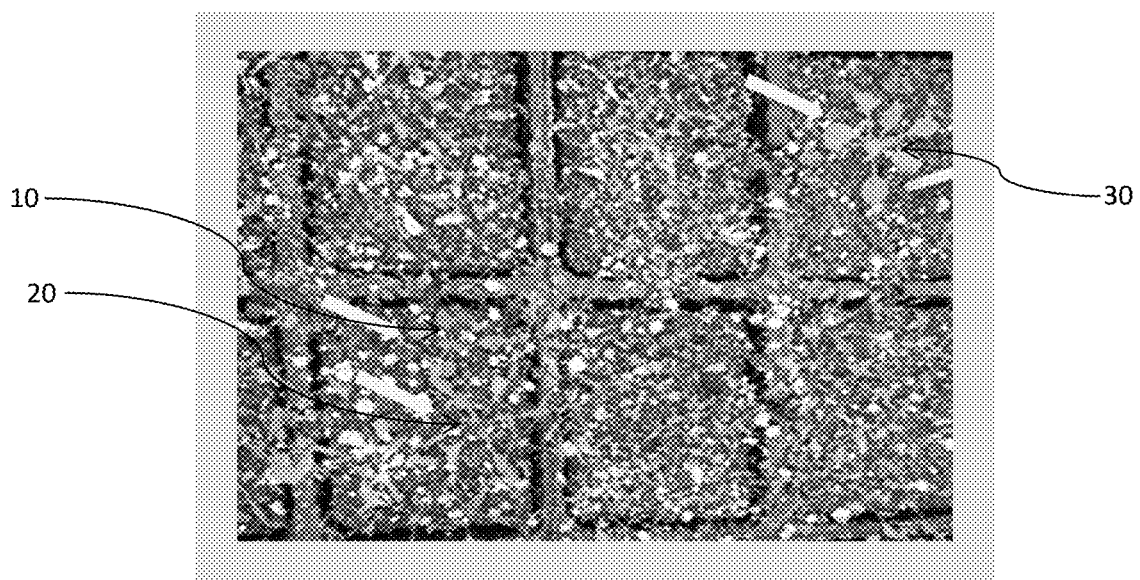
FIG. 6 presents photographic results of screening for transgenic plants resistance to drought.

Reference is now made to FIG. 6 showing photographic results of screening for transgenic plants resistance to drought grown under the conditions as described above. This figure shows that transgenic plants carrying drought resistance genes 10, 20 and 30 survive in severe drought conditions, while other transgenic plants that do not harbor drought resistant conferring genes do not survive the stress conditions. It is noted that within the small area shown in this figure (~15×25 cm), about 300 plants were screened while 3 survived the drought conditions.

When drought conditions start to develop, various measurements are taken, as shown in Table 3:
1) turgor observation, measured by scale of 1-10, when 1 is high turgor and 10 is total loss of turgor (see FIG. 7).
2) Weight of plant and pot, by scale in grams.
3) Death of plants observation, 10=dead and 1=alive (see FIG. 8)
4) State of plants observation in a scale of 1-10, when 1 is good state and 10 is poor.

TABLE 3

Measurements taken in drought experiments

| measurement | units | time of measurement |
| --- | --- | --- |
| Weight of pot | Grams | Start till end of experiment |
| Turgor | Observation units 1-10, where 1 is 0 turgor loss and 10 is 100% turgor loss | From beginning of turgor loss (~15-27 days from last irrigation) |
| Death | Observation units 1-10 | From first death observed |
| State of plants | Observation units 1-10 | During first 2 weeks and one day after revival |

Figure 7:
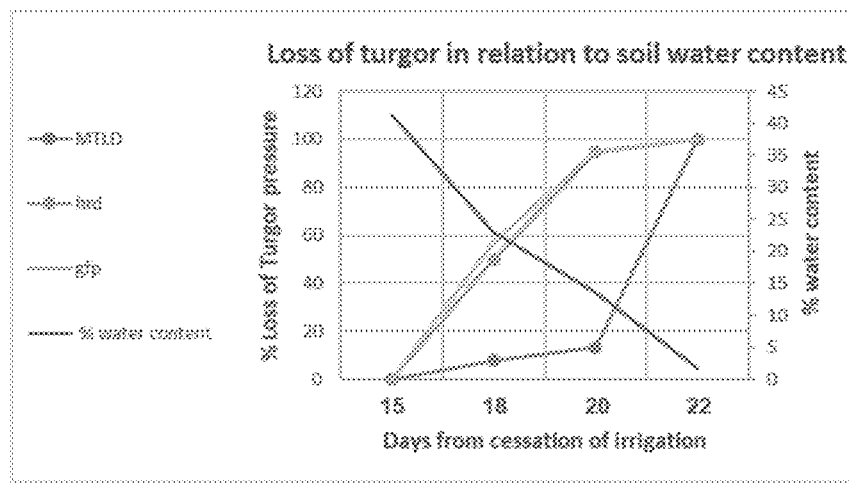
FIG. 7 presents a graphic illustration demonstrating loss of turgor pressure in plants expressing genes used as control relative to soil water content (dark gray), days after cessation of irrigation.

Reference is now made to FIG. 7, showing loss of turgor pressure in plants expressing genes used as control relative to soil water content (dark gray), days after cessation of irrigation. This figure shows curves of Arabidopsis plants, expressing different genes (indicated), as a response to growth under drought conditions. Dark line indicates soil water content from 40% in day 15 after water irrigation ceased, to close to 0% at day 22 after water irrigation ceased. The negative control GFP plant's loss of turgor pressure response is similar to that of HRD expressing plants, while mtlD expressing plants turgor pressure, seem to be less effected by drought until day 20 after water irrigation ceased.

It is demonstrated in this figure that plants expressing the positive control genes mtlD and HRD showed improved resistance to drought by showing significantly reduced loss of turgor pressure effects, while transgenic plants expressing the negative control GFP gene showed elevated loss of turgor pressure effect when exposed to the same water content loss.

Figure 8:
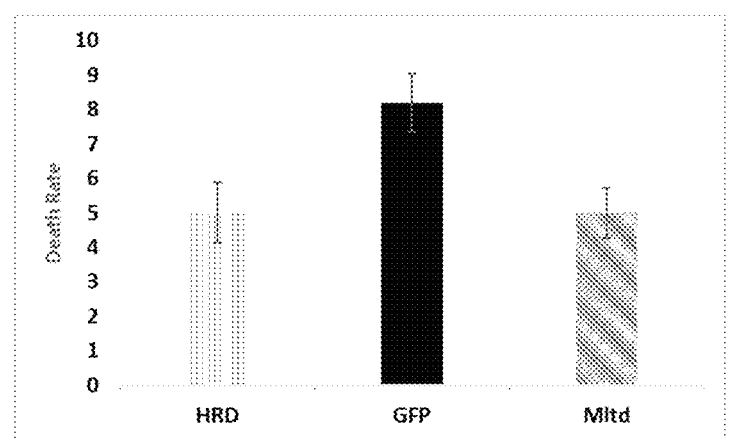
FIG. 8 presents a graphic illustration showing normalized death scale of positive control expressing transgenic plants as compared to GFP expressing plants.

Reference is now made to FIG. 8 showing normalized death scale of positive control expressing transgenic plants as compared to GFP expressing plants. As can be seen plants expressing the drought resistance positive control genes HRD and mtlD showed significantly reduced death rate as compared to the negative control GFP expressing plants.

Figure 9:
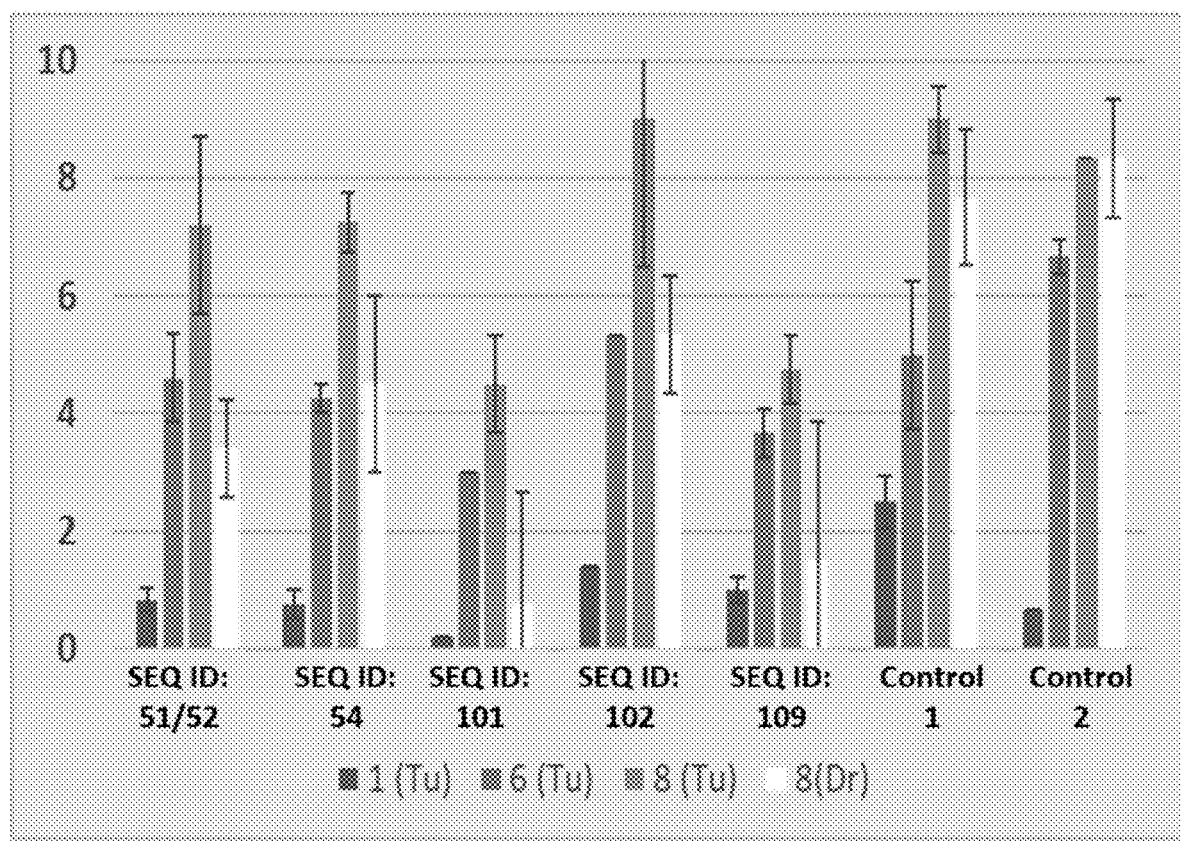
FIG. 9 graphically shows results of several drought resistance genes identified by the method of the present invention.

Reference is now made to FIG. 9 graphically showing phenotypic results of several drought resistance genes identified by the method of the present invention.

The graph shows average results of turgor pressure (Tu) and death rate (Dr) for several identified genes (see Table 4) under severe drought conditions. Scale for death and turgor loss is 1-10 when 10 is considered dry-brown and dead plants, or total loss of turgor, respectively. The results in the graph represent day 23 (1), day 28 (6) and day 30 (8) from sowing. Each column for each of the different expressed genes represents average of 5 repeats with 4 plants in each repeat. GFP expressing plants served as negative control and HRD as positive control. As can be seen, all tested genes identified by the method of the present invention showed significantly reduced turgor loss (by at least two fold after about 23 days from sowing) and reduced death rate (in the range of 9 to 2 fold after 30 days from sowing) as compared to plants expressing the negative control GFP gene. Moreover, plants expressing the newly discovered genes (see Table 4) demonstrated a significantly reduced death rated as compared to the positive control HRD expressing plants. These results indicate that by the method of the present invention, newly drought resistance genes are identified, which confer improved tolerance to drought in plants.

Another method used for evaluating plants performance in drought conditions is measuring their leaf area during the growth phase when drought conditions become prominent. About 10-14 days from sowing the plants, plant images were taken every 2-3 days together with a 50 mm$^2$ white surface. Image analysis was performed on pictures taken from the drought experiments and leaf area was calculated. The leaf area of several plant lines expressing novel genes identified as conferring drought resistance after re-cloning was compared to positive and negative controls (see Table 5 and FIG. 10).

Figure 10:
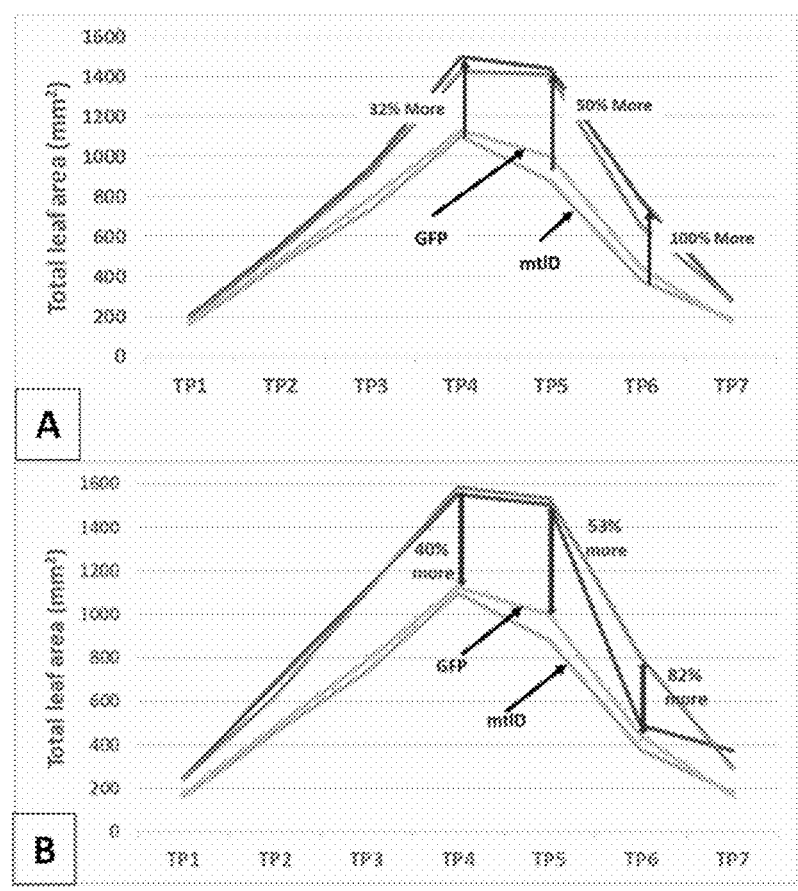
FIG. 10 graphically shows leaf area analysis of several transgenic plant lines expressing identified novel genes conferring drought resistance after re-cloning as compared to positive and negative controls.

The graph of FIG. 10 shows image analysis of leaf area of transformed plant lines. Two independent transformation events of the identified gene having SEQ ID NO:16 (FIG. 10A) and two independent transformation events of the identified gene having SEQ ID NO:25 (FIG. 10B) are shown in darker lines on top of each of the FIGS. 10A and 10B. These transgenic plants are compared to negative control plants expressing GFP, and positive control plants expressing mtlD, shown in lighter gray lines on the bottom of each of the FIGS. 10A and 10B. Improved performance under drought is shown as percentage from control plants at the indicated measured timepoint (TP) (arrows and percentages shown in the figure).

As can be seen in this figure, the total leaf area of plants expressing the newly identified tested genes was increased by between about 10% and about 82% (e.g. by about 45%) relative to plants expressing negative control genes.

To conclude, the present invention provides newly identified genes demonstrated to confer tolerance to drought conditions in plants.

C. Re-Cloning and Retransformation of Selected Genes into Plants

Selected genes from section B are re-cloned into the binary vectors as described above (i.e. FIGS. 1A-D) and sequenced to confirm that it has the same sequence as the original gene from T1 and T2 experiments. Plants are transformed with the re-cloned gene and seeds are collected. Experiments are repeated as in B except for each gene 3-5 individual transgenic plants with different unrelated transformation events are tested. Each individual transgenic plant/event is subjected to 5-10 times of repeats in experiments, hence for each event for every gene 20-40 plants are tested, and for every different gene 60-200 plants are tested.

Example 3

Polynucleotide Sequences Identified as Improving Drought and/or Salinity Resistance in Plants The process described above of screening of T1 transgenic seeds revealed about 1000 transgenes as candidate polynucleotide sequences for improving drought resistance in plants. Of these candidates, the screening of T2 seeds revealed about 140 best performing transgenes potentially improving drought resistance or tolerance in plants. These transgene sequences are subjected to further validation tests.

Reference is now made to Table 4, presenting examples of novel and unique polynucleotide sequences and polypeptides encoded by these sequences, found by the method of the present invention. These sequences are metatranscriptomes purified from environmentally challenged niches, SEQ ID NO:1 to SEQ ID NO:148 represent polynucleotide sequences found by the method of the present invention as candidates for improving drought resistance in plants (Table 4).

SEQ ID NO:149 to SEQ ID NO:321 represent polypeptide sequences encoded by the corresponding polynucleotide sequence found by the method of the present invention as candidates for improving drought resistance in plants (see Table 4).

Note that DNA sequences SEQ ID NO:9, SEQ ID NO:11, SEQ ID NO:20, SEQ ID NO:21, SEQ ID NO:28, SEQ ID NO:36, SEQ ID NO:43, SEQ ID NO:47, SEQ ID NO:51, SEQ ID NO:54, SEQ ID NO:55, SEQ ID NO:60, SEQ ID NO:75, SEQ ID NO:78, SEQ ID NO:80, SEQ ID NO:81, SEQ ID NO:85, SEQ ID NO:87, SEQ ID NO:97, SEQ ID NO:98, SEQ ID NO:105, SEQ ID NO:106, SEQ ID NO:107, SEQ ID NO:109, SEQ ID NO:111, SEQ ID NO:112, SEQ ID NO:120, SEQ ID NO:132, SEQ ID NO:134, SEQ ID NO:135, SEQ ID NO:140, SEQ ID NO:141 encode more than one open reading frame (ORF) (referred to as SEQ. ID NO X.1p and X.2p etc.) depending on different start codons.

TABLE 4

SEQ ID Nos of polynucleotide and polypeptide sequences

| Polynucleotide SEQ ID NO. | Polynucleotide name |
| --- | --- |
| SEQ ID NO: 1 | A454 |
| SEQ ID NO: 2 | A456 |
| SEQ ID NO: 3 | A458.1 |
| SEQ ID NO: 4 | A458.2 |
| SEQ ID NO: 5 | A460 |
| SEQ ID NO: 6 | A462 |
| SEQ ID NO: 7 | A463 |
| SEQ ID NO: 8 | A466 |
| SEQ ID NO: 9 | A468 |
| SEQ ID NO: 10 | A470 |
| SEQ ID NO: 11 | A475 |
| SEQ ID NO: 12 | A477 |
| SEQ ID NO: 13 | A480 |
| SEQ ID NO: 14 | A481 |
| SEQ ID NO: 15 | A483 |
| SEQ ID NO: 16 | A484 |
| SEQ ID NO: 17 | A485a |
| SEQ ID NO: 18 | A485b |
| SEQ ID NO: 19 | A486 |
| SEQ ID NO: 20 | A498 |
| SEQ ID NO: 21 | A499 |
| SEQ ID NO: 22 | A501 |
| SEQ ID NO: 23 | A504.1 |
| SEQ ID NO: 24 | A504 |
| SEQ ID NO: 25 | A506 |
| SEQ ID NO: 26 | A507.1 |
| SEQ ID NO: 27 | A507.2 |
| SEQ ID NO: 28 | A510a |
| SEQ ID NO: 29 | A510b |
| SEQ ID NO: 30 | A512 |
| SEQ ID NO: 31 | A513a |
| SEQ ID NO: 32 | A513b |
| SEQ ID NO: 33 | A518 |
| SEQ ID NO: 34 | A520a |
| SEQ ID NO: 35 | AC2510 |
| SEQ ID NO: 36 | AD2607.1 |
| SEQ ID NO: 37 | AD2607.3 |
| SEQ ID NO: 38 | D860a |
| SEQ ID NO: 39 | D860b |
| SEQ ID NO: 40 | D862 |
| SEQ ID NO: 41 | D863 |
| SEQ ID NO: 42 | D881 |
| SEQ ID NO: 43 | D890 |
| SEQ ID NO: 44 | De203 |
| SEQ ID NO: 45 | De214a |
| SEQ ID NO: 46 | De215a |
| SEQ ID NO: 47 | De215b.1 |
| SEQ ID NO: 48 | De215b.4 |
| SEQ ID NO: 49 | De215c |
| SEQ ID NO: 50 | De217 |
| SEQ ID NO: 51 | De223a |
| SEQ ID NO: 52 | De223b |
| SEQ ID NO: 53 | De227 |
| SEQ ID NO: 54 | De239a |
| SEQ ID NO: 55 | De245 |
| SEQ ID NO: 56 | De250.1 |
| SEQ ID NO: 57 | De250.2 |
| SEQ ID NO: 58 | De251 |
| SEQ ID NO: 59 | De313 |
| SEQ ID NO: 60 | F1022a |
| SEQ ID NO: 61 | F1022b |
| SEQ ID NO: 62 | G1085a |
| SEQ ID NO: 63 | G1181 |
| SEQ ID NO: 64 | G1190 |
| SEQ ID NO: 65 | H1301.1 |
| SEQ ID NO: 66 | H1301.2 |
| SEQ ID NO: 67 | K1464 |
| SEQ ID NO: 68 | K1475 |
| SEQ ID NO: 69 | M603 |
| SEQ ID NO: 70 | M606.1 |
| SEQ ID NO: 71 | M606.2 |
| SEQ ID NO: 72 | M607.1 |
| SEQ ID NO: 73 | M607.2 |
| SEQ ID NO: 74 | M609a.1 |
| SEQ ID NO: 75 | M609a.2 |
| SEQ ID NO: 76 | M609b |
| SEQ ID NO: 77 | M619a |
| SEQ ID NO: 78 | M619b |
| SEQ ID NO: 79 | M622a |
| SEQ ID NO: 80 | M622b |
| SEQ ID NO: 81 | M623a |
| SEQ ID NO: 82 | M623b.1 |
| SEQ ID NO: 83 | M623b.3 |
| SEQ ID NO: 84 | M623c |
| SEQ ID NO: 85 | M624 |
| SEQ ID NO: 86 | M625a.3 |
| SEQ ID NO: 87 | M625a |

TABLE 4-continued

SEQ ID Nos of polynucleotide and polypeptide sequences

| Polynucleotide SEQ ID NO. | Polynucleotide name |
|---|---|
| SEQ ID NO: 88 | M625b |
| SEQ ID NO: 89 | M631 |
| SEQ ID NO: 90 | M632a |
| SEQ ID NO: 91 | M635.1 |
| SEQ ID NO: 92 | M635.2 |
| SEQ ID NO: 93 | M638 |
| SEQ ID NO: 94 | M643 |
| SEQ ID NO: 95 | M649 |
| SEQ ID NO: 96 | M650a.3 |
| SEQ ID NO: 97 | M650a |
| SEQ ID NO: 98 | M650b |
| SEQ ID NO: 99 | M657 |
| SEQ ID NO: 100 | M659a |
| SEQ ID NO: 101 | M661 |
| SEQ ID NO: 102 | M663 |
| SEQ ID NO: 103 | M664.1 |
| SEQ ID NO: 104 | M664.2 |
| SEQ ID NO: 105 | M666 |
| SEQ ID NO: 106 | M671 |
| SEQ ID NO: 107 | M673 |
| SEQ ID NO: 108 | M676.3 |
| SEQ ID NO: 109 | M676 |
| SEQ ID NO: 110 | M677a |
| SEQ ID NO: 111 | M677b.1 |
| SEQ ID NO: 112 | M677b.3 |
| SEQ ID NO: 113 | M680 |
| SEQ ID NO: 114 | M691a.1 |
| SEQ ID NO: 115 | M691a.2 |
| SEQ ID NO: 116 | M691b |
| SEQ ID NO: 117 | M693 |
| SEQ ID NO: 118 | M697 |
| SEQ ID NO: 119 | M698 |
| SEQ ID NO: 120 | M705 |
| SEQ ID NO: 121 | M706 |
| SEQ ID NO: 122 | M715a |
| SEQ ID NO: 123 | M715b |
| SEQ ID NO: 124 | M719 |
| SEQ ID NO: 125 | M724 |
| SEQ ID NO: 126 | N1503a |
| SEQ ID NO: 127 | N1527.1 |
| SEQ ID NO: 128 | N1527.2 |
| SEQ ID NO: 129 | N1529 |
| SEQ ID NO: 130 | N1530 |
| SEQ ID NO: 131 | P1611 |
| SEQ ID NO: 132 | P1620.1 |
| SEQ ID NO: 133 | P1620.3 |
| SEQ ID NO: 134 | P1623a |
| SEQ ID NO: 135 | P1623b |
| SEQ ID NO: 136 | P1625a |
| SEQ ID NO: 137 | P1625b |
| SEQ ID NO: 138 | P1731 |
| SEQ ID NO: 139 | P1744 |
| SEQ ID NO: 140 | P1747.1 |
| SEQ ID NO: 141 | P1747.3 |
| SEQ ID NO: 142 | SN8 |
| SEQ ID NO: 143 | V1906b |
| SEQ ID NO: 144 | V1906c |
| SEQ ID NO: 145 | V1907a |
| SEQ ID NO: 146 | V1907b |
| SEQ ID NO: 147 | X2005 |
| SEQ ID NO: 148 | X2026 |
| SEQ ID NO: 149 | A454p |
| SEQ ID NO: 150 | A456p |
| SEQ ID NO: 151 | A458.1p |
| SEQ ID NO: 152 | A458.2p |
| SEQ ID NO: 153 | A460p |
| SEQ ID NO: 154 | A462p |
| SEQ ID NO: 155 | A463p |
| SEQ ID NO: 156 | A466p |
| SEQ ID NO: 157 | A468.1p |
| SEQ ID NO: 158 | A468.2p |
| SEQ ID NO: 159 | A470p |
| SEQ ID NO: 160 | A475.1p |
| SEQ ID NO: 161 | A475.2p |
| SEQ ID NO: 162 | A477p |
| SEQ ID NO: 163 | A480p |
| SEQ ID NO: 164 | A481p |
| SEQ ID NO: 165 | A483p |
| SEQ ID NO: 166 | A484p |
| SEQ ID NO: 167 | A485ap |
| SEQ ID NO: 168 | A485bp |
| SEQ ID NO: 169 | A486p |
| SEQ ID NO: 170 | A498.1p |
| SEQ ID NO: 171 | A498.2p |
| SEQ ID NO: 172 | A499.1p |
| SEQ ID NO: 173 | A499.2p |
| SEQ ID NO: 174 | A501p |
| SEQ ID NO: 175 | A504.1p |
| SEQ ID NO: 176 | A504.2p |
| SEQ ID NO: 177 | A506p |
| No ORF identified | No ORF identified |
| SEQ ID NO: 178 | A507.2p |
| SEQ ID NO: 179 | A510a.1p |
| SEQ ID NO: 180 | A510a.2p |
| No ORF identified | No ORF identified |
| SEQ ID NO: 181 | A512p |
| SEQ ID NO: 182 | A513ap |
| SEQ ID NO: 183 | A513bp |
| SEQ ID NO: 184 | A518p |
| SEQ ID NO: 185 | A520ap |
| SEQ ID NO: 186 | AC2510ap |
| SEQ ID NO: 187 | AD2607.1p |
| SEQ ID NO: 188 | AD2607.2p |
| SEQ ID NO: 189 | AD2607.3p |
| SEQ ID NO: 190 | D860ap |
| SEQ ID NO: 191 | D860bp |
| SEQ ID NO: 192 | D862p |
| SEQ ID NO: 193 | D863p |
| SEQ ID NO: 194 | D881p |
| SEQ ID NO: 195 | D890.1p |
| SEQ ID NO: 196 | D890.2p |
| SEQ ID NO: 197 | De203p |
| SEQ ID NO: 198 | De214ap |
| SEQ ID NO: 199 | De215ap |
| SEQ ID NO: 200 | De215b.1p |
| SEQ ID NO: 201 | De215b.2p |
| SEQ ID NO: 202 | De215b.3p |
| SEQ ID NO: 203 | De215b.4p |
| SEQ ID NO: 204 | De215cp |
| No ORF identified | No ORF identified |
| SEQ ID NO: 205 | De223a.1p |
| SEQ ID NO: 206 | De223a.2p |
| SEQ ID NO: 207 | De223bp |
| SEQ ID NO: 208 | De227p |
| SEQ ID NO: 209 | De239a.1p |
| SEQ ID NO: 210 | De239a.2p |
| SEQ ID NO: 211 | De245.1p |
| SEQ ID NO: 212 | De245.2p |
| SEQ ID NO: 213 | De250p |
| SEQ ID NO: 214 | De250.2p |
| SEQ ID NO: 215 | De251p |
| SEQ ID NO: 216 | De313p |
| SEQ ID NO: 217 | F1022a.1p |
| SEQ ID NO: 218 | F1022a.2p |
| SEQ ID NO: 219 | F1022bp |
| SEQ ID NO: 220 | G1085ap |
| SEQ ID NO: 221 | G1181p |
| SEQ ID NO: 222 | G1190p |
| SEQ ID NO: 223 | H1301.1p |
| SEQ ID NO: 224 | H1301.2p |
| No ORF identified | No ORF identified |
| SEQ ID NO: 225 | K1475p |
| SEQ ID NO: 226 | M603p |
| SEQ ID NO: 227 | M606.1p |
| SEQ ID NO: 228 | M606.2p |
| SEQ ID NO: 229 | M607.1p |
| SEQ ID NO: 230 | M607.2p |
| SEQ ID NO: 231 | M609a.1p |
| SEQ ID NO: 233 | M609a.3p |
| SEQ ID NO: 232 | M609a.2p |

TABLE 4-continued

SEQ ID Nos of polynucleotide and polypeptide sequences

| Polynucleotide SEQ ID NO. | Polynucleotide name |
|---|---|
| SEQ ID NO: 234 | M609bp |
| SEQ ID NO: 235 | M619ap |
| SEQ ID NO: 236 | M619b.1p |
| SEQ ID NO: 237 | M619b.2p |
| SEQ ID NO: 238 | M622ap |
| SEQ ID NO: 239 | M622b.1p |
| SEQ ID NO: 240 | M622b.2p |
| SEQ ID NO: 241 | M623a.1p |
| SEQ ID NO: 242 | M623a.2p |
| No ORF identified | No ORF identified |
| SEQ ID NO: 243 | M623b.3p |
| SEQ ID NO: 244 | M623cp |
| SEQ ID NO: 245 | M624.1p |
| SEQ ID NO: 246 | M624.2p |
| SEQ ID NO: 249 | M625a.3p |
| SEQ ID NO: 247 | M625a.1p |
| SEQ ID NO: 248 | M625a.2p |
| SEQ ID NO: 250 | M625bp |
| SEQ ID NO: 251 | M631p |
| SEQ ID NO: 252 | M632ap |
| SEQ ID NO: 253 | M635.1p |
| SEQ ID NO: 254 | M635.2p |
| SEQ ID NO: 255 | M638p |
| SEQ ID NO: 256 | M643p |
| SEQ ID NO: 257 | M649p |
| SEQ ID NO: 260 | M650a.3p |
| SEQ ID NO: 258 | M650a.1p |
| SEQ ID NO: 259 | M650a.2p |
| SEQ ID NO: 261 | M650b.1p |
| SEQ ID NO: 262 | M650b.2p |
| SEQ ID NO: 263 | M657p |
| SEQ ID NO: 264 | M659ap |
| SEQ ID NO: 265 | M661p |
| SEQ ID NO: 266 | M663p |
| SEQ ID NO: 267 | M664.1p |
| SEQ ID NO: 268 | M664.2p |
| SEQ ID NO: 269 | M666.1p |
| SEQ ID NO: 270 | M666.2p |
| SEQ ID NO: 271 | M671.1p |
| SEQ ID NO: 272 | M671.2p |
| SEQ ID NO: 273 | M673.1p |
| SEQ ID NO: 274 | M673.2p |
| SEQ ID NO: 277 | M676.3p |
| SEQ ID NO: 275 | M676.1p |
| SEQ ID NO: 276 | M676.2p |
| SEQ ID NO: 278 | M677ap |
| SEQ ID NO: 279 | M677b.1p |
| SEQ ID NO: 280 | M677b.2p |
| SEQ ID NO: 281 | M677b.3p |
| SEQ ID NO: 282 | M677b.4p |
| SEQ ID NO: 283 | M680p |
| SEQ ID NO: 284 | M691a.1p |
| SEQ ID NO: 285 | M691a.2p |
| SEQ ID NO: 286 | M691bp |
| SEQ ID NO: 287 | M693p |
| SEQ ID NO: 288 | M697p |
| SEQ ID NO: 289 | M698p |
| SEQ ID NO: 290 | M705.1p |
| SEQ ID NO: 291 | M705.2p |
| SEQ ID NO: 292 | M706p |
| SEQ ID NO: 293 | M715ap |
| SEQ ID NO: 294 | M715bp |
| SEQ ID NO: 295 | M719p |
| SEQ ID NO: 296 | M724p |
| SEQ ID NO: 297 | N1503ap |
| SEQ ID NO: 298 | N1527.1p |
| SEQ ID NO: 299 | N1527.2p |
| SEQ ID NO: 300 | N1529p |
| SEQ ID NO: 301 | N1530p |
| SEQ ID NO: 302 | P1611p |
| SEQ ID NO: 303 | P1620.1p |
| SEQ ID NO: 304 | P1620.2p |
| SEQ ID NO: 305 | P1620.3p |
| SEQ ID NO: 306 | P1623a.1p |
| SEQ ID NO: 307 | P1623a.2p |
| SEQ ID NO: 308 | P1623b.1p |
| SEQ ID NO: 309 | P1623b.2p |
| SEQ ID NO: 310 | P1625ap |
| SEQ ID NO: 311 | P1625bp |
| SEQ ID NO: 312 | P1731p |
| SEQ ID NO: 313 | P1744p |
| SEQ ID NO: 314 | P1747.1p |
| SEQ ID NO: 315 | P1747.2p |
| SEQ ID NO: 316 | P1747.3p |
| SEQ ID NO: 317 | P1747.4p |
| No ORF identified | No ORF identified |
| SEQ ID NO: 318 | V1906bp |
| No ORF identified | No ORF identified |
| SEQ ID NO: 319 | V1907ap |
| No ORF identified | No ORF identified |
| SEQ ID NO: 320 | X2005p |
| SEQ ID NO: 321 | X2026p |

Reference is now made to Table 5 presenting phenotypic results of several of the identified genes in the drought tolerance experiments. Plants were grown in soil in controlled greenhouses and tested for drought tolerance under the conditions mentioned above. During their growth, measurements and images were taken (see Table 3) and image analysis was applied converting the images to leaf area per plant. Results are shown as percentage of GFP expressing plants measurements that served as a negative control during the drought phase.

TABLE 5

Results of drought experiments conducted with T2 Arabidopsis plants

| Seq ID | DR | ± SD | Seq ID | DR | ± SD | Seq ID | DR | ± SD | Seq ID | DR | ± SD | Seq ID | DR | ± SD |
|---|---|---|---|---|---|---|---|---|---|---|---|---|---|---|
| SEQ ID NO: 1 | 116.00 | 3.13 | SEQ ID NO: 25 | 137.14 | 7.05 | SEQ ID NO: 55 | 144.00 | 5.56 | SEQ ID NO: 91/92 | 143.23 | 7.26 | SEQ ID NO: 122 | 120.00 | 10.25 |
| SEQ ID NO: 2 | 132.86 | 6.68 | SEQ ID NO: 26/27 | 135.00 | 7.64 | SEQ ID NO: 56/57 | 134.00 | 3.28 | SEQ ID NO: 93 | 133.33 | 6.84 | SEQ ID NO: 124 | 130.73 | 5.93 |
| SEQ ID NO: 17/18 | 151.43 | 10.52 | SEQ ID NO: 28 | 187.64 | 11.00 | SEQ ID NO: 58 | 151.6 | 20.7 | SEQ ID NO: 94 | 102.50 | 7.08 | SEQ ID NO: 125 | 139.10 | 9.76 |
| SEQ ID NO: 5 | 146.9 | 20.6 | SEQ ID NO: 30 | 118.57 | 1.88 | SEQ ID NO: 60 | 134.08 | 4.45 | SEQ ID NO: 97 | 133.41 | 7.61 | SEQ ID NO: 127/128 | 119.09 | 4.03 |

TABLE 5-continued

Results of drought experiments conducted with T2 Arabidopsis plants

| Seq ID | DR | ± SD | Seq ID | DR | ± SD | Seq ID | DR | ± SD | Seq ID | DR | ± SD | Seq ID | DR | ± SD |
|---|---|---|---|---|---|---|---|---|---|---|---|---|---|---|
| SEQ ID NO: 6 | 118.57 | 5.26 | SEQ ID NO: 31 | 112.56 | 4.97 | SEQ ID NO: 62 | 99.72 | 4.71 | SEQ ID NO: 99 | 137.50 | 8.80 | SEQ ID NO: 129 | 135.01 | 7.89 |
| SEQ ID NO: 7 | 156.7 | 23.4 | SEQ ID NO: 33 | 167.57 | 7.20 | SEQ ID NO: 63 | 277.71 | 16.80 | SEQ ID NO: 100 | 160.11 | 20.12 | SEQ ID NO: 130 | 196.80 | 9.06 |
| SEQ ID NO: 8 | 162.1 | 17.1 | SEQ ID NO: 34 | 118.92 | 5.31 | SEQ ID NO: 64 | 136.83 | 6.62 | SEQ ID NO: 101 | 182.50 | 10.00 | SEQ ID NO: 131 | 113.98 | 7.65 |
| SEQ ID NO: 9 | 138.24 | 20.36 | SEQ ID NO: 35 | 115.20 | 6.60 | SEQ ID NO: 65/66 | 107.77 | 10.82 | SEQ ID NO: 102 | 136.67 | 8.72 | SEQ ID NO: 132/133 | 110.33 | 6.64 |
| SEQ ID NO: 10 | 116.00 | 3.19 | SEQ ID NO: 36/37 | 109.71 | 7.79 | SEQ ID NO: 67 | 131.25 | 7.04 | SEQ ID NO: 103/104 | 121.79 | 7.45 | SEQ ID NO: 134 | 107.54 | 9.76 |
| SEQ ID NO: 11 | 107.14 | 2.93 | SEQ ID NO: 38 | 124.59 | 6.74 | SEQ ID NO: 68 | 186.67 | 9.85 | SEQ ID NO: 105 | 126.73 | 6.48 | SEQ ID NO: 137 | 114.17 | 5.84 |
| SEQ ID NO: 12 | 122.86 | 4.53 | SEQ ID NO: 40 | 154.29 | 10.83 | SEQ ID NO: 69 | 132.64 | 8.96 | SEQ ID NO: 106 | 125.00 | 5.94 | SEQ ID NO: 138 | 139.80 | 9.87 |
| SEQ ID NO: 13 | 160.00 | 12.32 | SEQ ID NO: 41 | 117.14 | 5.71 | SEQ ID NO: 70/71 | 145.00 | 7.07 | SEQ ID NO: 107 | 130.00 | 6.64 | SEQ ID NO: 139 | 115.04 | 6.38 |
| SEQ ID NO: 14 | 142.86 | 8.37 | SEQ ID NO: 42 | 118.27 | 3.56 | SEQ ID NO: 72/73 | 134.08 | 7.08 | SEQ ID NO: 109 | 175.00 | 7.38 | SEQ ID NO: 140/141 | 105.73 | 8.08 |
| SEQ ID NO: 15 | 145.71 | 7.24 | SEQ ID NO: 43 | 141.69 | 8.03 | SEQ ID NO: 74/75/76 | 187.50 | 10.00 | SEQ ID NO: 110 | 118.92 | 5.89 | SEQ ID NO: 142 | 141.43 | 3.65 |
| SEQ ID NO: 16 | 136.13 | 8.55 | SEQ ID NO: 44 | 144.00 | 6.36 | SEQ ID NO: 77 | 125.00 | 8.29 | SEQ ID NO: 113 | 113.14 | 8.47 | SEQ ID NO: 143 | 115.50 | 7.96 |
| SEQ ID NO: 17 | 108.33 | 2.73 | SEQ ID NO: 45 | 142.70 | 9.33 | SEQ ID NO: 79 | 123.73 | 6.78 | SEQ ID NO: 114/115/116 | 108.04 | 5.44 | SEQ ID NO: 145 | 112.59 | 7.32 |
| SEQ ID NO: 19 | 121.67 | 5.66 | SEQ ID NO: 46 | 119.36 | 9.40 | SEQ ID NO: 81 | 159.79 | 8.45 | SEQ ID NO: 117 | 167.50 | 9.13 | SEQ ID NO: 147 | 121.66 | 8.81 |
| SEQ ID NO: 20 | 118.68 | 2.48 | SEQ ID NO: 50 | 110.51 | 7.81 | SEQ ID NO: 85 | 180.00 | 7.07 | SEQ ID NO: 118 | 131.68 | 8.77 | SEQ ID NO: 148 | 121.07 | 5.86 |
| SEQ ID NO: 21 | 116.67 | 4.01 | SEQ ID NO: 51 | 158.00 | 13.73 | SEQ ID NO: 87 | 267.03 | 16.40 | SEQ ID NO: 119 | 121.04 | 6.30 | GFP | 100.00 | 6.55 |
| SEQ ID NO: 22 | 131.67 | 8.00 | SEQ ID NO: 53 | 119.42 | 8.70 | SEQ ID NO: 89 | 173.33 | 4.58 | SEQ ID NO: 120 | 104.85 | 7.51 | | | |
| SEQ ID NO: 23/24 | 124.29 | 6.45 | SEQ ID NO: 54 | 145.00 | 11.92 | SEQ ID NO: 90 | 135.00 | 9.29 | SEQ ID NO: 12 | 113.85 | 6.36 | | | |

DR—performance (leaf area) under Drought shown in % of GFP expressing plants
SD—value shown ± standard deviation As shown in Table 5, all plants expressing the tested genes identified by the method of the present invention revealed increased leaf area by about 15% to about 90% under drought conditions as compared to plants expressing the negative control gene (GFP). These results demonstrate that the method of the present invention provides novel genes conferring improved drought tolerance in plants.

Reference is now made to Table 6 presenting results of drought experiments conducted with T2 Arabidopsis plants re-cloned with the relevant Seq. IDs. Different Seq. IDs were re-cloned and re-transformed into Arabidopsis plants generating several independent events (represented by E1-3 in Table 6). Plants were grown in soil in controlled greenhouses and tested for drought tolerance under the conditions mentioned above. During their growth, images were taken and image analysis was applied, converting the images into leaf area per plant. Results are shown in Table 6 as percentage of GFP expressing plants that served as a negative control during the drought phase.

TABLE 6

Results of drought experiments conducted with T2 Arabidopsis plants re-cloned with the relevant Seq. IDs

| Seq ID | DR RC E1 | E1 ± SD | DR RC E2 | E2 ± SD | DR RC E3 | E3 ± SD |
|---|---|---|---|---|---|---|
| SEQ ID NO: 2 | 114.05 | 12.00 | 126.33 | 6.27 | 94.42 | 14.75 |
| SEQ ID NO: 7 | 125.74 | 7.50 | 118.43 | 12.40 | 82.39 | 17.20 |
| SEQ ID NO: 8 | 126.96 | 10.73 | 110.07 | 13.09 | 132.74 | 5.34 |
| SEQ ID NO: 9 | 159.34 | 19.75 | 151.99 | 27.05 | 113.97 | 18.65 |
| SEQ ID NO: 10 | 185.23 | 19.29 | 165.97 | 30.99 | 90.04 | 9.27 |
| SEQ ID NO: 11 | 116.91 | 9.54 | 106.90 | 10.41 | 106.32 | 10.87 |
| SEQ ID NO: 12 | 178.80 | 24.09 | 107.57 | 14.72 | 157.66 | 15.22 |
| SEQ ID NO: 14 | 162.78 | 14.10 | 151.93 | 9.90 | 123.68 | 10.10 |
| SEQ ID NO: 16 | 144.23 | 8.42 | 141.32 | 7.03 | 127.03 | 8.31 |
| SEQ ID NO: 18 | 176.30 | 26.57 | 126.24 | 11.63 | 138.53 | 23.03 |
| SEQ ID NO: 22 | 113.00 | 12.14 | 109.38 | 9.14 | 105.16 | 12.38 |
| SEQ ID NO: 25 | 150.56 | 7.57 | 153.02 | 9.91 | 120.25 | 13.63 |
| SEQ ID NO: 28 | 193.32 | 28.79 | | | | |
| SEQ ID NO: 30 | 123.33 | 11.83 | 113.97 | 8.18 | 112.53 | 16.34 |
| SEQ ID NO: 33 | 141.20 | 10.90 | 127.98 | 13.30 | 112.63 | 11.50 |
| SEQ ID NO: 34 | 167.25 | 12.60 | 150.19 | 13.30 | 138.48 | 10.20 |
| SEQ ID NO: 41 | 160.43 | 11.60 | 153.92 | 14.10 | 112.83 | 10.80 |
| SEQ ID NO: 43 | 229.50 | 18.12 | 136.33 | 32.37 | 106.83 | 26.53 |
| SEQ ID NO: 51 | 178.07 | 13.10 | 170.57 | 14.60 | 146.17 | 11.20 |
| SEQ ID NO: 54 | 169.39 | 15.50 | 131.72 | 11.30 | 120.10 | 16.70 |
| SEQ ID NO: 55 | 126.72 | 16.39 | 122.48 | 18.62 | 111.94 | 17.92 |
| SEQ ID NO: 56/57 | 138.08 | 8.64 | 134.76 | 9.21 | 127.74 | 10.65 |
| SEQ ID NO: 58 | 115.36 | 11.52 | 117.79 | 13.24 | 93.16 | 11.94 |
| SEQ ID NO: 60 | 151.90 | 12.80 | 137.24 | 11.90 | 93.80 | 5.60 |
| SEQ ID NO: 61 | 140.14 | 12.10 | 116.31 | 14.70 | 114.09 | 10.30 |
| SEQ ID NO: 74/75/76 | 175.07 | 13.50 | 160.92 | 12.30 | 105.95 | 11.30 |
| SEQ ID NO: 77 | 210.21 | 18.03 | 174.80 | 18.44 | 160.93 | 29.97 |
| SEQ ID NO: 78 | 182.00 | 15.30 | 175.52 | 16.80 | 115.61 | 11.10 |
| SEQ ID NO: 85 | 132.73 | 10.80 | 119.86 | 11.50 | 114.46 | 9.90 |
| SEQ ID NO: 89 | 167.95 | 21.26 | 154.64 | 21.46 | 142.21 | 29.65 |
| SEQ ID NO: 90 | 141.50 | 24.45 | 137.53 | 17.22 | 110.29 | 32.15 |
| SEQ ID NO: 91/92 | 219.30 | 29.16 | 192.51 | 22.47 | 92.77 | 20.90 |
| SEQ ID NO: 93 | 127.73 | 16.50 | 122.99 | 11.32 | 119.54 | 17.08 |
| SEQ ID NO: 94 | 123.64 | 13.85 | 120.32 | 9.86 | 107.77 | 15.59 |
| SEQ ID NO: 95 | 129.53 | 9.05 | 108.36 | 9.42 | 98.43 | 14.09 |
| SEQ ID NO: 101 | 161.68 | 14.10 | 141.20 | 11.30 | 134.68 | 13.60 |
| SEQ ID NO: 105 | 204.51 | 27.93 | 188.14 | 5.31 | 156.19 | 17.89 |
| SEQ ID NO: 106 | 153.33 | 12.60 | 143.91 | 10.80 | 130.47 | 11.50 |
| SEQ ID NO: 109 | 141.18 | 14.20 | 134.15 | 11.60 | 124.80 | 10.30 |
| SEQ ID NO: 110 | 118.66 | 10.30 | 113.58 | 8.40 | 104.01 | 7.60 |
| SEQ ID NO: 111/112 | 228.16 | 35.62 | 202.43 | 18.73 | 132.98 | 18.32 |
| SEQ ID NO: 113 | 158.59 | 24.54 | 155.03 | 21.36 | 135.44 | 17.44 |
| SEQ ID NO: 126 | 185.07 | 13.40 | 147.37 | 16.20 | 131.05 | 10.80 |

DR—performance (leaf area) under drought shown as % of GFP expressing plants
RC E1-3—performance with re-cloned relevant Seq. ID event 1-3
SD—value shown ± standard deviation As shown in Table 6, plants expressing the re-cloned genes identified by the method of the present invention presented enhanced leaf area as compared to plats expressing the negative control gene, in Arabidopsis plants subjected to drought conditions.

Reference is now made to Table 7 presenting results of drought experiments conducted with T2 tobacco plants. Different genes identified by the present invention were re-cloned and transformed into tobacco plants generating several independent events (represented by E1-3 in Table 7). Plants were grown in soil in controlled greenhouses and tested for drought tolerance under the conditions mentioned above. At the end of the experiment plant shoots fresh weight, leaves number, length of main branch and weight of main branch were evaluated. Results are shown in Table 7 as percentage of wild type (WT) plants that served as a negative control.

TABLE 7

Results of drought experiments conducted with T2 Tobacco plants

| Seq ID | FW | FW ± SD | LN | LN ± SD | BFW | BFW ± SD | BL | BL ± SD |
|---|---|---|---|---|---|---|---|---|
| SEQ ID NO: 1 E1 | 104.71 | 11.18 | 73.58 | 11.63 | 106.78 | 14.75 | 122.73 | 9.25 |
| SEQ ID NO: 1 E2 | 97.28 | 2.18 | 67.92 | 4.76 | 86.18 | 5.10 | 97.27 | 8.86 |
| SEQ ID NO: 1 E3 | 99.22 | 11.21 | 64.15 | 7.70 | 116.72 | 6.30 | 118.18 | 8.90 |
| SEQ ID NO: 2 E1 | 122.23 | 2.70 | 116.76 | 4.84 | 115.42 | 3.47 | 97.33 | 4.87 |
| SEQ ID NO: 2 E2 | 119.11 | 5.62 | 101.62 | 3.97 | 122.99 | 2.70 | 114.84 | 2.98 |
| SEQ ID NO: 2 E3 | 116.69 | 9.00 | 111.35 | 4.58 | 117.50 | 14.45 | 102.67 | 9.91 |
| SEQ ID NO: 15 E1 | 111.60 | 4.18 | 98.38 | 7.58 | 113.65 | 4.39 | 102.08 | 4.89 |
| SEQ ID NO: 15 E2 | 121.87 | 2.88 | 118.92 | 2.53 | 122.25 | 3.70 | 100.59 | 3.71 |

TABLE 7-continued

Results of drought experiments conducted with T2 Tobacco plants

| Seq ID | FW | FW ± SD | LN | LN ± SD | BFW | BFW ± SD | BL | BL ± SD |
|---|---|---|---|---|---|---|---|---|
| SEQ ID NO: 15 E3 | 113.93 | 5.39 | 116.76 | 6.42 | 103.32 | 7.79 | 95.25 | 9.41 |
| SEQ ID NO: 44 E1 | 124.04 | 4.23 | 118.92 | 6.69 | 130.31 | 5.23 | 94.66 | 6.12 |
| SEQ ID NO: 44 E2 | 121.17 | 8.34 | 108.11 | 3.54 | 128.45 | 14.00 | 112.02 | 8.14 |
| SEQ ID NO: 44 E3 | 113.80 | 10.36 | 117.84 | 7.28 | 118.83 | 9.15 | 90.80 | 8.89 |
| SEQ ID NO: 55 E1 | 120.52 | 3.43 | 123.24 | 5.53 | 122.56 | 5.65 | 102.08 | 5.33 |
| SEQ ID NO: 55 E2 | 117.85 | 8.35 | 113.51 | 3.42 | 121.35 | 11.26 | 95.55 | 7.40 |
| SEQ ID NO: 55 E3 | 123.13 | 5.02 | 111.35 | 9.31 | 127.92 | 8.75 | 110.09 | 7.81 |
| SEQ ID NO: 56/57 E1 | 101.58 | 5.17 | 75.47 | 8.92 | 80.26 | 23.40 | 109.55 | 6.45 |
| SEQ ID NO: 56/57 E2 | 106.93 | 9.10 | 79.25 | 8.50 | 101.30 | 10.14 | 103.64 | 7.22 |
| SEQ ID NO: 56/57 E3 | 98.16 | 10.90 | 75.47 | 8.92 | 81.97 | 10.54 | 100.91 | 15.84 |
| SEQ ID NO: 142 E1 | 110.50 | 5.07 | 94.34 | 15.46 | 109.37 | 7.31 | 116.82 | 16.89 |
| SEQ ID NO: 142 E2 | 119.83 | 5.07 | 94.34 | 1.98 | 105.75 | 5.15 | 118.64 | 19.00 |
| SEQ ID NO: 142 E3 | 114.89 | 2.74 | 98.11 | 6.86 | 101.90 | 5.94 | 95.45 | 19.44 |
| WT | 100.00 | 2.43 | 100.00 | 1.67 | 100.00 | 9.84 | 100.00 | 11.65 |

FW—fresh weight measured in grams
LN—leaf number
BFW—branch fresh weight measured in grams
BL—main branch length measured in cm
SD—value shown +/− standard deviation as % of measured trait
E1-3—different independent events The results presented in Table 7 show that most of the genes identified by the present invention confer improved tolerance to drought conditions in Tobacco plants, as shown by the tested parameters (e.g. fresh weight, leaf number, branch fresh weight, branch length) as compared to negative control plants.

Reference is now made to Table 8 presenting results of salinity experiments of transgenic tobacco plants as compared to control WT plants. Different tobacco lines expressing various genes identified by the method of the present invention (see Table 4), were germinated in soil. Seven days post germination; plants were irrigated with fertilized water containing 400 mM NaCl. Leaf images were taken 14 days after irrigation with salt and analyzed for leaf area for the different independent events. Results are shown in Table 8 as percentage leaf area difference from WT plants.

TABLE 8

Results of salinity experiments on tobacco plants

| Seq ID | HST | ±SD |
|---|---|---|
| SEQ ID NO: 1 | 225.12 | 12.65 |
| SEQ ID NO: 2 | 240.63 | 28.91 |
| SEQ ID NO: 15 | 505.52 | 17.57 |
| SEQ ID NO: 44 | 767.46 | 7.48 |
| SEQ ID NO: 55 | 206.71 | 26.27 |
| SEQ ID NO: 56/57 | 286.19 | 4.86 |
| SEQ ID NO: 70/71 | 1366.07 | 4.70 |
| SEQ ID NO: 142 | 318.54 | 29.75 |
| WT | 100.00 | 13.22 |

HST—high salinity tolerance shown as % difference of leaf area as compared to WT
SD—value shown +/− standard deviation between 4 independent events The results of Table 8 clearly show that plants expressing the novel salinity tolerance genes identified by the present invention revealed significantly higher leaf area as compared to WT control plants.

Reference is now made to Table 9 presenting salinity experiments conducted on Arabidopsis plants expressing novel genes having Seq. IDs as indicated. Ten plants per event per pot were grown in soil in controlled greenhouse. After germination, all pots with plants were irrigated by submerging them with 100 mM NaCl. The results of Table 9 represent average data of 4 different events per Seq. ID and wild type plants (WT).

TABLE 9

Results of salinity experiments conducted on Arabidopsis plants expressing novel identified genes

| Seq ID | Flower & Pod production | FP ± SD | Chlorosis | Chlor ± SD |
|---|---|---|---|---|
| SEQ ID NO: 1 | 2.50 | 0.50 | 4.17 | 0.00 |
| SEQ ID NO: 2 | 3.75 | 0.48 | 4.58 | 0.00 |
| SEQ ID NO: 5 | 1.00 | 0.41 | 2.33 | 1.00 |
| SEQ ID NO: 6 | 3.25 | 0.25 | 4.42 | 0.00 |
| SEQ ID NO: 7 | 3.50 | 0.50 | 4.42 | 0.25 |
| SEQ ID NO: 8 | 4.00 | 0.41 | 4.67 | 0.00 |
| SEQ ID NO: 9 | 3.25 | 0.25 | 4.33 | 0.25 |
| SEQ ID NO: 10 | 2.25 | 0.48 | 3.42 | 0.41 |
| SEQ ID NO: 11 | 1.50 | 0.50 | 3.00 | 0.50 |
| SEQ ID NO: 12 | 2.75 | 0.63 | 3.83 | 0.63 |
| SEQ ID NO: 13 | 2.75 | 0.25 | 3.58 | 0.00 |
| SEQ ID NO: 16 | 2.75 | 0.63 | 4.08 | 0.00 |
| SEQ ID NO: 18 | 1.50 | 0.29 | 2.92 | 0.25 |
| SEQ ID NO: 22 | 2.50 | 0.87 | 3.33 | 0.41 |
| SEQ ID NO: 23/24 | 3.50 | 0.29 | 4.50 | 0.00 |
| SEQ ID NO: 25 | 2.25 | 0.75 | 3.08 | 0.29 |
| SEQ ID NO: 26/27 | 1.75 | 0.48 | 3.00 | 0.25 |
| SEQ ID NO: 29 | 2.50 | 0.29 | 3.83 | 0.25 |
| SEQ ID NO: 30 | 3.25 | 0.48 | 4.25 | 0.29 |
| SEQ ID NO: 30 | 3.00 | 0.71 | 4.33 | 0.00 |
| SEQ ID NO: 33 | 2.50 | 0.87 | 3.42 | 0.25 |
| SEQ ID NO: 94 | 2.50 | 0.29 | 3.67 | 0.29 |
| SEQ ID NO: 40 | 1.25 | 0.48 | 2.33 | 1.25 |
| SEQ ID NO: 43 | 2.00 | 0.41 | 3.75 | 0.25 |
| SEQ ID NO: 44 | 3.50 | 0.29 | 4.42 | 0.25 |
| SEQ ID NO: 55 | 2.00 | 0.41 | 3.67 | 0.00 |
| SEQ ID NO: 56/57 | 2.50 | 0.29 | 3.58 | 0.25 |
| SEQ ID NO: 58 | 1.75 | 0.85 | 2.67 | 1.04 |
| SEQ ID NO: 59 | 3.00 | 0.41 | 3.75 | 0.48 |
| SEQ ID NO: 70/71 | 1.75 | 0.63 | 2.67 | 1.00 |
| SEQ ID NO: 77 | 2.00 | 0.00 | 3.50 | 0.29 |
| SEQ ID NO: 89 | 1.75 | 0.63 | 2.50 | 1.11 |
| SEQ ID NO: 90 | 3.00 | 0.71 | 3.83 | 0.25 |
| SEQ ID NO: 91/92 | 1.00 | 0.00 | 3.17 | 0.58 |
| SEQ ID NO: 93 | 2.75 | 0.25 | 4.17 | 0.25 |
| SEQ ID NO: 95 | 3.75 | 0.25 | 4.50 | 0.25 |
| SEQ ID NO: 99 | 2.00 | 0.41 | 3.00 | 0.25 |
| SEQ ID NO: 103/104 | 2.00 | 0.00 | 3.67 | 0.29 |
| SEQ ID NO: 106 | 1.00 | 0.00 | 2.25 | 0.29 |
| SEQ ID NO: 107 | 1.75 | 0.25 | 3.00 | 0.25 |
| SEQ ID NO: 110 | 1.75 | 0.25 | 2.83 | 0.25 |
| SEQ ID NO: 111/112 | 1.00 | 0.00 | 3.08 | 0.25 |
| SEQ ID NO: 113 | 1.25 | 0.75 | 1.83 | 1.44 |

TABLE 9-continued

Results of salinity experiments conducted on *Arabidopsis* plants expressing novel identified genes

| Seq ID | Flower & Pod production | FP ± SD | Chlorosis | Chlor ± SD |
|---|---|---|---|---|
| SEQ ID NO: 118 | 2.50 | 0.29 | 3.25 | 0.50 |
| SEQ ID NO: 119 | 2.25 | 1.03 | 2.75 | 1.19 |
| SEQ ID NO: 120 | 2.00 | 0.41 | 3.08 | 0.29 |
| SEQ ID NO: 124 | 1.75 | 0.25 | 3.00 | 0.00 |
| HRD | 1.25 | 0.25 | 2.83 | 0.48 |
| WT | 1.00 | 0.00 | 1.83 | 0.55 |

FP—Flowers and pods production
1—No Flowers
2—Few flowers formation with short flowering stems
3—Some flower formation almost no pods
4—Flowers and pods forming
Chlorosis—Chlorosis and damage to leaves
1—Completely dry leaves
2—Dry leaf edges
3—Yellow
4—Some Yellow
5—Green
±SD—standard deviation As shown in Table 9, plants expressing genes identified by the method of the present invention as conferring salinity tolerance, demonstrated significantly higher flowers and pods yield and significantly reduced chlorosis and damage effects to the leaves as compared to WT control plants subjected to the same salinity stress conditions.

To conclude, the experimental results presented above clearly demonstrate that by the unique method of the present invention, highly valuable stress tolerance (e.g. drought, salinity) genes in plants can be identified. The newly identified genes confer improved tolerance or resistance to the preselected stress in plants in various important parameters such as leaf area, turgor pressure, aerial yield and quality, flowers and fruits yield etc. These results show that the present invention provides a novel screening method that identifies stress tolerance plant genes that can be expressed in desirable and important crops to enable their growth and enhance their yield under various abiotic and biotic stress conditions.

REFERENCES

Gabor, E. M., Alkema, W. B. & Janssen, D. B. (2004) Quantifying the accessibility of the metagenome by random expression cloning techniques. Environ Microbiol 6, 879-886.

Culligan, E. P., Sleator, R. D., Marchesi, J. R. & Hill, C. (2014) Metagenomics and novel gene discovery: promise and potential for novel therapeutics. Virulence 5, 399-412

Venter, J. C. et al. Environmental genome shotgun sequencing of the Sargasso Sea. Science 304, 66-74.

Farooq, M., Wahid, A., Kobayashi, N., Fujita, D. & Basra, S. M. A. (2009) Plant drought stress: effects, mechanisms and management. Agron. Sustain. Dev. 29, 185-212.

Taiz L. & Zeiger E. (2006) Plant Physiology, 4th Ed., Sinauer Associates Inc. Publishers, Massachusetts.

Nonami H. (1998) Plant water relations and control of cell elongation at low water potentials, J. Plant Res. 111, 373-382.

Parida, A. K. & Das, A. B. (2005) Salt tolerance and salinity effects on plants: A review. Ecotoxicology and Environmental Safety, 60(3), 324-349.

Carillo P, Annunziata M G, Pontecorvo G, Fuggi A, & Woodrow P. 2011. Salinity stress and salt tolerance, abiotic stress in plants—mechanisms and adaptations. In: Arun Shanker, editor Tech, DOI: 10.5772/22331.

Yang T-T, Cheng L & Kain S R (1996) Optimized codon usage and chromophore mutations provide enhanced sensitivity with the green fluorescent protein. Nucleic Acids Res 24:4592-4593 Hema R, Vemanna R S, Sreeramulu S, Reddy C P, Senthil-Kumar M, & Udayakumar M (2014) Stable Expression of mtlD Gene Imparts Multiple Stress Tolerance in Finger Millet. PLoS ONE 9(6): e99110.

Karaba. A, Dixit S, Greco R, Aharoni A, Trijatmiko K R, Marsch-Martinez N, Krishnan A, Nataraja K N, Udayakumar M, & Pereira A (2007) improvement of water use efficiency in rice by expression of HARDY, an Arabidopsis drought and salt tolerance gene. Proc Natl Acad Sci USA 104:5270-15275.

The invention claimed is:

1. A plant comprising a transgene encoding a polypeptide sequences having at least 90% identity to the polypeptide sequences set forth in SEQ ID NO: 213 and wherein the plant has one or more of the following characteristics: improved drought resistance, increased biomass, increased salinity tolerance.

2. The plant according to claim 1, wherein said plant has at least two plant improving traits as compared to a plant of the same species lacking said transgene.

3. The plant of claim 1, wherein the transgene identified has a polynucleotide sequences having at least 80% identity to the polynucleotide sequences set forth in SEQ ID NO:56.

4. The plant according to claim 1, wherein the plant is further characterized by improved nutrition value of the crop, improved grain yield, increased herbicide or chemical resistance or tolerance, increased resistance to cold, increased resistance to hear, improved fertilizer uptake, improved fertilizer usage or any combination thereof.

* * * * *

SEQUENCE LISTING

```
<160> NUMBER OF SEQ ID NOS: 332

<210> SEQ ID NO 1
<211> LENGTH: 1019
<212> TYPE: DNA
<213> ORGANISM: Unknown
<220> FEATURE:
<223> OTHER INFORMATION: metagenomes purified from environmentally
      challenged niches

<400> SEQUENCE: 1
ggactttctc attttcagaa ttattttcta tactctgaca agagcaagca ataccaaaca      60
tcttccacat cgaagcttta accattttgc ccttaacatt tgaacaagac gaaatggcct     120
tcttcccaca ctacaccact aatctgtcgc ctctgctcta cttgttggac gacgactatg     180
ctgtctaccg ctcaacttgt ccaaagtcca actaccacca caagcaacac cacagccgcc     240
gtcagccttc gccagttcgt tactttagtc cgaattttga tatgcgagag gggaatgact     300
cctactacct tgacggagag ctccctggtg tcaaccagaa tgatgtcgat attgaattct     360
```

```
ctgaccctca gacactggtg atcaagggtc gagtggagcg gaattacaac aatctcgacg      420
gcatgaacga ggaaaaccag caagatgaag aacaattctc tgaaactctc tctagcaagt      480
cgtaccaacc cactgtcgag gacgaggacg aggcgaacca ttcaccaccc gtggcgacac      540
caacctactc tgagaagtct gttactgaga aaactcagaa gcctgcgtac aaataccgaa      600
attctgaacg tgctattggc gaattccacc gagccttcaa tctccctaca agagtcgatc      660
aagatgcggt cagggctaca ttgaggaatg gaatcctctc gctggagctc ccgaaggagc      720
cggcaccgaa gatgaagaag attcggattg aatagaggat ttcgaataaa attttttgatt     780 tgatgagtag ttggtgttta ttgttatgtc taattatatg gggctatgtc atgattggga      840
aatgggacac cgcatttgtt tcctttttcc ccatttcttc agacgccatc tatattacat      900
gtatgttgca tgaactatgg ttttttgctag gagcggttgc ttctgctctg cattttcatg      960
aactattttc ttttttattaa attaataact agcatatcaa ttaatgatct gtcatatgg     1019

<210> SEQ ID NO 2
<211> LENGTH: 712
<212> TYPE: DNA
<213> ORGANISM: Unknown
<220> FEATURE:
<223> OTHER INFORMATION: metagenomes purified from environmentally
      challenged niches

<400> SEQUENCE: 2
gatcatcaat caattaatca atctactcta ctttccaaaa cataactacc aaataaccag       60
aatgcagctc ctcagcaccc tcacccccct tgccctccta gtcaccgtcg cttccgccac      120
cggcaaagcc gtcaataatg ccgttggcaa cgccgtcgtc acaaaccact gtaaagaccc      180
aatctatctc tggtccgtcg gctcctccgt ctccccgaaa cacaccatcc cctccggctc      240
caactatacc gagcccttcc gccacgacga cgcatctggc ggcatcgcgc tgaagatcac      300
ccgtaacgac aacgggctgt atgacgggag tgcgcagtta gtttactcct acgctttgga      360
tggggaacag gtgtggtatg atttgtcgag tgtgtttggg gatgcgtttg caggggaggc      420
tgttgctgtg aagccggaga tgagggggtg tgggagtatt tgttggccta agggtaccac      480
gcctggtgga agccaggtta aggtctgtga tgcgagggg gatgttggat tggttgtttg       540
tgcgaagggg tgttaggggg tctgagtgaa ggttggtggt ggtaatgagc aattgggtat      600 gagagggaa aggatatgtt aatcgtttat gttatttact tgatcaaaat atttgtattg       660
acgtcggttg ttttgttatt gttgttttaa atgcaaatgt atatgaactt tc              712

<210> SEQ ID NO 3
<211> LENGTH: 580
<212> TYPE: DNA
<213> ORGANISM: Unknown
<220> FEATURE:
<223> OTHER INFORMATION: metagenomes purified from environmentally
      challenged niches

<400> SEQUENCE: 3
ggttcgtcaa cgcgacgatc cgcggggtc caagctagga cgtggcagtt gtgacacaac        60
aagagcatgc tatggcaaat gccattcgcg agctcgccac tacctgtga actgtggcct      120 tactcctata cccgccagag tctgacttat tcctgtcact ggaatctggc ttactgctgg      180
tgctggagtc tggtcccagt attttagtat agtacaattg ctagctgaag ccataaggcg      240
tggattgttg gggtggcgca gggctgaagc caaatgcag cggtgttgct gctggttgag       300
caccgggcat agcgccagaa agtgcacccg cgaacattcc ctggtattgc atgaacggct      360
```

```
gtccaggaat cgcgccaggc attggcaagg cgttgttgcg ctttgcctcc gctgccagca    420
gcctctctgc ttccgtaccg tgtctttcgc ccttaccgtc cttcttgaat gcataatcaa    480
ccgtcagagg cttgttcatc aagtactggc cattcatagc cgtgattgcc tggtccgagc    540
tgtcaaagtc gttgtactgg atgaatccat atcctttcaa                          580

<210> SEQ ID NO 4
<211> LENGTH: 580
<212> TYPE: DNA
<213> ORGANISM: Unknown
<220> FEATURE:
<223> OTHER INFORMATION: metagenomes purified from environmentally
      challenged niches

<400> SEQUENCE: 4
ttgaaaggat atggattcat ccagtacaac gactttgaca gctcggacca ggcaatcacg     60
gctatgaatg ccagtactt gatgaacaag cctctgacgg ttgattatgc attcaagaag    120
gacggtaagg gcgaaagaca cggtacgaaa gcagagaggc tgctggcagc ggaggcaaag    180
cgcaacaacg ccttgccaat gcctggcgcg attcctggac agccgttcat gcaataccag    240
ggaatgttcg cgggtgcact ttctggcgct atgcccggtg ctcaaccagc agcaacaccg    300
ctgccatttg gcttcagccc tgcgccaccc caacaatcca cgccttatgg cttcagctag    360
caattgtact atactaaaat actgggacca gactccagca ccagcagtaa gccagattcc    420
agtgacagga ataagtcaga ctctggcggg tataggagta aggccacagt tcacagggta    480
gtggcgagct cgcgaatggc atttgccata gcatgctctt gttgtgtcac aactgccacg    540
tcctagcttg accccgcg gatcgtcgcg ttgacgaacc                            580

<210> SEQ ID NO 5
<211> LENGTH: 780
<212> TYPE: DNA
<213> ORGANISM: Unknown
<220> FEATURE:
<223> OTHER INFORMATION: metagenomes purified from environmentally
      challenged niches

<400> SEQUENCE: 5
gaaaaaaact ttagaataca gtttaatcaa tcttcacagc tacaaggcta tatcatttga     60
tatagcatat caaagtggct ttgatttctg taaatttata tctaataata atagtgttta    120
tatcagctaa atacatattt ctatcctatc tatatatcac cgacagacca tatttgaaac    180
tgctgttgac actattattc atatgttcgg atttaatttt aatacgacaa aattgttaaa    240
aacaattctc gttgtttgtt atttgcaggc aacagtgtta gctgatcctt atacaagagt    300
atcttgggaa gcgtatatga atcatgtcaa tggatccgac gactatcgta ctcaagggga    360
tgataccaga gctacacgct ttccagagac taaacctcca aaacaaggaa aagatttcct    420
gtggtcgagt aaaccagtcc ccagttcaga tctatttctg gagttcttta tgtatgaggg    480
agaaccagat gaattcagca ggacgactga atcgtatcaa tcacttccga gcaacgcgtt    540
aactgctagg caaaatgccc ttacttgtca ggacatagag tcatgttcgt atcctccaca    600
ggtgaacaac tttcaagctt tattcgacga cctggggcca tcaacttgta atctcataaa    660
agacgaaact cgtgactgga tattgcagca gtggcccggg ttagctgtag agccgttat    720 atcgtttgcg gtagccgttg cgggaagctc ctgtgatata ttatattaat cagctttggc    780

<210> SEQ ID NO 6
```

```
<211> LENGTH: 661
<212> TYPE: DNA
<213> ORGANISM: Unknown
<220> FEATURE:
<223> OTHER INFORMATION: metagenomes purified from environmentally
      challenged niches

<400> SEQUENCE: 6
ggtcgagcta ctttcaaggt caagcaagat ggtccgttac gcacacaatg ctgagaaccc      60
agagaagacc gccaaggctc gtggtcagca cttgcgtacg cacttcaaga acacccgtga     120
agtcgctgct gctctgaccg gcttgaagct ttcaaaggct acaagtacc tcggcgatgt      180 ccaagagcac aaggatgtca tcccattccg tcgcttcaac ggtggtgttg cagagccgc     240 tcaggctaag aaccacggta cgacccaagg tcgttggcca gtcaagtcga ttggcttctt    300
gctcagactt tgaagaacg ctgaggccaa cgctgacgcc aagtcactcg acacggaaga    360
cctcttgatc aagcacattg ttgtccaaca agctccaaaa acccgtcgtc gtacttaccg    420
tgctcacggt cgtatcaacc cttaccaagg acacccatgc acattgaga tcactctggc     480 tgtcccagac gagcaagtcg ctcgcaacaa ggacgttgag gtgaaccaac caagaagat    540 ccaaggcaac aagcgtcaag tcgctgctca acgtcgcttg acctctgcat aaactggcta    600
ctcggttgtg taccactcta tacaaattat tcagtaaaat gctatccatc ttggcttcga    660
a                                                                     661

<210> SEQ ID NO 7
<211> LENGTH: 713
<212> TYPE: DNA
<213> ORGANISM: Unknown
<220> FEATURE:
<223> OTHER INFORMATION: metagenomes purified from environmentally
      challenged niches

<400> SEQUENCE: 7
agccacaacc acatcaatcc tccaccactt tcagctttcg acttcatcaa acaactcctt     60
ctaccactac tacctcaaca accttcatca aaatgactgg acgcggcaag ggcggcaagg    120
gtctcggaaa gggcggcgcc aagcgtcacc gcaagatctt gcgcgacaac atccagggca    180
tcaccaagcc cgccatccgc cgtctggcgc gtcgtggcgg tgtcaagcgt atctccgcca    240
tgatctacga ggagacccgc ggtgtcctca agaccttcct cgagggtgtc atccgcgacg    300
ccgtcaccta caccgagcac gccaagcgca agaccgtcac ctccctcgac gtcgtctacg    360
ccctcaagag gcaaggccgc accctctacg gtttcggtgg ttaagcagct cgctcttctc    420
tcttcgactg ctttgctttc ttcaaacaca ataacaatca cgacaacaac aacttcatca    480
gatatccacc cacaatgcga gagttgggct tgcgggtatg gcgcgaatgg gcaatgggct    540
atccgggttt tttcattttt ggggtttttt tctcttttcc tgtttcgatg ctgcgaggtg    600
agcacactgg gctgcggctc atgaggcttt gagtgtagaa taggctcaac atcatcaaag    660
aagcattcca cgagacgtgg cgctttcttc atcaaccaaa tgaatattgc agc           713

<210> SEQ ID NO 8
<211> LENGTH: 1021
<212> TYPE: DNA
<213> ORGANISM: Unknown
<220> FEATURE:
<223> OTHER INFORMATION: metagenomes purified from environmentally
      challenged niches

<400> SEQUENCE: 8
```

```
ggacttgcga ccacacacat ctttatacct caaaatgtcg ctcgatgtcg agatgtaga    60 cgcctggatc gacacgctat cgcagtgcaa gcagctatct gaatctgacg tgaagctcct  120
ctgcgacaag gccagagaaa ttcttataga ggagtccaac gtacagccag tcagatgccc  180
cgtcaccgtc tgcggcgata ttcacggtca attccacgac ttgattgagc tctttagaat  240
aggcggcaac tccccatcca ccaattacct cttcatgggc gattacgtag acaggggta   300 ctactcggtc gaaactgtca ccctcctcgt cgccttgaag ctccgctaca gggaaagaat  360
caccatcttg cgcggtaacc acgagtcgag acagatcacc caggtctacg gtttctacga  420
cgagtgcttg agaaagtatg gaaacgccaa cgtctggaag ttcttcaccg atctctttga  480
ctacctccca ctgacggcgc ttattgacaa tcaaatcttc tgtcttcacg gtggtttgtc  540
tccttccatc gacacgctcg accacatccg ctctatcgac cgtatccaag aggtgcctca  600
cgaaggtcct atgtgcgatc tcctctggtc cgatccagac gaccgctgcg gctggggcat  660
atcccctcgt ggtgccggtt acaccttcgg tcaggacatt tcagaggctt tcaaccactc  720
aaacggcttg acgtcgtag cccgtgctca ccaacttgtc atggaaggtt acaactggtc  780
ccaggacagg aatgtcgtca ctctcttctc tgcgccaaat tactgctaca gatgcggtaa  840
ccaagctgcg atcatggaga ttgacgagaa tctcaagtac actttcctcc aattcgatcc  900
agcaccaaga gctggcgaac cgatggtgtc tcgaagagtt ccggactact tcttataggc  960
tcttactcac tgtatttatg tttgcactgg gtattgttta cttgtacaat gtgtaactac 1020
g                                                                 1021
```

<210> SEQ ID NO 9
<211> LENGTH: 715
<212> TYPE: DNA
<213> ORGANISM: Unknown
<220> FEATURE:
<223> OTHER INFORMATION: metagenomes purified from environmentally challenged niches

<400> SEQUENCE: 9

```
ggagccacaa ccacatcaat cctccaccac tttcagcttt cgacttcatc aaacaactcc    60
ttctaccact actacctcaa caaccttcat caaaatgact ggacgcggca agggcggcaa   120
gggtctcgga aagggcggcg ccaagcgtca ccgcaagatc ttgcgcgaca acatccaggg   180
catcaccaag cccgccatcc gccgtctggc gcgtcgtggc ggtgtcaagc gtatctccgc   240
catgatctac gaggagaccc gcggtgtcct caagaccttc ctcgagggtg tcatccgcga   300
cgccgtcacc tacaccgagc acgccaagcg caagaccgtc acctccctcg acgtcgtcta   360
cgccctcaag aggcaaggcc gcaccctcta cggtttcggt ggttaagcag ctcgctcttc   420
tctcttcgac tgctttgctt tcttcaaaca caataacaat cacgacaaca caacttcat   480 cagatatcca cccacaatgc gagagttggg cttgcgggta tggcgcgaat gggcaatggg   540
ctatccgggt ttttcatttt tgggtgttt ttctctttt cctgtttcga tgctgcgagg     600
tgagcacact gggctgcggc tcatgaggct ttgagtgtag aataggctca acatcatcaa   660
agaagcattc cacgagacgt ggcgctttct tcatcaacca aatgaatatt gcagc        715
```

<210> SEQ ID NO 10
<211> LENGTH: 503
<212> TYPE: DNA
<213> ORGANISM: Unknown
<220> FEATURE:
<223> OTHER INFORMATION: metagenomes purified from environmentally challenged niches

<400> SEQUENCE: 10

```
aatcacccaa atgttctcta aactcatcgc catcgcctct cttgccctcg ctgccaacgc    60
tgcagtcatc gacccaagtg accacactgt ccaatacgaa gctgcaccag gaaaggttgt   120
gactgagcac tacgaggttc tcagccacgc cgaagcatcg cgcataatcg aagccaatcc   180
acacatcagc gactatcgct acagatgcaa ctaccaatgc aacgatagca gcggcaacta   240
catgagaaac ctgcagcagg gagttccaaa ccaagcatgc atcttctcta gctgctacga   300
ctgtgactgg aaattccaaa actgtagcta ctgtcgcttg tcgactggcc acaactaccg   360
tgatatcggt ggactcgaga gctggtgcta caacaacggc ggtactacag tgacgcacaa   420
ctgtggttat actgatggcg accaatgcta agagcggcct tgtaaagtaa aacttgtact   480
ctgaatttgc ctttatcttt ccc                                            503
```

<210> SEQ ID NO 11
<211> LENGTH: 580
<212> TYPE: DNA
<213> ORGANISM: Unknown
<220> FEATURE:
<223> OTHER INFORMATION: metagenomes purified from environmentally
    challenged niches

<400> SEQUENCE: 11

```
atcatctcaa acccaattat cttgaacacc tagtttctca agaacatcct caaaatgcac    60
ttcaaatctc tctttattgc tggcgccctc ttcatggtcg gtgccagtgc cgttgattgt   120
gccactcctg agattcactg cgagactagt gatggcagcc cctggtacga cgatgccgtc   180
caagccactg aatactggaa agaaatccag gacgccggca agacagctg cggtgatgct   240
ggttgcgcac agccccatgg ctctggatgc cacagcgacg tggtagcta tggtaccgcc   300
gagatcgttc tctgccagga tgactcgtcc tcttcaactc cccaatgtgc cgactgccgg   360
tgtgtctaca gctacctgaa gcctcttctc gaccaatgca agggtgccaa caacaagatt   420
ggtggatatg ctcatgttga catgggaggc aactacatca actatgaatt tgttaagaaa   480
tgagcggatc tcacgtgtgt gagaccatca tatagggttt tgaagtctgt ttcctttgta   540
tttaacgtcg aaagacaatt atgagccagg tttatactcc                          580
```

<210> SEQ ID NO 12
<211> LENGTH: 607
<212> TYPE: DNA
<213> ORGANISM: Unknown
<220> FEATURE:
<223> OTHER INFORMATION: metagenomes purified from environmentally
    challenged niches

<400> SEQUENCE: 12

```
cgcgccgggg gaaattggac catgatagac gacctcacca ctggctcaga ggacagcttc    60
tccaacagct ggatatcgtg gttcttatct accaaaggga acgagtactt ctgtgaggtg   120
gatgaggagt acatactgga cagattcaac ctcactggcc tcaacaacga cgtgcagaac   180
tactcgcagg cgctggagct catcacagac agcctcgacg acgaggacct cgatgatgag   240
cagagagacg ctatcgagaa cagtgccagg tatctctatg gcttgatcca cgccagatac   300
atcattacct cccgcggact ggcaaagatg ctcttcttgg tgtacccgca gcagctgccg   360
tcaaagacga cgaactcagt gccgagcacg aagccggcaa cttcagcaga cgcagcggtc   420
ggggtggaca ggtacctgcc caagatattc gggttcccgg tgcacgagat gtccaagcac   480
```

| | |
|---|---|
| gcgaggtggc aggaggcgca gagggatctg cagatttcga ggctgcagca aagtgcgagt | 540 |
| gacccgtcgt acgtgtagag cgttcaaaca tgtattacta ttggtataat aatttaactt | 600 |
| tactgcc | 607 |

<210> SEQ ID NO 13
<211> LENGTH: 1406
<212> TYPE: DNA
<213> ORGANISM: Unknown
<220> FEATURE:
<223> OTHER INFORMATION: metagenomes purified from environmentally
    challenged niches

<400> SEQUENCE: 13

| | |
|---|---|
| aagttacccg gcttattagt cctagattcc gagatgtcgc tcactcccga acaaaccgaa | 60 |
| atcatcaagg ccaccgtgcc tgtcgttaaa gaacatggca agaccatcac caccgttttc | 120 |
| tacaagaaca tgctcgaagc gcatcctgag ctgaacgcca ttttcaacac taccaatcag | 180 |
| gtcaatggtc accagcccaa cgcactcgcc ggagccctct tcgcctacgc ctccaacatt | 240 |
| gacaaccttg gcgccttggg ccctgccgtc gaactcatct gcaacaagca tgcttcgctg | 300 |
| tatatccaac ctgagcacta cggcatcgtc ggcaagttcc ttctcgaagc gatgggacag | 360 |
| gttttgggtg acgccttgac tccgcagatc ctcgacgcct gggcagctgc ctactggcag | 420 |
| ctcgccaacc tctttattgg tcgcgaaagt gctatctaca agcagagtga gggatggaca | 480 |
| cagtggcgcg agttccgggt tgcacagaag gtccctgagt ccgcggagat cacatcgttc | 540 |
| tacctcaagc ctgtcgacga gaagcctttg ccccgcttcc gccccggaca gtacatttcc | 600 |
| gtccaagtgc acgttcctca gcttgaatgc ccccaagctc gccaatactc cctcagcgac | 660 |
| aagccccgcg acgattacta ccgcatcagc gtgaagaagg agacgggtct caacacagca | 720 |
| aagccggagg ccaaggtcaa cccgggttac gtctcgaata ttctgcacga aacgtcaac | 780 |
| gagggcgacg tgatcaaggt gtcgcaccct tgcggcgatt tcttcttgac cgagcaggaa | 840 |
| ccgtcgcacc ctgtcgtcct catcgcagcc ggtgtgggtc tgacgccact tacctcgatg | 900 |
| ctcaacacat tggactccac ccccgcggac tctcagcgca agattcactt catccacggt | 960 |
| gcgcgcacca cttccgtccg cgcttttcaag gaccagatta agtctcgcgc tgagcgactc | 1020 |
| ccgaatctcc aggccacctt cttcaccagc tccccgtcgg cagatgaaaa gcaaggcgtc | 1080 |
| gactatgacg tccagggccg tatcgatgtg tccaagatgg atgccagcaa ggatcttttc | 1140 |
| ctcgacaatg cgcagaccga gttctacatt tgtggtccca cttccttcat gaatgatatc | 1200 |
| gcgaacagct tgaaagctcg gggggctacc tcggagcgta tccacatgga attgttcggc | 1260 |
| actggcggcg tgcctgtttta gatgatggct cagttagccg tgattgggtt ttatttcttt | 1320 |
| acgacgatat gactcaggtt tctaagttag tatacataat catgataaat tcttatatag | 1380 |
| atatatcaat aatacatctc ctctcg | 1406 |

<210> SEQ ID NO 14
<211> LENGTH: 750
<212> TYPE: DNA
<213> ORGANISM: Unknown
<220> FEATURE:
<223> OTHER INFORMATION: metagenomes purified from environmentally
    challenged niches

<400> SEQUENCE: 14

| | |
|---|---|
| gggtctcttc catttgaatt tttcaaccca cagcatggcc ttcatgaatc tcccatggcc | 60 |
| cactgaatgc ctgcatgccg ctctcaagaa cggatcctta cctttctggg gatttgtaat | 120 |

| | |
|---|---|
| ctatcgaacg acctacaccg ctcagtcaga tgccgcctgg ccgcagatta tcgagcttat | 180 |
| tgcctcctat atgaaagcct tactctacca cgagtataac gacaagaaaa aagatggaga | 240 |
| tgagcctaca gtctacgacg aaatctgggc aaggcatcag ttgacgatta tggatgatag | 300 |
| acaattcaac ggagcgtctg tgtttgatat ccaacttcac ttcgaaaagt gggttgaggc | 360 |
| gcagggaaag cgagatgaat ctactatgta tcgcatgtgt atggtcattg atgatgaatc | 420 |
| aatccagacg ttattggagg cgccacccgg ggaaaatagg aaactcggac gacgtatagg | 480 |
| gggccctgta cgctttgtca aagtcgtgga ggctttcccc gagctagaca gccttgacga | 540 |
| attccaggga tggatgaaat gtgagatcaa cgcgttatgg ccgctgtgga agatgatgtc | 600 |
| tgacggagat gaaatgagga tgtcatatga tgagatgaag gggaatggaa agcaggtcta | 660 |
| tggcgcaatt taatcggttt ttcttcatgt tatcctgatg gaaaaaatgg cagaacatat | 720 |
| gtctgtacat gcagaaaata aggtgattgg | 750 |

<210> SEQ ID NO 15
<211> LENGTH: 811
<212> TYPE: DNA
<213> ORGANISM: Unknown
<220> FEATURE:
<223> OTHER INFORMATION: metagenomes purified from environmentally
    challenged niches

<400> SEQUENCE: 15

| | |
|---|---|
| gacaccacct cttttcgac aaccacaccc cgtttcgcag gaagtccatt tccagcagtc | 60 |
| aaaatggccc gtcgtcccgc gagatgttac cgctactgca agaacaagcc ttaccctaag | 120 |
| tcccggttca accgtggtgt tcccgacccc aagatccgta tcttcgactt gggtcgtaag | 180 |
| aaggcttccg tggacgactt cccctgtgc gtccacatgg tctccaacga atacgaacag | 240 |
| ctttcctccg aagctctcga agctgcccgt atctgtgcca acaagtacct cgtcaagatc | 300 |
| gccggtaagg aaggttttca cctgcgtgtc cgcgcccacc ccttccacgt cgtccgtatc | 360 |
| aacaagatgt tgtcgtgcgc tggtgccgat cgtctccaga ccggtatgcg tggtgccttc | 420 |
| ggtaagccca acggtgttgt cgcccgtgtg aacatcggcc agatcctcct gtccatccgc | 480 |
| acccgtgact ccaaccgcgc cgccgccgtt gaggccatgc gccgctccac ctacaagttc | 540 |
| cctggtcgcc aaaagatcat tatctccaag aactggggct tcaccccgt ccgtcgtgag | 600 |
| gagtacgtca agctccgcca ggagggcaag ctcaagcagg acggtgccta cgtccagttc | 660 |
| ctgcgtggcc acggtttggt cgaggagaac atgaagcgct tcccccaggc ctacgagggc | 720 |
| gttgctcagt agattgggat gaattaggtg gtttatgtg ctggtcgtat ttatcgtttt | 780 |
| tactagggcc aaatgagaac aaaaaaaggc t | 811 |

<210> SEQ ID NO 16
<211> LENGTH: 923
<212> TYPE: DNA
<213> ORGANISM: Unknown
<220> FEATURE:
<223> OTHER INFORMATION: metagenomes purified from environmentally
    challenged niches

<400> SEQUENCE: 16

| | |
|---|---|
| gtctttagtt ggccattgaa cactgacaga tttgcattgc ttatatttgc atctacctca | 60 |
| catctactca actcctcctc tccgtttgtc atgtccttct accagtctcg tccagacact | 120 |
| atcaagggtc ctgatccttt gaccgacaat tggacttatg atagtgccat tgatctcttc | 180 |

```
tcttggaatc ccatgatgcc cgatcctttt acctttgacc tgcccgacga tcttatgaaa    240
tttgaatcta aggatatgtc tgctggcatg gtcgctcctt cggacattag tggttttgcc    300
attggtaacc atttgggcga ggatgctgcc tcgatatctg atcccgagag tgatgaccac    360
ccatggtccc cctccgctca tgctgccttc ccggagctct ctcccatcac atcgacagag    420
caagtccatc aagaaactgc tcgatactca actaccccg atgccacctc acctcaagaa     480
caaccctcct caccaccaac acgatctact cgccgccgat catccgctga cggtcccgtt    540
cgcaacgctg ccaaacgagc agcccacaac gtcattgaaa agcgctacag aacaaacatg    600
aatgccaaat tcgtggcact cgagaaagca atgaatggcg gtaatggcgt gcaaacatca    660
tcaagaggcg gagggtccgc gtcgcttaag aaatccgaaa tcctctctaa tgctattgcc    720
tacatgcatg gactgcaaga ggaaaatcgc tatttacaaa aggagcttgc tatcgttaaa    780
cagaatcttg taccggcagg gatatggcga ggggctccta gttgtaaacg ggagacgagt    840
tatcgttaac ttgttgattt ccctgtggtt gtttagattt tttttacgat gttacgtgta    900
taataatact ctcccctcgg gtc                                            923
```

<210> SEQ ID NO 17
<211> LENGTH: 1046
<212> TYPE: DNA
<213> ORGANISM: Unknown
<220> FEATURE:
<223> OTHER INFORMATION: metagenomes purified from environmentally challenged niches

<400> SEQUENCE: 17

```
ggacaagccc atcttcaatt cgagacagtc gccatgggtc gcgttatccg caaccagagg     60
aagggccgtg gctccatttt cacggctcac acccgtctga acaaggctcc cgcccagttc    120
cgtaccctcg acttcgctga gcgtcacgga tacacccgtg gtgttgtcaa ggagatcatc    180
cacgatgccg gccgtggtgc tcccctcgcc aaggtccagt tccgccaccc ctacaagttc    240
aagatggtga ccgagacctt catcgccaac gagggcatgt acaccggtca gttcatctac    300
gccggtaaga acgctcagct caccgtcggc aacgttctgc ccctcgcctc catgcccgag    360
ggtaccgtca tctccaacgt tgaggagaag tccggtgacc gtggtgcgct tggccgtacc    420
tccggtaact acgttaccgt cattggccac aaccccgagg acggcaagac ccgtgtcaag    480
cttccctccg gtgccaaaaa ggtcatcaag acaccgccc gtggtatggt tggtatcgtc    540
gccggtggtg tcgtaccgga caagcccctg ctcaaggctt cccgcgccaa gcacaagttc    600
gccgtcaagc gcaactcttg gcccaagact cgtggtgttg ccatgaaccc cgttgatcac    660
cctcacggtg gtggtaacca ccagcatatc ggtaaggcct ctaccatctc ccgctacgcc    720
gcccagggtc aaaaggccgg tctcattgct gcccggagaa ccggtctgct ccgtggtacc    780
cagaagacca aggattaagc gtgatattac gtggagtttt ctttgtgacg ggttgaaaat    840
ggacttctgc tatgagacat atgtacttag gcgagtgcgg ataagcgtcc catgcgccct    900
tagcgaatta aggttgtggt caccatcctt ttcttttat taaatcaaaa aagggtgatg    960
gaatggggtc cgaggctggc ctcaagtcaa ggcagaacgg aaaagtcaaa aatgccccct   1020
ggggttttgg aaatgataca cctttg                                        1046
```

<210> SEQ ID NO 18
<211> LENGTH: 780
<212> TYPE: DNA
<213> ORGANISM: Unknown
<220> FEATURE:

<223> OTHER INFORMATION: metagenomes purified from environmentally
     challenged niches

<400> SEQUENCE: 18

| ggcgcagagg | cctattactc | cccagtatca | tcgctaatag | gcatgtccac | gggtctaagg | 60 |
| ttcagcactt | tgccagctgc | ttccaatcca | cagtcgtcgt | cattgatacc | cagccctagt | 120 |
| gctcccatat | caacttttcc | atatacttta | acactcacgc | taactcccctt | gacgggatcc | 180 |
| ctctcaacct | catactcatt | acgcgcctct | cccaatctgt | catttagctc | tcggttcggt | 240 |
| ttcaatgttt | acagttggga | aagcgagatg | gtagcgggat | ttgaactatg | gcgacaatcg | 300 |
| aaaaagccca | agttggccgc | gggaagcgat | ggcgacgatc | ttgaatgggc | ccgcaggaag | 360 |
| gtccgtgtct | gggatccctc | agcttttccc | ctggcacccc | ctgaacctga | aatcccacaa | 420 |
| ccaaaccatg | aagatgagtc | tcaagagtca | gtacttaagc | tacgagtcga | ccaatcctgg | 480 |
| aatgttcgtc | ttctctggga | aggtcgggtg | aaggagcttt | tggtcagcgc | tggtgtcggg | 540 |
| ctcggcccga | gttccttctc | accatcgtca | tatgcaaatc | ccccgggtac | agccggggct | 600 |
| caaggcagcg | gtggggctc | accggcctca | tactggaggg | gcgtgggggg | tttcggtatc | 660 |
| atattcttca | tgagggattt | cttcggatct | atgtacttga | atgagcactg | tctagatgta | 720 |
| tatagtttat | cagattttat | gagacaatag | acaccatgaa | tctgcgttat | tgcgagacgg | 780 |

<210> SEQ ID NO 19
<211> LENGTH: 896
<212> TYPE: DNA
<213> ORGANISM: Unknown
<220> FEATURE:
<223> OTHER INFORMATION: metagenomes purified from environmentally
     challenged niches

<400> SEQUENCE: 19

| ggccctggcg | tgctttctgg | ctttcaacct | cccgacctcc | ctctaattac | ctcaattgaa | 60 |
| ctcgatttag | acgtggtgct | gccacctccc | gcctgccgca | caatgtttct | tcgcaccgtt | 120 |
| tctcgcgctg | tccctcgcag | caccgcggcc | atccgtgctg | caccgactgc | ctctgtgaac | 180 |
| gccctgcaga | cccgcgctgc | ctcggaccat | gctatcccca | accctaccct | cgccaacatt | 240 |
| gagaagcgct | gggaggtcat | gccccctcag | gagcaggccg | agctctggat | gcagctccgt | 300 |
| gaccgcatga | aggttgactg | gcaccagatg | accctgcagg | agaagaaggc | cgcttactac | 360 |
| attgccttcg | gcgcccacgg | ccccgcgcc | cagccccca | agggtgaggg | catgcgcgtg | 420 |
| ttcgccaagg | tgctccagct | cactgccgcc | tccgttgctg | tcttctacgc | catccacgcc | 480 |
| ttcgccggca | agcagcccgc | caccatgtcc | aaggagtggc | aggaggcctc | caacgaatat | 540 |
| gccctgaaag | agaagatcaa | ccccatccac | ggcatcagca | aagagggtta | cgaaggcaag | 600 |
| ggcttcgtcc | agagccccc | tgccgagaag | tcataggtgt | accagttgcc | cgaccgggaa | 660 |
| tgagttgata | tctacgccgg | acggacggcg | gcacccatcg | cacgatctat | atgtcgatct | 720 |
| tattacaagc | tactctttcc | atagccatgt | tcgacatgtc | tttgtgtcgg | aggatgggcc | 780 |
| tccgcccgtg | cgcgcggccg | tcgattgttc | cattctatct | tttttggcaa | gcattggaaa | 840 |
| atgcgtgtat | cccgtactgt | gctataatca | atgtatctct | tttgtagcca | tagagc | 896 |

<210> SEQ ID NO 20
<211> LENGTH: 641
<212> TYPE: DNA
<213> ORGANISM: Unknown
<220> FEATURE:
<223> OTHER INFORMATION: metagenomes purified from environmentally challenged niches

<400> SEQUENCE: 20

```
gtggcgcgcc ggggggggcat ctacctcgac ggcaacaacg acctggtcac tatgaagggt    60
aactacatct accacaccag cggccgctct cctaaggttc agggtaacac cttgctgcac   120
gctgtcaaca actactggca cgacaactcc ggccacgcct tcgagatcgg tgagggtggt   180
tacgttctgg ccgagggtaa cgtcttccag gatgttacta cccccgttga ggaccccgtt   240
gacggccagc tcttcacttc ccctgacccc agcaccaacg ctcagtgctc gtcataccct   300
ggccgggcct gcgaaatcaa cggcttcggt aactctggta ccttcaacca ggctgacact   360
agcctgctgt ctaaatttaa gggtcagaac attgcttctg ctgatgctta ctctaaggtt   420
gcctcgagcg ttgccagcaa cgccggtcag ggacacctgt aaaatggaaa gaggaggttc   480
agagcttaat ttgctcatgt cggacgacat agccctagcg gcttgctggt gaatttggca   540
taatagcgtt tctcttctca tacctacttt attactccgt ttggatcctt attaggtaaa   600
tattagccca ttgtatggtt caattcgatt gactttgagg c                       641
```

<210> SEQ ID NO 21
<211> LENGTH: 591
<212> TYPE: DNA
<213> ORGANISM: Unknown
<220> FEATURE:
<223> OTHER INFORMATION: metagenomes purified from environmentally
      challenged niches

<400> SEQUENCE: 21

```
gtggcgcgcc gggattctca tcatcagata aaatcaagat taatcttact ggacatcaca    60
acgatccaac acaaagttcc ttcatacttc aaacaaatct ctacaattga atcaaaatgc   120
catccaaaac cgaagcagcc cgtctacaaa acgacttcgg cgcagactac tgggttagaa   180
ataccccaaga acgccgccac tcaaccgctg gccgcggact attcgccggt ctccaggatg   240
tcaagcacta taacgtcgac catggctggg cccgtcgcaa gtctagcgat aaccccggac   300
tccttgcttc tttcttcagt cgattcaccg ggggatcata ccatccgccc tcggaataga   360
attccttttc ttaatgtgcg atattgggag gagtgtgatt tgaattggga ataagggaaa   420
agagtgcttg gaatatttga gtctcagact taactcgagt caagtttcat ttatgagtat   480
actgaggttt ttgtgttagt agcttggagt ttgggtggtt tattagtatt acctattgca   540
ttaccatgtt tatacatcgt gaatcatcga atgaatacca tgtcttcaat t            591
```

<210> SEQ ID NO 22
<211> LENGTH: 639
<212> TYPE: DNA
<213> ORGANISM: Unknown
<220> FEATURE:
<223> OTHER INFORMATION: metagenomes purified from environmentally
      challenged niches

<400> SEQUENCE: 22

```
gtggtatcaa cgcagagtga cgagcccacc atccccggag gcgccgctgt caccatccac    60
tcccgtaacg agaagaaggc ccgtaaggcc attggcaagc tcggtctcaa gcacgtcccc   120
ggcatcaccc gtgttactct ccgccgtcct aagaacatcc tttcgttgt taaccagccc   180
gatgtctaca gtcgccttc cagcaacacc tggatcatct tcggtgaggc caagatcgag   240
gacctgaact cccaggccca ggcttccgct gctcagcagc ttgccgccgc cgaggctgcc   300
gccggaggtg agcacgctgg tcacgaccac gagcacgaca tcctcggcaa gggcaaggcc   360
```

```
cccgagaccg agggcaagaa ggaagaagag gaggacgacg gcgaggaggt tgacgaggcc    420
ggcctcgagg ccaaggacat cgaccttgtc atggcccagg ccaacgtctc ccgcaagaag    480
gccgtcaagg ccctccggga aacgacaat gatatcgtga actcgatcat ggctctcagc    540
```
(Note: reading "gaacgacaat" as in image)
```
atatgatttg gctgcctgcc ggcaggatga atgagtgagc tttgggcgcg aggtcacgtt    600
gatatccctg ttctgggccc tctcccttaa gtgtatagc                           639
```

<210> SEQ ID NO 23
<211> LENGTH: 832
<212> TYPE: DNA
<213> ORGANISM: Unknown
<220> FEATURE:
<223> OTHER INFORMATION: metagenomes purified from environmentally
      challenged niches

<400> SEQUENCE: 23

```
gctcccaacg tcaacacccc ctccgccttc ccctcgaccg ttactcctgc ccgtccgatt     60
acaacaagga gaatgttcct tcagcgtacg gtatctaccc tcgcgaggcg cacccccgtg    120
cggggccttg ctgccgcgcg cccgttttct tcgtccgtta gccgattcaa caagtacgag    180
gttaaggagg ccaagctccg ttctcttgac gagatccaaa ctgaagaaga cctcatcccc    240
cctggtgcta agcccggtac cgtccctagc gatatcgaac acgccactgg tctcgagcgt    300
ctcgaactcg tcggtaaaat gcagggaatt gacatcttcg acttgaggcc tctggatgct    360
tcccgcaagg gaaccctcga aaaccccatt gttgtcaacg gtgctggtga cgagcagtac    420
gctggttgca ctggttaccc cgtcgactct caccaggtta actggttgac tgtctctcgt    480
gagcgcccca tcgagcgctg caacgaatgc ggtaacgttg tcaagctgaa ctatgtcgga    540
cctgaggagg accctcacgc tcacgaccac ggccacggcc accaccctgc ccccgaggag    600
cccaagacct tcgccgacta cgtcaagccc gagtactggt accggtaaat accccagcag    660
tacgacgcga gagttttcaa aaagagaat aagaaacaag caaagggacg gatcaagacg    720
```
(reading "gagttttcaa" / "aaagagaat" as shown)
```
ggctagtgcg ggaatgtcaa acgcaacata tttaagcatt gggtctacta tatacgggtt    780
cattcgtcca ttgattcctc ggtctagtgt tttcttgaac gtctttagct gg            832
```

<210> SEQ ID NO 24
<211> LENGTH: 832
<212> TYPE: DNA
<213> ORGANISM: Unknown
<220> FEATURE:
<223> OTHER INFORMATION: metagenomes purified from environmentally
      challenged niches

<400> SEQUENCE: 24

```
ccagctaaag acgttcaaga aaacactaga ccgaggaatc aatggacgaa tgaacccgta     60
tatagtagac ccaatgctta aatatgttgc gtttgacatt cccgcactag cccgtcttga    120
tccgtccctt tgcttgtttc ttattctctt ttttgaaaac tctcgcgtcg tactgctggg    180
gtatttaccg gtaccagtac tcgggcttga cgtagtcggc gaaggtcttg ggctcctcgg    240
gggcagggtg gtggccgtgg ccgtggtcgt gagcgtgagg gtcctcctca ggtccgacat    300
agttcagctt gacaacgtta ccgcattcgt tgcagcgctc gatggggcgc tcacgagaga    360
cagtcaacca gttaacctgg tgagagtcga cggggtaacc agtgcaacca gcgtactgct    420
cgtcaccagc accgttgaca acaatggggt tttcgagggt tcccttgcgg gaagcatcca    480
gaggcctcaa gtcgaagatg tcaattccct gcattttacc gacgagttcg agacgctcga    540
```

```
gaccagtggc gtgttcgata tcgctaggga cggtaccggg cttagcacca ggggggatga    600
ggtcttcttc agtttggatc tcgtcaagag aacggagctt ggcctcctta acctcgtact    660
tgttgaatcg gctaacggac gaagaaaacg ggcgcgcggc agcaaggccc cgcacggggg    720
tgcgcctcgc gagggtagat accgtacgct gaaggaacat tctccttgtt gtaatcggac    780
gggcaggagt aacggtcgag gggaaggcgg aggggggtgtt gacgttggga gc          832
```

```
<210> SEQ ID NO 25
<211> LENGTH: 1263
<212> TYPE: DNA
<213> ORGANISM: Unknown
<220> FEATURE:
<223> OTHER INFORMATION: metagenomes purified from environmentally
      challenged niches

<400> SEQUENCE: 25
```

```
acccaaaccc tgcgaagcaa aacgcgttac tcgatttggt catttcctcc aaagcatcat     60
tcctctttgg gcactgcctg tttcgtccat taatcaactg tgcttgaatc tctaactatc    120
ttttgatata ccctctttat ctctctcccc tttaatcttt ttttctctct ctctcttttc    180
ctttcttttt cggttactca ctatcatggc cgacatcact gccgtcggtg aggagaaccc    240
ttctcctacc caggatgagc tgcagcaggc cgcggccggt aacggcgctc ctgataaccg    300
cactcccaag cgtcgcatga gtgacgatga agaggacgag gagaagcagg gtcgcgagcg    360
cagaaagatt gagatcaagt tcattcagga taagtcgcgt cgccacatca ccttctccaa    420
gcggaaggcg ggtatcatga agaaggcata cgaattgtcc gtcctcacag gcacccaggt    480
gctgttgctg gtcgtgtccg agaccggcct ggtctatacc tttaccaccc ctaagctcca    540
accattggtc accaaggcgg agggcaagaa cctgattcag gcttgcctca acgccccga    600 ccctaccacc agcgagaatg cgtcgatgc ccccgaggtc ccagcggaga cccccgagga    660
tgtcaaccac gccaacgtca acgctgccgc agcccagcag accaacatcc ctcgtcccac    720
cggaatgcat cccggctaca tgaccaacga acaacagcag cagatggcct actaccaaaa    780
ccacctccag cagcaacagc aggccggtgg gcagtaccct ggcatgtctg tcggtggtcg    840
catgcctacg cagcaccagc ctaccgcata atcttattta ctcttatcta cgctcccacg    900
cacctcctct ttctgatttc cctgcatatg gtcttgtttt tagtagctga ggagtccaga    960
gttcagttgt ttttgccttc tttccgcatc taccctttat tttcccctct ttcgttatta   1020
tctctctccc ctgacatttg atacccgaca atcctgttgt tcaatccatc gtcgcatgaa   1080
aacgggtcct ataaatataa tgcatccccc tgtttacttt cgactgcgaa cgagagcatg   1140
caaatctgaa gaacagcatg gtcaattgtc tcagtaacct cgttaaggcg ccgatgagtt   1200
tggcgtttac atactctgct ttggaacgtg tgatgccttt ttaccgttca atgaaagcga   1260
ctc                                                               1263
```

```
<210> SEQ ID NO 26
<211> LENGTH: 1066
<212> TYPE: DNA
<213> ORGANISM: Unknown
<220> FEATURE:
<223> OTHER INFORMATION: metagenomes purified from environmentally
      challenged niches

<400> SEQUENCE: 26
```

```
aggctttgat ggcctcttca aaggggaaca ttgttcactc gaccagagtt gagtagagcc     60
aagaccattc cataatctcc aggggcatat cgccatgccg tcttgtcaag acgatctcct    120
```

```
tctcacacat attgatgata ggtaccgtta gattggactc ggttgaaccg agtccaattt      180
ggaactacga ctcctcccgg gcctgatttt gcaacgagga ttccactccc gtacactaca      240
gaactatatc gacaccgtcg ctgagattca atgtattctt tcattcgact ggcttcttcc      300
tccgggtgag acgagctgat atttgggaga aatattggac atcccagata atctcgcgca      360
aagtctagtt tggtctggtt gatatcggaa atgatcactt gtttggctcc aaacgctgtg      420
gccgtcgctg cacagaacag accgatagtc cccgacgctt gtaccaggac agtatgaccg      480
ggagtgatac ctgccacccg agctccatga attgcaacac tcaacggctc gaccaaaaca      540
gtttcttcaa gtgagaaatt tcgggaatcg gatacacca atcctcggg tgcgcggaat        600 agatgggtca gagtcccatg gttattgggg ggaggatccg cggcaaagct catctctgga      660
aaaatatcat atctccctgc tttacattgt ttacatcgtc gacgagagaa actagctcga      720
tggcaaagcg gtcgccagga atcacttttg tcactgccgg tccaattgag tgcacgatac      780
ctgatgcctc atgacccatg accagtggtt gctcgtcaga gaccattcga agtaccccgc      840
cgtgtttcca gaaatgggcc tatggaattg gaaattagca aagagaccc tggtgaaagg       900 aagagggatt tgtggggact catatcgctc ccatacacac ccatacgc gatgcgaact        960 aatatatcat agggatcact gagggtaggg acatcgcggt actcaagtcg agctttccca     1020
ggcccgtaga gtaggcagga caaattattc tgaaattatg atcaac                    1066
```

<210> SEQ ID NO 27
<211> LENGTH: 1066
<212> TYPE: DNA
<213> ORGANISM: Unknown
<220> FEATURE:
<223> OTHER INFORMATION: metagenomes purified from environmentally
      challenged niches

<400> SEQUENCE: 27

```
gttgatcata atttcagaat aatttgtcct gcctactcta cgggcctggg aaagctcgac       60
ttgagtaccg cgatgtccct accctcagtg atccctatga tatattagtt cgcatcgcgt      120
atgtgggtgt gtatgggagc gatatgagtc cccacaaatc cctcttcctt tcaccagggt      180
ctcttttgct aatttccaat tccataggcc catttctgga aacacggcgg ggtacttcga      240
atggtctctg acgagcaacc actggtcatg ggtcatgagg catcaggtat cgtgcactca      300
attggaccgg cagtgacaaa agtgattcct ggcgaccgct ttgccatcga gctagtttct      360
ctcgtcgacg atgtaaacaa tgtaaagcag ggagatatga tattttttcca gagatgagct      420 ttgccgcgga tcctccccccc aataaccatg ggactctgac ccatctattc cgcgcacccg      480
aggatttggt gtatccgatt cccgaaaatt tctcacttga agaaactgtt ttggtcgagc      540
cgttgagtgt tgcaattcat ggagctcggg tggcaggtat cactcccggt catactgtcc      600
tggtacaagc gtcggggact atcggtctgt tctgtgcagc gacggccaca gcgtttggag      660
ccaaacaagt gatcatttcc gatatcaacc agaccaaact agactttgcg cgagattatc      720
tgggatgtcc aatatttctc ccaaatatca gctcgtctca cccggaggaa gaagccagtc      780
gaatgaaaga atacattgaa tctcagcgac ggtgtcgata tagttctgta gtgtacggga      840
gtggaatcct cgttgcaaaa tcaggcccgg gaggagtcgt agttccaaat tggactcggt      900
tcaaccgagt ccaatctaac ggtacctatc atcaatatgt gtgagaagga gatcgtcttg     960
acaagacggc atggcgatat gccctggag attatgaat ggtcttggct ctactcaact      1020
ctggtcgagt gaacaatgtt ccccttgaa gaggccatca aagcct                    1066
```

<210> SEQ ID NO 28
<211> LENGTH: 504
<212> TYPE: DNA
<213> ORGANISM: Unknown
<220> FEATURE:
<223> OTHER INFORMATION: metagenomes purified from environmentally
      challenged niches

<400> SEQUENCE: 28

```
agaccaattc taccttaatc tccccaacac aactcaattg aaaacataca ccatgcctcg    60
cggagccgaa tacgccaacg gtcctctcca gagcgacaat gccatcgaag ctggcgaaaa   120
taaggcccac ggaacctccg gtaacaccgg cctcaaccgc gtcaacaagg tcgccgaatt   180
ccccgaaggc gccagaggaa ccggtaccgc tgctaacccg ctcagtgcc agggtagcgc    240 cggccatcag gatggaaagg gtggccatga cccgaagacc cttggagaga acaagggact   300
gggtactcaa tgatcttatg attcagaaga catgagttat ttgcatgagc tgggctcgct   360
gcgattctgt gggattctgt gatttgtaat atgatttgca tgggtcaggt cagacttaat   420
taagcatgcg ctattgtttc cgttatgctt atgatatgga tgggtccatg gttggagttg   480
ataatctaat atggaattga agtg                                          504
```

<210> SEQ ID NO 29
<211> LENGTH: 39
<212> TYPE: DNA
<213> ORGANISM: Unknown
<220> FEATURE:
<223> OTHER INFORMATION: metagenomes purified from environmentally
      challenged niches

<400> SEQUENCE: 29

```
attccatcta aagctaaata ttggcctgag accgatagc                           39
```

<210> SEQ ID NO 30
<211> LENGTH: 577
<212> TYPE: DNA
<213> ORGANISM: Unknown
<220> FEATURE:
<223> OTHER INFORMATION: metagenomes purified from environmentally
      challenged niches

<400> SEQUENCE: 30

```
gagactatga cgacgatcac agagttcccg ccattctaca cgcagcagcc gaatgcgagc    60
gcgctgacgc agcagctggg gctgtggcag aagcatatac tgagcacgtg caagcagcgg   120
cggcagttca agctgagcgt gagtgatgat atctgggcca acgagaggat aaagcgagct   180
gcttctcgtg aatttatttc tgtgattatc tcctcgctgg tgacagaagg gctagcgagc   240
tatacagacg ccaccaagga ggctgtgtgg gtgtactggc ggagtctatc tgattgggcg   300
caggcggcgt acgcgtacgc ggaaagcaca gcgcagctga acacgccgtt gacgtactat   360
gagctagtac aagggagta cagccatcta tctgagctgc atgagatgcc agtagagctg    420
ctcaagcttg ctgtgtcgct gctggtgaag cagaacaaag cggtgataat caaaacgagt   480
caaggggaag gtgtcaaatt cgtctagtat agaataactt aggttacatt ggaatctggt   540
aatcaattcc cttgtcattc agcttctgct gctttcc                            577
```

<210> SEQ ID NO 31
<211> LENGTH: 606
<212> TYPE: DNA
<213> ORGANISM: Unknown

<220> FEATURE:
<223> OTHER INFORMATION: metagenomes purified from environmentally
      challenged niches

<400> SEQUENCE: 31
gggaacaaac tctcattcta actaaatact ttttactctc tgctcccta tcgcattctt      60 tttaggacat tcagaaggtg atcgcttgac caaatgtcta tcccaaaagc ggcagctcat    120
accgacaagg cgcctcagcc tttcaaggac ctctattcgc aagcagttat tgctggtggc    180
gtggtctatt gctctggaat tgttgccatt gaccctgaaa ccggtagcct gattgaagga    240
gatgtcaagg ctcatacgga acgaatttta caaagccttt ctagtactct acaggccgcc    300
ggtaccagtc ttgatcgagc tgtaaagatc aatgtttacc tagcaaacat ggaagacttc    360
acatccatga actcagttta cgaaaagtat tttgtggatg gagtgaaacc ctgcagaacc    420
tgtgtggctg ttaagtctct accttttggc actgatgttg agatggaatg cattgcagta    480
ctgtaaatgt ttagttttat gcgcaactga gaaagacgga aggatcatcc tattacttt     540 tcgaatgtgc tctttggatt tctctgttgg atacacaaca atgccacaca ttgggtacaa    600
ccagat                                                              606

<210> SEQ ID NO 32
<211> LENGTH: 411
<212> TYPE: DNA
<213> ORGANISM: Unknown
<220> FEATURE:
<223> OTHER INFORMATION: metagenomes purified from environmentally
      challenged niches

<400> SEQUENCE: 32
ggaaccaatt acatccatca accaaaccaa caaaatgctg agatctcaat tcggtgtaat     60
ttcaaacgca gcaaagacag ccgcattcct caagcctgtt caaaccagat tgtacgctag    120
tggcgctctc tcgaagggcg acatccaaac tcgcattttt gatgtcctca agtcgtttga    180
taaggtgaag gctgataacc tcactgaatc ggcttctttc accaacgacc tcggcttgga    240
tagcttggac gccgttgaag tcgttatggc cattgaggag gagtttgcca tcgaaattcc    300
agacgctgaa gctgacgcaa tccaaaacgt gaaccaggct atcgaataca tcgccaaaac    360
ccctgaagca cactaaacac gctaaataat tttatcaatt catttcaaac g             411

<210> SEQ ID NO 33
<211> LENGTH: 619
<212> TYPE: DNA
<213> ORGANISM: Unknown
<220> FEATURE:
<223> OTHER INFORMATION: metagenomes purified from environmentally
      challenged niches

<400> SEQUENCE: 33
gtggtatcaa cgcagagtgg cgcgccggga acgaagaaag tttcttcgac ctacctatca     60
aagatatgta aggagcaaca taaatcaata ttcttttatc tgattgacct tcactctagt    120
gcctcgctac gatcagttac aaccttgccc gcgcgaatgg aacgtatacg actttccgaa    180
caggccgcga cgatttgcaa ccaaattcgt gaaatgatac cagagactgc cactttgccc    240
aatcaacctg gcaaggatca agctgaactc atgcatgaag atgaaaacgg gaataagata    300
tacggcggga aacttttaac ggagagagct gctcgactga agagcacat gaagattgac     360 caagtgagtg ccagatttat ctcacagtac tttactaatg gcattcagga ctggacagag    420
cgcttggtat attggacaaa gccgacgaaa ctattgaacc aacggaaaca aggatatatc    480

```
ataccgttat ctaaagacat cgttctacaa cctggggac ctttagaagc aaataacggc    540
tttcgggtca caaacgagcg gattctgagt tcaggagctg ccctttcat tatgccccaa    600 tgatattatt ttgaaaccc                                                619
```

<210> SEQ ID NO 34
<211> LENGTH: 1647
<212> TYPE: DNA
<213> ORGANISM: Unknown
<220> FEATURE:
<223> OTHER INFORMATION: metagenomes purified from environmentally
      challenged niches

<400> SEQUENCE: 34

```
accgctaccg tcatcactac aaatgctggc tcgcagctta cagcaaatca gacgctcaag     60
caggctgagc ttacaattgc gcgcctacgc cagcagtcca gaccgcagcg caagcttctc    120
taagctctca gagcaagatc tcccatcact cgcctccatc ttctcatccc ccgacacctc    180
cctcctcacc acgctcggcg acaagccaac agccaccagc gacgatctcg agccattcaa    240
cgtcgactgg atgggcaagt acaagggcca ctcttccata attgtgaaac caaagacgac    300
gcaagaagtc agcaaggtgc tgcagtgtg caacgagcgc aacgtagctg ttgttccaca    360
aggtggcaac accggtctcg ttggtggatc cgtgccttg cacgacgagg tcgtcttatc    420
tctctcctca atgaacagca tcagacactt cgaccctctt tccggttacg tttctgtcga    480
ttccggtatc gtgctcgaaa atttggataa ctacctcgca caacaaggac acattgtccc    540
tctcgatctg ggtgctaaag ctcctgtca gattggtggc aacgtcgcaa ccaacgctgg    600
tggtctgcgc atgttgagat acggtagttt gcacggcaac gtgctcggcc tcgaagtcgt    660
tctgccagat ggtagagtaa tcaatggtat gaagggactc aagaaggaca cactggtat    720 cgatctcaag cagctcttca tcggctcgga gggtgttctc ggtgttatca ctggtgtcac    780
tctcgccaca cccgtcagac catccgcaac taacgtcgct gtcttcgctt tgcctgacta    840
tgagtcagtg cagactgcct tctcatcagc tagacgcgat ctcggtgaga tcttgtcggc    900
gtttgagttc ttcgatgctg cctcatacaa gctcgtgcgc agccatggac acgcagctga    960
gcgcaaaacc ttcgaagatg gggaagacgc accattttc tgcttggtcg agacgtctgg   1020
ctcgaacaaa gaccacgacg atgagaaact gggtgctttc ctagagcagc tcatggagtc   1080
aggtatcgtc aatgacggtg tattggcaca agacgagacg caaattggcc agctgtggtc   1140
gctgcgtgag ggcattccag aagctgcagg caaagctggt cgcgtgtaca agtacgactt   1200
gagtttacca gtcgagaaga tgtactcgct ggtgccagag ctgcgccaaa agcttgctga   1260
gaagggtctg cttgccgctg agtcagaggg tggtaatgga gatgggccag tcaagacagt   1320
cttcggattt ggtcaccttg gcgatggcaa cctgcacatc aacattgttg ccgatgctta   1380
cagaaaggag gtggaggaag tcgtcgagcc atacatttac gagttggtag ccaagtacaa   1440
tggatctatc tcagcagagc atggtctcgg tctgatgaag gcaccttatg tcgcatacag   1500
tcaagacgcg ccatcgcttg acctcatgcg cactctcaag aagacactcg atccaaaggg   1560
cattctcaac ccatacaagt gcgtcaccgc ggaatagatt ggagttatag atttacgtta   1620
tatgcatgcg atcctgttac attatcc                                       1647
```

<210> SEQ ID NO 35
<211> LENGTH: 669
<212> TYPE: DNA
<213> ORGANISM: Unknown

<220> FEATURE:
<223> OTHER INFORMATION: metagenomes purified from environmentally
      challenged niches

<400> SEQUENCE: 35

```
gtcatcaact tcattcagca aaatggctct ctattacggc atcgtatttg gtatcttaac    60
atttgagatt attctctttt tcttattctt gttgcctatc ccaactcgtt ggcaaaaacc   120
agtgttccgt tggttagcta cctcacctac cattgcacat gctcaatata tcatgaaaat   180
tgtatttgta ttcatctttg tgctcttcct tgattccgtc aacactctcc gcgctttcta   240
cgaagtagtg aacactgaag atgagaatgg tggtattcca gctgccggta actctgattt   300
cagagctcaa gttggtcaag ctgcaaagaa gttttatgct caaagaaatt tgtatctcac   360
tggattcacc attctgttat tactcatttt gaacaagatc aagaacatgg ctatggacta   420
tattagattg gaagatcaat tcattgagct tgaaggatcc gtttccaaag atcccgccat   480
cagaaaggca agcaaagaaa tcgacactac tcccatcgaa gaccatgtta caagactcga   540
gcctgttgaa caagaacagg aaaacaaaaa ggatatctaa ttcacacctg taactaatat   600
gtaaacatct ccctcgctaa aagcgcaata aactaaaatc agcatcattg cgtatctctt   660
tcttctcac                                                           669
```

<210> SEQ ID NO 36
<211> LENGTH: 873
<212> TYPE: DNA
<213> ORGANISM: Unknown
<220> FEATURE:
<223> OTHER INFORMATION: metagenomes purified from environmentally
      challenged niches

<400> SEQUENCE: 36

```
gtggcgcgcc gggaggcgcc taacggtcat gaattgcctc ctcgcggtta tgatcccgga    60
gaaaacactt accaagcacc acctgatgaa cgtagtcaag tagatgttgc gattgaccct   120
aaatccaacc gtcttcagct gttgaagcct ttccagaagt gggacggcaa ggacatcacc   180
aatgttccta tcttgattaa ggtgcaaggc aaatgcacta cagatcatat ttccatggcc   240
ggcccttggc tcaagtatcg tggtcatttg gacaatatca gtaacaattt cctcattggc   300
gccaagagta gcgaaggcaa agtcaacagc atcaagaatg cttttactgg tgaatacaag   360
ggtgtccaga aacagctcgt gattacaaga aggaaggtgt tcgttgggtc gtggtaggtg   420
atgagaacta tggcgaaggc tcctctcgtg agcatgccgc tctagaacct cgattcctca   480
atggagctgc catcattacc aaatcatttg ctcgtatcca tgaaaccaat ctcaaaaagc   540
aaggaatgct tcctttaacc tttgctgatc ccaaggacta tgacaaggtg gacgcctcag   600
ataaagttga tattcttggc ttgactgatt tccaagaagg aaagccattg acccttcgct   660
tgcacaaaaa agatggatca actgtcgatg ttcctttgaa ccatacattc aacggtcagc   720
aaattgaatg gttcaagcat ggatctgcct tgaaccttat gaaggaaaat actgccaaga   780
acggaagctt gtaggtgcac cgttacgtta tcttcacaag catttgtatg tcaaataaac   840
tcgattagtt acttgcactt ttgttaagtt tat                                873
```

<210> SEQ ID NO 37
<211> LENGTH: 874
<212> TYPE: DNA
<213> ORGANISM: Unknown
<220> FEATURE:
<223> OTHER INFORMATION: metagenomes purified from environmentally
      challenged niches

<400> SEQUENCE: 37

```
gtggcgcgcc gggaggcgcc taacggtcat gaattgcctc ctcgcggtta tgatcccgga      60
gaaaacactt accaagcacc acctgatgaa cgtagtcaag tagatgttgc gattgaccct     120
aaatccaacc gtcttcagct gttgaagcct ttccagaagt gggacggcaa ggacatcacc     180
aatgttccta tcttgattaa ggtgcaaggc aaatgcacta cagatcatat ttccatggcc     240
ggccttggc tcaagtatcg tggtcatttg acaatatca gtaacaattt cctcattggc       300
gccaagagta gcgaaggcaa agtcaacagc atcaagaatg cttttactgg tgaatacaag     360
ggtgtcccag aaacagctcg tgattacaag aaggaaggtg ttcgttgggt cgtggtaggt     420
gatgagaact atggcgaagg ctcctctcgt gagcatgccg ctctagaacc tcgattcctc     480
aatggagctg ccatcattac caaatcattt gctcgtatcc atgaaaccaa tctcaaaaag     540
caaggaatgc ttcctttaac ctttgctgat cccaaggact atgacaaggt ggacgcctca     600
gataaagttg atattcttgg cttgactgat ttccaagaag aaagccatt gacccttcgc      660
ttgcacaaaa aagatggatc aactgtcgat gttcctttga accatacatt caacggtcag     720
caaattgaat ggttcaagca tggatctgcc ttgaacctta tgaaggaaaa tactgccaag     780
aacggaagct tgtaggtgca ccgttacgtt atcttcacaa gcatttgtat gtcaaataaa     840
ctcgattagt tacttgcact tttgttaagt ttat                                 874
```

<210> SEQ ID NO 38
<211> LENGTH: 718
<212> TYPE: DNA
<213> ORGANISM: Unknown
<220> FEATURE:
<223> OTHER INFORMATION: metagenomes purified from environmentally
      challenged niches

<400> SEQUENCE: 38

```
ggcgcgccct tgacacagga gcacgggttt cccgtgcgcg tcatcgttcc aggcgtggcg      60
ggcgcgaggg ccgtgaagtg gttggatcac atcacagtgc agcgggaaat gagcagcaat     120
cattatatgc atttcgacta caaggtccta ccaccagaag cggtcgatgc ggaaagggca     180
cgcaccttct ggcataaagt cccgccggtg atcgacatgc cagcgaattc tgccatcacg     240
tcgccacgaa atgaagacac ggtggaagtg gatgcagagg gatttatcac ggtggatggg     300
tacgctttgc cggggggaga agatgggccg gtgaaaagag tcgaggtctc cattgacaag     360
gagagatggg tcgacgcgga actgtttaca catcccatgg aaagcaagtg gacttggaaa     420
atctggaagg ccaaagtgca ggtcgagccg ggcgagcgaa gatgtctcta cagcagaacc     480
actgatgaag cgggcaactc gcagccgcag cgttctcagt ggaacctgag aggcgtatgt     540
tacaacggct atggagaagt gaggaatttg aaggtggtga aaggataggc caatcgttc     600
attccatcat ccatcaagat gtgtctgtat gtgtatgaag gcctgaagcg accacgggac     660
cccagggtgg tcactaaaca gtactcaaac ggactgtttg gttcgtttga cactttcg      718
```

<210> SEQ ID NO 39
<211> LENGTH: 160
<212> TYPE: DNA
<213> ORGANISM: Unknown
<220> FEATURE:
<223> OTHER INFORMATION: metagenomes purified from environmentally
      challenged niches

<400> SEQUENCE: 39

```
aatcaagttc gactgtcaaa atgccagcca acacgatgtc tgccactctc agatccctcc    60
acgttcccgg gaaaccagtc atcttcgcca atgtctggga caccgtctcc gccaaatcaa   120
tcgcacctct ggattcatgc aaagctctag caacggccag                         160
```

<210> SEQ ID NO 40
<211> LENGTH: 1274
<212> TYPE: DNA
<213> ORGANISM: Unknown
<220> FEATURE:
<223> OTHER INFORMATION: metagenomes purified from environmentally
      challenged niches

<400> SEQUENCE: 40

```
gccttgccca tgctactcat caaccctcct cgcaacctca tcggccaaag tcagtctggt    60
accggcaaga cggctgcatt caccctcaac atgctctcac gagtcgaccc aaacatcatg   120 accccctcagg ctatctgttt ggcaccgtcg cgagagcttg ctcgacagat tcaggaagta   180
gtcgacaaga ttggccagtt cacccagatc aagagtttcc tcgctgttcc gggctcttgg   240
tcgcgtaatg tcaagatcga caagcacatt cttgtcggta cgcctggtac actcgtcgac   300
atgctttcgc gaggaggcag gatcttcgac ccgaagcaga ttagagtctt tgtgctggat   360
gaagcggacg aaatgatcgc tttgcaaggt ctggggggacc agacgaagcg catcaagagg   420
atgctgccgc ctgggggtcca gaacgtcctg ttctccgcta cttttcccga caacgtccga   480
gactttgcag gcgacttcgc acccgaggcg aaccagatct tcctgaagaa agaggagatc   540
actgtcgacg ccatcaagca gctctacctc gagtgtgatg gagaggagca gaagtacaac   600 gcccttttctg ccttgtacga catcatgtcg atcggtcaga gtatcgtatt ctgcaagcga   660
aaagacacgg ccgaccgaat tgcggcgaga ctgacggatg agggtcactc tgtcgcttct   720
ctacacggtg acaaacagac tcgagaccgt gatgacatcc ttgacgcttt ccgagatggc   780
aaaaccaagg ttctgatcac caccaacgtc gttgctcgag gtatcgatat ccagcaagtg   840
aacatggtgg tcaactatga cgttcccgat ctcggtccag agggagattg gaagcctgat   900
atcgagacct atatccatcg aataggtcga accggtcgat ttggtcgaaa aggttgttcg   960
gtcatctttg cccatgatca gaggtcgatg caggatgttc agttcatcgc cgatacgctc  1020
ggcaagaaaa tgagcagaat caacgctacc aggcagactg atctcgatca gctcgaagcg  1080
gctttgaaag ccgccatcaa gggcaatcaa ccgaaagagt gaagagtggc accgaattcg  1140
aagagacggg cgctggaaga tatcctgaag caacagggag gagctcccct tatagcatga  1200
tcattgacga taaccatcta gggcctgaag tacattatga tagatagcag acatcaatgc  1260
aacgtcgcgt cgcc                                                    1274
```

<210> SEQ ID NO 41
<211> LENGTH: 919
<212> TYPE: DNA
<213> ORGANISM: Unknown
<220> FEATURE:
<223> OTHER INFORMATION: metagenomes purified from environmentally
      challenged niches

<400> SEQUENCE: 41

```
cacctccaac ctctttctag tttaccttca aaacacatcg gtgtaaggtc ttgcccaaca    60
tggctacctt ctcgacccgc atcaacctcg tccccacctc ccgaacgctc gctagcggcg   120
ttccattcgc acccaggatc gcccttgttc atcctcccgc gtctcacggt cacggaacga   180
gcggtcccag gagtgatgtc ccacccaggt gggctggtgt ccagggtgga ttcgcctcga   240
```

```
actcgagggt caatgtactc cccaccggca acttccagca acgattcatg tccaccacgc    300
cagcccgcaa gatcgaggct caaccccacg tccgaggtgt tcccgattgg tcggcatatc    360
agtcttcggg caagggcgag aacacccgat cccttcgta cttcatggtc ggatctctcg    420
gtgtcctcgc tgcttcaggt gccaagtcga ccgtcagcga cattctgagc aacatggccg    480
cttcggctga tgttttggct ttggccaaga tcgaagttga gatgggtgct atccctgagg    540
gcaagaacct gatcgtcaag tggcgaggaa agcccgtctt cattcgacac cgaacggaag    600
atgagattaa cgaggcacgc gcagtcgaca tcaagtcttt gcgtgatccg gagagcgacg    660
aggataggac ccaaaggga gagtggcttg tcatgctggg tgtctgcact cacttggggtt    720 gtgttcccat tggcgaggct ggtgattacg gaggatggtt ctgcccctgt cacggatctc    780
actacgatat ctctggccga atccgacgag gtcccgcccc tctcaacttg gaggttcccg    840
agtacgcttt caacgacgac gaggagaagc ttgtcattgg ttaggtgtag atggacatat    900
gcagtctatg gccatagcg                                                 919

<210> SEQ ID NO 42
<211> LENGTH: 1459
<212> TYPE: DNA
<213> ORGANISM: Unknown
<220> FEATURE:
<223> OTHER INFORMATION: metagenomes purified from environmentally
      challenged niches

<400> SEQUENCE: 42
ggggagcatc accatagtga cagggactgt agctcggtca agcgcgtatt cgcacttggg     60
cgcctggacg ttactctggc cgtggagtgc gggagtgtca ggacgatgtc ccttcgtgac    120
ctcgcttgct acactctcac gctcaagcca tctaccgaga ataccctcct gaccgagctc    180
acggctttgg agggaccgag tgaggagcca cgattcgcaa gagtgcggga aaggtggaa     240 ggagaggtct attcgtctgc catatacgat gcgttgacgg gagccaagct ggcctcggtg    300
ggtttcgctt ccgaaaagca gaagaacagg aggctacagc tacacaaccc ggatgagagt    360 gtgcctttg acaatactag caagctaggt ttcgaatgga cattcatctt cgaaggcaac    420
aagtacaggt ggacgagaga gctatacgga aaagattata tctgctcact agaccggaaa    480
cccgatccaa gggtggagat ctgcctagct cgagacgcag attcgaaagc gcctggacga    540
ctgcagattc tacactacaa catcgaacga ttcccgaacg agatcaagga tttgagggga    600
ctggaaacgc tactcattgc tacccctcatg tgcttcgtcg acgcggccga agatcggtcc    660
aattccggtc cgacccgcac ttcgcccttg cctgctaagc cggttgccaa tgctgcagca    720
ggtcaaagcg gcaccagcgc aagtggatct tctgatacc gagcgaaagt tgcgccggtg    780
acagtgccag taatcactgc agaggacttt gaggatgatt gtgacccgaa tgagatactg    840
gtaggaacgg agactgatgt gggcgagcac attgcacgag ctatagcgct tttggaggac    900
ccgaccatgc tgttcattgt cattcgaacg cgaactgcgg ccgcgagctc aagagcgtta    960
gaagtctcct taggggttac aaggttccgg caccgtgagg gcatgagcga gctgcatcaa   1020
tacgtggtag aggaagatcc ggtcggaag ccgaaaccca ttatgcctgc tcagggcctc   1080
aagttgatca acctggatga tcgaccagcg gcacaatcac ccaccaaacc ggaatggtct   1140
gccccaccta acatcgctgt ttacctatca tcgatcgagt tgccagatct cacgcccaag   1200
cccaagcctg tccaggggca cacacggccg ccaactcaag cacctcatgc tcggcctccg   1260
ccgccttctc aactaccaca aaagccgcag ccgcggccac gcccgcctcc atccgatggt   1320
```

| | |
|---|---|
| tcaggtagta gtcagactac actcgcttca acgcgaccgc cccaggacga cgggaaggat | 1380 |
| tcgagaaagt ctagctttgg aagactcttt ggcaggtagt acgatacact tagcagggca | 1440 |
| tatgcaggtg tatcgacgg | 1459 |

<210> SEQ ID NO 43
<211> LENGTH: 623
<212> TYPE: DNA
<213> ORGANISM: Unknown
<220> FEATURE:
<223> OTHER INFORMATION: metagenomes purified from environmentally
      challenged niches

<400> SEQUENCE: 43

| | |
|---|---|
| ggcgacgaca acaagaaaac aatacctcac ctgaacatat tcaataatgg cgtcccaatt | 60 |
| gatgcccctg gagctgatcg atcgttgcat cggatcaaga atgcgtgtga tcatgaaagg | 120 |
| cgacaaagag ttcagcggca cacttctcgg attcgacgac ttcgtcaata tggtgctcga | 180 |
| ggatgtcacc gagtacgact acaccggcgc aacgaccaag cttcccaaga tccttctgaa | 240 |
| cggcaacaac atctgcatgc tcatcccagg tggcatgccc gagggcgagt catgaatcac | 300 |
| ggacatatga tatcccttct tacgtctctt gaaatggcaa agcgagtctg atttaagaac | 360 |
| cacacgtgtc atgagaaggc agactatacc gctgtccagt ccaagctgct tgaacaataa | 420 |
| ttatcccgac ggagccacga aaacgtgaca agcggaagct cgcattcgca aagcgccggc | 480 |
| gcaataaaac gccttgttca gctcgccgac tttgtgcatg catgcagctc gccacacccc | 540 |
| gcagatatca ggctgccttc ttgttatcag gtatgcgtgt ttatactcta gcttatttca | 600 |
| gctatgcaaa acctatatca tcc | 623 |

<210> SEQ ID NO 44
<211> LENGTH: 489
<212> TYPE: DNA
<213> ORGANISM: Unknown
<220> FEATURE:
<223> OTHER INFORMATION: metagenomes purified from environmentally
      challenged niches

<400> SEQUENCE: 44

| | |
|---|---|
| gcaaaggagt tgtcgcctga cgtcaagcct gagccgacat ggtcttgtgg cgaggttgtc | 60 |
| aatgtcgtcg atgagcacgg caatgtcatc aaaccgtcag acctctgggt caagatgggt | 120 |
| atgcagcagc aggacaatgt ggacaaccta ttgatcgacg acctgtgtga tcagatgagg | 180 |
| gccaaggcca aatgcacaga gaacggcgct caattgaatg tcgacgacct gaaccacatg | 240 |
| atgtcgtatg acaagtcata taagcagaaa agggtagacg acctcaaaga caagtacggc | 300 |
| tggggagcag tctttggccc gaaatgagcc gcctccgcgg gggcaaggtg gacggacgat | 360 |
| ggtagacatg aatatgagag caaacagaca tagggtctga gtccagtagt gtgcttgtac | 420 |
| caccactgta aatatttgta cgatagccct acaccactta caattgatca tgtaactgtg | 480 |
| tgaaccgtg | 489 |

<210> SEQ ID NO 45
<211> LENGTH: 480
<212> TYPE: DNA
<213> ORGANISM: Unknown
<220> FEATURE:
<223> OTHER INFORMATION: metagenomes purified from environmentally
      challenged niches

<400> SEQUENCE: 45

| | |
|---|---|
| gggagcctga cccgccgtgc ttggttcatc caatccacct gcgccaccac tggtgatggt | 60 |
| ctctacgagg gtctggagtg gctcgccgac actctccgga aaacgaaccg cgattaaacg | 120 |
| cgtataatac gaaattgtga tggggaggat tgtgtacgta gcagagcaag agaaatacca | 180 |
| cgggaaatct gcaaatgatg gaatgatgat tatggcggga gtttcttcca atgttcttct | 240 |
| gcgaggccaa atatcccggc gatgaaaaag aattccctca ccggcatggc atggccatcc | 300 |
| tcaggagcaa ggtgtttgtg tttggctcgc cagggctcta tttctcttcg ctatgctatt | 360 |
| agcctcattt gttcttttct ctctggcgcc acgtcaaaat tgctggttta tctccttttg | 420 |
| attgcatgtt cagtatcggt atgatctcag tataccagca cttgggttga gcattcttct | 480 |

<210> SEQ ID NO 46
<211> LENGTH: 1139
<212> TYPE: DNA
<213> ORGANISM: Unknown
<220> FEATURE:
<223> OTHER INFORMATION: metagenomes purified from environmentally challenged niches

<400> SEQUENCE: 46

| | |
|---|---|
| acctcacttt gtgcgaatta tcctcctaca gcatcagctc tcttcagaaa gaggctaaat | 60 |
| ctatagaccg tccggaacag gttgtcaaca cgcgcgataa gagaagaagg gaatctactg | 120 |
| gtagacaaca gatcgatcgc tcttcagcaa acgcaagatg gagaaccttc ttcgtcagat | 180 |
| gcaaggggga ggtggtagga tgggtgcacg gccaggccct ggaggcgaaa ctatcctcgc | 240 |
| cgacaacggt gaaacagtcc atatttcatc tcttgctcta ttgaagatgc tcaagcatgg | 300 |
| acgagcgggt gtgcctatgg aagtcatggg tctcatgctt ggcgaatttg ttgatgacta | 360 |
| cactatctcc tgtgtcgacg tttttgcaat gcctcaatcc ggtacgacag tgacggtcga | 420 |
| atcagtggat cacgtctttc aaaccaagat gttggatatg ttaaaacaga cgggccgacc | 480 |
| cgagatggtc gtcggttggt accactcgca ccccggtttt ggttgttggc tgtccagtgt | 540 |
| cgatgtcaac actcagcagt ctttcgaaca gctacatccg cgagcagtag ccgttgtcat | 600 |
| cgaccctatc cagtctgttc gtggtaaagt cgtcatcgac gctttccgat ccatcaaccc | 660 |
| tcaatcactt gtcgctggac aagagtcgag gcaaacaacg agtaacattg gtcatctgaa | 720 |
| caaaccgtcc attcaggctc tcatacacgg tctgaatagg cattactaca gtctggccat | 780 |
| cgattacagg aaaacagaag gggagcaggg tatgttgttg aacctgcaca agcggggatg | 840 |
| gacagagggt ttgaagatgc gtgatcactc agagatgaag gagggtaatg agaaggcaat | 900 |
| caaggaaatg ctctctcttg cctcggccta cacgaaatct gttcaggaag agacgacaat | 960 |
| gacggccgaa cagcttaaaa cccgtcacgt aggaaagctt gatccaaaac gtcatttggg | 1020 |
| cgaggcggct gagaaagcga tgggtgatca agtgacgcag agtctggcca tgggtgtcct | 1080 |
| ggctgagctg tagacgtaga agagggaaga aaggaaacga catgcattgt acatatcgc | 1139 |

<210> SEQ ID NO 47
<211> LENGTH: 674
<212> TYPE: DNA
<213> ORGANISM: Unknown
<220> FEATURE:
<223> OTHER INFORMATION: metagenomes purified from environmentally challenged niches

<400> SEQUENCE: 47

| | |
|---|---|
| ggacacaccg gtgacgtctt gagcgtctcg ttctcggccg acaaccgaca aatcgtttct | 60 |

```
gcttcccgag accgaactac caagctctgg aacactctcg gagagtgcaa gttcaacatt    120
gttgacgatg gtcactcgga gtgggtctct tgcgttcgat tctctcctaa ccccgtcatt    180
cccgtcatcg tctctgctgg ttgggacaag gtcgtcaagg tctgggaatt gtccaagtgc    240
aagctcaaga ccaaccacca cggtcacact ggttacatca acaccctcgc cgtttcgccc    300
gacggatcgc tcgccgcatc cggtggaaag tatggcatca ccatgctttg ggatttgaac    360
gatggcaaac acctctactc tctagaggct ggagacattg tcaactcgct cgtcttctct    420
cctaaccgat actggctctg tgccgccact gcttcgtcaa tcaagatctt agacttggag    480
tccaagtcaa tcgttgacga cctcaagcca gacttctccg ccgagtaccc tgacaaggct    540
caaaagccac aatgtacttc cctcgcctgg tctgccgatg gtcagaccct ctttgccggt    600
ttctccgaca acctcgtccg agtctgggtt gtcactgctt agagtcgtga ggattgtatg    660
catggataac gtgg                                                      674
```

<210> SEQ ID NO 48
<211> LENGTH: 674
<212> TYPE: DNA
<213> ORGANISM: Unknown
<220> FEATURE:
<223> OTHER INFORMATION: metagenomes purified from environmentally
      challenged niches

<400> SEQUENCE: 48

```
ccacgttatc catgcataca atcctcacga ctctaagcag tgacaaccca gactcggacg     60
aggttgtcgg agaaaccggc aaagagggtc tgaccatcgg cagaccaggc gagggaagta    120
cattgtggct tttgagcctt gtcagggtac tcggcggaga agtctggctt gaggtcgtca    180
acgattgact tggactccaa gtctaagatc ttgattgacg aagcagtggc ggcacagagc    240
cagtatcggt taggagagaa gacgagcgag ttgacaatgt ctccagcctc tagagagtag    300
aggtgtttgc catcgttcaa atcccaaagc atggtgatgc catactttcc accggatgcg    360
gcgagcgatc cgtcgggcga aacggcgagg gtgttgatgt aaccagtgtg accgtggtgg    420
ttggtcttga gcttgcactt ggacaattcc cagaccttga cgaccttgtc ccaaccagca    480
gagacgatga cgggaatgac ggggttagga gagaatcgaa cgcaagagac ccactccgag    540
tgaccatcgt caacaatgtt gaacttgcac tctccgagag tgttccagag cttggtagtt    600
cggtctcggg aagcagaaac gatttgtcgg ttgtcggccg agaacgagac gctcaagacg    660
tcaccggtgt gtcc                                                      674
```

<210> SEQ ID NO 49
<211> LENGTH: 480
<212> TYPE: DNA
<213> ORGANISM: Unknown
<220> FEATURE:
<223> OTHER INFORMATION: metagenomes purified from environmentally
      challenged niches

<400> SEQUENCE: 49

```
gggagcctga cccgccgtgc ttggttcatc caatccacct gcgccaccac tggtgatggt     60
ctctacgagg gtctggagtg gctcgccgac actctccgga aaacgaaccg cgattaaacg    120
cgtataatac gaaattgtga tggggaggat tgtgtacgta gcagagcaag agaaatacca    180
cgggaaatct gcaaatgatg gaatgatgat tatgcggga gtttcttcca atgttcttct     240
gcgaggccaa atatcccggc gatgaaaaag aattcccctca ccggcatggc atggccatcc    300
tcaggagcaa ggtgtttgtg tttggctcgc cagggctcta tttctcttcg ctatgctatt    360
```

| | |
|---|---|
| agcctcattt gttctttct ctctggcgcc acgtcaaaat tgctggttta tctccttttg | 420 |
| attgcatgtt cagtatcggt atgatctcag tataccagca cttgggttga gcattcttct | 480 |

<210> SEQ ID NO 50
<211> LENGTH: 1170
<212> TYPE: DNA
<213> ORGANISM: Unknown
<220> FEATURE:
<223> OTHER INFORMATION: metagenomes purified from environmentally
challenged niches

<400> SEQUENCE: 50

| | |
|---|---|
| aaagttgatc gaccacattg ggtctgagaa aaacccaatg cttttttgta cagcagtgag | 60 |
| gaatattggt caatggccga aaggctaac cagtaacttg gaagaatgaa attgtatttg | 120 |
| tataaataca atagtggtta aaccacataa aattctaaat agattatata taatgacaaa | 180 |
| atctatttat aagtcttgac caaactacgt gccagcagtc gcggtaatac gtagaaggct | 240 |
| agtgttagtt atctttattg ggtttaaagg gtaagtagac ggtaaattaa actctaaaag | 300 |
| agtacttatt tactagagtt atatgagaga aggaagaatt cctggagtag agataaaatt | 360 |
| ttttgatacc aggaggactg tcaacggcga aggcgtcctt ctatgtaata actgacgttg | 420 |
| agagacgaag gcttgggtag caaacaggat tagataccct aatagtccaa gcagacaatg | 480 |
| atgaatgtca tacattagat agattttaat gtataaacga aagtgtaagc attccacctc | 540 |
| aagagtacta tggcaacata taaactgaaa tcattagacc gtttctgaaa ccagtagtga | 600 |
| agtatgttat ttaattcgat gatccgcgaa aaaccttacc acagcttgta tagcagttat | 660 |
| gaaaaattgt tacaagcgct gcatggctgt ctttagttaa tgtcgtgaga tttggttaac | 720 |
| tcctctaatt aacgaaaacc ctcactttat ttatatatat aaagtggttc gctattacat | 780 |
| tggttgataa tagggattaa gacaagtcat tatggcctaa atgctgtggg ctatagacgt | 840 |
| gccacatacg cctttacaaa gggatgcgat attgtgaaat ggagctaacc cccaaaaaag | 900 |
| gaaatactat ggatagtagt ctgtaactcg actgcttgaa taaggaatta ctagtaatcg | 960 |
| tgaatcacca tcgtcacggt gaattatttc tcagttaggg actaaccact cgtcaggcgc | 1020 |
| tgaaagaaga agatgcagta agtttgatgt tttctgtgta tgattataca taaagttgtt | 1080 |
| gtataactac gcagaaaagt tttcgtatgc aaaactttga ttggtgttaa gtcgaaataa | 1140 |
| ggttcgtgta atggaaattg cacggggagc | 1170 |

<210> SEQ ID NO 51
<211> LENGTH: 1231
<212> TYPE: DNA
<213> ORGANISM: Unknown
<220> FEATURE:
<223> OTHER INFORMATION: metagenomes purified from environmentally
challenged niches

<400> SEQUENCE: 51

| | |
|---|---|
| ggacgatatg acttcaagca gcctcagcga attcgagacg cttctgtcac ggccacgcca | 60 |
| gaatggaacc tgcttgaaga gatcgagttt ggccgattgg gcaagctcaa cctttccgtc | 120 |
| gaagagcccg aagacctcga atcgcacggt accctccaag gttacgacaa gacgtttgac | 180 |
| cgcatcaaca ctcgtaccga aagacctctc gagatcattg atcgagcatg gtacaatcaa | 240 |
| accacttctg acgatcccgt tattgctcag ctcgctcaaa cgcagtctgc ccaaatcttc | 300 |
| gcgacagatg ccattcttgc ggttctgatg tgcaccactc gttccgtaaa ctcgtgggat | 360 |

| | |
|---|---|
| atcattctcg agcgacgagg taaccagctt ttcctcgaca aacgagattc tggtccattc | 420 |
| gactacgtca ctgttcacga aaacgccgcc gacccacctg ccgactctga cgatcccaac | 480 |
| aacgtaaact cggcttcttc cctttcgctc gaggccacct acattacccg aaatttctcg | 540 |
| tctcaagtca ttgatgccaa gtccaagcca tattcgccta gccccaatcc gttctattcg | 600 |
| gaggacgagc catcacccgt cgcttcctgc ttgtacaggt accgaaagtt cgacctgtct | 660 |
| gttggcgagg aagataccct ggacctcatt gtacgaaccg aagtcgacgc ctatcaaggc | 720 |
| aagaaggact ctctcgtcac tgtcaaggca ttgaacgagt ttgatcctcg agcttcaggt | 780 |
| ggtggcaaag ccctagactg gcgaaagtac ctcgacactc aaaagggtgc cattgtcgcc | 840 |
| tcggaaatga agaacaactc ggctaaactc gctcgatggg ctatccagtc tgtcttggcc | 900 |
| ggtgccgaag tcatgaagat gggatacatc tcgcgagctt cgcccaggga tacaactcat | 960 |
| cacgtcattg tcggtgtgca aaattacaag ccaaaagact ttgccgctca aatgaatgtg | 1020 |
| tccctcaaca acggttgggg tatcgtccga acgattgccg atcttgtcct caagcagcca | 1080 |
| gagggcaagt atgtcctcgt caaggaccca aatgcaggca tcattcgtct ctacagtgtg | 1140 |
| ccagagaatg ctttcgaggc agaggaggag gaggagcaat agtcgaaaag tctagacagg | 1200 |
| ccgtgtcgga catgcatcat atacttcaag g | 1231 |

<210> SEQ ID NO 52
<211> LENGTH: 788
<212> TYPE: DNA
<213> ORGANISM: Unknown
<220> FEATURE:
<223> OTHER INFORMATION: metagenomes purified from environmentally
      challenged niches

<400> SEQUENCE: 52

| | |
|---|---|
| gagcgctcaa ggtccttggc cccagaagcc gatcaaggtg tcgcgactca gtgtcacgaa | 60 |
| gtcagatcgt caggtagcta cgacacgttc gagatcggcc atcaccaacc tgacagcgat | 120 |
| acctcgggag tagctgactt gcgcacttcc agtcgtatgg acacctgcga cgcgcatctt | 180 |
| ctacggcggg tcaaaagctg ccctcttttc agctaccgcg aagacgaggt gtccgaaact | 240 |
| gtacaattgc ctacaggcga atggacgacg atcagagata tcactccgag tgcaccaaag | 300 |
| atcggctttg aagtgcgcga ctcgctctcc gcgttcccga cagccaagcc tgtcgaagcg | 360 |
| aagcacgagt ccgcctccag catatccaat gatttaccct ctcagccatc ctcaaggccg | 420 |
| ctgattgagt gtccgacact ggtcgccgat tcacgcacaa cgacggggtc caactctgtg | 480 |
| cgcagtttcg acgcccagac cgaacgcctg agcggcttga gcgacgtgca ccacagatac | 540 |
| atgcaggaca agccgtcaca gcgttctgat tcctggaccg acgtcaaatc ctccgctccg | 600 |
| tcctcccagt cgatggcagt ccccaacaaa gcggcttacc tggctccgat cccagctggc | 660 |
| ccaaatgaca gtaagacttc gagttccggt cgcgccccgt cagacgccgc gaccgaacac | 720 |
| gagtgttcgc tacaataagt cagacttgct gttggaacgt ttcctacctc atgcatacct | 780 |
| ggcatgct | 788 |

<210> SEQ ID NO 53
<211> LENGTH: 706
<212> TYPE: DNA
<213> ORGANISM: Unknown
<220> FEATURE:
<223> OTHER INFORMATION: metagenomes purified from environmentally
      challenged niches

<400> SEQUENCE: 53

```
acccctccaaa ctccaagctc ttttcaaccc tttcctacct tacacaacaa cttcaacaac    60
aactatggca cccaagtcca ctgacaagcc cgcatccacc gctggcaagg cccctctgc    120 tggaggcaag gctcctgcct ccaagactgt cggtgctaag aagaccgcag caagaagtc    180 tgctaagtct actggcgagg gcggcgagaa gaagaagcgt gtcaagtcca gaaggagac    240 ctactctacc tacatctaca aggtcctcaa gcaggtccac cctgacactg gtatctccaa    300
caaggccatg cttatcctca actctttcgt gaacgacatt ttcgagcgta ttgccggtga    360
agcctccaag ctcgctactt acaacaagaa gtctaccatc tcctcccgcg agatccagac    420
tgctgtccgc ctgatcctcc ccggtgaact gtccaagcac gctatttctg agggcaccaa    480
gggtgtcacc aagtactcca gctccaagta aacttgtctt ttgcttggct gagagtcttt    540
cccctttcct tcttcattgt ccctaccctc ctgttcttcc cctctccctc acattcatca    600
tgttgtctat taggcgagct gcctgcagac ttgctcgctg tcaaggctga agcagtcgcg    660
tagttagtgt aatggagcca caaatgtaat tctagagcac atgcag                   706
```

<210> SEQ ID NO 54
<211> LENGTH: 1203
<212> TYPE: DNA
<213> ORGANISM: Unknown
<220> FEATURE:
<223> OTHER INFORMATION: metagenomes purified from environmentally
      challenged niches

<400> SEQUENCE: 54

```
gatgtcaagc gattcaccaa ggatctgctg ttcaactcgg agggcaacct aaccttcaag     60
ccccacttgt ggaacgacat ccgtcacacc ctcctcccca cctttatccg acagatcgga    120
tacgttccca tcccacgagc cgagttctcc tcgcctgaca ttgaccttgt catcgagaat    180
ctggtcctgt ccggacccaa cctcttcccc aacgtcgtct cgctcgagag ccacaactcg    240
ttcaagttct cgccttacca gcagctcaac aagggtatgg acacgcatca ccacaagttc    300
aggctgggta tgagccagat ccaggccgat atccgagatg tccgattctc gttccgacga    360
aagactggat ggcccaagct caaggaccac ggtctcgccg atgtcatcct tgccggtaag    420
ggtatgtcga tcgacgtcga gctcgagtct gtcgagggac gacgagactc tgttgtgcga    480
gtcaaccacg tccacaccac catcgacacc ctcaccttct ccatccgaga ctccaagcac    540
gacttgctct acaagttcgt caagtcggtg gccacgggta cgatcaagaa ggcaatccag    600
gccgccgtcg acaatgccat ccgtacggct gtcggtcacc tcgacgacca gctcgtccag    660
gtccgaaaca ccgtcgatga cgccaagaag tctgacgaga ccacccgaac gcaagccctc    720
aaggacttgt actcgaagaa ggcggacacg gcacagaaga agcaggccga gtccaaggag    780
cagcctggta ctttccgaat cgtcgccaac cgagactctg ttctcaaccc cgacatgggc    840
ggtggcaagg gcgccatgac caacaagatg tggaagaccg aggaccttgc acactctggc    900
aaggaatggc actctcccgc tttcgacttg ctcgactcca gcacccagc acgtaccggt    960 cagacccacc ccgaggccaa ggagggtgct ggacacggaa acagcttgag ctcaaaggct   1020
cagcccggcg ccaacgcggc cgaccagctc aaggctactc acggtcagtc tgaggctgag   1080
gccatcgctg gtcagaagcg acagcaatag gtggaagaga gggagccgcg tattgagaag   1140
taggaaggac tagctgtata cccccttata cttttgtgtc tatagtaatg aatgcgtgaa   1200
acc                                                                 1203
```

```
<210> SEQ ID NO 55
<211> LENGTH: 962
<212> TYPE: DNA
<213> ORGANISM: Unknown
<220> FEATURE:
<223> OTHER INFORMATION: metagenomes purified from environmentally
      challenged niches

<400> SEQUENCE: 55
ggacctttca tccatcagcg tatcgcatat cagcttcctg acaaagtaag aggtaataac    60
aagacaccac actctttcag cacgtacctc ataccggacc gccatgtaca catccgccgt   120
gacactgctc tctttggtct tgctcctggc gacttccgtt attgcacaag aacaagctgg   180
tcggcctggc actcagcgag gcggcgtctt ctttgggtgt tatgccgatc gacctacagg   240
caatgccaac cagcccatca ctcgagtcgc caactccgac acattctttg aatgcatgga   300
gaattgtgct gcgataacgt ctccttcgtt gctgggatac tatcaaccct cctccggtca   360
atgcttctgc ggcaaccttt tatttaaccc tcaagctcaa ttgaacggta acggttgtca   420
aggtagtgat tggtcctttg gccggacttc gaccaccttc aggaggttcg gtgacgcttg   480
tcgacctttc ggtggtgtcg gattttctgc gaatcaatac actacagtca ctggtcccgt   540
agcttgtcat gttcaatgcg catcaaacag attcgcctat gtctggtccg atactggaag   600
caactcatgg caatgtgctt gcagcaacaa tgtccgtgtt caggaggact ccagtacac    660 ttgtcaaggt ggcggtgtat ttgtgtttga acattcagta caagctcagg cttcttcgct   720
taacaggaag cggacggtgg aggaacaatg ggctgttccg aaagacgccc tctgtccatt   780
cggaatgtca gcgtgcaagg tatcaggtgt cgataatgct tacgaggtat gcttcttttc   840
agaccgctag gccctggtt ccctggccac gaggtttgaa acacgccatt gacctgtagt    900
gcctcgatac ctcagccgag ctagaatcgt gcggtggttg tctgcatggt caattgttct   960
ga                                                                  962

<210> SEQ ID NO 56
<211> LENGTH: 909
<212> TYPE: DNA
<213> ORGANISM: Unknown
<220> FEATURE:
<223> OTHER INFORMATION: metagenomes purified from environmentally
      challenged niches

<400> SEQUENCE: 56
gggggaggaa cggtcgttag caatgctttg ctggagaatg ccaagctctg caagacccag    60
ggcaaggaga gctctcttcg agtcatcgtg tgtggccgaa ataggttgga gaatgggtct   120
gcacctcatt gggccgaggc gtttgctacg catggcaaat tggtggaagt gaggatgccg   180
caaaacggca ttcgcatgga gggcatcaaa gctatcgccg acggactggc caagtgtccg   240
acattggaag tgcttgattt gcaggacaac acggctacca agacaggaac acggagtatt   300
gtccgacacc tctcaacttg gcctaaactt cgaatactca atctctcgga ctgtcttttg   360
ggttcggtcg gcggtatcgc tcttgcaacc gcattgtcca ctggctcgaa caagcacctc   420
gaacagctca aactgcaata tggcgagttt gacaagagga cggttgagat actgtcgacg   480
gcaattagcc agcatttgcc aaaattgacg acactcgaac tgaatggaaa ccgtttcgat   540
gccgaagacg aatgcgttga daccctgaag aaggcacttg agctacatgg gaacgaggat   600
gctttggacg aacttgacga tatggaggag gtggacgagg acgaagagga tgatgatgac   660
gaggacgagg aggacgaaga cgaggacaag gacactagcg ccgacgatgg gatcgatgca   720
```

```
ggagctgctg gagaagacgc tctaccacca gtcacgaaga aggacgagga cgtacttgcg    780
gatctcctgt ccaaggtcca cgttcagcct agctgagtcc aagcgctttc cggtcggcaa    840
gtagatagac tagacagcat aataccttga ccctcatgat gccacccgca tgtacacatt    900
tgttctccg                                                             909

<210> SEQ ID NO 57
<211> LENGTH: 909
<212> TYPE: DNA
<213> ORGANISM: Unknown
<220> FEATURE:
<223> OTHER INFORMATION: metagenomes purified from environmentally
      challenged niches

<400> SEQUENCE: 57
cggagaacaa atgtgtacat gcgggtggca tcatgagggt caaggtatta tgctgtctag     60
tctatctact tgccgaccgg aaagcgcttg gactcagcta ggctgaacgt ggaccttgga    120
caggagatcc gcaagtacgt cctcgtcctt cttcgtgact ggtggtagag cgtcttctcc    180
agcagctcct gcatcgatcc catcgtcggc gctagtgtcc ttgtcctcgt cttcgtcctc    240
ctcgtcctcg tcatcatcat cctcttcgtc ctcgtccacc tcctccatat cgtcaagttc    300
gtccaaagca tcctcgttcc catgtagctc aagtgccttc ttcagggtct caacgcattc    360
gtcttcggca tcgaaacggt ttccattcag ttcgagtgtc gtcaattttg gcaaatgctg    420
gctaattgcc gtcgacagta tctcaaccgt cctcttgtca aactcgccat attgcagttt    480
gagctgttcg aggtgcttgt tcgagccagt ggacaatgcg gttgcaagag cgataccgcc    540
gaccgaaccc aaaagacagt ccgagagatt gagtattcga agtttaggcc aagttgagag    600
gtgtcggaca atactccgtg ttcctgtctt ggtagccgtg ttgtcctgca aatcaagcac    660
ttccaatgtc ggacacttgg ccagtccgtc ggcgatagct ttgatgccct ccatgcgaat    720
gccgttttgc ggcatcctca cttccaccaa tttgccatgc gtagcaaacg cctcggccca    780
atgaggtgca gacccattct ccaacctatt tcggccacac acgatgactc gaagagagct    840
ctccttgccc tgggtcttgc agagcttggc attctccagc aaagcattgc taacgaccgt    900
tcctccccc                                                             909

<210> SEQ ID NO 58
<211> LENGTH: 596
<212> TYPE: DNA
<213> ORGANISM: Unknown
<220> FEATURE:
<223> OTHER INFORMATION: metagenomes purified from environmentally
      challenged niches

<400> SEQUENCE: 58
ggatggtgaa gcttagtaac agtcttgtcc gtcgtcttaa atggcaacac gttcgcagtc     60
tcggcgtggt ggcgctgact gcccaattgc gaggaccaca acctcagagc gccgaggacg    120
aagattctga agcagctggc aagaagctca aactggctgg cgaccaagct acatctgcgg    180
tcattcccaa gtccgcagac aagcccgata cttcctct actcgacaca ctacctgcta     240
ctatggctgc tggcaccagg tctatgacta ggcccttgca tgtcggtgat ctgaggttgg    300
ctgatctgcg taaaatcatg caggcagctg gccacacggc tgagttccga ggtgagggaa    360
cactactcat tgacaagtcc gtcgctgtca gaaaatcagg cacagggcag attgaaatcg    420
aggcatctgc tcaagcagct gcaaaccaag ctactcctgg ccgaggtgcg agtagcttcc    480
tcgctgtcaa aagaaagata tacgagggtc tcgctgttgt cacaggaagt taaatgaccg    540
```

```
tgtaccctat attcaatttt tgtataattt acgcaatacc aacgatattc tctcgt          596
```

<210> SEQ ID NO 59
<211> LENGTH: 418
<212> TYPE: DNA
<213> ORGANISM: Unknown
<220> FEATURE:
<223> OTHER INFORMATION: metagenomes purified from environmentally
      challenged niches

<400> SEQUENCE: 59

```
gaaaatgaaa attgatgtgg agaagctgaa taaagatatc agccttttcc cgcaggtgca      60
tccgattacg gaagatatga aaatcacgca caaaggtgtt tcgcgccttg taatgctgga     120
caggtattca tttaaagaca ctgaaaaaat tacgctatct gaaggcgatt ttgtagtgct     180
gacgatcaag gaagatccaa aatttcctgc aagagggcta ggctacatta agaaattga     240
ttgggaaaat aaaaaggcaa aggttcaggt cgaagaagag tttcgtcata ctcttgaaaa     300
gcctgaagaa cgggagacgg gaatcatcgt tcgctcttta gatgtcatcg aaaaaccgct     360
tgaaattttt tatgaacaaa ttgccaaaag aaatgcaaca ggtcttgctg ctgttgaa       418
```

<210> SEQ ID NO 60
<211> LENGTH: 988
<212> TYPE: DNA
<213> ORGANISM: Unknown
<220> FEATURE:
<223> OTHER INFORMATION: metagenomes purified from environmentally
      challenged niches

<400> SEQUENCE: 60

```
ggggatgcaa cggtgactca actgcgcgaa atcatggacg acccagctgg ctatttcttg      60
ccaaatctca aacatggcgc cgataacatg ttctacgtcg gtccacgcgg acttgcacaa     120
gagctcgagg agctttttac cttcccaagc acaatcctca gaaagcgcca ggataccagt     180
cagcatgacg aaaggcaggc aaagaaggcg cgcacgcaag aggacgaagc ggctggtgac     240
gcgttggagg agcccgagac tgggcgacgc gacagtgtgc ttccgactga acgggccgct     300
tttggtctcg agggtgatga ctcgggcttt ttccttggcg accagacgat gggagacgac     360
atgctgccta tggacgacat gggagccatg gacaccggag tggaccagcg acgcatgcga     420
acaccatcag tcgcaccgtc ggtcaccgaa tcgatcgcac gtcagattca gaatgaccga     480
agcgctggca cacccact ggctatattc gagaaggagg caagggacga cacgcagtcg      540
caatcgcagg ctacgcccaa caaatcggtg gcctccgagt ctatcagcaa gacttcttct     600
ggccaatcaa agaatactgg catggccatg ggtttgttgc gaagggagat tgaggcgatc     660
gaggaggaag acaagatggt cgggtttgat cacttggcag acaaggcgtc caagcgagca     720
gcgtctgcat tcttcttcga gctgttggtg cttggtacca acatgcggt caagcttgaa      780
caagctcagg ctttcggcga catccacata cgcggcaaag acaagctgtt tgcagaggtt     840
gttgcataga caaacttgaa gagccacgat cttacgcgca acggagggag atctaatgac     900
catcttgatg tcgactttaa tgttatttgg tacttgtaca tgagctgcta agagggtctt     960
gaatgagatg atgcatcgct tcatgagg                                       988
```

<210> SEQ ID NO 61
<211> LENGTH: 614
<212> TYPE: DNA
<213> ORGANISM: Unknown
<220> FEATURE:

<223> OTHER INFORMATION: metagenomes purified from environmentally
      challenged niches

<400> SEQUENCE: 61

| | | | | | |
|---|---|---|---|---|---|
| gcagaccgtc | tcttttaaat | ctcctccttg | acaccgtct | cctttgcaca | tttactacac | 60 |
| tccacatatc | tccataacaa | ccttatatct | ttacacaatg | ggtgaccacg | ccactaccaa | 120 |
| cgacccctcc | aacgccacct | tcgaggagaa | gggcaagggc | aaggacgtcc | aggatcaaat | 180 |
| cgcggaggac | tccagcgacg | aggagagtga | ccaggagcct | gagatggttg | acgaggaaga | 240 |
| ggatgacaac | aacctcgagc | ccatctccca | agacaacatc | atctcaggtg | gtcgccgtac | 300 |
| acgcggcaag | atcatcgatt | atgccgccga | agccgagaag | aacaaggatg | agatggagga | 360 |
| ctctgaggat | gacgaggatt | accaaggcgc | taatgacgac | gaggatgacc | agatgcgcga | 420 |
| ctaagcgcat | ggtcttgatg | acggatctca | attaacatag | gactttggag | gattggcgct | 480 |
| atggtttctg | aaggaggttc | tctcgtgcgc | ctttgtggtt | agcatctcac | ctatgaaatg | 540 |
| tcatggcctg | agcctggcaa | tggacatgac | tatgaataaa | tgaaatgaag | cctgcttctg | 600 |
| tctttgtgta | acag | | | | | 614 |

<210> SEQ ID NO 62
<211> LENGTH: 418
<212> TYPE: DNA
<213> ORGANISM: Unknown
<220> FEATURE:
<223> OTHER INFORMATION: metagenomes purified from environmentally
      challenged niches

<400> SEQUENCE: 62

| | | | | | |
|---|---|---|---|---|---|
| gaacttaagt | attttaaagc | agttgcacta | tacaacctga | gccggtactt | ggatgcacgg | 60 |
| aaagcaatca | atgacctcat | tcagagctac | ccggacttcc | ggcaagctga | ggccctcaag | 120 |
| tcagccattg | atgacaaggt | ggtgcgcgat | gggctgattg | gcgtgagtgt | ggcaggagca | 180 |
| gtggtggctg | gcgtcgtggg | cttggctgtg | gctcttgcac | gtggcaacag | aggatgatgc | 240 |
| tacaggaggc | agcaggttgt | tggacagttc | agtgcaccgt | gccaatgctt | caacggtctg | 300 |
| gcacaggagg | cagcaggttg | tgaccctgca | caagcttggg | ccatgattct | acagacacac | 360 |
| cttatggcaa | tcaaatgtgt | gtttgcatgt | gcgttgaaga | gtgtaaatgt | gctcttcc | 418 |

<210> SEQ ID NO 63
<211> LENGTH: 94
<212> TYPE: DNA
<213> ORGANISM: Unknown
<220> FEATURE:
<223> OTHER INFORMATION: metagenomes purified from environmentally
      challenged niches

<400> SEQUENCE: 63

| | | | | | |
|---|---|---|---|---|---|
| tatcccgagt | agcatgggac | acgtggaatc | ccgtgtgaat | cagcgaggac | cacctcgtaa | 60 |
| ggctaaatac | tcctgggtga | ccgatagcga | aaaa | | | 94 |

<210> SEQ ID NO 64
<211> LENGTH: 371
<212> TYPE: DNA
<213> ORGANISM: Unknown
<220> FEATURE:
<223> OTHER INFORMATION: metagenomes purified from environmentally
      challenged niches

<400> SEQUENCE: 64

| | | | | | |
|---|---|---|---|---|---|
| cacgatttaa | ataccegggg | gacgttttgg | attcgacagg | gatagatcga | gcttaagctg | 60 |

```
cgagccggag ggatcgtctc cgtcatcaac gtcgcctaaa gataactggc aaacaaaaca    120
actacgcttt agctgcttaa tgctaaaggc tcctttcttc catcgcccat gtggaggaaa    180
aggggttcaa cttaagtggg ctacgcccga ttccgccgtc tgaggaagag ggaagagacg    240
aatcagacta gctgtccgga tgcctgccga caggctaagg aacagtgaaa tgttaaatat    300
gtcggatacg ctcgtagatg cttaagtggc gatatctctg gacgtgggtt cgattcccac    360
cgtctccacc a                                                         371

<210> SEQ ID NO 65
<211> LENGTH: 681
<212> TYPE: DNA
<213> ORGANISM: Unknown
<220> FEATURE:
<223> OTHER INFORMATION: metagenomes purified from environmentally
      challenged niches

<400> SEQUENCE: 65
gccatcagca ccgcaaagct acctcatcaa ccattgaaag cacgcaaata actccccaaa     60
gttaatgccc gtacgaccct acctggaaga aatggccgac atgcccgtgc ccctgttcgc    120
gtacgacgca ccgcccaccc tggccgacca ccctcacgcc cgcgagcacc aacacacgac    180
cttcatgcaa taccttgcgc gcaagcagcc ggacccaaag aactacccca actaccctga    240
cgtggacatc cgcgacgcca tcaatcacta cctgatcgag ctcgaatgcc ggggatcaa     300 agacgcagcc gacatccact gccagtggac gagctcgcgg cacctgaccg tcaccggcga    360
catcgcccgt cctgaggaaa gccagatcga agcgcagatc gagagcaggc ccgtctacct    420
ggttctggga gagagacgca ttggctcttt ccgtcgcaac tttaccttcc ctgtggaggt    480
cgagcaggaa aatatgactg ccaagttgga ggccggattg ttgaagattg tcttgcccaa    540
gcacaagcac catactccga agggaacagg aaaggtcgac attgatgtca ttgagtgaac    600 gtctttggg tctgcgatta tatgcgagga gttcttagat tgccggagtg ggtacctgta    660
tgggaattat gtatctgcaa c                                              681

<210> SEQ ID NO 66
<211> LENGTH: 681
<212> TYPE: DNA
<213> ORGANISM: Unknown
<220> FEATURE:
<223> OTHER INFORMATION: metagenomes purified from environmentally
      challenged niches

<400> SEQUENCE: 66
gttgcagata cataattccc atacaggtac ccactccggc aatctaagaa ctcctcgcat     60
ataatcgcag acccaaaaga cgttcactca atgacatcaa tgtcgacctt tcctgttccc    120
ttcggagtat ggtgcttgtg cttgggcaag acaatcttca acaatccggc ctccaacttg    180
gcagtcatat tttcctgctc gacctccaca gggaaggtaa agttgcgacg gaaagagcca    240
atgcgtctct ctcccagaac caggtagacg ggcctgctct cgatctgcgc ttcgatctgg    300
ctttcctcag gacgggcgat gtcgccggtg acgtcaggt gccgcgagct cgtccactgg    360
cagtggatgt cggctgcgtc tttgatcccc gggcattcga gctcgatcag gtagtgattg    420
atggcgtcgc ggatgtccac gtcagggtag ttggggtagt tctttgggtc cggctgcttg    480
cgcgcaaggt attgcatgaa ggtcgtgtgt tggtgctcgc gggcgtgagg gtggtcggcc    540
agggtgggcg gtgcgtcgta cgcgaacagg ggcacgggca tgtcggccat ttcttccagg    600
```

```
tagggtcgta cgggcattaa cttttggggag ttatttgcgt gctttcaatg gttgatgagg    660
tagctttgcg gtgctgatgg c                                              681
```

<210> SEQ ID NO 67
<211> LENGTH: 50
<212> TYPE: DNA
<213> ORGANISM: Unknown
<220> FEATURE:
<223> OTHER INFORMATION: metagenomes purified from environmentally
      challenged niches

<400> SEQUENCE: 67

```
gggatgatat gcatcatata gatcttgaga aatcaaggta agtatacaaa               50
```

<210> SEQ ID NO 68
<211> LENGTH: 558
<212> TYPE: DNA
<213> ORGANISM: Unknown
<220> FEATURE:
<223> OTHER INFORMATION: metagenomes purified from environmentally
      challenged niches

<400> SEQUENCE: 68

```
gggaaaaaaa ctttagaata cagtttaatc aatcttcaca gctacaaggc tatatcattt    60
gatatagcat atcaaagtgg ctttgatttc tgtaaattta tatctaataa taatagtgtt   120
tatatcagct aaatacatat ttctatccta tctatatatc accgacagac catatttgaa   180
actgctgttg acactattat tcatatgttc ggatttaatt ttaatacgac aaaattgtta   240
aaaacaattc tcgttgtttg ttatttgcag gcaacagtgt tagctgatcc ttatacaaga   300
gtatcttggg aagcgtatat gaatcatgtc aatggatccg acgactatcg tactcaaggg   360
gatgatacca gagctacacg ctttccagag actaaacctc caaacaagg aaaagatttc    420 ctgtggtcga gtaaaccagt ccccagttca gatctatttc tggagttctt tatgtatgag   480
ggagaaccag atgaattcag caggacgact gaatcgtatc aatcacttcc gagcaacgcg   540
ttaactgcta ggcaaaaa                                                 558
```

<210> SEQ ID NO 69
<211> LENGTH: 1164
<212> TYPE: DNA
<213> ORGANISM: Unknown
<220> FEATURE:
<223> OTHER INFORMATION: metagenomes purified from environmentally
      challenged niches

<400> SEQUENCE: 69

```
ggacacatca cacaacaaca atgtctccaa caccaacatc accacacaac aagctctcgc    60
tccccgcaag agcttcttcc cacgactcga cagacggcat ccgtaagcga gtatgcaagg   120
cttgcgacag gtgtcgattg aagaagagca aatgcgacgg atcaagtcca tgctctcgat   180
gcaaagcaga caacgccatc tgcgtgttcg gagagcgcaa acgatcacat gataaacact   240
atcccaaagg ctatgtcgag atgctcgaac aacagcaggg tcagctcgtc tcaggcctca   300
aagaaatgta ccacagactc cagaaagcct ccgcctggga tggccctgtg ttggacgaaa   360
gcaccggaca gcctctcact cacgacatcc tgtcagcatt agacctcctc gaaccaaagc   420
atgacgacag caacgagcca gaagtcttcg aagagaactg cgaaaagctg caatcaaaat   480
tgctcgcaga cggcgcgggc tttgcccacc gacgaggatc gatcagttcg gattctgaac   540
acagccatca cgatcgaccc aaaacatcct cacgccacga cacgcccgtg caacccaaac   600
```
cgtcgatctt caaggagaac ctgagcttcg ccagcgcggc ctcatcacca ctcacgcaaa    660
gccccatccc tcgatcgaaa cccttgaacg tcatgccata ccaaacgctg caaccgtcgt    720
caagaccatc cccactccag atgccctcag catacaacga cccgcaacta tacgcacccg    780
aatgggcaca agcactggca gacatgagcg gcgatcccaa ctaccgccaa agattctcca    840
tgcagcagca acaacaaaac gacttcgaca acctgctctg ggatccctca gcgcaagcgc    900
ccatggaatc gcccttcagc caaccagcct tcttcaacca ggcgcaactg atcggcagcg    960
gcaacgtctt tgggctgtct gacatcaacg atctgggccc caaccccgcg gatggcggga   1020
tggactttga cttcagcaag ttcgtgcagc agaccgaagt catgacatga acatgattct   1080
tgccttctgt caatacgcgc gagaattttg cttcagagtt ccagtccgtg taattcttgt   1140
gtatttatta cgatacgaac acgc                                          1164

<210> SEQ ID NO 70
<211> LENGTH: 923
<212> TYPE: DNA
<213> ORGANISM: Unknown
<220> FEATURE:
<223> OTHER INFORMATION: metagenomes purified from environmentally
      challenged niches

<400> SEQUENCE: 70
agagctcttc gtactccaca ccaccatctt ccatccgacc acactttcat cccaaatcca     60
tcaacaaccc atctcaactc catctcacca cctcaccatc atcacaatgt cttccttccg    120
cgtcgccgcc cccaagatgg cctccatggc cgctcagtcc tccgtgaagg tcgcccgccc    180
ggccttccag gctgctcagc tccagaagtt cacccgcgcc tactccgcgg tccccaagaa    240
caccgtcttc aacaccatga agcgcaccca gatgatggcc cgccaggcct cccccatcgc    300
caagcgtgcc tactcctctg agatggccaa cgccctcgtc caggtctccc agaacatcgg    360
tatgggttcc gccgccatcg gtcttgccgg tgctggtgtc ggtatcggtc tcgtcttcgc    420
cgccctcatc caggccgtcg cccgcaaccc ctccctccgt ggccagcttt tctcttacgc    480
cattcttggt ttcgctttcg tcgaggccat cggtctcttc gacctcatgg ttgccatgat    540
ggccaagttc ttgtaaaaat gtgcattcca ttacctaccg agatggagat ggatgcgaag    600
gcgattgggg acggagacag tgcgttgctg cagcagcatt agtaccggtg ttggtcgtgt    660
accagtagtc tgatggagac ggatagatgg atagaaagct ggtgaatggg ggctacgaag    720
aaaacgtacc tctcgatcca tttgtaccca tactcatgaa gtatatccgt cttctttcct    780
tctatcattc gcgcgcactt ccttgctggt ggcttttggg ggttgcgctc tcaccgaaaa    840
gcaacgtcac tcttgtatat aacttattcg accacggcca tatcttggtt tggctgggga    900
aataacaatg tctcatttgt acc                                           923

<210> SEQ ID NO 71
<211> LENGTH: 923
<212> TYPE: DNA
<213> ORGANISM: Unknown
<220> FEATURE:
<223> OTHER INFORMATION: metagenomes purified from environmentally
      challenged niches

<400> SEQUENCE: 71
ggtacaaatg agacattgtt atttccccag ccaaaccaag atatggccgt ggtcgaataa     60
gttatataca agagtgacgt tgcttttcgg tgagagcgca accccaaaaa gccaccagca    120
aggaagtgcg cgcgaatgat agaaggaaag aagacggata tacttcatga gtatgggtac    180

| | | |
|---|---|---|
| aaatggatcg agaggtacgt tttcttcgta gcccccattc accagctttc tatccatcta | 240 |
| tccgtctcca tcagactact ggtacacgac caacaccggt actaatgctg ctgcagcaac | 300 |
| gcactgtctc cgtccccaat cgccttcgca tccatctcca tctcggtagg taatggaatg | 360 |
| cacatttta caagaacttg gccatcatgg caaccatgag gtcgaagaga ccgatggcct | 420 |
| cgacgaaagc gaaaccaaga atggcgtaag agaaaagctg ccacggagg aggggttgc | 480 |
| gggcgacggc ctggatgagg gcggcgaaga cgagaccgat accgacacca gcaccggcaa | 540 |
| gaccgatggc ggcggaaccc ataccgatgt tctgggagac ctggacgagg gcgttggcca | 600 |
| tctcagagga gtaggcacgc ttggcgatgg ggaggcctg gcgggccatc atctgggtgc | 660 |
| gcttcatggt gttgaagacg gtgttcttgg ggaccgcgga gtaggcgcgg gtgaacttct | 720 |
| ggagctgagc agcctggaag gccgggcggg cgaccttcac ggaggactga gcggccatgg | 780 |
| aggccatctt gggggcggcg acgcggaagg aagacattgt gatgatggtg aggtggtgag | 840 |
| atggagttga gatgggttgt tgatggattt gggatgaaag tgtggtcgga tggaagatgg | 900 |
| tggtgtggag tacgaagagc tct | 923 |

<210> SEQ ID NO 72
<211> LENGTH: 1368
<212> TYPE: DNA
<213> ORGANISM: Unknown
<220> FEATURE:
<223> OTHER INFORMATION: metagenomes purified from environmentally
      challenged niches

<400> SEQUENCE: 72

| | | |
|---|---|---|
| ggaggattct cggtcaagtt caggaccgca gaaggaaatt gggactttgt ggccaacaac | 60 |
| accccgtct tcttcctccg agacccggcc aagttccccc acttcatcca cacccagaag | 120 |
| cgagatcccg ccacccactt gtctggtgac gatgactcga ccatgttctg ggactacctg | 180 |
| tcgcagaacc ccgagtcgat ccaccaagtc atgatcctca tgggtgatcg aggtatcccc | 240 |
| aagggctggc gattcatgca tggctactac ggccacaccc tcaagattgt caatgacaag | 300 |
| ggcgaatggg tctacgccca gttccacctc atctctgatc agggcaccca gaacttcacg | 360 |
| ggtgacgagg ctgctcagca atccaacgat tacggacaga aggatctgta cgaagccatc | 420 |
| gagaagggag acttccccct cgtggacgatg aaggttcaga tcatgaccga gaagcaagcc | 480 |
| gaggaggcat gggagcaaaa gaggatcaac gtctttgatt tgacccacgt ctggcctcat | 540 |
| ggtgattacc cacttcgaac agtcggtaaa ttcacccta acgagaatgc caagaactac | 600 |
| ttcgccgagg tggaacaagt cgcattcaac ccgtctcaca tgattcccgg tgtcgagccg | 660 |
| tccaacgacc cagtgttgca gtcgcgactg ttctcttacc ccgatgctca ccgacaccga | 720 |
| atcggagcca actatcagca actgcccgtt aaccagaatg tgtgcccctt cgccttgggc | 780 |
| aacttccagc gagacggcca gatggcattc tacaatcaag gtagtcgacc caactacctt | 840 |
| tcttcgattg agccaatctc attcaaggag agggcgtatg atctcaacaa ggtccacggc | 900 |
| aaattcgtcg gagaagccgt cgccttcttg tctgaaatca ggccagagga cttcaatgcc | 960 |
| ccaagggcac tgtggcagaa agtctttagc gaggaaagca agcagcgatt cgtcgacacc | 1020 |
| gtctctggtc acatgtcgac agtccgagac aaagccatca ccgctcgaat gatgactatc | 1080 |
| ttccgagaag tttcgcctga tcttggtgat cgacttgaga aggccactgg tgtcaagggc | 1140 |
| gaatccacca ttgccgggat gaagttcaac ggaacgcaca tgggtttgga caaggccaac | 1200 |
| aagatcccgg ctaatgggat gaagaagggt ggagaagtca tctttgacaa tggtgcacct | 1260 |

| | |
|---|---|
| gctactgctg ccaggtaaat gagcggtcag gcgtacttga tatatgttgt tacgatatgt | 1320 |
| cggtctcgta gtcatgtagc caggataaat gaagcggatg tggcagtg | 1368 |

<210> SEQ ID NO 73
<211> LENGTH: 1368
<212> TYPE: DNA
<213> ORGANISM: Unknown
<220> FEATURE:
<223> OTHER INFORMATION: metagenomes purified from environmentally
      challenged niches

<400> SEQUENCE: 73

| | |
|---|---|
| cactgccaca tccgcttcat ttatcctggc tacatgacta cgagaccgac atatcgtaac | 60 |
| aacatatatc aagtacgcct gaccgctcat ttacctggca gcagtagcag gtgcaccatt | 120 |
| gtcaaagatg acttctccac ccttcttcat cccattagcc gggatcttgt tggccttgtc | 180 |
| aaacccattg tgcgttccgt tgaacttcat cccggcaatg gtggattcgc ccttgacacc | 240 |
| agtggccttc tcaagtcgat caccaagatc aggcgaaact tctcggaaga tagtcatcat | 300 |
| tcgagcggtg atggctttgt ctcggactgt cgacatgtga ccagagacgg tgtcgacgaa | 360 |
| tcgctgcttg ctttcctcgc taaagacttt ctgccacagt gcccttgggg cattgaagtc | 420 |
| ctctggcctg atttcagaca agaaggcgac ggcttctccg acgaatttgc cgtggacctt | 480 |
| gttgagatca tacgccctct ccttgaatga gattggctca atcgaagaaa ggtagttggg | 540 |
| tcgactacct tgattgtaga atgccatctg gccgtctcgc tggaagttgc ccaaggcgaa | 600 |
| ggggcacaca ttctggttaa cgggcagttg ctgatagttg gctccgattc ggtgtcggtg | 660 |
| agcatcgggg taagagaaca gtcgcgactg caacactggg tcgttggacg gctcgacacc | 720 |
| gggaatcatg tgagacgggt tgaatgcgac ttgttccacc tcggcgaagt agttcttggc | 780 |
| attctcgtta agggtgaatt taccgactgt tcgaagtggg taatcaccat gaggccagac | 840 |
| gtgggtcaaa tcaaagacgt tgatcctctt ttgctcccat gcctcctcgg cttgcttctc | 900 |
| ggtcatgatc tgaaccttca tcgtccacga ggggaagtct cccttctcga tggcttcgta | 960 |
| cagatccttc tgtccgtaat cgttggattg ctgagcagcc tcgtcacccg tgaagttctg | 1020 |
| ggtgccctga tcagagatga ggtggaactg ggcgtagacc cattcgccct tgtcattgac | 1080 |
| aatcttgagg gtgtggccgt agtagccatg catgaatcgc cagcccttgg ggataccctcg | 1140 |
| atcacccatg aggatcatga cttggtggat cgactcgggg ttctgcgaca ggtagtccca | 1200 |
| gaacatggtc gagtcatcgt caccagacaa gtgggtggcg ggatctcgct tctgggtgtg | 1260 |
| gatgaagtgg gggaacttgg ccgggtctcg gaggaagaag acgggggtgt tgttggccac | 1320 |
| aaagtcccaa tttccttctg cggtcctgaa cttgaccgag aatcctcc | 1368 |

<210> SEQ ID NO 74
<211> LENGTH: 1377
<212> TYPE: DNA
<213> ORGANISM: Unknown
<220> FEATURE:
<223> OTHER INFORMATION: metagenomes purified from environmentally
      challenged niches

<400> SEQUENCE: 74

| | |
|---|---|
| ggacaccatt gacgcagagg tgctcgacag tttgggtgtc acccaagaga acttccagtt | 60 |
| tgcccttggc gtcagcaacc cctctgccct tcgcgaggtc gcagtggtcg aggttcccaa | 120 |
| cgtcagatgg gaggacattg gtggtctcga ggaggtcaag agggagctca tcgagagcgt | 180 |

| | |
|---|---|
| gcaataccccc gtcgaccacc ccgagaagtt cctcaagttt ggcatgtccc catcaaaggg | 240 |
| tgtgcttttc tacggtcccc ctggtactgg taagactctt ctggccaagg ctgtcgccaa | 300 |
| cgagtgcgcg gccaacttta tttccgtcaa gggtcccgag cttctctcca tgtggttcgg | 360 |
| tgagtctgag agcaacattc gtgacatctt cgacaaggct cgtgctgccg cgccttgcgt | 420 |
| tgtcttcctc gacgagctgg actccatcgc caagtctcgt ggcggttctc agggcgatgc | 480 |
| tggcggtgct tccgaccgtg tggtcaacca gcttctcact gagatggacg gtatgaccag | 540 |
| caagaagaac gttttcgtca tcggtgccac caacaggcct gagcagctcg acaacgctct | 600 |
| ctgccgtcct ggtcgtctcg acactctcgt ctacgttccc ctgcctgacc aggagggccg | 660 |
| tgagagcatt ctcaaggccc agctccgcaa gactcctatc gccgacgaca tcgacctttc | 720 |
| ctacatggcc tccaagactc acggtttctc tggtgccgat cttggcttca tcacccagcg | 780 |
| tgccgtcaag ctggccatca agcagtctat tgacctggcc atccagaacc aaaaggctag | 840 |
| agaggccgag ggtgacaccg ccatggacga ggacatcgag gaggacgacc ccgtgcccga | 900 |
| gctgaccaag gctcactttg aggaggctat gagcatggct cgtcgctccg tcaccgacac | 960 |
| cgagatcagg cgctacgagg ctttcgccca gagcatgaag agctccggtg gcggcagcgc | 1020 |
| tttcttccgc ttccctgaga gcggtgccga tggcaacgca gccgagcagc agcaaaatgg | 1080 |
| tgctggcgag gaggacctct acgactaaat tggtttcacg aacctcacga cctaatcctt | 1140 |
| tgctgttatc ggagtaatat tccagatgga gagagcaatc atgcattcag gcgcgtctat | 1200 |
| ggactgaagg ggaagatgga tagagtgttc cagtagccct tttctctttt tttctgggaa | 1260 |
| ctcttgctgt ttggctggtc gcctcttatc gagtgtggtt gtgctagagt aggcagttca | 1320 |
| gagtttccct gttatgttat gcctttccgg gcagtatgag aataatttcc ttgcaaa | 1377 |

<210> SEQ ID NO 75
<211> LENGTH: 1377
<212> TYPE: DNA
<213> ORGANISM: Unknown
<220> FEATURE:
<223> OTHER INFORMATION: metagenomes purified from environmentally challenged niches

<400> SEQUENCE: 75

| | |
|---|---|
| tttgcaagga aattattctc atactgcccg gaaaggcata acataacagg gaaactctga | 60 |
| actgcctact ctagcacaac cacactcgat aagaggcgac cagccaaaca gcaagagttc | 120 |
| ccagaaaaaa agagaaaagg gctactggaa cactctatcc atcttcccct tcagtccata | 180 |
| gacgcgcctg aatgcatgat tgctctctcc atctggaata ttactccgat aacagcaaag | 240 |
| gattaggtcg tgaggttcgt gaaaccaatt tagtcgtaga ggtcctcctc gccagcacca | 300 |
| ttttgctgct gctcggctgc gttgccatcg gcaccgctct cagggaagcg gaagaaagcg | 360 |
| ctgccgccac cggagctctt catgctctgg gcgaaagcct cgtagcgcct gatctcggtg | 420 |
| tcggtgacgg agcgacgagc catgctcata gcctcctcaa agtgagcctt ggtcagctcg | 480 |
| ggcacggggt cgtcctcctc gatgtcctcg tccatggcgg tgtcaccctc ggcctctcta | 540 |
| gccttttggt tctggatggc caggtcaata gactgcttga tggccagctt gacggcacgc | 600 |
| tgggtgatga agccaagatc ggcaccagag aaaccgtgag tcttggaggc catgtaggaa | 660 |
| aggtcgatgt cgtcggcgat aggagtcttg cggagctggg ccttgagaat gctctcacgg | 720 |
| ccctcctggt caggcagggg aacgtagacg agagtgtcga gacgaccagg acggcagaga | 780 |
| gcgttgtcga gctgctcagg cctgttggtg gcaccgatga cgaaaacgtt cttcttgctg | 840 |

| | |
|---|---|
| gtcataccgt ccatctcagt gagaagctgg ttgaccacac ggtcggaagc accgccagca | 900 |
| tcgccctgag aaccgccacg agacttggcg atggagtcca gctcgtcgag gaagacaacg | 960 |
| caaggcgcgg cagcacgagc cttgtcgaag atgtcacgaa tgttgctctc agactcaccg | 1020 |
| aaccacatgg agagaagctc gggacccttg acggaaataa agttggccgc gcactcgttg | 1080 |
| gcgacagcct tggccagaag agtcttacca gtaccagggg gaccgtagaa aagcacaccc | 1140 |
| tttgatgggg acatgccaaa cttgaggaac ttctcggggt ggtcgacggg gtattgcacg | 1200 |
| ctctcgatga gctccctctt gacctcctcg agaccaccaa tgtcctccca tctgacgttg | 1260 |
| ggaacctcga ccactgcgac ctcgcgaagg gcagaggggt tgctgacgcc aagggcaaac | 1320 |
| tggaagttct cttgggtgac acccaaactg tcgagcacct ctgcgtcaat ggtgtcc | 1377 |

<210> SEQ ID NO 76
<211> LENGTH: 699
<212> TYPE: DNA
<213> ORGANISM: Unknown
<220> FEATURE:
<223> OTHER INFORMATION: metagenomes purified from environmentally
      challenged niches

<400> SEQUENCE: 76

| | |
|---|---|
| gaaggtgacg acgagcagac tttgcgcccc acgacgatac taacgtaacg acccagcaca | 60 |
| cattaatcca caatgggtca ctccgccggt ctcaggaagg gcactcgcta tgccttctct | 120 |
| cgcgacttca agaagagggg catgatcccc ctctccacct accttaagca gtacaaggtc | 180 |
| ggcgacatcg tccacgtcgt ctgcaacggt gccgtccaga agggcatgcc ccacaaggac | 240 |
| ttccacggca agactggtgt cgtctacaac gtgaccaagt ccgccgtcgg cgtcatcctg | 300 |
| tacaagcagg ttggcaaccg ttacatcgag aagcgcgtca acctccgcat cgagcacgtc | 360 |
| cgcctctccc gctcgcgtga ggagttcatc gtccgcgtca agaccaacgc tgagaagaag | 420 |
| cgcaaggcca aggaggaggg caccaccgtc ttcctcaagc gccaggccga caagcccgc | 480 |
| gaggcccgca ccatcagcgc caaggacaac aagcccgaga gcatcgctcc tatcgcctac | 540 |
| gacacccaca tttaagcgtg cttgtttcga aagggagggc gtacgggctg gtatgatggc | 600 |
| gaggctagga ggttggtatc ggcggatcgg attccaccgg atgggaaata cctgccggat | 660 |
| gagccagcta gcttcgcaag gtgcatgaat tctagcgcc | 699 |

<210> SEQ ID NO 77
<211> LENGTH: 1664
<212> TYPE: DNA
<213> ORGANISM: Unknown
<220> FEATURE:
<223> OTHER INFORMATION: metagenomes purified from environmentally
      challenged niches

<400> SEQUENCE: 77

| | |
|---|---|
| ggggacatgg gcatcggtgg tcttgatacg gagttctcgg ctatcttccg acgagcattt | 60 |
| gccagtcgta tttccccgcc gggactggtc gagaaattag gtatccagca cgtcaagggt | 120 |
| atcttactgt ttggcccgcc aggaacagga aaaaccttga tggcacggca gatcggaacg | 180 |
| atgctcaacg ccagagagcc taaggtggtc aacggtcccg aaatcctcaa caagttcgtc | 240 |
| ggtcagagtg aggagaatat cagaaagctg tttgccgatg ctgagaaaga gcaaaaggaa | 300 |
| aaggggggatg aaagtggctt gcacatcatc atcttcgatg agctggacgc tatctgtaaa | 360 |
| cagcgaggat ctacaaacag cggtaccggc gttgagact cggttgtcaa tcagctgtta | 420 |
| tcgaagatgg acggtgtaga tcaactgaac aatgtcttga tcatcggtat gactaatcga | 480 |

```
atggacatga tcgacgaagc gctcctccga cctggacgtc tggaagtcca cattgagatc        540
tcgttgcctg acgaagctgg ccgattccag atcctcaaca ttcataccaa caagatgagg        600
acgaatggtg tcatggacag cgatgtggat ctgggcgaac tagcggccct gacgaagaac        660
ttctcgggtg ccgagattgg tggtctggtc aaatcagcga ccagtttcgc tttcaaccgt        720
cacgtcaagg ttggctccgt cgccgcgttt gatgatatcg acaatatgaa gatctcacga        780
gccgacttcc tccacgccct agacgaggtt acacctgcgt ttggtgtctc cgaagaagag        840
ctgcaacagg tcgtgcagaa cggtatcatt cactactcgc aacacgtcaa tgacacacta        900
aacgatggaa gtctgcttgt ggagcaagtg cgaaaatccg accgcacccc gcttgtctcg        960
gccctccttc acgtccatc tggcgcgggc aagacggctt tggcagccac gatcgccatg       1020
gcatccgagt tccctttcat caagctcatc tcgcctgaaa caatggttgg gttttctgag       1080
ccgcagaaga ttgctcaact caacaaggtg ttcacagaca gctacaagag tccgatgagc       1140
atcatcgttg tcgacagtct cgagagattg ctggactgga cccgatcgg acccaggttc       1200 tcgaatggtg tgcttcaggc tttggttgtc ctctttggca acgtccgcc caagggtcgg       1260 cgtcttctca ttctggccac cacgtcaaat cgcaacatcc tcacggatat ggacgtcctt       1320
tcggctttcg acactgatat ccccattaac cccatctcat cgatcgatgc agtggtgcac       1380
gttctagatg aggtcaagtt attcccgaac tcgaaggaaa agcagagagc aacacagatg       1440
cttcgcgagg cgagactggg cgaaggtggt cgaccagact tgttggtcgg agtgaaaaag       1500
ctgttgagta tggcagagat ggcccggcag gatccggatc ccacgatgaa gatcgtgacg       1560
agcattctca gggaggcgag ttaggatgtg tgaagcgtga tcatgataga gtgtagtcca       1620
aacaatgtac tagtgcaaca gaagctatgc agatgaataa cgtt                       1664

<210> SEQ ID NO 78
<211> LENGTH: 1368
<212> TYPE: DNA
<213> ORGANISM: Unknown
<220> FEATURE:
<223> OTHER INFORMATION: metagenomes purified from environmentally
      challenged niches

<400> SEQUENCE: 78
ggaggattct cggtcaagtt caggaccgca gaaggaaatt gggactttgt ggccaacaac         60
acccccgtct tcttcctccg agacccggcc aagttccccc acttcatcca cacccagaag        120
cgagatcccg ccacccactt gtctggtgac gatgactcga ccatgttctg ggactacctg        180
tcgcagaacc ccgagtcgat ccaccaagtc atgatcctca tgggtgatcg aggtatcccc        240
aagggctggc gattcatgca tggctactac ggccacaccc tcaagattgt caatgacaag        300
ggcgaatggg tctacgccca gttccacctc atctctgatc agggcaccca gaacttcacg        360
ggtgacgagg ctgctcagca atccaacgat tacggacaga aggatctgta cgaagccatc        420
gagaagggag acttcccctc gtggacgatg aaggttcaga tcatgaccga agcaagcc         480 gaggaggcat gggagcaaaa gaggatcaac gtctttgatt tgacccacgt ctggcctcat        540
ggtgattacc cacttcgaac agtcggtaaa ttcaccctta acgagaatgc caagaactac        600
ttcgccgagg tggaacaagt cgcattcaac ccgtctcaca tgattcccgg tgtcgagccg        660
tccaacgacc cagtgttgca gtcgcgactg ttctcttacc ccgatgctca ccgacaccga        720
atcggagcca actatcagca actgcccgtt aaccagaatg tgtgccccct tcgccttggc        780
aacttccagc gagacggcca gatggcattc tacaatcaag gtagtcgacc caactacctt        840
```

```
tcttcgattg agccaatctc attcaaggag agggcgtatg atctcaacaa ggtccacggc      900
aaattcgtcg agaagccgt cgccttcttg tctgaaatca ggccagagga cttcaatgcc       960
ccaagggcac tgtggcagaa agtctttagc gaggaaagca agcagcgatt cgtcgacacc      1020
gtctctggtc acatgtcgac agtccgagac aaagccatca ccgctcgaat gatgactatc     1080
ttccgagaag tttcgcctga tcttggtgat cgacttgaga aggccactgg tgtcaagggc     1140
gaatccacca ttgccgggat gaagttcaac ggaacgcaca atgggtttga caaggccaac     1200
aagatcccgg ctaatgggat gaagaagggt ggagaagtca tctttgacaa tggtgcacct    1260
gctactgctg ccaggtaaat gagcggtcag gcgtacttga tatatgttgt tacgatatgt    1320
cggtctcgta gtcatgtagc caggataaat gaagcggatg tggcagtg                 1368
```

<210> SEQ ID NO 79
<211> LENGTH: 1280
<212> TYPE: DNA
<213> ORGANISM: Unknown
<220> FEATURE:
<223> OTHER INFORMATION: metagenomes purified from environmentally
      challenged niches

<400> SEQUENCE: 79

```
gagcacatac acacaccacc gcaatcatgc ctccccgcca accagcaaca cggctctttg       60
ccctaccgcc tcgcttcctc tgcccttcgc tgcccaccac gcaaacgcgc accatccgct      120
ccatcgacaa acccgcccca aaacccagcc gattcaatgc ctcactcaat ctccccgtgc     180
tgggctcctc gtccaccgcc gccttcgcgc gcaaagagca ctcgctcccc ctgcgcaccg    240
gcgcgctcgc catcaaaaag ggcatgacgg cactcttcga cccggtcaca gcgaagcgca    300
cgccctgcac cgtcctgcaa ctcgacagat gccaggtggt cagccacaag cgacgcgaca    360
tccacggcta ctgggcggtg caagtgggcg cgggcgccaa agaagcgagg aacgtcacgc    420
ggccggagag gggccacttc gccgcctaca acgtgcccct tgagcaggcac ctggccgagt   480 tcagagtcaa gaacgccgag ggcctgcccc ccgttggctc ggctattacc gccgacctgt    540
tcatcgaggg ccagttcatc gatgccaaag ccgaccgcag aggcatgggt ttcgagggtg    600
gtatgaagcg ctggaacttc ggcggacagc ccgcgtcgca cggtaactcg ctcgcgcaca    660
gattgatggg ttcgtccggt ggtggacagg gcagcggtag cagagtcttg cccggcaaga    720
agatgccggg tcgcatgggt ggcgagcagg cgaccgttgc gaacctgagg gtcatgcagg    780
tggacaagga gaacggtatc gtggttgtga gtggcgctgt gcctggcccg aagaactgca    840
tggtcaagct gcaggatgcg ctcaagaagc cttggcctga tgcgacttgg ccgccgtcta    900
ttgagggcgc gacggaggtt ctgagggagg ccactgagaa ggcgcctgct gcgtaagggg    960
gtcggtcgag gtcaagaaat atcgttgcaa tttgggagat gatgctgtcc gatgcctgtc   1020
gaaaaggggt tcttgtgggg aggtctggag aatcatcgat gcaagcatta acatgagcgt   1080
gatctcacga gcaatcccag agaagcggtt acagctgctt gctcgaaatg tacactgctc   1140
aaagcttgcc ggagaagttg gccaaagtca tcactctcgg cacaggaata tactttgtaa   1200 ccataggaa aagaggagag ggtctcgagc caggatcaaa aataggaaat gtacattata   1260
attgcatatc gtcatcatcc                                                1280
```

<210> SEQ ID NO 80
<211> LENGTH: 677
<212> TYPE: DNA
<213> ORGANISM: Unknown

<220> FEATURE:
<223> OTHER INFORMATION: metagenomes purified from environmentally
      challenged niches

<400> SEQUENCE: 80

```
ggaatcgacg aacgacacct caatcgaaac caccactcgc cattgtgaat ctttccacct      60
gtcgcaatgg gtatctggga cgctttcacc gatattgtcg aggctgtgac gccatggagc     120
gtcgttgagg ccgaggctcc tgctgaggag ccccaggagg agaacgagtc caagaccgag     180
tccaaggacg agcccgagga ggaggaagag gatgaggaag aagaggagga tgaggatgat     240
gaggaggagc tcgtcgaccc caaggagact ctcgaggaag agtgcaagaa ctctcctcaa     300
tgtgcccccg ccaagcacca cttcgacgag tgtgttgagc gcgttcagca gcaggagagc     360
gagggtggtg ctaaggagga ctgtgtcgag gagttcttcc accttgccca ctgtgcgacc     420
gcttgcgccg ctcccaagct ttggtctcag ctcaagtaaa ctcacaacat tgggttatcg     480
gttactacga cgacgcaatg gctacataca cgtcgaaaag atgcctggag ccggaacgag     540
gcaatgctgc ccactacgga aggctgttcc cttgtacgaa tgctcatctg ccgggtatca     600
agtcggccag agattactct gatgtcgact ctctctgtac catacgctct tacgcctgaa     660
tagatttctt gcacttt                                                    677
```

<210> SEQ ID NO 81
<211> LENGTH: 1019
<212> TYPE: DNA
<213> ORGANISM: Unknown
<220> FEATURE:
<223> OTHER INFORMATION: metagenomes purified from environmentally
      challenged niches

<400> SEQUENCE: 81

```
gggagatact accgtgcgcc cgagatcatg ttgacatggc aaaaatacga tgtcgccgtc      60
gacatttgga gcacaggatg tatcttcgcc gagatgctcg agggaaagcc cctgttcccg     120
ggcaaggacc acgttaatca gttctcgatc atcacagaat tgctcggcac acctcctgac     180
gatgtcatcc agaccatcgc atctgagaac accctccgat tcgtccagtc gctgcccaag     240
cgtgagaagg tcccattcac tacgaaattc gccaatgccg acccgctttc gcttgacttg     300
ttggagaaga tgcttgtctt cgatccacgt acccgtatct cggcatcaga agggctgtcg     360
cacgagtacc ttgcgccata ccatgacccg acggatgagc ccgtcgctgc cgaggtgttt     420
gactggagtt tcaacgatgc ggatctacca gtagacacct ggaaggtcat gatgtactcc     480
gagatcctgg acttccacaa cttgggtgat atccagcaag accaggccgc cgaaggaccc     540
gtcactggcg acctagcccc accttccgct acgacttcgg catagacagc ttgcctttag     600
gggtttttt ctcgtttttc tcttctcgtc tcattacgtt cctagtcaac atgtgtccat     660
tagcatccca aattattggt ggtagaaagg agggaaggaa ttggtgcaac atgatctctc     720
ctagaaaatc gtttctcttc atctctcgtc catgatccac gctttcccaa gctttatctc     780
ccccttcccc ttcctcacgc ctcaacttct cctgtaccaa caaatcttcg ctaccgcttt     840
ctcgaccgtc gaacgaacat cacaaagaat caagaaaggt agaagaggtg tgaatagacc     900
aggaaaggca ttcttggagc gagggggag gaggaagtaa tctggaacga aagcccatca     960
cactgttttc tttgaaccta catacacgga cagaggggaa tgcatgtgca tggtaatgt    1019
```

<210> SEQ ID NO 82
<211> LENGTH: 391
<212> TYPE: DNA

<213> ORGANISM: Unknown
<220> FEATURE:
<223> OTHER INFORMATION: metagenomes purified from environmentally
      challenged niches

<400> SEQUENCE: 82

| cgctaccggt cgccggcgcg ccggggttga cctcggatca ggtagggata cccgctgaac | 60 |
| ttaagcatat caataagcgg aggaaaagaa accaaccggg attgccctag taacggcgag | 120 |
| tgaagcggca agagctcaaa tttgaaagct ggccccctcg ggtccgcat tgtaatttgc | 180 |
| agaggatgct tcgggaacgg ccccatcta agtgccctgg aacgggccgt catagagggt | 240 |
| gagaatcccg tctgggatgg ggtggccgcg cccgtgtgaa gctccttcga cgagtcgagt | 300 |
| tgtttgggaa tgcagctcta attgggtggt aaatttcatc taaagctaaa tattggccgg | 360 |
| agaccgatag cgcacaagta gagtgatcga a | 391 |

<210> SEQ ID NO 83
<211> LENGTH: 391
<212> TYPE: DNA
<213> ORGANISM: Unknown
<220> FEATURE:
<223> OTHER INFORMATION: metagenomes purified from environmentally
      challenged niches

<400> SEQUENCE: 83

| cgctaccggt cgccggcgcg ccggggttga cctcggatca ggtagggata cccgctgaac | 60 |
| ttaagcatat caataagcgg aggaaaagaa accaaccggg attgccctag taacggcgag | 120 |
| cgaagcggca agagctcaaa tttgaaagct ggccccctcg ggtccgcat tgtaatttgc | 180 |
| agaggatgct tcgggaacgg ccccatcta agtgccctgg aacgggccgt catagagggt | 240 |
| gagaatcccg tctgggatgg ggtggccgcg cccgtgtcaa gctccttcga cgagtcgagt | 300 |
| tgtttgggaa tgcagctcaa attgggtggt aaatttcatc taaagctaaa tattggccgg | 360 |
| agaccgatag cgcacaagta gagtgatcga a | 391 |

<210> SEQ ID NO 84
<211> LENGTH: 124
<212> TYPE: DNA
<213> ORGANISM: Unknown
<220> FEATURE:
<223> OTHER INFORMATION: metagenomes purified from environmentally
      challenged niches

<400> SEQUENCE: 84

| gggtctggtg gcgatagcga gacggccaca cccgttccca tgccaaacac ggaagttaag | 60 |
| cgtctcagcg ccgaaagtag ttgggggatc tccccctgtg aggataggac gttgccaggc | 120 |
| aaaa | 124 |

<210> SEQ ID NO 85
<211> LENGTH: 717
<212> TYPE: DNA
<213> ORGANISM: Unknown
<220> FEATURE:
<223> OTHER INFORMATION: metagenomes purified from environmentally
      challenged niches

<400> SEQUENCE: 85

| agatggagcc tgaccaagaa gagtctgaag aggaagaaga ggaagaggat gacgagatgg | 60 |
| atgaagatga ggatgagggc cagcagcagg acgccagtgg catgcagaca ccctctgggc | 120 |
| tcgccacgcc ctcaggctat gcctctacta catctacaat gcctggtggc atggagacgc | 180 |

| | |
|---|---|
| ctgactttat ggacttgcgc aagcagcgac agacgcgcga cgagaccgct gatcaagagg | 240 |
| accagggtgc accgcgagac ctctatacgg tcgtgcccga gcgcagagcc accgcttctg | 300 |
| gcttcctcgg ttctgaccgc gcctatgact tgtccaatgc ccacagtct tccaacatgc | 360 |
| ctgtgttggg tcaagaagac tcgcgcaaga agaaaggcgg cagatctggt gcagacgacg | 420 |
| tcgacctggc cttggatcca gctgagctcg agggcatgtc tgagcaagag cttaggcaga | 480 |
| agtacgactc gcacaggcgc tcctcgtcca gtcaaggcgc cggcggacag caggacaaag | 540 |
| aagatttctc agatttcgtc gcgcaagagg tcgcaaagaa gaggcagagg gctcagcagc | 600 |
| gcggcggcag tggacgcgac cgcgaaagct ctcggagcaa ggaaaagttc aagtttaga | 660 |
| gtgtatgttt gtattgtatg aagatcagac aaaaatgcta tgggtggcgt tgctgct | 717 |

<210> SEQ ID NO 86
<211> LENGTH: 872
<212> TYPE: DNA
<213> ORGANISM: Unknown
<220> FEATURE:
<223> OTHER INFORMATION: metagenomes purified from environmentally
      challenged niches

<400> SEQUENCE: 86

| | |
|---|---|
| cgtgtagcat aaagctagaa gtaatattca cagctaactc tacagtagaa caaagttctt | 60 |
| gtttcgttct ccagatccaa gtgatagcaa ctgcttcaca aggatggaag aaccaaattg | 120 |
| ttgaaagatt cggcacctaa taggcggcac ccatgttgaa atcgtcagtc atgttgaaac | 180 |
| tccgtaaacc cgcttttggt gccctctaat ccgcaaaacc ttgaaaccct atgttgaact | 240 |
| tttggtatca tcttcgtaat cgtcataaaa cagaactccc cgtgccagag gcggcaggtt | 300 |
| gagaataccg ccccttgaat taacacatta taggaagtgg aacaaaggaa aaatgagaaa | 360 |
| tgttaatgcg cacagaatta ctgagtgtac ttctggcggt agaacttagc agcctcgacc | 420 |
| agagaggtca gctggccgat agtctgctca gtggtacggg tcttcagacc gcagtcaggg | 480 |
| ttgatccaga gctgctcagg cttgaggtac tggagcatct gctcgatacg ctccttgatc | 540 |
| tcatccacgg agggaacacg aggagagtgg atatcgtaga caccaggtcc aatgtgggcg | 600 |
| gggaaactct gatcaacgaa gacctggagg agcttggcat cggacttgct gttctcgatg | 660 |
| gacaaaacat cggtatcaag ggcagcaata gcgtggaaga agtcctggaa ttcactgtag | 720 |
| cagaagtggg agtggacctg ggtgctgtcg gtgacaccag cagtagacag cttgaaagca | 780 |
| ttgacagccc acttaacata agcatcacgg gcagcgccag tacgcagagg aagaccctca | 840 |
| cgcagggcag gctcgtcgac ttggatgacc cc | 872 |

<210> SEQ ID NO 87
<211> LENGTH: 872
<212> TYPE: DNA
<213> ORGANISM: Unknown
<220> FEATURE:
<223> OTHER INFORMATION: metagenomes purified from environmentally
      challenged niches

<400> SEQUENCE: 87

| | |
|---|---|
| ggggtcatcc aagtcgacga gcctgccctg cgtgagggtc ttcctctgcg tactggcgct | 60 |
| gcccgtgatg cttatgttaa gtgggctgtc aatgctttca agctgtctac tgctggtgtc | 120 |
| accgacagca cccaggtcca ctcccacttc tgctacagtg aattccagga cttcttccac | 180 |
| gctattgctg cccttgatac cgatgttttg tccatcgaga acagcaagtc cgatgccaag | 240 |

| | |
|---|---|
| ctcctccagg tcttcgttga tcagagtttc cccgcccaca ttggacctgg tgtctacgat | 300 |
| atccactctc ctcgtgttcc ctccgtggat gagatcaagg agcgtatcga gcagatgctc | 360 |
| cagtacctca agcctgagca gctctggatc aaccctgact gcggtctgaa gacccgtacc | 420 |
| actgagcaga ctatcggcca gctgacctct ctggtcgagg ctgctaagtt ctaccgccag | 480 |
| aagtacactc agtaattctg tgcgcattaa catttctcat ttttcctttg ttccacttcc | 540 |
| tataatgtgt taattcaagg ggcggtattc tcaacctgcc gcctctggca cggggagttc | 600 |
| tgttttatga cgattacgaa gatgatacca aaagttcaac atagggtttc aaggttttgc | 660 |
| ggattagagg gcaccaaaag cgggtttacg gagtttcaac atgactgacg atttcaacat | 720 |
| gggtgccgcc tattaggtgc cgaatctttc aacaatttgg ttcttccatc cttgtgaagc | 780 |
| agttgctatc acttggatct ggagaacgaa acaagaactt gttctactg tagagttagc | 840 |
| tgtgaatatt acttctagct ttatgctaca cg | 872 |

<210> SEQ ID NO 88
<211> LENGTH: 362
<212> TYPE: DNA
<213> ORGANISM: Unknown
<220> FEATURE:
<223> OTHER INFORMATION: metagenomes purified from environmentally
challenged niches

<400> SEQUENCE: 88

| | |
|---|---|
| gttgacctcg gatcaggtag ggatacccgc tgaacttaag catatcaata agcggaggaa | 60 |
| aagaaaccaa cagggattgc tctagtaacg gcgagtgaag cagcaatagc tcaaatttga | 120 |
| aatctggcgt cttcggcgtc cgagttgtaa tttgtagagg atgcttctgg gcagccaccg | 180 |
| acctaagttc cttggaacag gacgtcatag agggtgagaa tcccgtatgc ggtcggaaag | 240 |
| gcaccctaca cgtagctcct tcgacgagtc gagttgtttg ggaatgcagc tctaaatggg | 300 |
| aggtaaattt cttctaaagc taaatattgg ccagagaccg atagcgcaca agtagagtaa | 360 |
| cc | 362 |

<210> SEQ ID NO 89
<211> LENGTH: 663
<212> TYPE: DNA
<213> ORGANISM: Unknown
<220> FEATURE:
<223> OTHER INFORMATION: metagenomes purified from environmentally
challenged niches

<400> SEQUENCE: 89

| | |
|---|---|
| gaccctcact ctctttctcc ctctcttaca tagcgagctg gtctccatcc ttgttgtttg | 60 |
| atttgatctt ctttgcattt ccctatccca gtgatgaagt tatccaattc cgctcattac | 120 |
| tcgcttttcc tcctatcctc catcctcggc ttctccagcg cgtcggccaa ctctcacctc | 180 |
| agtgatgatt ctccttgtgt ggcccgctcg ccaacaagtg ggctctatta tgatctgaat | 240 |
| gctatctcat tagcaccgcc ggaatggaag aacgggaaga aagttgatca ggaagcgcga | 300 |
| gatgaaagct ggcatgccaa ggggcatgac taccccgcga acttcacaat caatgtctgc | 360 |
| gcgccggttc ttgagaatgt aaccaatgtt gtcggggtag atgcctctcg atgggcgaat | 420 |
| gtcagtgctt tctatgagca agctgggaag atatactcaa tgggagagca agcctccgag | 480 |
| cctttcttcc gcggccgcaa gctagtactc aactacacgg acggttcgcc atgtcccggt | 540 |
| gattcgaata ctgctagcgg caatagctct attcgaacca agtccactct gatgtccttc | 600 |
| ctctgcgatc gcgcggccga attccccggg ctcgagaagc ttggatccac cggatctaga | 660 | taa                                                              663

<210> SEQ ID NO 90
<211> LENGTH: 1243
<212> TYPE: DNA
<213> ORGANISM: Unknown
<220> FEATURE:
<223> OTHER INFORMATION: metagenomes purified from environmentally
      challenged niches

<400> SEQUENCE: 90
atgtccatcc gcaatgaatg gcttcaatga gaaaggcctc gacggggatg cctttggaga      60
gaagtccaat ctctccgggc taaagacatt tgacgctttc cccaaaacaa aaacatccta     120
cacaacccca acccgacgag gcggccaatg gaccgttctc atcctagcag tatgcacact     180
attcagcctc cacgaactcc gcacctggtg gcgcggcaca gaagcccacc acttcagcgt     240
ggaaaaaggc gtatcccacg atctccaatt aaacctcgat atggtcgttc acatgccctg     300
tgacactctc cgcataaaca ttcaagacgc ctccggagac cgcgttttag ctggcgaact     360
cctaacccgc gaagacacaa actgggacct ttggatgaag aagcgcaatt tcgaatccca     420
cggcgaacac gaataccaaa cgctcaatca tgaagcggct gatcgattaa gtgcgcagga     480
tgaagacgcg cacgtacacc atgtcctggg tgaagtgcgc cgtaacccgc gccgcaagtt     540
ttctaagggt ccacgtctac gctggggcga taacaaggat tcttgtcgaa tttatggaag     600
tcttgaaggg aataaagtgc aaggggattt ccatattacg gcacggggac atggatatat     660
ggaattggcg ccgcatttgg atcacgaagt cttcaatttc tcccacatga ttacagaact     720
gtccttcgga ccacactatc catcccttct aaaccctctt gacaagacca tcgccgaaag     780
cgaaacccac taccagaaat tccaatactt cctttccgtc gtcccgaccc tctactcaaa     840
gggccacaat gcacttgacc tcgtgacaac aaataaagat aactccgtcc gctacggccg     900
taacacaatc ttcacaaacc aatacgcagc cacaagccag agtaccgccc tccctgaaat     960
ccccacccta atcccgggaa tcttttttcaa gtataatatc gagccgatct tgctacttgt    1020
cagcgaagag cggacgggat tcttggctct tgtcattcga gtcattaata ccgtttctgg    1080
ggtcttggtt acgggtggtt ggatctacca gatttctggg tggattgttg agatccttgg    1140
gaaaaggaaa cggcagtctg agggtgtttt gactgggaag cattattcgg attgatttgt    1200
ttctagtagt ttcgtctcaa tataagtttg attttccttt tcc                       1243

<210> SEQ ID NO 91
<211> LENGTH: 1007
<212> TYPE: DNA
<213> ORGANISM: Unknown
<220> FEATURE:
<223> OTHER INFORMATION: metagenomes purified from environmentally
      challenged niches

<400> SEQUENCE: 91
gaacggtgat agtagtagta ggctcgtcat ctatctacaa cccctctctc ctcactcccc      60
tctctcgacg ccatgttcac gcgtactctc cgaccggccg tggcggtcgc caggactcag     120
gctgtccagc agcaacaggc cggtatggcc acattgaagg aaatcgacca gcgtttgaaa     180
tccgtcaaga acattgggaa gatcaccaag tcgatgaagg tcgttgcctc gaccaagttg     240
acgcgagctg agaaggccat gcgtgaagcc aagaagtacg gtgccgccaa caacgttctg     300
ttcgagcaga ccaaggctgg tgaggaggag cccaaggagc gcaagatcct ctacctcgcc     360

| | |
|---|---|
| atgacatccg acggtggtct gtgcggtggt atccactcca acattacgcg atacatgaag | 420 |
| aaggctgtgg ccaaggaacc cggaatgctg gctgttgtcg gtgacaagcc caaggctcag | 480 |
| ctctctcgag cgatgcccaa ggctttgacc atgtctttca acggcgtcgg caaggatgtc | 540 |
| cccactttcg tcgaggccag cgctatcgcc gatgagatta tgaaatctgc cggtgacttt | 600 |
| gacgagatcc gaatcgtctc taacaagtac ctttccgcta tcgcctacga acctcacacc | 660 |
| aacgccgtca tctccgctga ggcactccga caagccgccg gtttccagca atacgagatg | 720 |
| gaggaggatg tctccaagga cttggccgag ttcgctcttg ccaacgccat ctacactgcc | 780 |
| ctggtcgagg acacgccgc cgagatctct gcaaggaggc aagctatgga gaacgcttcc | 840 |
| aacaacgcca acgacatgat caactctctc cagctgcagt acaaccgtgg tcgacaggct | 900 |
| gtcattacca ccgagctgat cgatatcatt accggtgcct cggctctgta agcgggtgta | 960 |
| gactagatgg acaaaacaac aaaaatggca tgcagcgaat gacattg | 1007 |

<210> SEQ ID NO 92
<211> LENGTH: 1007
<212> TYPE: DNA
<213> ORGANISM: Unknown
<220> FEATURE:
<223> OTHER INFORMATION: metagenomes purified from environmentally challenged niches

<400> SEQUENCE: 92

| | |
|---|---|
| caatgtcatt cgctgcatgc cattttttgtt gttttgtcca tctagtctac accgcttac | 60 |
| agagccgagg caccggtaat gatatcgatc agctcggtgg taatgacagc ctgtcgacca | 120 |
| cggttgtact gcagctggag agagttgatc atgtcgttgg cgttgttgga agcgttctcc | 180 |
| atagcttgcc tccttgcaga gatctcggcg gcgtgtccct cgaccagggc agtgtagatg | 240 |
| gcgttggcaa gagcgaactc ggccaagtcc ttggagacat cctcctccat ctcgtattgc | 300 |
| tggaaaccgg cggcttgtcg gagtgcctca gcggagatga cggcgttggt gtgaggttcg | 360 |
| taggcgatag cggaaaggta cttgttagag acgattcgga tctcgtcaaa gtcaccggca | 420 |
| gatttcataa tctcatcggc gatagcgctg gcctcgacga aagtggggac atccttgccg | 480 |
| acgccgttga aagacatggt caaagccttg ggcatcgctc gagagagctg agccttgggc | 540 |
| ttgtcaccga caacagccag cattccgggt tccttggcca cagccttctt catgtatcgc | 600 |
| gtaatgttgg agtggatacc accgcacaga ccaccgtcgg atgtcatggc gaggtagagg | 660 |
| atcttgcgct ccttgggctc ctcctcacca gccttggtct gctcgaacag aacgttgttg | 720 |
| gcggcaccgt acttcttggc ttcacgcatg gccttctcag ctcgcgtcaa cttggtcgag | 780 |
| gcaacgacct tcatcgactt ggtgatcttc ccaatgttct tgacggattt caaacgctgg | 840 |
| tcgatttcct tcaatgtggc cataccggcc tgttgctgct ggacagcctg agtcctggcg | 900 |
| accgccacgg ccggtcggag agtacgcgtg aacatggcgt cgagagaggg gagtgaggag | 960 |
| agaggggttg tagatagatg acgagcctac tactactatc accgttc | 1007 |

<210> SEQ ID NO 93
<211> LENGTH: 1139
<212> TYPE: DNA
<213> ORGANISM: Unknown
<220> FEATURE:
<223> OTHER INFORMATION: metagenomes purified from environmentally challenged niches

<400> SEQUENCE: 93

| | |
|---|---|
| acctcacttt gtgcgaatta tcctcctaca gcatcagctc tcttcagaaa gaggctaaat | 60 |

-continued

```
ctatagaccg tccggaacag gttgtcaaca cgcgcgataa gagaagaagg gaatctactg      120
gtagacaaca gatcgatcgc tcttcagcaa acgcaagatg gagaaccttc ttcgtcagat      180
gcaaggggga ggtggtagga tgggtgcacg gccaggccct ggaggcgaaa ctatcctcgc      240
cgacaacggt gaaacagtcc atatttcatc tcttgctcta ttgaagatgc tcaagcatgg      300
acgagcgggt gtgcctatgg aagtcatggg tctcatgctt ggcgaatttg ttgatgacta      360
cactatctcc tgtgtcgacg tttttgcaat gcctcaatcc ggtacgacag tgacggtcga      420
atcagtggat cacgtctttc aaaccaagat gttggatatg ttaaaacaga cgggccgacc      480
cgagatggtc gtcggttggt accactcgca ccccggtttt ggttgttggc tgtccagtgt      540
cgatgtcaac actcagcagt ctttcgaaca gctacatccg cgagcagtag ccgttgtcat      600
cgaccctatc cagtctgttc gtggtaaagt cgtcatcgac gctttccgat ccatcaaccc      660
tcaatcactt gtcgctggac aagagtcgag gcaaacaacg agtaacattg gtcatctgaa      720
caaaccgtcc attcaggctc tcatacacgg tctgaatagg cattactaca gtctggccat      780
cgattacagg aaaacagaag gggagcaggg tatgttgttg aacctgcaca agcggggatg      840
gacagagggt ttgaagatgc gtgatcactc agagatgaag gagggtaatg agaaggcaat      900
caaggaaatg ctctctcttg cctcggccta cacgaaatct gttcaggaag agacgacaat      960
gacggccgaa cagcttaaaa cccgtcacgt aggaaagctt gatccaaaac gtcatttggg     1020
cgaggcggct gagaaagcga tgggtgatca agtgacgcag agtctggcca tgggtgtcct     1080
ggctgagctg tagacgtaga agagggaaga aaggaaacga catgcattgt acatatcgc     1139
```

<210> SEQ ID NO 94
<211> LENGTH: 526
<212> TYPE: DNA
<213> ORGANISM: Unknown
<220> FEATURE:
<223> OTHER INFORMATION: metagenomes purified from environmentally
      challenged niches

<400> SEQUENCE: 94

```
aacccacccc gccattctca attcttcgtc cgtgttcttc tcgagaagct acacttcgca       60
aaaatgggtg ccattccgga atatgatccc gaggagcccc tcgagaccaa gcccttcaag      120
ttcgtgactg ctggttacga cgctcgtttc ccccagcaga accagaccaa gcactgctgg      180
caaaactacg tcgactacta caagtgtgtc gaggccaagg gtgaagactt ccgcccctgc      240
aagcagttct accacgcttt ccgctcgctc tgccccaagg cctggactga ccgctgggac      300
acccagcgcg agggtggtaa cttccctgct atccttaaca aatagataac caatggctgc      360
tttgtgttgg tgaattgggt tatagcagat tctgtattga caaactttcc aatgtactct      420
acctggtcat gcggggatac atttcttttc tgtttggatg taattttccc actctgatga      480
agaaagtgtg tctataaact cgctgttttg aaactaaacg tcttcc                    526
```

<210> SEQ ID NO 95
<211> LENGTH: 839
<212> TYPE: DNA
<213> ORGANISM: Unknown
<220> FEATURE:
<223> OTHER INFORMATION: metagenomes purified from environmentally
      challenged niches

<400> SEQUENCE: 95

```
gggccattgc tcgaggagct cgatgtcgag gcgtacgcca agaagtaccg ttacctgaga       60
```

| | |
|---|---|
| ttcatgtgcc aggagacgct ggaccatctc gcctttctca aggacaaagt gaaggatgtc | 120 |
| gaagggttct gggcatccac cttgttgaag caccgcgatc tcaggggcta catcacttca | 180 |
| cgatccgaca aggacgcatt gaagtacttg actcacattg agctcgttca ggatcccaag | 240 |
| gatccccgtc cgttcgctct caaattctac ttcaaggaga acccatactt ctccgacttg | 300 |
| gtcttggaga agaagtacga tatgtccgag ggttccgaac ccgcacctgc cgatggtagc | 360 |
| attacggagg gaatgcgcaa tttcaaagaa gacgagctgg tcaccaaggc taccacgatc | 420 |
| aactggaagt cggacgacaa gaatctagtc gccaagcagc ccagatccaa aattcccgac | 480 |
| aatgacgacg atgaagattt cgacggggac gtcggatcgt tcttcaacta ctttacagat | 540 |
| gacacagata ttttccagat tggggccctc ctgcagtcgg agctactgcc tgatgccatc | 600 |
| gactactttg ttggccgagg cgagcaggtg gactctgaag gagaggagct agacgagctg | 660 |
| gaagaggatg atgaagacga cgatgaggat gatgagggca gtatcgacct cgaagacgag | 720 |
| gaggagcagc cgagtaaaaa gaagcccaag agggcctaag aaacatttga tccgtcaaca | 780 |
| tgtacgacg aggtaatcgt gttcgaatgt taatgatcat gcatatgcta gtaaattcg | 839 |

<210> SEQ ID NO 96
<211> LENGTH: 804
<212> TYPE: DNA
<213> ORGANISM: Unknown
<220> FEATURE:
<223> OTHER INFORMATION: metagenomes purified from environmentally
      challenged niches

<400> SEQUENCE: 96

| | |
|---|---|
| ggatctttcc tcacccctca acacactcac acaccattcg gacgcgctat gcacaatgcc | 60 |
| ttgacggttt cgaggctcaa cgacaagttc aagagccgc tcgttgttct tgtggagctt | 120 |
| ttgcgtgctc gtgttctgca cgaccgcaac ttctcgaaca gacaattctc aggtggtcct | 180 |
| tcattcggga cagacaatca gaagagaagc atgcttttga tcttccgtac tctgtccatt | 240 |
| attccgctcc aattcaaggc cgagcactgg tcaggaccat tgtcaagaga gctgcttgtc | 300 |
| ttcaactcat tccacaagac actgtcaaga tccctgagaa cgctggtcga atcaatcact | 360 |
| atgaacgcct tcctcaagaa caatgcgaga agagcacgtg acgactatct tgacattgca | 420 |
| ctttcactac cattccaaaa cgataccaac actggattcg gtatcttctt taagatttac | 480 |
| ttggatgcat tgactacatt tgcagaaggc aacatcactg aagagaacaa agacagcgag | 540 |
| tctgtgaaag aggccaagca gtcagcaatg gagatcctag gtgacgccat accgaacgtg | 600 |
| aaggacccag aggccgagct tttgcggggt ttcagattct gggatgctgt gctcgtgtgc | 660 |
| gtccgtacac tcaaagcaga cagggcaatc gatctcaagc tagctgagtc tttcgaggcg | 720 |
| gcaaacagct accttaatat gatgagacca aattgatacg gcgttttgta gcaatcttga | 780 |
| gctttatgca atctacttct gtcg | 804 |

<210> SEQ ID NO 97
<211> LENGTH: 848
<212> TYPE: DNA
<213> ORGANISM: Unknown
<220> FEATURE:
<223> OTHER INFORMATION: metagenomes purified from environmentally
      challenged niches

<400> SEQUENCE: 97

| | |
|---|---|
| ggatctttcc tcacccctca acacactcac acaccattcg gacgcgctat gcacaatgcc | 60 |
| ttgacggttt cgaggctcaa cgacaagttc aagagccgc tcgttgttct tgtggagctt | 120 |

```
ttgcgtgctc gtgttctgca cgaccgcaac ttctcgaaca gacaattctc aggtggtcct    180
tcattcggga cagacaatca gaagagaagc atgcttttga tcttccgtac tctgtccatt    240
attccgctcc aattcaaggc cgagcactgg tcaggaccat tgtcaagaga gctgcttgtc    300
ttcaactcat tccacaagac actgtcaaga tccctgagaa cgctggtcga atcaatcact    360
atgaacgcct tcctcaagaa caatgcgaga agagcacgtg acgactatct tgacattgca    420 cttttcactac cattccaaaa cgataccaac actggattcg gtatcttctt taaggttggt    480
ggccttgcag gagtctgaca tagcgctgac gcagacagat ttacttggat gcattgacta    540
catttgcaga aggcaacatc actgaagaga acaaagacag cgagtctgtg aaagaggcca    600
agcagtcagc aatggagatc ctaggtgacg ccataccgaa cgtgaaggac ccagaggccg    660
agcttttgcg gggtttcaga ttctgggatg ctgtgctcgt gtgcgtccgt acactcaaag    720
cagacagggc aatcgatctc aagctagctg agtctttcga ggcggcaaac agctacctta    780
atatgatgag accaaattga tacggcgttt tgtagcaatc ttgagcttta tgcaatctac    840
ttctgtcg                                                              848
```

<210> SEQ ID NO 98
<211> LENGTH: 628
<212> TYPE: DNA
<213> ORGANISM: Unknown
<220> FEATURE:
<223> OTHER INFORMATION: metagenomes purified from environmentally challenged niches

<400> SEQUENCE: 98

```
ggggcatcta cctcgacggc aacaacgacc tggtcactat gaagggtaac tacatctacc    60
acaccagcgg ccgctctcct aaggttcagg gtaacacctt gctgcacgct gtcaacaact   120
actggcacga caactccggc cacgccttcg agatcggtga gggtggttac gttctggccg   180
agggtaacgt cttccaggat gttactaccc ccgttgagga ccccgttgac ggccagctcc   240
tcacttcccc tgaccccagc accaacgctc agtgctcgtc ataccttggc cgggcctgcg   300
aaatcaacgg cttcggtaac tctggtacct tcaaccaggc tgacactagc ctgctgtcta   360
aatttaaggg tcagaacatt gcttctgctg atgcttactc taaggttgcc tcgagcgttg   420
ccagcaacgc cggtcaggga cacctgtaaa atggaaagag gaggttcaga gcttaatttg   480
ctcatgtcgg acgacatagc cctagcggct tgctggtgaa tttggcataa tagcgtttct   540
cttctcatac ctactttatt actccgtttg gatccttatt aggtaaatat tagcccattg   600
tatggttcaa ttcgattgac tttgaggc                                      628
```

<210> SEQ ID NO 99
<211> LENGTH: 804
<212> TYPE: DNA
<213> ORGANISM: Unknown
<220> FEATURE:
<223> OTHER INFORMATION: metagenomes purified from environmentally challenged niches

<400> SEQUENCE: 99

```
agttggaaat ctgatcaatt actctccatc ttctcgttct actatctaat cctctcttcc    60
ttccaaaaca tatcatcatg tctgctcaac ctctccgcat tgtcatggcc tgtgacgagg   120
ctggtgttcc ttacaaggat gccatcaagg ccgttctcga gaagagcccc ctcgtcgcct   180
ccgtctctga cgtcggtgtc aacgatgcct ccgataagac cgcctacccc cacccgccg   240
```

```
tcgagggtgc tcaacagatc aaggccggta aggctgaccg tggcctcttc atctgcggta    300
ctggtctagg tgtcgctatc gccgccaaca aggttcccgg tattcgtgcc gttactgccc    360
acgacccttt ctccgtcgag cgttccattc tgagcaacga tgctcaggtc ctctgcatgg    420
gtcaacgtgt cattggcgtc gaacttgcga agaagcttgc cctcgattgg ctcaactacc    480
gtttcgatcc taagagtgcc tctgccgcga aggtccaggc tatctccgac tacgagacca    540
agttcgctgg ctcttcttaa atgcattatc ttgcatgaat gacggtcttc gtacatactt    600
tgccacatat gggttctaat tgcactgcgt ctgcagtctc gatatgaaac cattggattg    660
cgatggatgt ccctttttcca tttgcaactt tttatatact ttcttttcta ccaagcgctt    720
catgatacca cgattcgatt accgagttct gctgtttgct ttggtcggta gatctagata    780
cacaatgcag tatattcgag tttc                                           804

<210> SEQ ID NO 100
<211> LENGTH: 782
<212> TYPE: DNA
<213> ORGANISM: Unknown
<220> FEATURE:
<223> OTHER INFORMATION: metagenomes purified from environmentally
      challenged niches

<400> SEQUENCE: 100
acttctcctt ttctgttagc tttgactcta ctatcctgct cctcctctaa atccgtggaa     60
tccaattttt tcacaataac ttcgctacca taatgtccgt cactaccact tcctccgccg    120
ccgcagcctc ctgcactccc tcttggcaga ttcctgtcga cgatgttgcc tgtgccggtc    180
agatcagcgg taatatcacc aaggttttcg atacctgctg taagggaaac agccctgtca    240
agtacaacga cgactgcaac atctactgtc ttgcccaagg acaaaccaag caagagttga    300
ccgactgttt gaccgagaag agcggaaaca accagatctt ctgtggtcat ggcaagcaga    360
atgccactgc tacagctgaa gccaccacca ccaaggagac tggcacatcg accggcactt    420
caacctcttc cactggcact tctaccgaga ccaacgctgc cgtgctcaac caacccatct    480
ccaagaccgg tcttggactc gtcgccatgc tcttctgctc tgccctcgtt ggtgttgtcg    540
cctaagttat gactccaaaa cgaacacatt actgcggtat ggatacggca attatgacaa    600
ccagaggacc gcagggacgg agaatggtaa ttgatgaacc cggaaaagat acgtggtgca    660
tggacataaa tgtttgattt actcttactg tctgcttcaa cttccgaga ggaatattgt    720 ttcttctgta ccaatagcga tagcattaac agcatcttaa ttctaatttt gcatatcact    780
tc                                                                   782

<210> SEQ ID NO 101
<211> LENGTH: 693
<212> TYPE: DNA
<213> ORGANISM: Unknown
<220> FEATURE:
<223> OTHER INFORMATION: metagenomes purified from environmentally
      challenged niches

<400> SEQUENCE: 101
gccggggtcg atcgaggtgt catcaccaag gacgagaagg acagcagtat caatagacta     60
ctcgtcactg gttacggtct ggccgaggtc atgggtacag atggtgtgaa cggcatcaag    120
acgcgaacca atcacgtcat ggagacgtgc gaggttctgg gcatcgaagc cgctcgacag    180
accatctaca acgagattca gcataccatg acatcgcacg gaatgtcaat cgatcctcga    240
cacgttatgc tgctcggaga cgtcatgact tacaagggcg aggtgctcgg tatcactcga    300
```

```
ttcggtgtgc aaaagatgaa ggactcggtt ctcatgttgg ccagtttcga gaagaccact    360
gatcatctgt tcgatgcctc gctgttttcg aaaaaggatg aaatccaagg cgtctccgag    420
tgtatcatta tgggcacacc cgcgccaggt tgtggcacct cacttgcatc gatcgtcaca    480
cctgcccctc tcctcccacg caaaaagcct tgctgtttg aaacagcgtt caaagctggt     540
caggatcgat tgagctatca cgaaaacaat ggcggcatgg aggtggacat gtgaacccgg    600
tccctcatac atcttcttct gattgtctgt accatacata catcgcattg cttcttttca    660
catacgacac gacatgcatc tgacatctac gac                                 693

<210> SEQ ID NO 102
<211> LENGTH: 776
<212> TYPE: DNA
<213> ORGANISM: Unknown
<220> FEATURE:
<223> OTHER INFORMATION: metagenomes purified from environmentally
      challenged niches

<400> SEQUENCE: 102
gcaggatcag gaggagcata ttccttctct ctgaccacct tctcgccttc tggaaagctt     60
gtccagatcg aacatgcatt ggcagcgta gcgggtggaa caacatcact gggtatcaaa    120
gctaccaacg tgttgtcct tgcgactgag aagaagtcac cgtcactcct gctcgatacg    180
tctgttctcg aaaaggtagc tcctatatgt cccaacattg gtttcgtcta ctcgggtatg    240
ggacccgatt tccgagtcct ggtcgccaaa gctaggaaga tcgcccaagc gtactataaa    300
gtgtatggcg agtacccacc tacaaaggtt ctagtgcagg aggtggcggg cgtgatgcaa    360
aaggctacgc aatctggtgg tgtgcgacca tatggtatct ccctcttgat cgctggttgg    420
gattcgcacc gaggtcagag cctgtaccaa gtggatccgt caggtagcta ctgggcgtgg    480
aaggcaagcg cgatcggcaa gaacatggtc aacggaaaga cattccttga agcgatac     540 aatgacgacc tgtcactcga agatgccatt cacacggccc ttctcacgct gaaagaaggt    600
ttcgagggac agatgactga gaacacgatc gagatcggtg tagtgacggt accgacggcc    660
gagcagatgc aggagaagcc aggagagagg ctacctccca cgttcaggaa gttgacggag    720
caggaagtga gggactatct cgccttgtag acgatgcaga cagaacatga ccatcc        776

<210> SEQ ID NO 103
<211> LENGTH: 1191
<212> TYPE: DNA
<213> ORGANISM: Unknown
<220> FEATURE:
<223> OTHER INFORMATION: metagenomes purified from environmentally
      challenged niches

<400> SEQUENCE: 103
aagtctacga ctcctccagc caatttactt tgatccaaaa tgttgaccag cgccttttct     60
acatctgctt ccaagatgct cggcaagaga gcagtctcgt cttccagcgc cttgaacgga    120
aaggttgccg tcctcggtgc tgctggcggt attggccagc ccctctcctt gctggtcaag    180
cagaaccctg ctgtctccag cctctcccctt tacgatgttc gcggctcccc tggtgttgct    240
gctgacatta gccacatcaa caccccctgct gtcaccgagg gcttcctccc cgacaacgat    300
ggcctcaagc aagccctcga gggtgctgag gtggtcctca ttcctgctgg tgttcctcgc    360
aagcccggca tgacccgtga cgaccttttc aacaccaacg cttccatcgt caagatgctt    420
gctgaggctt ctgccaagta ctgccccaag gctatgatgc tcatcattgc caaccccgtc    480
```

| | |
|---|---|
| aactccaccg tgccgatcgt cgctgagacc ttcaagcgtg ctggtgtcta cgaccctgcc | 540 |
| cgtctcttcg gtgtcaccac cctcgacgtt gtccgctctt ccactttcgt ctctggcatc | 600 |
| accggtgcca agccctccga caccgtggtc caggtcatcg gtggtcactc tggcgccacc | 660 |
| atcgtgcccc tgctctccca gatccctcag ggcgacaaga ttgtcaaggc tggcggccag | 720 |
| cagtacgctg acctcgtcaa gcgcatccag tttggcggtg acgaagtcgt caaggccaag | 780 |
| gacggcactg gctccgctac cctctccatg gcttacgccg ctgccgtctt caacgacgct | 840 |
| ctcctcaagg ctatggacgg ccaaaagggt ctcgttcaac ccgcttacgt cgagagcccc | 900 |
| cacttcgcca aggagggtgc taagtacttc gcctccaacg tcgagctcgg ccccaacggt | 960 |
| gttgagaaga tcctcgacat cggcaacatg tcctctgagg agcaggagct ccttaaggag | 1020 |
| tgccttcccc agctcgccaa gaacattgct gctggtgaga agttcgtcgc tgacaactag | 1080 |
| aggatatccc acgacgttgc tccctataat aatgagagca agcgagaaca agagaaataa | 1140 |
| agacatagca aattgaatag ggcttccaac tgcaccaaaa agcagtgatg c | 1191 |

<210> SEQ ID NO 104
<211> LENGTH: 1191
<212> TYPE: DNA
<213> ORGANISM: Unknown
<220> FEATURE:
<223> OTHER INFORMATION: metagenomes purified from environmentally
    challenged niches

<400> SEQUENCE: 104

| | |
|---|---|
| gcatcactgc tttttggtgc agttggaagc cctattcaat ttgctatgtc tttatttctc | 60 |
| ttgttctcgc ttgctctcat tattataggg agcaacgtcg tgggatatcc tctagttgtc | 120 |
| agcgacgaac ttctcaccag cagcaatgtt cttggcgagc tggggaaggc actccttaag | 180 |
| gagctcctgc tcctcagagg acatgttgcc gatgtcgagg atcttctcaa caccgttggg | 240 |
| gccgagctcg acgttggagg cgaagtactt agcaccctcc ttggcgaagt gggggctctc | 300 |
| gacgtaagcg ggttgaacga gacccttttg gccgtccata gccttgagga gagcgtcgtt | 360 |
| gaagacggca gcggcgtaag ccatggagag ggtagcggag ccagtgccgt ccttggcctt | 420 |
| gacgacttcg tcaccgccaa actggatgcg cttgacgagg tcagcgtact gctggccgcc | 480 |
| agccttgaca atcttgtcgc cctgagggat ctgggagagc aggggcacga tggtggcgcc | 540 |
| agagtgacca ccgatgacct ggaccacggt gtcgagggc ttggcaccgg tgatgccaga | 600 |
| gacgaaagtg gaagagcgga caacgtcgag ggtggtgaca ccgaagagac gggcagggtc | 660 |
| gtagacacca gcacgcttga aggtctcagc gacgatcggc acggtggagt tgacggggtt | 720 |
| ggcaatgatg agcatcatag ccttgggca gtacttggca gaagcctcag caagcatctt | 780 |
| gacgatggaa gcgttggtgt tgaaaaggtc gtcacgggtc atgccgggct tgcgaggaac | 840 |
| accagcagga atgaggacca cctcagcacc ctcgagggct tgcttgaggc catcgttgtc | 900 |
| ggggaggaag ccctcggtga cagcagggt gttgatgtgg ctaatgtcag cagcaacacc | 960 |
| aggggagccg cgaacatcgt aaagggagag gctggagaca gcaggttct gcttgaccag | 1020 |
| caaggagagg ggctggccaa taccgccagc agcaccgagg acggcaacct ttccgttcaa | 1080 |
| ggcgctggaa gacgagactg ctctcttgcc gagcatcttg gaagcagatg tagaaaaggc | 1140 |
| gctggtcaac attttggatc aaagtaaatt ggctggagga gtcgtagact t | 1191 |

<210> SEQ ID NO 105
<211> LENGTH: 1505
<212> TYPE: DNA

<213> ORGANISM: Unknown
<220> FEATURE:
<223> OTHER INFORMATION: metagenomes purified from environmentally
     challenged niches

<400> SEQUENCE: 105

| | | | | | |
|---|---|---|---|---|---|
| ggggcaagcg | tgctgcttcc | ggcactgcat | ttcgacgagc | gggagcaacg | acctggacgt | 60 |
| acgtcttcga | ctgcaagtct | gctgcagcgt | cacgatcgca | atgaaccttt | atcgctcaac | 120 |
| tcgcactcgc | cgacatctgt | ggaccacact | cccactactg | cgcatttcac | tggtgctgaa | 180 |
| gagttgctcg | cctccgacgt | cggaccgacc | gcgacagctg | ggctaccgg | tgatgcggag | 240 |
| cttgagagca | agctcaagct | gcttgaagag | gtcaaacgtg | cacgggaatc | ggtacatagc | 300 |
| tcgctcgaga | ggatcagagc | cggcacgcct | accccgtcta | tcagccaggg | aatgcccagc | 360 |
| ccgacaccct | ctggtgcccc | tggttacgct | agaactccgt | cgtctgtcgg | cctgtcggac | 420 |
| gacgtgcgct | cgagacgagg | ctcaacgacc | agctccaagg | ttcttgacgc | tatcgacaag | 480 |
| cctcgagtcg | ctacccaatc | cgaatggac | gagtacgttc | gcaaccggca | tgtcatctca | 540 |
| cctccaccca | ctcagtttgc | cgtattgccc | acatctgctg | cgatggtcga | tcgtggtacc | 600 |
| agtcgacaca | gccagtatgc | ccttgtttcc | gacggcgttg | ccaaagcgct | tgacaggcgg | 660 |
| gagcgaacta | tttcaatgat | ggagccgcaa | gttgccgagg | actggggacc | aagagagacg | 720 |
| ctcgacagca | ctccggctca | tgtctcgatg | ggcgtcgag | ccatgtcatt | ccatgagata | 780 |
| cctctggcat | cgcctgtcgc | tgcctctcga | cctcaggacc | gctcctccta | ctctgccgga | 840 |
| ccacgtcagg | tcatagggtc | agctgctggc | cacacgcagc | gaccgggtat | cagtcaatcg | 900 |
| agatcagccc | acggccggac | tatgacatac | gacgagctga | cggagagaca | tcgtcagcgc | 960 |
| ttgtcggcat | tgcaagcgcc | agtcagcgcc | aaaatcaggg | agccgatgga | catcgcgtcc | 1020 |
| gccaaagcca | gctgggacaa | gcaaaagcgg | gtcgagcggg | acgaaatgaa | gaggcgagaa | 1080 |
| gccgagaagc | tcgctcaggc | tcacgcaaga | gagcgacgag | ggcccgctgt | cgacaagaag | 1140 |
| gaagttctca | gtcgaccga | cgaatggagg | cgaagcgtcc | acggcggtct | cgacggtttc | 1200 |
| gccgttccgc | acctaccggc | ccacgctcga | ggttccacgc | agcctggtgg | atccggcgcc | 1260 |
| aagcgatctt | cactctctca | aaggcccagc | aactacttcg | ccaactaggc | ataatcgaat | 1320 |
| cgcggacagt | catctgtaca | tagaaccgta | cctgtattac | caaccctgca | cttccgctca | 1380 |
| cacctgttgc | ctataccctcg | tctaccaacg | ctcattccaa | tatcatagct | acattcattt | 1440 |
| gcaaggacac | tatcacaccg | cagtcatgac | tccgtatgga | tattcaatgc | atacctcttc | 1500 |
| cagag | | | | | | 1505 |

<210> SEQ ID NO 106
<211> LENGTH: 1391
<212> TYPE: DNA
<213> ORGANISM: Unknown
<220> FEATURE:
<223> OTHER INFORMATION: metagenomes purified from environmentally
     challenged niches

<400> SEQUENCE: 106

| | | | | | |
|---|---|---|---|---|---|
| aacctcggcc | gagaggacaa | gattatcaag | aatgggatct | cctgcgcctc | accaccgcca | 60 |
| tcaatcctca | cttgaaggag | tcattgactt | ttctactggt | agagggcatc | cattgaatcc | 120 |
| ctatcaacgc | gacaaggccg | agagcgtttt | tactggcatt | atcaaccgct | tcgaggactc | 180 |
| gtcgaccgta | gagaaaccat | acaaccgtgc | caagctggtt | cgcctgacgt | atgagtatgc | 240 |
| tcgctcggaa | gattctcgat | gcaatttctt | gcaagcattc | ttcggatcag | taaacgttac | 300 |

```
gatggatgac tctattgatt tcgacgatga agcggtagaa gagggattc gctcgagcct    360 gaattccttc gcagatttct tggtggagaa cttcttcctt ccactcaagg cttccgccag    420
caggacgccc ccagccccc agcccaagtt ccgagcagac gtcctgctgt ggggtctgtg     480
gaaagagtgg cctcgctcag acgcgactgc ctcatccgcg atcgacatcg ttgcgtaatc    540
tctcgcaact tcgacatgaa agaagctgag cgacgtcttg acgatagcgg atatgaccat    600
gcctcggacg atgaaggaca tttactgaaa gatcaggagc atgggtcatt cgcggaacta    660
gaagttgcgc atatacttcc tcactcattg atgactacga cagcgaactc cgagctgaac    720
aagtccaaag aaacggcatt gacaatactt aatatgttcg acagtggcat tgtccatcta    780
atcgacggtc cagacattga tcgccctcga aatgctctta ccttaagcat tgacctccat    840
cgacagtttg gcaacttcaa ggttttttt gagcctatgc ctgagcccca tacctaccgg     900
attgattcaa ccctccgcca gccatttaga aacccgattt tccctgtaac ccgtgcactc    960
tacctcaccc ctgagcgaac tattgatccc ccgtccggtc gacttcttgc cgttcatcgc   1020
gcaatttgcc acattttaca tctcagtgct gctgggaatt acatcgacag catacttcgc   1080
gacatggatg acgggactgt acaagccaac ggctcgactc gcctggctag catagttcgt   1140
ctgaaactgg ggggttggtg ggatggcact gttgttggat agtcaaccac ttcgaccctc   1200
tccatacacc acaacggcaa ctcgagctga tgcatcaccg atctacctac gccattcgcg   1260
tggaggattg tcgcatatca ccactaggtt cgtgcgactg gatatgaaac gcggcccgta   1320
ctttggggtc gtgtatccgg tttcacatcc agcttgtcgc atcaaggatt ccaatcctaa   1380
cgacatgagc c                                                        1391

<210> SEQ ID NO 107
<211> LENGTH: 665
<212> TYPE: DNA
<213> ORGANISM: Unknown
<220> FEATURE:
<223> OTHER INFORMATION: metagenomes purified from environmentally
      challenged niches

<400> SEQUENCE: 107
ggacgaccga ataccgtca aaatggtcaa catcccgaag acgcgcagga cctactgcaa      60
gggcaaggaa tgcaagaagc acacccagca caaggtcacc cagtacaagg ctggcaaggc    120
ctccctcttc gcgcagggta agcgtcgtta cgaccgtaag cagtccggtt acggtggtca    180
gaccaagccc gtcttccaca agaaggccaa gaccaccaag aaggtcgtcc tcagattaga    240
atgcacttcg tgcaagacca aggcgcagct cgctctcaag cgctgcaagc acttcgagct    300
tggtggtgac aagaagacca agggtgccgc tcttgtcttc tagatgggtg cataacggtt    360
atggcgctag ggatgatgat ggagcggtct gtgcatgtag cctccttgag tacatgatcc    420
tcgagggctc ggaatcaaag cttcgtttct cctacgatcg tcccactcgc aaagacatgt    480
ctcgtcatat catggcttgc gcacaacatt cttcgagggt ccatcagaga tgcccgaccc    540
tgccgctacg ctgcgtggga tgtgactcca gcacaaccgc cttccagtat catctcttcg    600
cgtgcagaag tgaggacgat tttacgacag tccatataac aaatcggaaa tgccaacaag    660
atcaa                                                               665

<210> SEQ ID NO 108
<211> LENGTH: 1327
<212> TYPE: DNA
<213> ORGANISM: Unknown
```

```
<220> FEATURE:
<223> OTHER INFORMATION: metagenomes purified from environmentally
      challenged niches

<400> SEQUENCE: 108
ggcccctctt gaactttgga cttttttagca tctattttct ctacttctct ctccctcctc    60
ctatctacct tctctatcat ctccttcagc tccctacaac atgaagctca cctttaagga   120
cctgaagcag gagaagttcg taatcgaggt cgagccctcc gagactgttc gcgaagtcaa   180
gcaaaaaatt gctcaagaaa aaggcgaata tgaggcggaa cgaatgaaag ttatctactc   240
gggcaagatc cttcaggatg acaagaccgt cgaatcatac aacatccagg agaaggattt   300
cctagtctgt ctgccttcaa agggtcctaa gcccgctgcc tcgtcgtctg cctcccaggc   360
acccgccact ccggccccta gagctcctgt tgctactcct gctgctcctg ccccgctgc    420 tcctgcacct gctagttcta cgcctgctgt ccctgcgact ccctcgcctg ctggcgccca   480
gaccggtccc tctttcggtg acccatctgc attgaccatg ggttctgcgg ctgagggtgc   540
cgtcactcag atggaagcaa tgggatttgc cagaagcgat attgaccggg ccatgcgggc   600
tgcattcttc aatcctgacc gcgctgtcga ttacctcttg aacggtattc ccgccgatgt   660
tcaacaggaa caacagcagc ggcaacaaga gcaacaagcg gaccgtgctg cagaacaagc   720
tcctgtgccc agcgctgagg atgctgctgc tgccgccgct ctgggtggcg atgagggttt   780
taacatgttc gaggctgccg ctcaggctgg tgatggtcgt ggtggtggtg ctcggtctgg   840
aggtagcgag gcccttgcga acctggactt tctccgcagt aaccccccatt tccagcaact   900 gagacagttg gtccagcagc agccgcacat gctcgaaccc atcctgcaac aggttgctgc   960
cggaaaccca cagatttccc agatcattgg ccaaaactct gaacagtttc tccaactgct  1020
aagtgaggag ggtgatgagg aagatgcggc cctgcctcct ggtacacaag ctatctccgt  1080
tacagaggag gagcgggacg ccattgagcg gttgtgccgt ctgggtttcc cccgggattc  1140
cgtcatccag gcctacttcg cctgcgacaa gaacgaagaa ctcgcagcaa acttcctctt  1200
cgaccagccg gacgatgatg aggagtaaat ctgatccacg atgctgtggt tcacttcttt  1260
actccatgtc ttatccccct ccccttttgc ttctttacgt tctgatgaat accaagcatg  1320
cctgttg                                                            1327

<210> SEQ ID NO 109
<211> LENGTH: 1326
<212> TYPE: DNA
<213> ORGANISM: Unknown
<220> FEATURE:
<223> OTHER INFORMATION: metagenomes purified from environmentally
      challenged niches

<400> SEQUENCE: 109
ggcccctctt gaactttgga cttttttagca tctattttct ctacttctct ctccctcctc    60
ctatctacct tctctatcat ctccttcagc tccctacaac atgaagctca cctttaagga   120
cctgaagcag gagaagttcg taatcgaggt cgagccctcc gagactgttc gcgaagtcaa   180
gcaaaaattg ctcaagaaaa aggcgaatat gaggcggaac gaatgaaagt tatctactcg   240
ggcaagatcc ttcaggatga caagaccgtc gaatcataca acatccagga gaaggatttc   300
ctagtctgtc tgccttcaaa gggtcctaag cccgctgcct cgtcgtctgc ctcccaggca   360
cccgccactc cggcccctag agctcctgtt gctactcctg ctgctcctgc cccgctgct    420 cctgcacctg ctagttctac gcctgctgtc cctgcgactc cctcgcctgc tggcgcccag   480
```

| | |
|---|---|
| accggtccct ctttcggtga cccatctgca ttgaccatgg gttctgcggc tgagggtgcc | 540 |
| gtcactcaga tggaagcaat gggatttgcc agaagcgata ttgaccgggc catgcgggct | 600 |
| gcattcttca atcctgaccg cgctgtcgat tacctcttga acggtattcc cgccgatgtt | 660 |
| caacaggaac aacagcagcg gcaacaagag caacaagcgg accgtgctgc agaacaagct | 720 |
| cctgtgccca gcgctgagga tgctgctgct gccgccgctc tgggtggcga tgagggtttt | 780 |
| aacatgttcg aggctgccgc tcaggctggt gatggtcgtg gtggtggtgc tcggtctgga | 840 |
| ggtagcgagg cccttgcgaa cctggacttt ctccgcagta accccatttt ccagcaactg | 900 |
| agacagttgg tccagcagca gccgcacatg ctcgaaccca tcctgcaaca ggttgctgcc | 960 |
| ggaaacccac agatttccca gatcattggc caaaactctg aacagtttct ccaactgcta | 1020 |
| agtgaggagg gtgatgagga agatgcggcc ctgcctcctg gtacacaagc tatctccgtt | 1080 |
| acagaggagg agcgggacgc cattgagcgg ttgtgccgtc tgggtttccc ccgggattcc | 1140 |
| gtcatccagg cctacttcgc ctgcgacaag aacgaagaac tcgcagcaaa cttcctcttc | 1200 |
| gaccagccgg acgatgatga ggagtaaatc tgatccacga tgctgtggtt cacttcttta | 1260 |
| ctccatgtct tatccccttc ccctttttgct tctttacgtt ctgatgaata ccaagcatgc | 1320 |
| ctgttg | 1326 |

<210> SEQ ID NO 110
<211> LENGTH: 1162
<212> TYPE: DNA
<213> ORGANISM: Unknown
<220> FEATURE:
<223> OTHER INFORMATION: metagenomes purified from environmentally
      challenged niches

<400> SEQUENCE: 110

| | |
|---|---|
| gcgccggggg acatggagac tgccgacgcc aagaacaggg ctatgcgagc cgctggcttc | 60 |
| atcgttcccg acaccttcga agacctgccc gaggtcctca agaccaccta cactggtctg | 120 |
| gttcaaaagg gtgtcatcgt tcccaaggcc gagatcgacc cacccaacat ccccatggac | 180 |
| taccagtggg cttccaagtt gggtcttatc cgaaagcccg ccgccttcat ctcgaccatc | 240 |
| tcggacgagc gaggtcagga gttgatgtac gccggtatgc gaatctccga cgttttcaag | 300 |
| gaggagatcg gtatcggtgg tgtcatctcc ctcctgtggt tcaagcgacg attgccacct | 360 |
| ttcgcctgca aattcatcga gatggttctg caattgactg ccgaccacgg acccgccgtt | 420 |
| tcgggtgcca tgaacaccat catcaccgct cgagcaggca aggacctgat ctcgtccctg | 480 |
| gccgctggtc tcttgaccat cggtgaccga ttcgtggcg ctctcgatgg tgccgccgcc | 540 |
| gagttctctc gaggtctcaa ctctggtgct accccacgag aatttgtcga ctcgatgcga | 600 |
| aaggccaacc gattgattcc cggtatcgga cacaagatca agtcaaagac caaccccgat | 660 |
| ctccgagtcg ttctcgttgt cgattacgtc aagaagcact tcccgtctca caagacgctc | 720 |
| gactttgcct tggccgtcga ggacgtcacg acgcaaaagt ccaacacgct catcttgaac | 780 |
| gttgatggtg ctattgccgc ttccttctgt gatttgctta gcggttgcgg tgctttcact | 840 |
| gaggatgagg ctgccgatta cctcaagaac ggtactctta acggtctttt cgttcttggt | 900 |
| cgatcgatcg gtttcatcgg tcactacctc gaccaaaggc cctcaagca gcctctctac | 960 |
| cgacaccccg ccgacgacat tttcatcaac atgcaagagc gagttgtctt ccagcctggg | 1020 |
| tccaactaag aggcgaccgc gactacgggt ctcggccaat ttctcccttg ggtttcctcc | 1080 |
| ttcaattaaa actactgtac ataccaccca catcatttat ctcttctttc atgactatag | 1140 |

| | |
|---|---:|
| acgcatgcac gggatcgctc gg | 1162 |

<210> SEQ ID NO 111
<211> LENGTH: 965
<212> TYPE: DNA
<213> ORGANISM: Unknown
<220> FEATURE:
<223> OTHER INFORMATION: metagenomes purified from environmentally
      challenged niches

<400> SEQUENCE: 111

| | |
|---|---:|
| ggggcataca aggagggcaa gttcaccagc gaaagcatcc aaaagtcaaa gctcagattc | 60 |
| caggacatcc tcgttgagct gcccctcagg gttcacaact cccaccttct caccagcttc | 120 |
| ctgcaccagg tcccgcaggc gccgccggca agaaccccc tcgacttccc ttcatcccctt | 180 |
| gcagagcttt cgcgcgactc cgatgtcagc tccaacccct tcgcacccaa ccttgacacc | 240 |
| ctggacctca gcatcgaccc cttccagtac tggcagcgcg ccctcggccg cgagcagcag | 300 |
| aagatcaccg catggcaaca gaagcgcaag gctgagaatg ctgcacgcgc cgcgagcaag | 360 |
| cagccgcccc ttgacgagaa tgagtggcag aagctgttca agctgcccac ggagcccagc | 420 |
| aggctcgagg ctctgcttgt cggcaggcag gtcgagcagt acgcccgcca ggtcgacgga | 480 |
| ttctccgcca ccgtttccgc caagatgttt ggcgtcaggg gcaacctcct ccctaacgag | 540 |
| atcgagtaga ggacgaatat tacgagacg ggaccggcgt ttatgcatag cgaggcgttc | 600 |
| tcggctgggt ggggtagagt acatgcggca tggctacaaa aaaaaggatg atgtggttcc | 660 |
| gccatcgacg agttcagggc aacgctgcat agaatcccaa aagaagaaag gattttaacg | 720 |
| tttttgaatt tggaacttct tcgcattgga cgattgcttt cttgacgact ccgtcagttg | 780 |
| cgcgcttttt ccatggccca taccctcttt atctctaatg agggtgcgcc accgcagacc | 840 |
| caccagctac tcgaagaaaa gtcgctatt tttatttgga gttattagcg agtacaaacg | 900 |
| gaggcatgtc tagaggctga ggagtgtggt agtaagatta tagatgtctt tatgctcgat | 960 |
| atgag | 965 |

<210> SEQ ID NO 112
<211> LENGTH: 965
<212> TYPE: DNA
<213> ORGANISM: Unknown
<220> FEATURE:
<223> OTHER INFORMATION: metagenomes purified from environmentally
      challenged niches

<400> SEQUENCE: 112

| | |
|---|---:|
| ctcatatcga gcataaagac atctataatc ttactaccac actcctcagc ctctagacat | 60 |
| gcctccgttt gtactcgcta ataactccaa ataaaaaata gcgactttc ttcgagtagc | 120 |
| tggtgggtct gcggtggcgc accctcatta gagataaaga gggtatgggc catggaaaaa | 180 |
| gcgcgcaact gacggagtcg tcaagaaagc aatcgtccaa tgcgaagaag ttccaaattc | 240 |
| aaaaacgtta aaatcctttc ttcttttggg attctatgca gcgttgccct gaactcgtcg | 300 |
| atggcggaac cacatcatcc ttttttttgt agccatgccg catgtactct accccaccca | 360 |
| gccgagaacg cctcgctatg cataaacgcc ggtcccgtct ccgtaatatt cgtcctctac | 420 |
| tcgatctcgt tagggaggag gttgcccctg acgccaaaca tcttggcgga aacggtggcg | 480 |
| gagaatccgt cgacctggcg ggcgtactgc tcgacctgcc tgccgacaag cagagcctcg | 540 |
| agcctgctgg gctccgtggg cagcttgaac agcttctgcc actcattctc gtcaagggc | 600 |
| ggctgcttgc tcgcggcgcg tgcagcattc tcagccttgc gcttctgttg ccatgcggtg | 660 |

```
atcttctgct gctcgcggcc gagggcgcgc tgccagtact ggaagggtc gatgctgagg      720 tccagggtgt caaggttggg tgcgaagggg ttggagctga catcggagtc gcgcgaaagc      780
tctgcaaggg atgaagggaa gtcgagggg ttctttgccg gcggcgcctg cgggacctgg       840
tgcaggaagc tggtgagaag gtgggagttg taaccctga ggggcagctc aacgaggatg        900
tcctggaatc tgagctttga cttttggatg ctttcgctgg tgaacttgcc ctccttgtat       960
gcccc                                                                   965
```

<210> SEQ ID NO 113
<211> LENGTH: 1160
<212> TYPE: DNA
<213> ORGANISM: Unknown
<220> FEATURE:
<223> OTHER INFORMATION: metagenomes purified from environmentally
      challenged niches

<400> SEQUENCE: 113

```
gacttcggcg aaggcgatga gcaactcttt cataaggcac cttccttcga ctcttcgtgc      60
gtttcgttca tctactgcat tctctcttac acgttcattc tcttccacca tggcatccaa     120
cgggacatcc acaaatggcg ttcagcatga cgctcgcaag gtcttcttct tcgacatcga     180
caactgtctt tacccgaaat cgtatcaaat acacgacaag atggccgtgc tgatcgacaa     240
ctactttcaa aaccatctgt cgctgtccca agaagatgcg accactcttc atcagcggta     300
ctataaggac tacggcctcg ccatcgaggg gcttgttcgc caccacaaag tcgacccact     360
tgagtacaac gagaaggtcg acgatgcgtt gcctctggat gatatcatca acccgatcc      420 gaaacttcga aaattgctgc aagacataga caccgacaag gtgaagctgt ggctattcac     480
caacgcctac gtgaaccacg ccaaaagggt gactcgcctg cttggtgtag acgatttgtt     540
cgaaggcatg acttttgcg actacgccgc ggaacgcctc ctctgcaagc ccacgacgga      600
gatgtacaac aaggctatgc aagaggcgaa cgccaccgat atcgatcagt gctactttgt     660
tgatgattca gcgctgaatg cggctgctgc tatgaaatac ggttggaaaa ctgcgcatct     720
ggtcgagcct accgcgaagc ctccgcccca gcccgtctca caacaccaga tcagcaacct     780
tgaagagctg cgcaaggtct tccctgaagt atttaagact tcatgatggc atggaaattt     840
taacgaagac acgagtgtat tttacgaaaa ctactcagga ttcccttgcc ttgtaagatg     900
cgaccatcgc tactgggttg ggattggaga tggtgcccag caacgctttt gcgacactat     960
caggtctaag gactctattg taaaacccgg gtcgatttgc atatggttaa ttcgaatctt    1020
ccatgaacac agcatttcgt gaaccaaaga gcacacacgt cgaagtgttg ggatgtcttt    1080
gagcagccag cttggatttc ttgagaggtc ggaagcaatt ctataggata gacagcataa    1140
atgcaataaa gccactattg                                                1160
```

<210> SEQ ID NO 114
<211> LENGTH: 982
<212> TYPE: DNA
<213> ORGANISM: Unknown
<220> FEATURE:
<223> OTHER INFORMATION: metagenomes purified from environmentally
      challenged niches

<400> SEQUENCE: 114

```
atacaagact taccatcaac acaatggctc gcatctttat cactggcagc accgacggcc       60
tcggtcttct ttctgcgaag cttctctcgg aacaaggcca cagcgtcttc ctccatgccc      120
```

```
gcaatgccga acgagcatcc caggccaaag cagcagtgcc caaagcccaa ggtgtcatca    180
tcggcgatct ttcaaacgtc tcagacgtga agcagctcgc cgccgatgcc aacaaggctg    240 gacctttga cgccgttgtt cacaatgctg gcctcggact caccaccaat ggccagaaga    300
ctgctgaggg cgtagcccag attttttgccg ttaacagcat ggcacccttac attctgaccg   360 ctctcatgga caagccgaag aggctcttgt acgtcagctc cggactgcac ttcggtggcg    420
accccagcct cgaggacgtc acttgggcca caagggagtt ccgaccatcg gatgcataca    480
acgatacaaa gatgcaaaac gtcatgctct cgaaagcagt cgccaaacgc tggcctgatg    540
tgcagagcgg ctctcttgac ccaggctggg tgaagactaa gctcggcggg tcggccgcgc    600
ctggcaccac cgacgctcca gcagagatga ttgctgagta cgctgccggc aaatcttgcg    660
caggcgatca aacaggtgcc tacttgactc cgcgtggcgt ggaagagccg catgatgcga    720
ctaagctggc cgagaagcag gatcgtctga tgcagattta caaggaggta tcgggtgttt    780
cgttccccca gtaaacacag cttcatggct ttgcctcgcg gagacctcac attttcaatt    840
agatctccct gccgattgca gcagaccagt actcactagg ctgtgcaggg ggcatgttga    900
tcaagaacga gccataacga catgccatgt caacggacaa tgagtgggcg aagtaacaca    960
tgaaattcat tatctaagcg cc                                             982
```

<210> SEQ ID NO 115
<211> LENGTH: 982
<212> TYPE: DNA
<213> ORGANISM: Unknown
<220> FEATURE:
<223> OTHER INFORMATION: metagenomes purified from environmentally
      challenged niches

<400> SEQUENCE: 115

```
ggcgcttaga taatgaattt catgtgttac ttcgcccact cattgtccgt tgacatggca     60
tgtcgttatg gctcgttctt gatcaacatg cccctgcac agcctagtga gtactggtct    120
gctgcaatcg gcagggagat ctaattgaaa atgtgaggtc tccgcgaggc aaagccatga    180
agctgtgttt actgggggaa cgaaacaccc gatacctcct tgtaaatctg catcagacga    240
tcctgcttct cggccagctt agtcgcatca tgcggctctt ccacgccacg cggagtcaag    300
taggcacctg tttgatcgcc tgcgcaagat ttgccggcag cgtactcagc aatcatctct    360
gctggagcgt cggtggtgcc aggcgcggcc gacccgccga gcttagtctt cacccagcct    420
gggtcaagag agccgctctg cacatcaggc cagcgtttgg cgactgcttt cgagagcatg    480
acgttttgca tctttgtatc gttgtatgca tccgatggtc ggaactccct gtggcccaa     540 gtgacgtcct cgaggctggg gtcgccaccg aagtgcagtc cggagctgac gtacaagagc    600
ctcttcggct tgtccatgag agcggtcaga atgtaaggtg ccatgctgtt aacggcaaaa    660
atctgggcta cgccctcagc agtcttctgg ccattggtgg tgagtccgag gccagcattg    720
tgaacaacgg cgtcaaaagg tccagccttg ttggcatcgg cggcgagctg cttcacgtct    780
gagacgtttg aaagatcgcc gatgatgaca ccttgggctt tgggcactgc tgctttggcc    840
tgggatgctc gttcggcatt gcgggcatgg aggaagacgc tgtggccttg ttccgagaga    900
agcttcgcaa aaagaagacc gaggccgtcg gtgctgccag tgataaagat gcgagccatt    960
gtgttgatgg taagtcttgt at                                             982
```

<210> SEQ ID NO 116
<211> LENGTH: 821
<212> TYPE: DNA

```
<213> ORGANISM: Unknown
<220> FEATURE:
<223> OTHER INFORMATION: metagenomes purified from environmentally
      challenged niches

<400> SEQUENCE: 116
agcgactccg acaacaacga ccaccgggac gactcatatc cttcacaatg gccattggac      60
aatcctcgca gcagcaggcc gacggccaga atgtcgtcac ccagggcaac tctgacaagg     120
ccgccaaccc catgcgcgag ctgcgcatcc agaagctcgt cctcaacatc tccgtcggcg     180
agtctggtga cagacttact cgtgccgcca aggtgctcga gcagctgagc ggtcagaccc     240
ccgtctacag caaggcccgc tacaccgtcc gtaccttcgg tatccgccgt aacgagaaga     300
tctccgtcca cgttaccgtc cgtggcgcca aggccgagga gatcctcgag cgtggcctca     360
aggtcaagga gtacgagctc cgcaagcgca acttctctgc caccggtaat ttcggtttcg     420
gtatctccga gcacatcgac ctgggtatca agtacgaccc tgcgatcggt atctacggca     480
tggacttcta cgtcgtcatg tcccgtcccg gtgagcgtgt cgcccgccgc cgtcgcgcga     540
agacccgcgt tggtgcttct cacaaggtca acgctcccga ggtcatcaag tggtacaaga     600
accgcttcga gggcatcgtc aggtaaaaag cttgaaaggt ggtctgggat gatgaaaaat     660
tcaacttgtg gttttggcaa cggcgcaaaa gagcgaggct attttccgt agcttgagga      720 tatatccggc ctatcggagc tttactttta cgcttgagca agatcgcaaa aatggaggcc     780
tcgtatacca agcgagcgtg ccgcataacc attgatcgct c                         821

<210> SEQ ID NO 117
<211> LENGTH: 673
<212> TYPE: DNA
<213> ORGANISM: Unknown
<220> FEATURE:
<223> OTHER INFORMATION: metagenomes purified from environmentally
      challenged niches

<400> SEQUENCE: 117
gacacaccgg tgacgtcttg agcgtctcgt tctcggccga caaccgacaa atcgtttctg      60
cttcccgaga ccgaactatc aagctctgga cactctcgg agagtgcaag ttcaacattg      120
ttgacgatgg tcactcggag tgggtctctt gcgttcgatt ctctcctaac cccgtcattc     180
ccgtcatcgt ctctgctggt tgggacaagg tcgtcaaggt ctgggaattg tccaagtgca     240
agctcaagac caaccaccac ggtcacactg gttacatcaa cccctcgcc gtttcgcccg      300 acggatcgct cgccgcatcc ggtggaaagg atggcatcac catgctttgg gatttgaacg     360
atggcaaaca cctctactct ctagaggctg gagacattgt caactcgctc gtcttctctc     420
ctaaccgata ctggctctgt gccgccactg cttcgtcaat caagatcttc gacttggagt     480
ccaagtcaat cgttgacgac ctcaagccag acttctccgc cgagtactct gacaaggctc     540
aaaagccaca atgtacttcc ctcgcctggt ctgccgatgg tcagaccctc tttgccggtt     600
tctccgacaa cctcgtccga gtctgggttg tcactgctta gagtcgtgag gattgtatgc     660
atggataacg tgg                                                        673

<210> SEQ ID NO 118
<211> LENGTH: 1183
<212> TYPE: DNA
<213> ORGANISM: Unknown
<220> FEATURE:
<223> OTHER INFORMATION: metagenomes purified from environmentally
      challenged niches
```

```
<400> SEQUENCE: 118
gaagtaccgt tttctgtgca gtttttttta aacccagaac ttgcaattga gatcacgcgt      60
cgcaatggca ccctctaccc agaagcaatg gaccgttaaa aacggggagc aggactttga     120
cggcctcgtt tacggcgacg cgccagttcc gactgcgggg gactcggaag tcgttgtcaa     180
gctccatggt gcctcgctca actaccgtga cctgattatc cccaagggaa agtacccctt     240
cccgctctcg ttcccggtcg tccccggctc tgacggtgcc ggtgaagtcg tcgaggtcgg     300
atccaaggtc aagcaattca agaagggcga caaggttgtt accctcttca accagctcca     360
tcagtacggt cccgttgacg ctgctgcggc atcgtcgggc ctcggtggtg cggttgacgg     420
aaccctgcgc cagtacggtg tcttcaatga gaacggcgtc gtcagggccc cgaccaacct     480
gaacttcctt gagtcgagca cactaacctg tgcgggacta acaagctgga atgcgctgta     540
tgggctgaag ccgcttcttc ctggccagac cgtcctggtg cagggcactg gcggtgtgag     600
tatctttgct ttgcagttcg caaaagcagc gggcgcaact gtgatcgcaa caacctcatc     660
cgaagagaaa ggcaagcgcc ttaaggacct cggtgccgat cacgtcatta actacaagac     720
ccaaaccaac tggggcgaga tcgcgcgcgg tttgacgcgc gacaacatcg gggttgacca     780
catcattgag gttggaggcg ccggcaccct ggagcagagc ttcaagtgca tcaagttcga     840
gggagtcatt agtattattg gcttcttggg cggaatgaac cccagcacca tacccaatgt     900
tctgcagacc ctgagcaaca tctgcactgt gcgcggtgtg tatgttggca gcaaggcgct     960
gatgaacgac atgatcaacg ccatcgaggc gaacaatatc caccctgttg tggatggaac    1020
tgtgttcacc cttgagaaga cacgagaggc ctatgagtac atgtgggcgc agaagcactt    1080
cggaaagctg accatccaga tcgcttaatc acttgatgaa tataatgagg gatatatgcg    1140
actaggaatt atgcgctaat gaatataata accatgcaat tag                      1183

<210> SEQ ID NO 119
<211> LENGTH: 1563
<212> TYPE: DNA
<213> ORGANISM: Unknown
<220> FEATURE:
<223> OTHER INFORMATION: metagenomes purified from environmentally
      challenged niches

<400> SEQUENCE: 119
ggggccatgc tcgagcagca gtaccagatg cgaaaggagc agcaagtgca atttacacct      60
atggcatcgc cgtccagcac tccttaccac atgcatcaag atttcactgt tccgggcgac     120
tttttctccc ccctcacatc gcctgcgctc cacgctcaga atcagccaca atcgcgacag     180
caattcacgg ctcatcaaca gggctactac acgaatccca gcaccgctgc gagctcggcg     240
gctccgagtc caatcgacgc gaacggagat gtggaaatgg gtggcgacgg tgttgcgctg     300
ccagagtcag cgagccaacc gaagaagcct tcccgaagga agcctgcgac accgaggact     360
ttcgccatga acaaggtcaa gcaaagtccc atacaaaaac cgcaaaaaag gaagtctgtg     420
gcgttggcac acaaggatgc agatgctgtg gtgcaggacg cccaacggtc tggccatatc     480
gcgcccaaat ccgcaggtct ccaaatgccg cctccgtttg agagctcgga aaacgacagt     540
gtttcgccgg aagcgctgaa cgacctgcct atggcccccc cgcctagacc tggatcggtt     600
tcgcagtcgc ccgccatcgc tcctcagaat cagagcgttt ctggaccggc cgcgactccc     660
aaatctctcc tttctatgaa gggcgctcaa gatatgaatg cacctgccag tactggtatt     720
tctggccaaa tgggacaggc atccttagaa gatctcgaac ttcccgaagc tgccgaaaat     780
```

```
ccaggatcga ctgcgacaca ctcgcaagtc ttgaactcgc aagagccgac acctcgcctc    840
atgccctccc gtaaaacgcc aaaactcggc cctcttagca cgccttcatc gggcaagcct    900
acttctgctt ccaacagtcc cgctcatgcg ttgtctccca tgacagcgag tacccctgct    960
ggtctgctga aggacaagaa ggacaacaaa ggcggacgtg caaccagcaa gaagcgtggt   1020
agtgtcagta ccaccaattc agcaatggtc tctccggcac tccgaccgaa ggtcagcccg   1080
agtatcaagc ctctgctacc cgaaggcacc agcctcaact ccccgaccca tgccctcctc   1140
ctcgcctcca atccaatta ccagaacctc ctggaaggca accacctccc cggcatctcc    1200
tacccggact ccctctcaac cggcctcacc agcaaacgca cctcgcacaa agtcgccgag   1260
caaggccgcc gcaaccgcat caacgacgcc ctcaaagaaa tgcaagccct catccccgcc   1320
tcgtccggcg cccgcgccga agagctcatg accgccgacg ccggcgacga cgacagccag   1380
gaaaccaagg agaaggaccg cgacgccgct gtcaagagca atagctccaa agccgcgacc   1440
gtcgagagtg cgaatcggta tattcgcgtg ttgaaggaga gcgacgcggc gcagaaggat   1500
gcgatcgcgc ggccgaattc cccgggctcg agaagcttgg atccaccgga tctagataac   1560
tga                                                                1563
```

<210> SEQ ID NO 120
<211> LENGTH: 939
<212> TYPE: DNA
<213> ORGANISM: Unknown
<220> FEATURE:
<223> OTHER INFORMATION: metagenomes purified from environmentally challenged niches

<400> SEQUENCE: 120

```
gacgacacaa tgagaaacat cctcctagta ttggcgtctg cagcgcttgc tgttgtggca     60
caaaagccag atctcgacgt gaaaggcacg tttggagacg cgaacccctt ctccaaggtc    120
gtcaacggcc aaagcaacaa gctctacctc acgctggaca accacagccc tgagtctctg    180
gtggtcaagt ctatcagcgg gtcatggtct gagaagacgt ccgcttcatc cggtcaagag    240
aagtttctta agaactctac cacccaagag aagctcactg tccccatccc tcccaagtcc    300
gagggcgcat tccagcctcc tacagtcttg acctaccagt tctggagcga attcaagcct    360
agagagttgc tcttgaccgt tttgggttga ctatgttgat gctaccggtc actcgtacag    420
agaaacagcc tacgaaggcc aagtgactgt cgttgaggcc ccgggatctt tctttgaccc    480
cgccttgctc tttgcctacg ccatggtgct ggctctcgtc ggcggcgccg gctaccttgc    540
ctacaacatc tactttccac ctgcccgcaa gcccagaaga agcgccaaca ccgcacctac    600
agatgctcct gctgctccgg ctgaccctga cgaatggatt cctgtccacc acaagagggc    660
caaaaagacg tctggcggcg gggccaccag tggtgaagag agcgaagcca ctgaaggcta    720
tgcaagcgag aagtctgcca gtggagccaa gaagagaggc aaaggtggca gaaaataaat    780
actgacatgt gcctcgagct gcagacgacg ctcgtcaaaa gtgtagcaag ttgaagaagc    840
ccagcacgaa gtccccagct tgactgctgc cgtttggctt aatggcacag aaagcgagtg    900
tacgtcgtac acggcttata gtctcgaatg caacaaagg                           939
```

<210> SEQ ID NO 121
<211> LENGTH: 836
<212> TYPE: DNA
<213> ORGANISM: Unknown
<220> FEATURE:
<223> OTHER INFORMATION: metagenomes purified from environmentally challenged niches

<400> SEQUENCE: 121

```
gaaatcacgg gggaggcgta ggcgcgtctt actactatgg cggcatcgcg attgcgctgt      60
gtcttgtgat tgtgttgacg cttgtatcaa gaatattata tcgacgacgt gtaaggaaca     120
gactcctgcg agccaacaga caagagcgca ttactttgcg agaccgggga gaagcgccag     180
gcctgccaac ctatcgggag tctcgcaatc agccctcatt accgcgatac acggccgagg     240
cagactacgc acctccaccc ggcccgcctc cttccaacag cccggacaac gaaggccacc     300
acttccactt ccatttcccc tctttacatg tgcctcaggc actgcacttg cggcctaggc     360
aggcagacga tcctgctgac cagatcccca ccgtgccccc tccgtcctac gagccgccca     420
agtatgagcc gcccagtgga gcgcctccag agcagcaaca agagcctgtg gctagcggga     480
gtagcgagca tcatcaccag cagtctgctt gggcgaaca taccgcggcg caacagccg      540
ctgccacaac tccggcagag cacagtggcg agtcgacaga gcttaggagt gcgtcgcctt     600
ctcagccaca atctcaatcc caacctcaag caccagcaca accacaagag caggattacg     660
gctacgacga tgccgacttt atccatcctg aagagcgacg caggatcgag gctgcgcagc     720
gcaatgatcc gcagacatga ttcaaacatg tgttgtaaag tgtactacta tgaactcgtt     780
gaccagtata atcgaagcgt atataacggc acaaatgcaa agctgccatc atcccg        836
```

<210> SEQ ID NO 122
<211> LENGTH: 697
<212> TYPE: DNA
<213> ORGANISM: Unknown
<220> FEATURE:
<223> OTHER INFORMATION: metagenomes purified from environmentally
     challenged niches

<400> SEQUENCE: 122

```
cattacggcc gggaagcttt cagaagctaa tcgagttctt cctatccctt tcaactttac      60
acaccatgtc tagaattggc gatccaacga acaaccctgc tacccagcaa ctgtactctg     120
ataggccctt gcatctccct ggccccggcc tcaagccatc caggcagctc actatcagct     180
cggctgttgc gttccgcgag gattcgggcc aaacacgctt caacctcatc agctctgacc     240
accgcgaggt gttgcacatt agtattcgtg caagggacaa cgttctcgtg ctcaacacca     300
aggcccccga tggcgattgg ggcaaagaag agcgacatga tctcaaaccc cttttcgata     360
ccccactgct gccttacatc accgtaatgg caacgaagaa cagctatatc ctttctgttc     420
ctggtaaacg ggagatcatc ttcaataaga ggaaagggtt catggagcct gctgtgagga     480
ttgagtatga ctatgatgag atgtctgcgt tctccgaccc ctgctacatt acagtcccat     540
cttcatctta aagctttcct agttggcttg gagttggcgg atatggtcac attggttttt     600
tcacacggca aacggtaaag aattacggct tctctctcct gtcatgttca gcggacgatg     660
tatgatgtag tgttctgttc aattgatctg gttgttg                             697
```

<210> SEQ ID NO 123
<211> LENGTH: 329
<212> TYPE: DNA
<213> ORGANISM: Unknown
<220> FEATURE:
<223> OTHER INFORMATION: metagenomes purified from environmentally
     challenged niches

<400> SEQUENCE: 123

```
ggaacgacca cgagcagttt ttaaaatgcc acaagaaatc aaggacatca agaacttact      60
```

```
cgaaatcgct cgtcgtaagg acgctcgttc cgcccgcatc aagaagacca agaccgttgg    120
tgctaagggc gagccagctc aacttaccaa gttcaagatt cgttgctctc gctacctcta    180
cactctcgtc gtctctgacg gtgagaaggc agagaagctt aagcaatcac tcccaccaac    240
cctcaacgtc gaggagattg gtaaggtttc aaagaagtag attagtgatg taatttgctg    300
ccttgattga ttgtccttgt tggtatttt                                      329
```

<210> SEQ ID NO 124
<211> LENGTH: 747
<212> TYPE: DNA
<213> ORGANISM: Unknown
<220> FEATURE:
<223> OTHER INFORMATION: metagenomes purified from environmentally
      challenged niches

<400> SEQUENCE: 124

```
gtacacataa ctcttcattc ctcatcatgt ctcacacttt ctacgatggc accatcgtgg     60
tgcttcaagg cattcttgaa acttttctc atatccttca caaagccgaa gaaagcccaa    120
actctagcgc ttttcccgca gctcgtctgc acgaggacat gtatccattg accgaccaaa   180
ttcgcctagc aactcaattt tctgagtata ttctggctaa agtgaccggc cgcgagccaa    240
ggaagttcga aggcaatcca ttgaccttcg ctgaattcta tgagcgtatc gataccatgc    300
tgaagtcact caaagaagca gataaggatg tcgtcaatgc aaatgccgac aaggaggagc    360
ttactcaagt tggacctacc gcaaaaattg aattgagtaa tgctatatac gcccatcgca    420
tagccttgcc caacatttac ttccatctca acattgctta cggcattttg cggaaggagg    480
gcgtgcctct tggcaagctt gactattttg cgggcttttt cccaccgagc atggctcaag    540
gcaagtaaag aagtgatgtt ggttatgttt ccggatggag agggtgctga tctatgagaa    600
tgagttccga gtagaccatg atggtctaga tgtggacttg agctttcatt tgccaaattc    660
ttgtggaaag atagcaatga cggaacaagc gatttgtatg tacatttaat gaagtctatc    720
tatagaatta atctccgatc tatcgcg                                        747
```

<210> SEQ ID NO 125
<211> LENGTH: 693
<212> TYPE: DNA
<213> ORGANISM: Unknown
<220> FEATURE:
<223> OTHER INFORMATION: metagenomes purified from environmentally
      challenged niches

<400> SEQUENCE: 125

```
aagctcttca aagctaatta tcgagttctc ctatctcttg cacttataca caccatgtct     60
agaattggcg atttgcgaa caacaaccag gctacccagc agctgttctc tgatagaccc    120
atgcagctcc ctggccccgg ccttaagccg tccaggcagc tcacggtcag ctcagctatg    180
gcgttccgct gggactctgg ccaaacccgc ttcaacctca tcagtctga ccgtcgtgaa     240 gtgctgcaca tcagcatccg cgcaaaagac gacgtccttg tgcttaacac taaggctcct    300
gatggcaatt ggggcaagga agagcgacac gagctcaaac cccttttcga cacccccgatg   360 ctgccttata tcaccgtaac ggcgactaag actagctata tcctgtccgt tcctggtaat    420
caggagatca tcttcaataa gaggaaaggg ttcatggagc tgctgtcaa gattgagtat     480 gactatgacg agaaccctgc gttctctgat ccgtgctacg tcacagttcc gcatttatct    540
taaggtctta ttggcttgga gttggcggat agtcacaccg ttttttttca cacggcaaaa    600
ggcaaagtat tacggctttt ctctcctgtc ctgtttagcg gatgtacgat gtatgttgta    660
```
gtagtgttct ggaatttgtg ttcaagttgt tgg    693

<210> SEQ ID NO 126
<211> LENGTH: 1030
<212> TYPE: DNA
<213> ORGANISM: Unknown
<220> FEATURE:
<223> OTHER INFORMATION: metagenomes purified from environmentally
      challenged niches

<400> SEQUENCE: 126
gagcgacttc atcaaaaatg tcagagcaac ttcactacaa gggttcattg gccggccacg    60
gcaactgggt tactgccatc gctacctctg cagagaaccc agacatgatc ctcactgctt    120
cccgtgacaa gtctgtcatc gtctggcaac tcacccgtga cgacgctcag tacggttacc    180
caaagagaat cctcaagggc cacaaccact tcgtctctga cgtctccatc tcatacgacg    240
gtcaattcgc tttgtcctcc tcatgggaca agaccctccg tctctgggac ctcaacactg    300
gtcttaccac cagacgtttc gttggccacg aagcagacgt tctctccgtc tccttctccg    360
ccgacaacag acaaatcgtc tctggctccc gcgaccgcac catcaagctc tggaacaccc    420
ttggtgaatg caagttcgac atcaaggatg aaggccactc cgaatgggtt tcatgcgttc    480
gtttctctcc aaacccaatg aacccagtca tcgtctcagc tggttgggac aaggttgtca    540
aggtttggga actctcaaac tgcaagctca agaccaacca ctacggtcac actggctaca    600
tcaacaccgt ctctgtctcc ccagacggat cccttgctgc ctccggcggt aaggacggca    660
tcaccatgct ttgggacctc aacgagggca agcacctcta ctccctcgag ctggtgacaa    720
ttgtcaacgc actcgtcttc tcaccaaacc gttactggtt gtgcgctgct actgcctcat    780
gcatcaagat cttcgacctc gagtccaagt ccatcgtcga cgagctcaag ccagactttg    840
tcgacgtcgg caagaactcc cgcgagccag aagctgtctc cctctcctgg tccgctgatg    900
gtcaaaccct cttcgctggt ttcaccgaca acgccgtccg tgtctggacc gtcgcataaa    960
actaagctgt atctaataga cagggtattg ggttttgtaa cactattgcg aggaactcat   1020
gatttttaccg                                                          1030

<210> SEQ ID NO 127
<211> LENGTH: 668
<212> TYPE: DNA
<213> ORGANISM: Unknown
<220> FEATURE:
<223> OTHER INFORMATION: metagenomes purified from environmentally
      challenged niches

<400> SEQUENCE: 127
ggggaaggtg gtggtatcca cggaaccacc ttcaactcca tcatgaagtg tgatgttgac    60
gtccgtaagg atctctatgg caacattgtc atgtctggtg gtactactat gtaccctggt    120
attgccgacc gtatgcagaa ggaaatcacc gctcttgctc cttcgtcgat gaaggtcaag    180
atcattgctc ctcctgagcg taaatactct gtgtggattg gtggttccat cctggcttct    240
ctgtccacct tccagcagat gtggatctcg aagcaggagt acgacgagag cggcccttcg    300
atcgtccacc gcaagtgctt ctaagcttaa gcgcatggtt gatttgcttg tttgtacttc    360
ttttctggcg tatcaaaagg caggacagtg tggcatgcgg accttttctg acctgatgac    420
gagagggatc gcctaagaaa aaggaacttt atttttagttg tggaatagag acggtttatt    480
tgacgctagt tctcgtccag agcatcctcg agacgatagt ctgggttcgt cttaagcgat    540

```
ggatggtggt gattctcttc gtattgttcc tgtacctgta ctacatattg cctacaccat    600
gtcctgttca tttcttctct gtttgcgttg cgttagacct tataaattta aatgtcgtat    660
tgctcccc                                                             668
```

<210> SEQ ID NO 128
<211> LENGTH: 668
<212> TYPE: DNA
<213> ORGANISM: Unknown
<220> FEATURE:
<223> OTHER INFORMATION: metagenomes purified from environmentally
      challenged niches

<400> SEQUENCE: 128

```
ggggagcaat acgacattta aatttataag gtctaacgca acgcaaacag agaagaaatg     60
aacaggacat ggtgtaggca atatgtagta caggtacagg aacaatacga agagaatcac    120
caccatccat cgcttaagac gaacccagac tatcgtctcg aggatgctct ggacgagaac    180
tagcgtcaaa taaaccgtct ctattccaca actaaaataa agttcctttt tcttaggcga    240
tccctctcgt catcaggtca gaaaaggtcc gcatgccaca ctgtcctgcc ttttgatacg    300
ccagaaaaga agtacaaaca agcaaatcaa ccatgcgctt aagcttagaa gcacttgcgg    360
tggacgatcg aagggccgct ctcgtcgtac tcctgcttcg agatccacat ctgctggaag    420
gtggacagag aagccaggat ggaaccacca atccacacag agtatttacg ctcaggagga    480
gcaatgatct tgaccttcat cgacgaagga gcaagagcgg tgatttcctt ctgcatacgg    540
tcggcaatac cagggtacat agtagtacca ccagacatga caatgttgcc atagagatcc    600
ttacggacgt caacatcaca cttcatgatg gagttgaagg tggttccgtg gataccacca    660
ccttcccc                                                             668
```

<210> SEQ ID NO 129
<211> LENGTH: 1018
<212> TYPE: DNA
<213> ORGANISM: Unknown
<220> FEATURE:
<223> OTHER INFORMATION: metagenomes purified from environmentally
      challenged niches

<400> SEQUENCE: 129

```
gactttctca tttcagaatt attttctata ctctgacaag agcaagcaat accaaacatc     60
ttccacatcg aagctttaac cattttgccc ttaacatttg aacaagacga aatggccttc    120
ttcccacact acaccactaa tctgtcgcct ctgctctact tgttggacga cgactatgct    180
gtctaccgct caacttgtcc aaagtccaac taccaccaca agcaacacca cagccgccgt    240
cagccttcgc cagttcgtta ctttagtccg aattttgata tgcgagaggg gaatgactcc    300
tactaccttg acggagagct ccctggtgtc aaccagaatg atgtcgatat tgaattctct    360
gaccctcaga cactggtgat caagggtcga gtggagcgga attacaacaa tctcgacggc    420
atgaacgagg aaaaccagca agatgaagaa caattctctg aaactctctc tagcaagtcg    480
taccaaccca ctgtcgagga cgaggacgag gcgaaccatt caccaccccgt ggcgacacca    540 acctactctg agaagtctgt tactgagaaa actcagaagc ctgcgtacaa ataccgaaat    600
tctgaacgtg ctattggcga attccaccga gccttcaatc tccctacaag agtcgatcaa    660
gatgcggtca gggctacatt gaggaatgga atcctctcgc tggagctccc gaaggagccg    720
gcaccgaaga tgaagaagat tcggattgaa tagaggattt cgaataaaat ttttgatttg    780
atgagtagtt ggtgtttatt gttatgtcta attatatggg gctatgtcat gattgggaaa    840
```

```
tgggacaccg catttgtttc cttttttcccc atttcttcag acgccatcta tattgcatgt    900
atgttgcatg aactatggtt tttgctagga gcggttgctt ctgctttgca ttttcatgaa    960
ctattttctt tttattaaat taataactag catatcaatt aatgatctgt catatggc     1018
```

<210> SEQ ID NO 130
<211> LENGTH: 686
<212> TYPE: DNA
<213> ORGANISM: Unknown
<220> FEATURE:
<223> OTHER INFORMATION: metagenomes purified from environmentally
      challenged niches

<400> SEQUENCE: 130

```
aagctttcag aagctaatcg agttcttcct atccctttca actttacaca ccatgtctag     60
aattggcgat ccaacgaaca accctgctac ccagcaactg tactctgata ggcccttgca    120
tctccctggc cccggcctca agccatccag gcagctcact atcagctcgg ctgttgcgtt    180
ccgcgaggat tcgggccaaa cacgcttcaa cctcatcagc tctgaccacc gcgaggtgtt    240
gcacattagt attcgtgcaa gggacaacgt tctcgtgctc aacaccaagg cccccgatgg    300
cgattggggc aaagaagagc gacatgatct caaacccctt ttcgataccc cactgctgcc    360
ttacatcacc gtaatggcaa cgaagaacag ctatatcctt tctgttcctg gtaaacggga    420
gatcatcttc aataagagga aagggttcat ggagcctgct gtgaggattg agtatgacta    480
tgatgagatg tctgcgttct ccgacccctg ctacattaca gtcccatctt catcttaaag    540 cttcctagt tggcttggag ttggcggata tggtcacatt ggttttttca cacggcaaac    600
ggtaaagaat tacggcttct ctctcctgtc atgttcagcg gacgatgtat gatgtagtgt    660
tctgttcaat tgatctggtt gttgac                                        686
```

<210> SEQ ID NO 131
<211> LENGTH: 698
<212> TYPE: DNA
<213> ORGANISM: Unknown
<220> FEATURE:
<223> OTHER INFORMATION: metagenomes purified from environmentally
      challenged niches

<400> SEQUENCE: 131

```
gggcatataa ccacaggtca ttcgcatccg tcgcagaact tcttacatct gagctttcct     60
gtccgttaga tataggcaaa atgaaggcct actggtacga taaccaaccg ggcgaccagc    120
gcttgcctca cgactccggc cgccccgtca ccgagtccta cctcgagtcc atcggcgtct    180
tctaccgcca ctgcccaaca attgaccttg tcgactccct ggccgccgag cgcggctaca    240
agaaccgcga cgaggtctgc gtctcgccgc agactatggg cgatgtctac gaggagaagg    300
tgaagacgtt ctttagtgaa catttgcacg aggacgagga gattcggtac attcgagatg    360
gggaggggta ctttgatgtg cgtgggcagg aggatgagtg ggtacggatt cggttgagta    420
aggatgatct gatcattctt ccggctggga tctaccatcg gtttacgaca gatgataaga    480
actacgtcaa ggctatgcgt ctcttccagg aggagcccaa gtggacgccc ttgaaccgtg    540
gccctgaggt tgatgtcaac cctcaccgga agacatacct ggaaaccgtc cccagccctg    600
ctgtggctgc gaactaagtg agcatcgaat gctcttgttg aacaatctat ttgcacatct    660
ttagccttta tacacctcaa tgcatcaatg gatttagg                           698
```

<210> SEQ ID NO 132

| | |
|---|---|
| <211> LENGTH: 884 | |
| <212> TYPE: DNA | |
| <213> ORGANISM: Unknown | |
| <220> FEATURE: | |
| <223> OTHER INFORMATION: metagenomes purified from environmentally challenged niches | |

<400> SEQUENCE: 132

```
gtggctgccg gctacacccc cgaggccctc gagatcctct ccaagaagaa gggcggcaag      60
tacctcgtcc tcgagatgga cgagacctac aaccccccg ccgaggagac acgtactctc     120
tacggtgtcc agctcaccca ggcccgcaac gatgctgtca tctccccca gaagaccttc     180
aataccatca ttaccccaa gaacaccgag tccctcccg agtccgccct ccgcgacctc     240
accgtcgcca ccctcgccct gaaatacaca cagtccaact ccgtctgcta cgcgctcaac     300
ggacaggtcg tcggcctcgg tgccggccag caaagtcgta tccactgcac tcgtcttgcc     360
ggcgacaaga ccgacaactg gtggatgcgc ttccacgagc gcgtgctcaa catcaagtgg     420
aagcagggca ccaagcgtgc tgacaagagc aacgccatcg acctgctctg ctcgggccag     480
acgccccgca atgacgctga aaggtcgag tacgagcgtg tgttcgcgga ggttcctgct     540
ccgttcaccc aggaggagcg tgatgcttgg ctctcgcagt tgaccaacgt tgctatttct     600
tcggatgctt tcgtatgtct ctcccctctg ttagagcatt ctaagttcta agatcatgct     660
aattggtgaa atagttcccc ttcatcgaca acgtcttccg agccgcccgc tccggcgtca     720
agtacatcgc tgcacccagc ggttcgcaga acgacggccc tgtcttcgag actgccgaga     780
agcttggtat ctcgttcgtt gagcagggta ctcgtctgtt ccaccactaa cttgcttttc     840
cggtggcgtg gtattatggt ataaaaagaa aaagggtttg gggg      884
```

| | |
|---|---|
| <210> SEQ ID NO 133 | |
| <211> LENGTH: 822 | |
| <212> TYPE: DNA | |
| <213> ORGANISM: Unknown | |
| <220> FEATURE: | |
| <223> OTHER INFORMATION: metagenomes purified from environmentally challenged niches | |

<400> SEQUENCE: 133

```
gtggctgccg gctacacccc cgaggccctc gagatcctct ccaagaagaa gggcggcaag      60
tacctcgtcc tcgagatgga cgagacctac aaccccccg ccgaggagac acgtactctc     120
tacggtgtcc agctcaccca ggcccgcaac gatgctgtca tctccccca gaagaccttc     180
aataccatca ttaccccaa gaacaccgag tccctcccg agtccgccct ccgcgacctc     240
accgtcgcca ccctcgccct gaaatacaca cagtccaact ccgtctgcta cgcgctcaac     300
ggacaggtcg tcggcctcgg tgccggccag caaagtcgta tccactgcac tcgtcttgcc     360
ggcgacaaga ccgacaactg gtggatgcgc ttccacgagc gcgtgctcaa catcaagtgg     420
aagcagggca ccaagcgtgc tgacaagagc aacgccatcg acctgctctg ctcgggccag     480
acgccccgca atgacgctga aaggtcgag tacgagcgtg tgttcgcgga ggttcctgct     540
ccgttcaccc aggaggagcg tgatgcttgg ctctcgcagt tgaccaacgt tgctatttct     600
tcggatgctt tcttcccctt catcgacaac gtcttccgag ccgcccgctc cggcgtcaag     660
tacatcgctg cacccagcgg ttcgcagaac gacggccctg tcttcgagac tgccgagaag     720
cttggtatct cgttcgttga gcagggtact cgtctgttcc accactaact tgcttttccg     780
gtggcgtggt attatggtat aaaaagaaaa agggtttggg gg     822
```

<210> SEQ ID NO 134
<211> LENGTH: 996
<212> TYPE: DNA
<213> ORGANISM: Unknown
<220> FEATURE:
<223> OTHER INFORMATION: metagenomes purified from environmentally
      challenged niches

<400> SEQUENCE: 134

| | | | | | | |
|---|---|---|---|---|---|---|
| tgaagcagtg | gtatcaacgc | aagcagtggt | atcaacgcag | aatgtgcgat | cgctctagaa | 60 |
| tcggtcccaa | gggttgggaa | gcagtggtat | caacgcaagc | agtggtatca | acgcaagcag | 120 |
| tggtatcaac | gcaagcagtg | gtatcaacgc | aagcagtggt | atcaacgcaa | gcagtggtat | 180 |
| caacgcagag | tgcgcagccc | ggtgctatct | ctgctcctgt | ggcagctggt | aaggacgttg | 240 |
| agctgcagtg | gaccgaatgg | ccggaaagtc | atcatggccc | tgtcattact | tacctggcca | 300 |
| actgcaacgg | tgactgctct | gaggtcgaca | aatcctctct | ggagttttc | aagatcgatc | 360 |
| agaagggtct | catcgatgac | agcaatgtcc | ctggcacatg | gctaccgac | aaactaatct | 420 |
| ccaacaacaa | cagctacacc | gtcaccatcc | ccagcgacat | tgctgccggt | aactacgtcc | 480 |
| tccgccatga | aatcattgct | ctgcactccg | ctggcaacga | ggatggtgcc | cagaactacc | 540 |
| cccagtgtct | caacctcaag | gttactggtg | gtggcaacgc | ttctccctca | ggtactcttg | 600 |
| gtaccaagct | ctacaacgag | gacgactcgg | gtatccttgt | cagtatctac | cagcagcttg | 660 |
| actcctacga | catccccggc | cctgctctgt | actctggcgc | ttcctcgtcc | tccaactctg | 720 |
| gttcttcttc | cagcgttgct | tcggccactg | cttctgccac | ttctgccgct | gcttcctctc | 780 |
| cctcgtcctc | tcaggcttcc | ggtacccccg | cttcccaggt | caaggctcag | accgctagct | 840 |
| ctactcctag | cgcttcgtcc | ggtgccactt | ccggcagtct | gtccgactac | ttcagctctc | 900 |
| tgagcgctga | ggagttcctc | aacgttatca | gcgagactct | gtcttggttg | gtcactgaca | 960 |
| agattcacgc | tcgtgacttg | tcgaccgcat | aaatgg | | | 996 |

<210> SEQ ID NO 135
<211> LENGTH: 823
<212> TYPE: DNA
<213> ORGANISM: Unknown
<220> FEATURE:
<223> OTHER INFORMATION: metagenomes purified from environmentally
      challenged niches

<400> SEQUENCE: 135

| | | | | | | |
|---|---|---|---|---|---|---|
| gtggtatcaa | cgcagagtgc | gcagcccggt | gctatctctg | ctcctgtggc | agctggtaag | 60 |
| gacgttgagc | tgcagtggac | cgaatggccg | gaaagtcatc | atggccctgt | cattacttac | 120 |
| ctggccaact | gcaacggtga | ctgctctgag | gtcgacaaat | cctctctgga | gtttttcaag | 180 |
| atcgatcaga | agggtctcat | cgatgacagc | aatgtccctg | gcacatgggc | taccgacaaa | 240 |
| ctaatctcca | acaacaacag | ctacaccgtc | accatcccca | gcgacattgc | tgccggtaac | 300 |
| tacgtcctcc | gccatgaaat | cattgctctg | cactccgctg | gcaacgagga | tggtgcccag | 360 |
| aactacccc | agtgtctcaa | cctcaaggtt | actggtggtg | gcaacgcttc | tccctcaggt | 420 |
| actcttggta | ccaagctcta | caacgaggac | gactcgggta | tccttgtcag | tatctaccag | 480 |
| cagcttgact | cctacgacat | ccccggccct | gctctgtact | ctggcgcttc | ctcgtcctcc | 540 |
| aactctggtt | cttcttccag | cgttgcttcg | gccactgctt | ctgccacttc | tgccgctgct | 600 |
| tcctctccct | cgtcctctca | ggcttccggt | accccgctt | cccaggtcaa | ggctcagacc | 660 |
| gctagctcta | ctcctagcgc | ttcgtccggt | gccacttccg | gcagtctgtc | cgactacttc | 720 |

```
agctctctga gcgctgagga gttcctcaac gttatcagcg agactctgtc ttggttggtc    780
actgacaaga ttcacgctcg tgacttgtcg accgcataaa tgg                      823
```

<210> SEQ ID NO 136
<211> LENGTH: 1000
<212> TYPE: DNA
<213> ORGANISM: Unknown
<220> FEATURE:
<223> OTHER INFORMATION: metagenomes purified from environmentally
      challenged niches

<400> SEQUENCE: 136

```
gacggtgaag ttggaataga ataaaatgtt gagcatgttt accagagtgg ccagaggaca     60
ggccaaggtg tttacccgca acgcatccac agcatcatcc aaaccaacga atcaatcatc    120
caacaaggct gccactatcg cagcttcaat ttcaggtgtt accgccgcgt tatacgccca    180
ccaatacggc ctcattgaca gcgtcttcgc tagtggctta aagagggtt tgcacgctcc     240 tcatttccct tggtcacaca atggctggtt ggacagcttt gaccacaact ccattagacg    300
cggttaccaa gtttaccgtg aggtgtgcag ctcgtgtcac tctttggaca gaatagcgtg    360
gagaaacctt gtcgctgtgt cacacacttc agatgaagcc agagcgatgg ctgaagagca    420
agagtacact gatggtccaa atgaccaagg agagtctttc caaagacctg gtaaattggc    480
tgattacatg ccagctcctt atccaaatga ggaagcttcg agggccgcca atggtggtgc    540
tcttcctcct gatctttctc tcatcgttaa agcaagacac ggaggagctg attacattat    600
ggctctgctc actggttacc aggatcctcc tgctggtatt caagttcaag agggcatgaa    660 cttcaacccca tatttcccag gtggtggtat tgccatgggt agagttttgt tcgatggtct    720
ggtagaatac gacgatggca ctcctgctac tactacacaa atggctaagg atgtcgctac    780
tttcctcagc tgggctagtg agccagaaca cgacgacaga aagaagatgg gcttccaagc    840
tgtcattatc ctctcagcta tgaccgccat ctcactctac gtcaagagac tcaagtggtc    900
gcctatcaag acgaggaaac tgacttacaa cccaccaaag tgatctgaat gtagagaaaa    960
gtttgacccg tataaaaaat ttcatcctct ccttttccg                          1000
```

<210> SEQ ID NO 137
<211> LENGTH: 544
<212> TYPE: DNA
<213> ORGANISM: Unknown
<220> FEATURE:
<223> OTHER INFORMATION: metagenomes purified from environmentally
      challenged niches

<400> SEQUENCE: 137

```
ggaggtagtc cagccaaaaa gagtttgata ggcgcgatgg aggcacaaaa tctcaagact     60
ttcccaaagc aacctatctt ccaaaactca aagacccgtg gtaacaagaa ggtcaccaag    120
gaccgtcgtt ggtacaagga cgtcggtctc ggtttcaaga ctcctcaaga agccatcacc    180
ggtacttaca tcgacaagaa gtgccccatgg accggtgagg tttccatcag aggccgtatc    240
ttgtccggca aggtggtctc taccaagatg acccgtacga tcgtcatcag aagagagtac    300
cttcactacg tgccaaagta caacagatac gagaagcgtc acaagaacct cccagtgcac    360
gcatcacctg cattccgtat cgagaatggt gaccaagtcg tcgttggcca atgccgtcca    420
ctttcaaaga ctgtgagatt caacgtcctc cgtgtcatca agaacaaggc tgctgctaag    480
gctttcgcaa agttctaaac ttgttattaa tgtagttggt ccattcacag aattttgaaa    540
gtcc                                                                 544
```

<210> SEQ ID NO 138
<211> LENGTH: 938
<212> TYPE: DNA
<213> ORGANISM: Unknown
<220> FEATURE:
<223> OTHER INFORMATION: metagenomes purified from environmentally
      challenged niches

<400> SEQUENCE: 138

| | | | | | |
|---|---|---|---|---|---|
| acgttcaatt | gacttttcca | ttcttttgtt | cgttctgaag | agttttctttt | tttctttcat | 60 |
| tgtcgcctcc | tttctttcgc | cttcccgttg | tttccgatca | tcgggtgttg | ccagagtata | 120 |
| tatagagttg | gggctcccct | ttatctatct | caccgcaacc | gtcctcctga | tcctctctcc | 180 |
| tgatcctcct | ccttcattcc | ttgactcctc | ttcacgctcc | tcctgaccag | ccaagtctta | 240 |
| catccctctc | tacaactact | actcttcaaa | taatcctctc | ctctcggtgg | gcttgaatcc | 300 |
| cttatcttcc | gcctccccc | acgaaccgga | ccggatcgtc | ttatcgcctc | cgcaccagct | 360 |
| ggcgcttact | acctcatcca | cctctttccc | gtctcgccac | cgaaaccagt | ctacaatgcc | 420 |
| tcctcgcaag | cccagatgct | cctttaagga | gtgcaaggaa | caagcccagc | gcattgtcgg | 480 |
| agactgcagc | ttctgcagcg | gtcacttctg | ctccaagcat | cgcatgctcg | aagcccactc | 540 |
| ctgctccggt | ctggaagact | gcaagaagga | gtcccacgcc | cgcaatgctg | ataagttgaa | 600 |
| cagcgagcgc | acacaggtta | tcaagggtgt | atgacgggga | cacatctaca | ctactacaac | 660 |
| aatctcggcg | catttcgatt | gcatttactt | gccattttta | tccgacgttg | agttagcgcg | 720 |
| gtgttattta | caatttcttc | tttctttat | tttgcctacg | atgtctcccc | ctatcggtat | 780 |
| ggtggtgtct | cgtttcggga | gcgacatggt | ttacaatgat | tttggtttgg | ggtggtctct | 840 |
| cggtatttgt | ctattatcca | cttatttcc | ggggtattat | gcgcatggcg | ttactatatg | 900 |
| gagtttgata | ttctatctcg | aatcgatact | tttacaac | | | 938 |

<210> SEQ ID NO 139
<211> LENGTH: 687
<212> TYPE: DNA
<213> ORGANISM: Unknown
<220> FEATURE:
<223> OTHER INFORMATION: metagenomes purified from environmentally
      challenged niches

<400> SEQUENCE: 139

| | | | | | |
|---|---|---|---|---|---|
| aagctctccc | aagctaatcg | agtttttact | gtcacttgca | tttatacata | ccatgtctag | 60 |
| gaacttcggc | gattttcga | ctaaccaggc | tactcagcag | ctgtactccg | atagacccctt | 120 |
| gcatctccct | ggaaatggcc | ttaagccggc | tagacagctc | acgatcagtt | cagctgtcgc | 180 |
| attccgctgg | gactctgacc | aaacccgctt | caacctgatc | agctctgacc | gtcgcgaagt | 240 |
| gttgcacatc | agcattcgcg | caaaagacaa | cgttctcgtc | ctcaacacca | aggcgcccga | 300 |
| tggtgactgg | ggcagggaag | agcgacacga | gctcaagaaa | ctttcgata | ccctatgct | 360 |
| gccttacatc | accgtgacgg | cgacgaagat | gacctataac | atcactgtcc | ctagtggtca | 420 |
| agaaatcatc | ttcaacaaga | ggaaaggatt | catggaacct | gctgtgaaga | ttgagtatga | 480 |
| ctatgatgag | cactctgcgt | tctccgaccc | atgctacatt | acgttccat | cttcttaaag | 540 |
| gctcgtcggc | ttagagttgg | cggatagtca | cactggtttt | tcatacggca | acggcaatg | 600 |
| tattacggct | tttctctcct | gtcctgttca | gcggtagatg | tacgatgtat | gttgtagtgt | 660 |
| ttcaaatttg | agttcaagtt | gttggcc | | | | 687 |

<210> SEQ ID NO 140
<211> LENGTH: 601
<212> TYPE: DNA
<213> ORGANISM: Unknown
<220> FEATURE:
<223> OTHER INFORMATION: metagenomes purified from environmentally
      challenged niches

<400> SEQUENCE: 140

| | |
|---|---:|
| gtctgcttgc ttcaacgagc gctgaatttc ttgttggccg gtgttgattc cccggattcc | 60 |
| ctgttatcgc ctgctgtgtt cgccttggta gcaggtgttt gaattggtcc tgcaatttcg | 120 |
| ctgattgctg gcctcgaact cccgatcgaa cgaactctcc tctcctccgt caacgcacct | 180 |
| tcacatatcg caaagcacaa tggtttccaa gattctcttc tggagtggct tcggcatcgc | 240 |
| cgtccgtctc tggcaactcg gtatcgaaat gcgtcccatt cttgccaagc agggtctctg | 300 |
| ggcctacccc gtcttcgcag gtgtcggtgg aagcttcggt tactggctcc agggtgtcga | 360 |
| ggaccgtcag ctgaagattc ttgcgcagcg ccgcgaagcc atcctcgaca agcgccggag | 420 |
| acgggacgag cgtgagggtc tgagcaacat tgagaaggag ggtactttgg ctgcgacccc | 480 |
| atgatttgtt gcgttggctg ttgtttattt tcactgcctt cggagaaaga ccggcaattg | 540 |
| cattgctggg catgtatcat accaaaacag aggaaggtta atggtcaatt gtttaatgac | 600 |
| c | 601 |

<210> SEQ ID NO 141
<211> LENGTH: 601
<212> TYPE: DNA
<213> ORGANISM: Unknown
<220> FEATURE:
<223> OTHER INFORMATION: metagenomes purified from environmentally
      challenged niches

<400> SEQUENCE: 141

| | |
|---|---:|
| ggtcattaaa caattgacca ttaaccttcc tctgttttgg tatgatacat gcccagcaat | 60 |
| gcaattgccg gtctttctcc gaaggcagtg aaaataaaca acagccaacg caacaaatca | 120 |
| tggggtcgca gccaaagtac cctccttctc aatgttgctc agaccctcac gctcgtcccg | 180 |
| tctccggcgc ttgtcgagga tggcttcgcg gcgctgcgca agaatcttca gctgacggtc | 240 |
| ctcgacaccc tggagccagt aaccgaagct tccaccgaca cctgcgaaga cggggtaggc | 300 |
| ccagagaccc tgcttggcaa gaatgggacg catttcgata ccgagttgcc agagacggac | 360 |
| ggcgatgccg aagccactcc agaagagaat cttggaaacc attgtgcttt gcgatatgtg | 420 |
| aaggtgcgtt gacggaggag aggagagttc gttcgatcgg gagttcgagg ccagcaatca | 480 |
| gcgaaattgc aggaccaatt caaacacctg ctaccaaggc gaacacagca ggcgataaca | 540 |
| gggaatccgg ggaatcaaca ccggccaaca agaaattcag cgctcgttga agcaagcaga | 600 |
| c | 601 |

<210> SEQ ID NO 142
<211> LENGTH: 380
<212> TYPE: DNA
<213> ORGANISM: Unknown
<220> FEATURE:
<223> OTHER INFORMATION: metagenomes purified from environmentally
      challenged niches

<400> SEQUENCE: 142

| | |
|---|---:|
| gggggcgaca tggcttcgac gccggtgaca atccctgagg tgcatgccga gagcgtaacg | 60 |

```
tatctcgtaa atccaacgtt acgataaaat agtcgcaaac gacgacaact acgctcaggg    120
cgcgctggca gcgtaacaac tgctagcttc tagtccggcc cggaggtgat gtgcccattc    180
atcaccgaag ggatacgagc tcagactgat gggatcgcgg ctggctttgt cctcgcgtca    240
gccgctaaaa cttagaggaa tcgcgtcgct ggatcctgcc cgtcggagcc agaggcgcta    300
aatcaaaaga cggacctaag catgtagagc cgatgggtga gtgccggcgg acggggttc     360 aattcccccc gcctccacca                                                380

<210> SEQ ID NO 143
<211> LENGTH: 977
<212> TYPE: DNA
<213> ORGANISM: Unknown
<220> FEATURE:
<223> OTHER INFORMATION: metagenomes purified from environmentally
      challenged niches

<400> SEQUENCE: 143
gggaccagaa cagcttcagc tacaatgcca ttcatcaagg aagccaagag caacagctac     60
ttctctcgct accaagtcaa gtaccgcaga cgtcgtgaag gcaagactga cttctacgca    120
cgtaagcgct tggtaacgca agctaagaac aagtacaacg caccaaagta ccgtctcgta    180
gttagattca cgaacaagga catcatctgt caaatcgtgt catcaaagct tcaaggtgac    240
gttgttctca ctcacgctcg cgcccgcgaa cttccacgtt acggcatcaa gcacggtctc    300
acgtcatggt catccgctta cgcggttggt ctcctcgtcg caagaagagc gctcaccaag    360
ctcggtcttg ctgacaagta cgagggtgac gttgaagcta ctggtgaata caacctcacc    420
gagccacttg gcgatgatga accacgtcct ttcaaggtct tccttgacgt tggtcttaag    480
cgtacctcta ctggttctag agtcttcggt gctcttaagg gcgcctcaga cggtggtctc    540
tacatccctc actctgagaa ccgtttccca ggttacgata tcgagagcaa ggaactcgac    600
gctgaaatct tgaacaagta catcttgggt ggtcacattg ctgagtacat ggaggctctt    660
gaggaggaag atgaggagag attcaaggct caattctcta cctatcttga agacggtatt    720
ggatctgagg acattgaaga aatcttctcg ggcgcacacg aggctatccg tgctgaccca    780
accttcaagc caagtgaggc tgccaagggc accgactgga agtccgagtc aaagaagcac    840
cgcgctgtca gactcaccaa gcaacaacgc gaggacgcta ccaacagcg tatcaagtac     900 taccagcaag ctggcgacct cgagtaaacg gtaattgtag cggtctacat agacaatcaa    960
tgtctgttgt tccttag                                                   977

<210> SEQ ID NO 144
<211> LENGTH: 73
<212> TYPE: DNA
<213> ORGANISM: Unknown
<220> FEATURE:
<223> OTHER INFORMATION: metagenomes purified from environmentally
      challenged niches

<400> SEQUENCE: 144
gattacccgc tgaacttaag catatcaata agcggaggaa aagaaactaa caaggattcc     60
cctagtaacg gcg                                                        73

<210> SEQ ID NO 145
<211> LENGTH: 823
<212> TYPE: DNA
<213> ORGANISM: Unknown
<220> FEATURE:
<223> OTHER INFORMATION: metagenomes purified from environmentally
``` challenged niches

<400> SEQUENCE: 145

| | |
|---|---|
| gggtctcttc catttgaatt tttcaaccca cagcatggcc ttcatgaatc tcccatggcc | 60 |
| cactgaatgc ctacatgccg ctctcaagaa cggatcctta cctttctggg gatttgtaat | 120 |
| ctatcgaacg acctacaccg ctcagtcaga tgccgcctgg ccgcagatta tcgagcttat | 180 |
| tgcctcctat atgaaagcct tactctacca cgagtataac gacaagaaaa agatggaga | 240 |
| tgagcctaca gtctacgacg aaatctgggc aaggcatcag ttgacgatta tggatgatag | 300 |
| acaattcaac ggagcgtctg tgtttgatat ccaacttcac ttcgaaaagt gggttgaggc | 360 |
| gcagggaaag cgagatgaat ctactatgta tcgcatgtgt atggtcattg atgatgaatc | 420 |
| aatccagacg ttattggagg cgccacccgg ggaaaatagg aaactcggac gacgtatagg | 480 |
| gggccctgta cgctttgtca agtcgtgga ggctttcccc gagctagaca gccttgacga | 540 |
| attccaggga tggatgaaat gtgagatcaa cgcgttatgg ccgctgtgga agatgatgtc | 600 |
| tgacggagat gaaatgagga tgtcatatga tgagatgaag gggaatggaa agcaggtcta | 660 |
| tggcgcaatt taatcggttt ttcttcatgt tatcctgatg gaaaaaatgg cagaacatat | 720 |
| gtctgtacat gcagaaaata aggtgattgg aaaatacttg aatgctatga agttagatag | 780 |
| tagctgttct agcggccaga taaagccgcg catgtgaatt tcg | 823 |

<210> SEQ ID NO 146
<211> LENGTH: 181
<212> TYPE: DNA
<213> ORGANISM: Unknown
<220> FEATURE:
<223> OTHER INFORMATION: metagenomes purified from environmentally
    challenged niches

<400> SEQUENCE: 146

| | |
|---|---|
| gtactaacca ctcgtcaggc gctgaaagaa gaagatgcag taagtttgat gttttctgtg | 60 |
| tatgattata cataaagttg ttgtataact acgcagaaaa gttttcgtat gcaaaacttt | 120 |
| gattggtgtt aagtcgaaat aaggttcgtg taatggaaat tgcacgggga gtataaaatg | 180 |
| t | 181 |

<210> SEQ ID NO 147
<211> LENGTH: 734
<212> TYPE: DNA
<213> ORGANISM: Unknown
<220> FEATURE:
<223> OTHER INFORMATION: metagenomes purified from environmentally
    challenged niches

<400> SEQUENCE: 147

| | |
|---|---|
| atgacagaga aactttacac cgagcaagtg aatgcgttcg gaaacgaatt acctcctcta | 60 |
| tcatacaaag acctggacaa actccccta caccaaaacg tcatcaaaga aactcttcga | 120 |
| atccacaact caattcatac actcatgcgt aaagtgaaaa atccctcc agtcccagga | 180 |
| acaagattcg ttataccaac cagtcacacc ctcctcgcgt ccccgggcgt aacaacccgc | 240 |
| gacgattcac acttccgaaa cgcaatgacc tgggatccac accgttggga aacacgaagt | 300 |
| gaggtcgaag atgatggtga gacaatcgat tatggatatg gggttgtttc aaaggggacg | 360 |
| aagagtcctt atttgccctt tggagcgggt cgacatcgat gtattgggga gaaattcgca | 420 |
| tacttgaatc ttactgttat tgttgctact cttgtgagga attttcggtt ttctgaacct | 480 |
| gatgatagag agggtgttcc tgaaacggat tattcgtcac tcttttctag acctatgcgg | 540 |

-continued

```
ccggcgactg ctcggtggga acgacgtggg gagtactaga ggtgggatta ttggggattt      600
gattgctttt tggaattggg atggaagagt tcttgggata tattcttgtt cttcgaggct      660
ttcccaggtg attttcaca gggcttggta ttatcgtatt taatcaatca attcactaca      720
cttttcgagc ttgc                                                        734
```

<210> SEQ ID NO 148
<211> LENGTH: 741
<212> TYPE: DNA
<213> ORGANISM: Unknown
<220> FEATURE:
<223> OTHER INFORMATION: metagenomes purified from environmentally
      challenged niches

<400> SEQUENCE: 148

```
ttatggccca ttggagagag gagtacctaa ctgcactggc agtgcgagat cagagggaga       60
aggccaatct cagtatttac gatgcctata cccgactcgc agatagcacg gccaaacttc      120
cagctacaat agatacaagt ggcagcccct caggtgataa agggccatct ggtacctacg      180
agtccgaaaa gacggcattt tctcaatcaa ggacagccaa gaagcagcag acagaagtgg      240
agccttcagt tacggagctt ctaaatacta cacgtgcaga actagccgaa gcacagcgct      300
ctcgggcaga attgcgagat cgtctagagc gagctactaa cgaagcggag aaattgcgga      360
aacagattgg caaagatggt cgacgaatac atggactgga aaatgaagtt gctcaacagc      420
aaaagcgccg caaagatgtt gaagaagagt tgagaggaaa ggctaagcta ctcaatgaat      480
tccaagacga aattgcagct ctgactctcc aggtgaacat ggccgagaga aaagctaaga      540
agcttggaga ggagaacgat gatcttgtta atcgttggat gaagagaatg ggccaggaag      600
ctgatgcaat gaatgatgcc tccaagttttt cgtgactgcc gaatcagaat agaatcaaat      660
ggcccagata ggccttcgca ttgttatgac atgatcgaat tccgaggcaa attcgcctat      720
catggtaatg aacggataaa g                                                741
```

<210> SEQ ID NO 149
<211> LENGTH: 213
<212> TYPE: PRT
<213> ORGANISM: Unknown
<220> FEATURE:
<223> OTHER INFORMATION: metagenomes purified from environmentally
      challenged niches

<400> SEQUENCE: 149

```
Met Ala Phe Phe Pro His Tyr Thr Thr Asn Leu Ser Pro Leu Leu Tyr
1               5                   10                  15

Leu Leu Asp Asp Asp Tyr Ala Val Tyr Arg Ser Thr Cys Pro Lys Ser
            20                  25                  30

Asn Tyr His His Lys Gln His His Ser Arg Arg Gln Pro Ser Pro Val
        35                  40                  45

Arg Tyr Phe Ser Pro Asn Phe Asp Met Arg Glu Gly Asn Asp Ser Tyr
    50                  55                  60

Tyr Leu Asp Gly Glu Leu Pro Gly Val Asn Gln Asn Asp Val Asp Ile
65                  70                  75                  80

Glu Phe Ser Asp Pro Gln Thr Leu Val Ile Lys Gly Arg Val Glu Arg
                85                  90                  95

Asn Tyr Asn Asn Leu Asp Gly Met Asn Glu Glu Asn Gln Gln Asp Glu
            100                 105                 110

Glu Gln Phe Ser Glu Thr Leu Ser Ser Lys Ser Tyr Gln Pro Thr Val
```

```
            115                 120                 125
Glu Asp Glu Asp Glu Ala Asn His Ser Pro Pro Val Ala Thr Pro Thr
    130                 135                 140

Tyr Ser Glu Lys Ser Val Thr Glu Lys Thr Gln Lys Pro Ala Tyr Lys
145                 150                 155                 160

Tyr Arg Asn Ser Glu Arg Ala Ile Gly Glu Phe His Arg Ala Phe Asn
                165                 170                 175

Leu Pro Thr Arg Val Asp Gln Asp Ala Val Arg Ala Thr Leu Arg Asn
            180                 185                 190

Gly Ile Leu Ser Leu Glu Leu Pro Lys Glu Pro Ala Pro Lys Met Lys
            195                 200                 205

Lys Ile Arg Ile Glu
    210

<210> SEQ ID NO 150
<211> LENGTH: 164
<212> TYPE: PRT
<213> ORGANISM: Unknown
<220> FEATURE:
<223> OTHER INFORMATION: metagenomes purified from environmentally
      challenged niches

<400> SEQUENCE: 150

Met Gln Leu Leu Ser Thr Leu Thr Pro Leu Ala Leu Leu Val Thr Val
1               5                   10                  15

Ala Ser Ala Thr Gly Lys Ala Val Asn Asn Ala Val Gly Asn Ala Val
            20                  25                  30

Val Thr Asn His Cys Lys Asp Pro Ile Tyr Leu Trp Ser Val Gly Ser
        35                  40                  45

Ser Val Ser Pro Lys His Thr Ile Pro Ser Gly Ser Asn Tyr Thr Glu
    50                  55                  60

Pro Phe Arg His Asp Asp Ala Ser Gly Gly Ile Ala Leu Lys Ile Thr
65                  70                  75                  80

Arg Asn Asp Asn Gly Leu Tyr Asp Gly Ser Ala Gln Leu Val Tyr Ser
                85                  90                  95

Tyr Ala Leu Asp Gly Glu Gln Val Trp Tyr Asp Leu Ser Ser Val Phe
            100                 105                 110

Gly Asp Ala Phe Ala Gly Glu Ala Val Ala Val Lys Pro Glu Asn Glu
        115                 120                 125

Gly Cys Gly Ser Ile Cys Trp Pro Lys Gly Thr Thr Pro Gly Gly Ser
    130                 135                 140

Gln Val Lys Val Cys Asp Ala Glu Gly Asp Val Gly Leu Val Val Cys
145                 150                 155                 160

Ala Lys Gly Cys

<210> SEQ ID NO 151
<211> LENGTH: 149
<212> TYPE: PRT
<213> ORGANISM: Unknown
<220> FEATURE:
<223> OTHER INFORMATION: metagenomes purified from environmentally
      challenged niches

<400> SEQUENCE: 151

Leu Leu Ala Glu Ala Ile Arg Arg Gly Leu Leu Gly Trp Arg Arg Ala
1               5                   10                  15

Glu Ala Lys Trp Gln Arg Cys Cys Cys Trp Leu Ser Thr Gly His Ser
            20                  25                  30
```

```
Ala Arg Lys Cys Thr Arg Glu His Ser Leu Val Leu His Glu Arg Leu
         35                  40                  45

Ser Arg Asn Arg Ala Arg His Trp Gln Gly Val Val Ala Leu Cys Leu
 50                  55                  60

Arg Cys Gln Gln Pro Leu Cys Phe Arg Thr Val Ser Phe Ala Leu Thr
 65                  70                  75                  80

Val Leu Leu Glu Cys Ile Ile Asn Arg Gln Arg Leu Val His Gln Val
                 85                  90                  95

Leu Ala Ile His Ser Arg Asp Cys Leu Val Arg Ala Val Lys Val Val
                100                 105                 110

Val Leu Asp Glu Ser Ile Ser Phe Gln Lys Lys Lys Lys Lys Lys Lys
            115                 120                 125

Lys Lys Thr Gly Gly Gln Val Leu Lys Leu Pro Glu Gly Ile Ser Pro
        130                 135                 140

His Gly Gln Lys Phe
145

<210> SEQ ID NO 152
<211> LENGTH: 119
<212> TYPE: PRT
<213> ORGANISM: Unknown
<220> FEATURE:
<223> OTHER INFORMATION: metagenomes purified from environmentally
      challenged niches

<400> SEQUENCE: 152

Leu Lys Gly Tyr Gly Phe Ile Gln Tyr Asn Asp Phe Asp Ser Ser Asp
 1               5                  10                  15

Gln Ala Ile Thr Ala Met Asn Gly Gln Tyr Leu Met Asn Lys Pro Leu
             20                  25                  30

Thr Val Asp Tyr Ala Phe Lys Lys Asp Gly Lys Gly Glu Arg His Gly
         35                  40                  45

Thr Glu Ala Glu Arg Leu Leu Ala Ala Glu Ala Lys Arg Asn Asn Ala
 50                  55                  60

Leu Pro Met Pro Gly Ala Ile Pro Gly Gln Pro Phe Met Gln Tyr Gln
 65                  70                  75                  80

Gly Met Phe Ala Gly Ala Leu Ser Gly Ala Met Pro Gly Ala Gln Pro
                 85                  90                  95

Ala Ala Thr Pro Leu Pro Phe Gly Phe Ser Pro Ala Pro Gln Gln
                100                 105                 110

Ser Thr Pro Tyr Gly Phe Ser
        115

<210> SEQ ID NO 153
<211> LENGTH: 188
<212> TYPE: PRT
<213> ORGANISM: Unknown
<220> FEATURE:
<223> OTHER INFORMATION: metagenomes purified from environmentally
      challenged niches

<400> SEQUENCE: 153

Met Phe Gly Phe Asn Phe Asn Thr Thr Lys Leu Leu Lys Thr Ile Leu
 1               5                  10                  15

Val Val Cys Tyr Leu Gln Ala Thr Val Leu Ala Asp Pro Tyr Thr Arg
             20                  25                  30

Val Ser Trp Glu Ala Tyr Met Asn His Val Asn Gly Ser Asp Asp Tyr
         35                  40                  45
```

```
Arg Thr Gln Gly Asp Asp Thr Arg Ala Thr Arg Phe Pro Glu Thr Lys
    50                  55                  60

Pro Pro Lys Gln Gly Lys Asp Phe Leu Trp Ser Ser Lys Pro Val Pro
65                  70                  75                  80

Ser Ser Asp Leu Phe Leu Glu Phe Phe Met Tyr Glu Gly Glu Pro Asp
                85                  90                  95

Glu Phe Ser Arg Thr Thr Glu Ser Tyr Gln Ser Leu Pro Ser Asn Ala
                100                 105                 110

Leu Thr Ala Arg Gln Asn Ala Leu Thr Cys Gln Asp Ile Glu Ser Cys
                115                 120                 125

Ser Tyr Pro Pro Gln Val Asn Asn Phe Gln Ala Leu Phe Asp Asp Leu
                130                 135                 140

Gly Pro Ser Thr Cys Asn Leu Ile Lys Asp Glu Thr Arg Asp Trp Ile
145                 150                 155                 160

Leu Gln Gln Trp Pro Gly Leu Ala Val Gly Ala Val Ile Ser Phe Ala
                165                 170                 175

Val Ala Val Ala Gly Ser Ser Cys Asp Ile Leu Tyr
                180                 185
```

```
<210> SEQ ID NO 154
<211> LENGTH: 187
<212> TYPE: PRT
<213> ORGANISM: Unknown
<220> FEATURE:
<223> OTHER INFORMATION: metagenomes purified from environmentally
      challenged niches

<400> SEQUENCE: 154
```

```
Met Val Arg Tyr Ala His Asn Ala Glu Asn Pro Glu Lys Thr Ala Lys
1               5                   10                  15

Ala Arg Gly Gln His Leu Arg Thr His Phe Lys Asn Thr Arg Glu Val
                20                  25                  30

Ala Ala Ala Leu Thr Gly Leu Lys Leu Ser Lys Ala Tyr Lys Tyr Leu
                35                  40                  45

Gly Asp Val Gln Glu His Lys Asp Val Ile Pro Phe Arg Arg Phe Asn
50                  55                  60

Gly Gly Val Gly Arg Ala Ala Gln Ala Lys Asn His Gly Thr Thr Gln
65                  70                  75                  80

Gly Arg Trp Pro Val Lys Ser Ile Gly Phe Leu Leu Arg Leu Leu Lys
                85                  90                  95

Asn Ala Glu Ala Asn Ala Asp Ala Lys Ser Leu Asp Thr Glu Asp Leu
                100                 105                 110

Leu Ile Lys His Ile Val Val Gln Gln Ala Pro Lys Thr Arg Arg Arg
                115                 120                 125

Thr Tyr Arg Ala His Gly Arg Ile Asn Pro Tyr Gln Gly His Pro Cys
                130                 135                 140

His Ile Glu Ile Thr Leu Ala Val Pro Asp Gln Val Ala Arg Asn
145                 150                 155                 160

Lys Asp Val Glu Val Asn Gln Pro Lys Lys Ile Gln Gly Asn Lys Arg
                165                 170                 175

Gln Val Ala Ala Gln Arg Arg Leu Thr Ser Ala
                180                 185
```

```
<210> SEQ ID NO 155
<211> LENGTH: 103
<212> TYPE: PRT
```

<213> ORGANISM: Unknown
<220> FEATURE:
<223> OTHER INFORMATION: metagenomes purified from environmentally
      challenged niches

<400> SEQUENCE: 155

Met Thr Gly Arg Gly Lys Gly Gly Lys Gly Leu Gly Lys Gly Gly Ala
1               5                   10                  15

Lys Arg His Arg Lys Ile Leu Arg Asp Asn Ile Gln Gly Ile Thr Lys
            20                  25                  30

Pro Ala Ile Arg Arg Leu Ala Arg Arg Gly Gly Val Lys Arg Ile Ser
        35                  40                  45

Ala Met Ile Tyr Glu Glu Thr Arg Gly Val Leu Lys Thr Phe Leu Glu
    50                  55                  60

Gly Val Ile Arg Asp Ala Val Thr Tyr Thr Glu His Ala Lys Arg Lys
65                  70                  75                  80

Thr Val Thr Ser Leu Asp Val Val Tyr Ala Leu Lys Arg Gln Gly Arg
                85                  90                  95

Thr Leu Tyr Gly Phe Gly Gly
            100

<210> SEQ ID NO 156
<211> LENGTH: 307
<212> TYPE: PRT
<213> ORGANISM: Unknown
<220> FEATURE:
<223> OTHER INFORMATION: metagenomes purified from environmentally
      challenged niches

<400> SEQUENCE: 156

Met Ser Leu Asp Val Gly Asp Val Asp Ala Trp Ile Asp Thr Leu Ser
1               5                   10                  15

Gln Cys Lys Gln Leu Ser Glu Ser Asp Val Lys Leu Leu Cys Asp Lys
            20                  25                  30

Ala Arg Glu Ile Leu Ile Glu Glu Ser Asn Val Gln Pro Val Arg Cys
        35                  40                  45

Pro Val Thr Val Cys Gly Asp Ile His Gly Gln Phe His Asp Leu Ile
    50                  55                  60

Glu Leu Phe Arg Ile Gly Gly Asn Ser Pro Ser Thr Asn Tyr Leu Phe
65                  70                  75                  80

Met Gly Asp Tyr Val Asp Arg Gly Tyr Tyr Ser Val Glu Thr Val Thr
                85                  90                  95

Leu Leu Val Ala Leu Lys Leu Arg Tyr Arg Glu Arg Ile Thr Ile Leu
            100                 105                 110

Arg Gly Asn His Glu Ser Arg Gln Ile Thr Gln Val Tyr Gly Phe Tyr
            115                 120                 125

Asp Glu Cys Leu Arg Lys Tyr Gly Asn Ala Asn Val Trp Lys Phe Phe
        130                 135                 140

Thr Asp Leu Phe Asp Tyr Leu Pro Leu Thr Ala Leu Ile Asp Asn Gln
145                 150                 155                 160

Ile Phe Cys Leu His Gly Gly Leu Ser Pro Ser Ile Asp Thr Leu Asp
                165                 170                 175

His Ile Arg Ser Ile Asp Arg Ile Gln Glu Val Pro His Glu Gly Pro
            180                 185                 190

Met Cys Asp Leu Leu Trp Ser Asp Pro Asp Asp Arg Cys Gly Trp Gly
        195                 200                 205

Ile Ser Pro Arg Gly Ala Gly Tyr Thr Phe Gly Gln Asp Ile Ser Glu

```
                    210                 215                 220
Ala Phe Asn His Ser Asn Gly Leu Thr Leu Val Ala Arg Ala His Gln
225                 230                 235                 240

Leu Val Met Glu Gly Tyr Asn Trp Ser Gln Asp Arg Asn Val Val Thr
                245                 250                 255

Leu Phe Ser Ala Pro Asn Tyr Cys Tyr Arg Cys Gly Asn Gln Ala Ala
                260                 265                 270

Ile Met Glu Ile Asp Glu Asn Leu Lys Tyr Thr Phe Leu Gln Phe Asp
            275                 280                 285

Pro Ala Pro Arg Ala Gly Glu Pro Met Val Ser Arg Arg Val Pro Asp
            290                 295                 300

Tyr Phe Leu
305

<210> SEQ ID NO 157
<211> LENGTH: 103
<212> TYPE: PRT
<213> ORGANISM: Unknown
<220> FEATURE:
<223> OTHER INFORMATION: metagenomes purified from environmentally
      challenged niches

<400> SEQUENCE: 157

Met Thr Gly Arg Gly Lys Gly Lys Gly Leu Gly Lys Gly Ala
1               5                   10                  15

Lys Arg His Arg Lys Ile Leu Arg Asp Asn Ile Gln Gly Ile Thr Lys
                20                  25                  30

Pro Ala Ile Arg Arg Leu Ala Arg Arg Gly Gly Val Lys Arg Ile Ser
            35                  40                  45

Ala Met Ile Tyr Glu Glu Thr Arg Gly Val Leu Lys Thr Phe Leu Glu
        50                  55                  60

Gly Val Ile Arg Asp Ala Val Thr Tyr Thr Glu His Ala Lys Arg Lys
65                  70                  75                  80

Thr Val Thr Ser Leu Asp Val Val Tyr Ala Leu Lys Arg Gln Gly Arg
                85                  90                  95

Thr Leu Tyr Gly Phe Gly Gly
            100

<210> SEQ ID NO 158
<211> LENGTH: 151
<212> TYPE: PRT
<213> ORGANISM: Unknown
<220> FEATURE:
<223> OTHER INFORMATION: metagenomes purified from environmentally
      challenged niches

<400> SEQUENCE: 158

Gly Ala Thr Thr Thr Ser Ile Leu His His Phe Gln Leu Ser Thr Ser
1               5                   10                  15

Ser Asn Asn Ser Phe Tyr His Tyr Leu Asn Asn Leu His Gln Asn
                20                  25                  30

Asp Trp Thr Arg Gln Gly Arg Gln Gly Ser Arg Lys Gly Arg Arg Gln
            35                  40                  45

Ala Ser Pro Gln Asp Leu Ala Arg Gln His Pro Gly His His Gln Ala
        50                  55                  60

Arg His Pro Pro Ser Gly Ala Ser Trp Arg Cys Gln Ala Tyr Leu Arg
65                  70                  75                  80

His Asp Leu Arg Gly Asp Pro Arg Cys Pro Gln Asp Leu Pro Arg Gly
```

```
                    85                  90                  95
Cys His Pro Arg Arg His Leu His Arg Ala Arg Gln Ala Gln Asp
            100                 105                 110

Arg His Leu Pro Arg Arg Leu Arg Pro Gln Glu Ala Arg Pro His
        115                 120                 125

Pro Leu Arg Phe Arg Trp Leu Ser Ser Ser Leu Ser Leu Arg Leu
    130                 135                 140

Leu Cys Phe Leu Gln Thr Gln
145                 150

<210> SEQ ID NO 159
<211> LENGTH: 146
<212> TYPE: PRT
<213> ORGANISM: Unknown
<220> FEATURE:
<223> OTHER INFORMATION: metagenomes purified from environmentally
      challenged niches

<400> SEQUENCE: 159

Met Phe Ser Lys Leu Ile Ala Ile Ala Ser Leu Ala Leu Ala Ala Asn
1               5                   10                  15

Ala Ala Val Ile Asp Pro Ser Asp His Thr Val Gln Tyr Glu Ala Ala
            20                  25                  30

Pro Gly Lys Val Val Thr Glu His Tyr Glu Val Leu Ser His Ala Glu
        35                  40                  45

Ala Ser Arg Ile Ile Glu Ala Asn Pro His Ile Ser Asp Tyr Arg Tyr
    50                  55                  60

Arg Cys Asn Tyr Gln Cys Asn Asp Ser Ser Gly Asn Tyr Met Arg Asn
65                  70                  75                  80

Leu Gln Gln Gly Val Pro Asn Gln Ala Cys Ile Phe Ser Ser Cys Tyr
                85                  90                  95

Asp Cys Asp Trp Lys Phe Gln Asn Cys Ser Tyr Cys Arg Leu Ser Thr
            100                 105                 110

Gly His Asn Tyr Arg Asp Ile Gly Gly Leu Glu Ser Trp Cys Tyr Asn
        115                 120                 125

Asn Gly Gly Thr Thr Val Thr His Asn Cys Gly Tyr Thr Asp Gly Asp
    130                 135                 140

Gln Cys
145

<210> SEQ ID NO 160
<211> LENGTH: 142
<212> TYPE: PRT
<213> ORGANISM: Unknown
<220> FEATURE:
<223> OTHER INFORMATION: metagenomes purified from environmentally
      challenged niches

<400> SEQUENCE: 160

Met His Phe Lys Ser Leu Phe Ile Ala Gly Ala Leu Phe Met Val Gly
1               5                   10                  15

Ala Ser Ala Val Asp Cys Ala Thr Pro Glu Ile His Cys Glu Thr Ser
            20                  25                  30

Asp Gly Ser Pro Trp Tyr Asp Asp Ala Val Gln Ala Thr Glu Tyr Trp
        35                  40                  45

Lys Glu Ile Gln Asp Ala Gly Lys Asp Ser Cys Gly Asp Ala Gly Cys
    50                  55                  60

Ala Gln Pro His Gly Ser Gly Cys His Ser Asp Gly Gly Ser Tyr Gly
```

```
                65                  70                  75                  80
Thr Ala Glu Ile Val Leu Cys Gln Asp Asp Ser Ser Ser Thr Pro
                    85                  90                  95

Gln Cys Ala Asp Cys Arg Cys Val Tyr Ser Tyr Leu Lys Pro Leu Leu
                    100                 105                 110

Asp Gln Cys Lys Gly Ala Asn Asn Lys Ile Gly Tyr Ala His Val
            115                 120                 125

Asp Met Gly Gly Asn Tyr Ile Asn Tyr Glu Phe Val Lys Lys
        130                 135                 140

<210> SEQ ID NO 161
<211> LENGTH: 100
<212> TYPE: PRT
<213> ORGANISM: Unknown
<220> FEATURE:
<223> OTHER INFORMATION: metagenomes purified from environmentally
      challenged niches

<400> SEQUENCE: 161

Leu Leu Ala Pro Ser Ser Trp Ser Val Pro Val Pro Leu Ile Val Pro
1               5                   10                  15

Leu Leu Arg Phe Thr Ala Arg Leu Val Met Ala Ala Pro Gly Thr Thr
                20                  25                  30

Met Pro Ser Lys Pro Leu Asn Thr Gly Lys Lys Ser Arg Thr Pro Ala
            35                  40                  45

Lys Thr Ala Ala Val Met Leu Val Ala His Ser Pro Met Ala Leu Asp
        50                  55                  60

Ala Thr Ala Thr Val Val Ala Met Val Pro Pro Arg Ser Phe Ser Ala
65                  70                  75                  80

Arg Met Thr Arg Pro Leu Gln Leu Pro Asn Val Pro Thr Ala Gly Val
                85                  90                  95

Ser Thr Ala Thr
            100

<210> SEQ ID NO 162
<211> LENGTH: 185
<212> TYPE: PRT
<213> ORGANISM: Unknown
<220> FEATURE:
<223> OTHER INFORMATION: metagenomes purified from environmentally
      challenged niches

<400> SEQUENCE: 162

Arg Ala Gly Gly Asn Trp Thr Met Ile Asp Asp Leu Thr Gly Ser
1               5                   10                  15

Glu Asp Ser Phe Ser Asn Ser Trp Ile Ser Trp Phe Leu Ser Thr Lys
                20                  25                  30

Gly Asn Glu Tyr Phe Cys Glu Val Asp Glu Glu Tyr Ile Leu Asp Arg
            35                  40                  45

Phe Asn Leu Thr Gly Leu Asn Asn Asp Val Gln Asn Tyr Ser Gln Ala
        50                  55                  60

Leu Glu Leu Ile Thr Asp Ser Leu Asp Asp Asp Leu Asp Glu
65                  70                  75                  80

Gln Arg Asp Ala Ile Glu Asn Ser Ala Arg Tyr Leu Tyr Gly Leu Ile
                85                  90                  95

His Ala Arg Tyr Ile Ile Thr Ser Arg Gly Leu Ala Lys Met Leu Phe
            100                 105                 110

Leu Val Tyr Pro Gln Gln Leu Pro Ser Lys Thr Thr Asn Ser Val Pro
```

```
            115                 120                 125
Ser Thr Lys Pro Ala Thr Ser Ala Asp Ala Val Gly Val Asp Arg
            130                 135                 140

Tyr Leu Pro Lys Ile Phe Gly Phe Pro Val His Glu Met Ser Lys His
145                 150                 155                 160

Ala Arg Trp Gln Glu Ala Gln Arg Asp Leu Gln Ile Ser Arg Leu Gln
                165                 170                 175

Gln Ser Ala Ser Asp Pro Ser Tyr Val
            180                 185

<210> SEQ ID NO 163
<211> LENGTH: 415
<212> TYPE: PRT
<213> ORGANISM: Unknown
<220> FEATURE:
<223> OTHER INFORMATION: metagenomes purified from environmentally
      challenged niches

<400> SEQUENCE: 163

Met Ser Leu Thr Pro Glu Gln Thr Glu Ile Ile Lys Ala Thr Val Pro
1               5                   10                  15

Val Val Lys Glu His Gly Lys Thr Ile Thr Thr Val Phe Tyr Lys Asn
            20                  25                  30

Met Leu Glu Ala His Pro Glu Leu Asn Ala Ile Phe Asn Thr Thr Asn
        35                  40                  45

Gln Val Asn Gly His Gln Pro Asn Ala Leu Ala Gly Ala Leu Phe Ala
    50                  55                  60

Tyr Ala Ser Asn Ile Asp Asn Leu Gly Ala Leu Gly Pro Ala Val Glu
65                  70                  75                  80

Leu Ile Cys Asn Lys His Ala Ser Leu Tyr Ile Gln Pro Glu His Tyr
                85                  90                  95

Gly Ile Val Gly Lys Phe Leu Leu Glu Ala Met Gly Gln Val Leu Gly
            100                 105                 110

Asp Ala Leu Thr Pro Gln Ile Leu Asp Ala Trp Ala Ala Ala Tyr Trp
        115                 120                 125

Gln Leu Ala Asn Leu Phe Ile Gly Arg Glu Ser Ala Ile Tyr Lys Gln
    130                 135                 140

Ser Glu Gly Trp Thr Gln Trp Arg Glu Phe Arg Val Ala Gln Lys Val
145                 150                 155                 160

Pro Glu Ser Ala Glu Ile Thr Ser Phe Tyr Leu Lys Pro Val Asp Glu
                165                 170                 175

Lys Pro Leu Pro Arg Phe Arg Pro Gly Gln Tyr Ile Ser Val Gln Val
            180                 185                 190

His Val Pro Gln Leu Glu Cys Pro Gln Ala Arg Gln Tyr Ser Leu Ser
        195                 200                 205

Asp Lys Pro Arg Asp Asp Tyr Tyr Arg Ile Ser Val Lys Lys Glu Thr
    210                 215                 220

Gly Leu Asn Thr Ala Lys Pro Glu Ala Lys Val Asn Pro Gly Tyr Val
225                 230                 235                 240

Ser Asn Ile Leu His Glu Asn Val Asn Glu Gly Asp Val Ile Lys Val
                245                 250                 255

Ser His Pro Cys Gly Asp Phe Phe Leu Thr Glu Gln Glu Pro Ser His
            260                 265                 270

Pro Val Val Leu Ile Ala Ala Gly Val Gly Leu Thr Pro Leu Thr Ser
        275                 280                 285
```

```
Met Leu Asn Thr Leu Asp Ser Thr Pro Ala Asp Ser Gln Arg Lys Ile
    290                 295                 300

His Phe Ile His Gly Ala Arg Thr Thr Ser Val Arg Ala Phe Lys Asp
305                 310                 315                 320

Gln Ile Lys Ser Arg Ala Glu Arg Leu Pro Asn Leu Gln Ala Thr Phe
                325                 330                 335

Phe Thr Ser Ser Pro Ser Ala Asp Glu Lys Gln Gly Val Asp Tyr Asp
            340                 345                 350

Val Gln Gly Arg Ile Asp Val Ser Lys Met Asp Ala Ser Lys Asp Leu
        355                 360                 365

Phe Leu Asp Asn Ala Gln Thr Glu Phe Tyr Ile Cys Gly Pro Thr Ser
370                 375                 380

Phe Met Asn Asp Ile Ala Asn Ser Leu Lys Ala Arg Gly Ala Thr Ser
385                 390                 395                 400

Glu Arg Ile His Met Glu Leu Phe Gly Thr Gly Val Pro Val
                405                 410                 415

<210> SEQ ID NO 164
<211> LENGTH: 212
<212> TYPE: PRT
<213> ORGANISM: Unknown
<220> FEATURE:
<223> OTHER INFORMATION: metagenomes purified from environmentally
      challenged niches

<400> SEQUENCE: 164

Met Ala Phe Met Asn Leu Pro Trp Pro Thr Glu Cys Leu His Ala Ala
1               5                   10                  15

Leu Lys Asn Gly Ser Leu Pro Phe Trp Gly Phe Val Ile Tyr Arg Thr
            20                  25                  30

Thr Tyr Thr Ala Gln Ser Asp Ala Ala Trp Pro Gln Ile Ile Glu Leu
        35                  40                  45

Ile Ala Ser Tyr Met Lys Ala Leu Leu Tyr His Glu Tyr Asn Asp Lys
    50                  55                  60

Lys Lys Asp Gly Asp Glu Pro Thr Val Tyr Asp Glu Ile Trp Ala Arg
65                  70                  75                  80

His Gln Leu Thr Ile Met Asp Asp Arg Gln Phe Asn Gly Ala Ser Val
                85                  90                  95

Phe Asp Ile Gln Leu His Phe Glu Lys Trp Val Glu Ala Gln Gly Lys
            100                 105                 110

Arg Asp Glu Ser Thr Met Tyr Arg Met Cys Met Val Ile Asp Asp Glu
        115                 120                 125

Ser Ile Gln Thr Leu Leu Glu Ala Pro Pro Gly Glu Asn Arg Lys Leu
    130                 135                 140

Gly Arg Arg Ile Gly Gly Pro Val Arg Phe Val Lys Val Val Glu Ala
145                 150                 155                 160

Phe Pro Glu Leu Asp Ser Leu Asp Glu Phe Gln Gly Trp Met Lys Cys
                165                 170                 175

Glu Ile Asn Ala Leu Trp Pro Leu Trp Lys Met Met Ser Asp Gly Asp
            180                 185                 190

Glu Met Arg Met Ser Tyr Asp Glu Met Lys Gly Asn Gly Lys Gln Val
        195                 200                 205

Tyr Gly Ala Ile
    210

<210> SEQ ID NO 165
```

<211> LENGTH: 222
<212> TYPE: PRT
<213> ORGANISM: Unknown
<220> FEATURE:
<223> OTHER INFORMATION: metagenomes purified from environmentally
     challenged niches

<400> SEQUENCE: 165

Met Ala Arg Arg Pro Ala Arg Cys Tyr Arg Tyr Cys Lys Asn Lys Pro
1               5                   10                  15

Tyr Pro Lys Ser Arg Phe Asn Arg Gly Val Pro Asp Pro Lys Ile Arg
            20                  25                  30

Ile Phe Asp Leu Gly Arg Lys Lys Ala Ser Val Asp Asp Phe Pro Leu
        35                  40                  45

Cys Val His Met Val Ser Asn Glu Tyr Glu Gln Leu Ser Ser Glu Ala
    50                  55                  60

Leu Glu Ala Ala Arg Ile Cys Ala Asn Lys Tyr Leu Val Lys Ile Ala
65                  70                  75                  80

Gly Lys Glu Gly Phe His Leu Arg Val Arg Ala His Pro Phe His Val
                85                  90                  95

Val Arg Ile Asn Lys Met Leu Ser Cys Ala Gly Ala Asp Arg Leu Gln
            100                 105                 110

Thr Gly Met Arg Gly Ala Phe Gly Lys Pro Asn Gly Val Val Ala Arg
        115                 120                 125

Val Asn Ile Gly Gln Ile Leu Leu Ser Ile Arg Thr Arg Asp Ser Asn
    130                 135                 140

Arg Ala Ala Ala Val Glu Ala Met Arg Arg Ser Thr Tyr Lys Phe Pro
145                 150                 155                 160

Gly Arg Gln Lys Ile Ile Ile Ser Lys Asn Trp Gly Phe Thr Pro Val
                165                 170                 175

Arg Arg Glu Glu Tyr Val Lys Leu Arg Gln Glu Gly Lys Leu Lys Gln
            180                 185                 190

Asp Gly Ala Tyr Val Gln Phe Leu Arg Gly His Gly Leu Val Glu Glu
        195                 200                 205

Asn Met Lys Arg Phe Pro Gln Ala Tyr Glu Gly Val Ala Gln
    210                 215                 220

<210> SEQ ID NO 166
<211> LENGTH: 252
<212> TYPE: PRT
<213> ORGANISM: Unknown
<220> FEATURE:
<223> OTHER INFORMATION: metagenomes purified from environmentally
     challenged niches

<400> SEQUENCE: 166

Met Ser Phe Tyr Gln Ser Arg Pro Asp Thr Ile Lys Gly Pro Asp Pro
1               5                   10                  15

Leu Thr Asp Asn Trp Thr Tyr Asp Ser Ala Ile Asp Leu Phe Ser Trp
            20                  25                  30

Asn Pro Met Met Pro Asp Pro Phe Thr Phe Asp Leu Pro Asp Asp Leu
        35                  40                  45

Met Lys Phe Glu Ser Lys Asp Met Ser Ala Gly Met Val Ala Pro Ser
    50                  55                  60

Asp Ile Ser Gly Phe Ala Ile Gly Asn His Leu Gly Glu Asp Ala Ala
65                  70                  75                  80

Ser Ile Ser Asp Pro Glu Ser Asp Asp His Pro Trp Ser Pro Ser Ala
                85                  90                  95

```
His Ala Ala Phe Pro Glu Leu Ser Pro Ile Thr Ser Thr Glu Gln Val
                100                 105                 110

His Gln Glu Thr Ala Arg Tyr Ser Thr Thr Pro Asp Ala Thr Ser Pro
            115                 120                 125

Gln Glu Gln Pro Ser Ser Pro Pro Thr Arg Ser Thr Arg Arg Arg Ser
        130                 135                 140

Ser Ala Asp Gly Pro Val Arg Asn Ala Ala Lys Arg Ala Ala His Asn
145                 150                 155                 160

Val Ile Glu Lys Arg Tyr Arg Thr Asn Met Asn Ala Lys Phe Val Ala
                165                 170                 175

Leu Glu Lys Ala Met Asn Gly Asn Gly Val Gln Thr Ser Ser Arg
            180                 185                 190

Gly Gly Gly Ser Ala Ser Leu Lys Lys Ser Glu Ile Leu Ser Asn Ala
        195                 200                 205

Ile Ala Tyr Met His Gly Leu Gln Glu Glu Asn Arg Tyr Leu Gln Lys
    210                 215                 220

Glu Leu Ala Ile Val Lys Gln Asn Leu Val Pro Ala Gly Ile Trp Arg
225                 230                 235                 240

Gly Ala Pro Ser Cys Lys Arg Glu Thr Ser Tyr Arg
                245                 250

<210> SEQ ID NO 167
<211> LENGTH: 254
<212> TYPE: PRT
<213> ORGANISM: Unknown
<220> FEATURE:
<223> OTHER INFORMATION: metagenomes purified from environmentally
      challenged niches

<400> SEQUENCE: 167

Met Gly Arg Val Ile Arg Asn Gln Arg Lys Gly Arg Gly Ser Ile Phe
1               5                   10                  15

Thr Ala His Thr Arg Leu Asn Lys Ala Pro Ala Gln Phe Arg Thr Leu
            20                  25                  30

Asp Phe Ala Glu Arg His Gly Tyr Thr Arg Gly Val Val Lys Glu Ile
        35                  40                  45

Ile His Asp Ala Gly Arg Gly Ala Pro Leu Ala Lys Val Gln Phe Arg
    50                  55                  60

His Pro Tyr Lys Phe Lys Met Val Thr Glu Thr Phe Ile Ala Asn Glu
65                  70                  75                  80

Gly Met Tyr Thr Gly Gln Phe Ile Tyr Ala Gly Lys Asn Ala Gln Leu
                85                  90                  95

Thr Val Gly Asn Val Leu Pro Leu Ala Ser Met Pro Glu Gly Thr Val
            100                 105                 110

Ile Ser Asn Val Glu Glu Lys Ser Gly Asp Arg Gly Ala Leu Gly Arg
        115                 120                 125

Thr Ser Gly Asn Tyr Val Thr Val Ile Gly His Asn Pro Glu Asp Gly
    130                 135                 140

Lys Thr Arg Val Lys Leu Pro Ser Gly Ala Lys Lys Val Ile Lys Asn
145                 150                 155                 160

Thr Ala Arg Gly Met Val Gly Ile Val Ala Gly Gly Arg Thr Asp
                165                 170                 175

Lys Pro Leu Leu Lys Ala Ser Arg Ala Lys His Lys Phe Ala Val Lys
            180                 185                 190

Arg Asn Ser Trp Pro Lys Thr Arg Gly Val Ala Met Asn Pro Val Asp
```

```
                195              200              205
His Pro His Gly Gly Asn His Gln His Ile Gly Lys Ala Ser Thr
    210              215              220

Ile Ser Arg Tyr Ala Ala Gln Gly Gln Lys Ala Gly Leu Ile Ala Ala
225              230              235              240

Arg Arg Thr Gly Leu Leu Arg Gly Thr Gln Lys Thr Lys Asp
            245              250
```

<210> SEQ ID NO 168
<211> LENGTH: 249
<212> TYPE: PRT
<213> ORGANISM: Unknown
<220> FEATURE:
<223> OTHER INFORMATION: metagenomes purified from environmentally
      challenged niches

<400> SEQUENCE: 168

```
Gly Ala Glu Ala Tyr Tyr Ser Pro Val Ser Ser Leu Ile Gly Met Ser
1               5                   10                  15

Thr Gly Leu Arg Phe Ser Thr Leu Pro Ala Ala Ser Asn Pro Gln Ser
            20                  25                  30

Ser Ser Leu Ile Pro Ser Pro Ser Ala Pro Ile Ser Thr Phe Pro Tyr
        35                  40                  45

Thr Leu Thr Leu Thr Leu Thr Pro Leu Thr Gly Ser Leu Ser Thr Ser
50                  55                  60

Tyr Ser Leu Arg Ala Ser Pro Asn Leu Ser Phe Ser Ser Arg Phe Gly
65                  70                  75                  80

Phe Asn Val Tyr Ser Trp Glu Ser Glu Met Val Ala Gly Phe Glu Leu
                85                  90                  95

Trp Arg Gln Ser Lys Lys Pro Lys Leu Ala Ala Gly Ser Asp Gly Asp
            100                 105                 110

Asp Leu Glu Trp Ala Arg Arg Lys Val Arg Val Trp Asp Pro Ser Ala
        115                 120                 125

Phe Pro Leu Ala Pro Pro Glu Pro Glu Ile Pro Gln Pro Asn His Glu
130                 135                 140

Asp Glu Ser Gln Glu Ser Val Leu Lys Leu Arg Val Asp Gln Ser Trp
145                 150                 155                 160

Asn Val Arg Leu Leu Trp Glu Gly Arg Val Lys Glu Leu Leu Val Ser
                165                 170                 175

Ala Gly Val Gly Leu Gly Pro Ser Ser Phe Ser Pro Ser Ser Tyr Ala
            180                 185                 190

Asn Pro Pro Gly Thr Ala Gly Ala Gln Gly Ser Gly Gly Ser Pro
        195                 200                 205

Ala Ser Tyr Trp Arg Gly Val Gly Gly Phe Gly Ile Ile Phe Phe Met
210                 215                 220

Arg Asp Phe Phe Gly Ser Met Tyr Leu Asn Glu His Cys Leu Asp Val
225                 230                 235                 240

Tyr Ser Leu Ser Asp Phe Met Arg Gln
                245
```

<210> SEQ ID NO 169
<211> LENGTH: 211
<212> TYPE: PRT
<213> ORGANISM: Unknown
<220> FEATURE:
<223> OTHER INFORMATION: metagenomes purified from environmentally
      challenged niches

<400> SEQUENCE: 169

```
Gly Pro Gly Val Leu Ser Gly Phe Gln Pro Asp Leu Pro Leu Ile
1               5                   10                  15

Thr Ser Ile Glu Leu Asp Leu Asp Val Val Leu Pro Pro Ala Cys
            20                  25                  30

Arg Thr Met Phe Leu Arg Thr Val Ser Arg Ala Val Pro Arg Ser Thr
                35                  40                  45

Ala Ala Ile Arg Ala Ala Pro Thr Ala Ser Val Asn Ala Leu Gln Thr
50                  55                  60

Arg Ala Ala Ser Asp His Ala Ile Pro Asn Pro Thr Leu Ala Asn Ile
65                  70                  75                  80

Glu Lys Arg Trp Glu Val Met Pro Pro Gln Glu Gln Ala Glu Leu Trp
                85                  90                  95

Met Gln Leu Arg Asp Arg Met Lys Val Asp Trp His Gln Met Thr Leu
                100                 105                 110

Gln Glu Lys Lys Ala Ala Tyr Tyr Ile Ala Phe Gly Ala His Gly Pro
            115                 120                 125

Arg Ala Gln Pro Pro Lys Gly Glu Gly Met Arg Val Phe Ala Lys Val
130                 135                 140

Leu Gln Leu Thr Ala Ala Ser Val Ala Val Phe Tyr Ala Ile His Ala
145                 150                 155                 160

Phe Ala Gly Lys Gln Pro Ala Thr Met Ser Lys Glu Trp Gln Glu Ala
                165                 170                 175

Ser Asn Glu Tyr Ala Leu Lys Gly Lys Ile Asn Pro Ile His Gly Ile
            180                 185                 190

Ser Lys Glu Gly Tyr Glu Gly Lys Gly Phe Val Gln Ser Pro Pro Ala
195                 200                 205

Glu Lys Ser
    210
```

<210> SEQ ID NO 170
<211> LENGTH: 153
<212> TYPE: PRT
<213> ORGANISM: Unknown
<220> FEATURE:
<223> OTHER INFORMATION: metagenomes purified from environmentally challenged niches

<400> SEQUENCE: 170

```
Val Ala Arg Arg Gly Gly Ile Tyr Leu Asp Gly Asn Asp Leu Val
1               5                   10                  15

Thr Met Lys Gly Asn Tyr Ile Tyr His Thr Ser Gly Arg Ser Pro Lys
            20                  25                  30

Val Gln Gly Asn Thr Leu Leu His Ala Val Asn Asn Tyr Trp His Asp
            35                  40                  45

Asn Ser Gly His Ala Phe Glu Ile Gly Glu Gly Tyr Val Leu Ala
50                  55                  60

Glu Gly Asn Val Phe Gln Asp Val Thr Thr Pro Val Glu Asp Pro Val
65                  70                  75                  80

Asp Gly Gln Leu Phe Thr Ser Pro Asp Pro Ser Thr Asn Ala Gln Cys
                85                  90                  95

Ser Ser Tyr Leu Gly Arg Ala Cys Glu Ile Asn Gly Phe Gly Asn Ser
            100                 105                 110

Gly Thr Phe Asn Gln Ala Asp Thr Ser Leu Leu Ser Lys Phe Lys Gly
            115                 120                 125
```

Gln Asn Ile Ala Ser Ala Asp Ala Tyr Ser Lys Val Ala Ser Ser Val
            130                 135                 140

Ala Ser Asn Ala Gly Gln Gly His Leu
145                 150

<210> SEQ ID NO 171
<211> LENGTH: 120
<212> TYPE: PRT
<213> ORGANISM: Unknown
<220> FEATURE:
<223> OTHER INFORMATION: metagenomes purified from environmentally
      challenged niches

<400> SEQUENCE: 171

Val Arg Val Val Thr Phe Trp Pro Arg Val Thr Ser Ser Arg Met Leu
1               5                   10                  15

Leu Pro Pro Leu Arg Thr Pro Leu Thr Ala Ser Ser Leu Pro Leu
            20                  25                  30

Thr Pro Ala Pro Thr Leu Ser Ala Arg His Thr Leu Ala Gly Pro Ala
            35                  40                  45

Lys Ser Thr Ala Ser Val Thr Leu Val Pro Ser Thr Arg Leu Thr Leu
50                  55                  60

Ala Cys Cys Leu Asn Leu Arg Val Arg Thr Leu Leu Leu Met Leu
65                  70                  75                  80

Thr Leu Arg Leu Pro Arg Ala Leu Pro Ala Thr Pro Val Arg Asp Thr
                85                  90                  95

Cys Lys Met Glu Arg Gly Gly Ser Glu Leu Asn Leu Leu Met Ser Asp
            100                 105                 110

Asp Ile Ala Leu Ala Ala Cys Trp
            115                 120

<210> SEQ ID NO 172
<211> LENGTH: 80
<212> TYPE: PRT
<213> ORGANISM: Unknown
<220> FEATURE:
<223> OTHER INFORMATION: metagenomes purified from environmentally
      challenged niches

<400> SEQUENCE: 172

Met Pro Ser Lys Thr Glu Ala Ala Arg Leu Gln Asn Asp Phe Gly Ala
1               5                   10                  15

Asp Tyr Trp Val Arg Asn Thr Gln Glu Arg Arg His Ser Thr Ala Gly
            20                  25                  30

Arg Gly Leu Phe Ala Gly Leu Gln Asp Val Lys His Tyr Asn Val Asp
            35                  40                  45

His Gly Trp Ala Arg Arg Lys Ser Ser Asp Asn Pro Gly Leu Leu Ala
50                  55                  60

Ser Phe Phe Ser Arg Phe Thr Gly Gly Ser Tyr His Pro Pro Ser Glu
65                  70                  75                  80

<210> SEQ ID NO 173
<211> LENGTH: 137
<212> TYPE: PRT
<213> ORGANISM: Unknown
<220> FEATURE:
<223> OTHER INFORMATION: metagenomes purified from environmentally
      challenged niches

<400> SEQUENCE: 173

Val Ala Arg Arg Asp Ser His His Gln Ile Lys Ser Arg Leu Ile Leu

```
                1               5                  10                 15
            Leu Asp Ile Thr Thr Ile Gln His Lys Val Pro Ser Tyr Phe Lys Gln
                            20                 25                 30

Ile Ser Thr Ile Glu Ser Lys Cys His Pro Lys Pro Lys Gln Pro Val
                            35                 40                 45

Tyr Lys Thr Thr Ser Ala Gln Thr Thr Gly Leu Glu Ile Pro Lys Asn
                            50                 55                 60

Ala Ala Thr Gln Pro Leu Ala Ala Asp Tyr Ser Pro Val Ser Arg Met
             65                 70                 75                 80

Ser Ser Thr Ile Thr Ser Thr Met Ala Gly Pro Val Ala Ser Leu Ala
                            85                 90                 95

Ile Thr Pro Asp Ser Leu Leu Leu Ser Ser Val Asp Ser Pro Gly Asp
                           100                105                110

His Thr Ile Arg Pro Arg Asn Arg Ile Pro Phe Leu Asn Val Arg Tyr
                           115                120                125

Trp Glu Glu Cys Asp Leu Asn Trp Glu
                           130                135
```

<210> SEQ ID NO 174
<211> LENGTH: 181
<212> TYPE: PRT
<213> ORGANISM: Unknown
<220> FEATURE:
<223> OTHER INFORMATION: metagenomes purified from environmentally
      challenged niches

<400> SEQUENCE: 174

```
            Val Val Ser Thr Gln Ser Asp Glu Pro Thr Ile Pro Gly Gly Ala Ala
             1               5                  10                 15

Val Thr Ile His Ser Arg Asn Glu Lys Lys Ala Arg Lys Ala Ile Gly
                            20                 25                 30

Lys Leu Gly Leu Lys His Val Pro Gly Ile Thr Arg Val Thr Leu Arg
                            35                 40                 45

Arg Pro Lys Asn Ile Leu Phe Val Val Asn Gln Pro Asp Val Tyr Lys
                            50                 55                 60

Ser Pro Ser Ser Asn Thr Trp Ile Ile Phe Gly Glu Ala Lys Ile Glu
             65                 70                 75                 80

Asp Leu Asn Ser Gln Ala Gln Ala Ser Ala Ala Gln Gln Leu Ala Ala
                            85                 90                 95

Ala Glu Ala Ala Ala Gly Gly Glu His Ala Gly His Asp His Glu His
                           100                105                110

Asp Ile Leu Gly Lys Gly Lys Ala Pro Glu Thr Glu Gly Lys Lys Glu
                           115                120                125

Glu Glu Glu Asp Asp Gly Glu Glu Val Asp Glu Ala Gly Leu Glu Ala
                           130                135                140

Lys Asp Ile Asp Leu Val Met Ala Gln Ala Asn Val Ser Arg Lys Lys
            145                150                155                160

Ala Val Lys Ala Leu Arg Glu Asn Asp Asn Asp Ile Val Asn Ser Ile
                           165                170                175

Met Ala Leu Ser Ile
                           180
```

<210> SEQ ID NO 175
<211> LENGTH: 191
<212> TYPE: PRT
<213> ORGANISM: Unknown
<220> FEATURE:

<223> OTHER INFORMATION: metagenomes purified from environmentally
      challenged niches

<400> SEQUENCE: 175

Met Phe Leu Gln Arg Thr Val Ser Thr Leu Ala Arg Arg Thr Pro Val
1               5                   10                  15

Arg Gly Leu Ala Ala Arg Pro Phe Ser Ser Val Ser Arg Phe
            20                  25                  30

Asn Lys Tyr Glu Val Lys Glu Ala Lys Leu Arg Ser Leu Asp Glu Ile
            35                  40                  45

Gln Thr Glu Glu Asp Leu Ile Pro Pro Gly Ala Lys Pro Gly Thr Val
50                  55                  60

Pro Ser Asp Ile Glu His Ala Thr Gly Leu Glu Arg Leu Glu Leu Val
65                  70                  75                  80

Gly Lys Met Gln Gly Ile Asp Ile Phe Asp Leu Arg Pro Leu Asp Ala
                85                  90                  95

Ser Arg Lys Gly Thr Leu Glu Asn Pro Ile Val Val Asn Gly Ala Gly
            100                 105                 110

Asp Glu Gln Tyr Ala Gly Cys Thr Gly Tyr Pro Val Asp Ser His Gln
            115                 120                 125

Val Asn Trp Leu Thr Val Ser Arg Glu Arg Pro Ile Glu Arg Cys Asn
130                 135                 140

Glu Cys Gly Asn Val Val Lys Leu Asn Tyr Val Gly Pro Glu Glu Asp
145                 150                 155                 160

Pro His Ala His Asp His Gly His Gly His His Pro Ala Pro Glu Glu
                165                 170                 175

Pro Lys Thr Phe Ala Asp Tyr Val Lys Pro Glu Tyr Trp Tyr Arg
            180                 185                 190

<210> SEQ ID NO 176
<211> LENGTH: 261
<212> TYPE: PRT
<213> ORGANISM: Unknown
<220> FEATURE:
<223> OTHER INFORMATION: metagenomes purified from environmentally
      challenged niches

<400> SEQUENCE: 176

Met Asn Pro Tyr Ile Val Asp Pro Met Leu Lys Tyr Val Ala Phe Asp
1               5                   10                  15

Ile Pro Ala Leu Ala Arg Leu Asp Pro Ser Leu Cys Leu Phe Leu Ile
            20                  25                  30

Leu Phe Phe Glu Asn Ser Arg Val Leu Leu Gly Tyr Leu Pro Val
            35                  40                  45

Pro Val Leu Gly Leu Asp Val Val Gly Glu Gly Leu Gly Leu Gly
50                  55                  60

Gly Arg Val Val Ala Val Ala Val Val Ser Val Arg Val Leu Leu
65                  70                  75                  80

Arg Ser Asp Ile Val Gln Leu Asp Asn Val Thr Ala Phe Val Ala Ala
                85                  90                  95

Leu Asp Gly Ala Leu Thr Arg Asp Ser Gln Pro Val Asn Leu Val Arg
            100                 105                 110

Val Asp Gly Val Thr Ser Ala Thr Ser Val Leu Leu Val Thr Ser Thr
            115                 120                 125

Val Asp Asn Asn Gly Val Phe Glu Gly Ser Leu Ala Gly Ser Ile Gln
130                 135                 140

```
Arg Pro Gln Val Glu Asp Val Asn Ser Leu His Phe Thr Asp Glu Phe
145                 150                 155                 160

Glu Thr Leu Glu Thr Ser Gly Val Phe Asp Ile Ala Arg Asp Gly Thr
                165                 170                 175

Gly Leu Ser Thr Arg Gly Asp Glu Val Phe Phe Ser Leu Asp Leu Val
                180                 185                 190

Lys Arg Thr Glu Leu Gly Leu Leu Asn Leu Val Leu Val Glu Ser Ala
                195                 200                 205

Asn Gly Arg Arg Lys Arg Ala Arg Gly Ser Lys Ala Pro His Gly Gly
210                 215                 220

Ala Pro Arg Glu Gly Arg Tyr Arg Thr Leu Lys Glu His Ser Pro Cys
225                 230                 235                 240

Cys Asn Arg Thr Gly Arg Ser Asn Gly Arg Gly Glu Gly Gly Gly
                245                 250                 255

Val Asp Val Gly Ser
                260

<210> SEQ ID NO 177
<211> LENGTH: 221
<212> TYPE: PRT
<213> ORGANISM: Unknown
<220> FEATURE:
<223> OTHER INFORMATION: metagenomes purified from environmentally
      challenged niches

<400> SEQUENCE: 177

Met Ala Asp Ile Thr Ala Val Gly Glu Glu Asn Pro Ser Pro Thr Gln
1               5                   10                  15

Asp Glu Leu Gln Gln Ala Ala Ala Gly Asn Gly Ala Pro Asp Asn Arg
                20                  25                  30

Thr Pro Lys Arg Arg Met Ser Asp Asp Glu Glu Asp Glu Glu Lys Gln
                35                  40                  45

Gly Arg Glu Arg Arg Lys Ile Glu Ile Lys Phe Ile Gln Asp Lys Ser
            50                  55                  60

Arg Arg His Ile Thr Phe Ser Lys Arg Lys Ala Gly Ile Met Lys Lys
65                  70                  75                  80

Ala Tyr Glu Leu Ser Val Leu Thr Gly Thr Gln Val Leu Leu Leu Val
                85                  90                  95

Val Ser Glu Thr Gly Leu Val Tyr Thr Phe Thr Thr Pro Lys Leu Gln
                100                 105                 110

Pro Leu Val Thr Lys Ala Glu Gly Lys Asn Leu Ile Gln Ala Cys Leu
                115                 120                 125

Asn Ala Pro Asp Pro Thr Thr Ser Glu Asn Gly Val Asp Ala Pro Glu
130                 135                 140

Val Pro Ala Glu Thr Pro Glu Asp Val Asn His Ala Asn Val Asn Ala
145                 150                 155                 160

Ala Ala Ala Gln Gln Thr Asn Ile Pro Arg Pro Thr Gly Met His Pro
                165                 170                 175

Gly Tyr Met Thr Asn Glu Gln Gln Gln Met Ala Tyr Tyr Gln Asn
                180                 185                 190

His Leu Gln Gln Gln Gln Ala Gly Gly Tyr Pro Gly Met Ser
                195                 200                 205

Val Gly Gly Arg Met Pro Thr Gln His Gln Pro Thr Ala
    210                 215                 220

<210> SEQ ID NO 178
```

<211> LENGTH: 176
<212> TYPE: PRT
<213> ORGANISM: Unknown
<220> FEATURE:
<223> OTHER INFORMATION: metagenomes purified from environmentally
      challenged niches

<400> SEQUENCE: 178

Met Ser Phe Ala Ala Asp Pro Pro Asn Asn His Gly Thr Leu Thr
1               5                   10                  15

His Leu Phe Arg Ala Pro Glu Asp Leu Val Tyr Pro Ile Pro Glu Asn
                20                  25                  30

Phe Ser Leu Glu Glu Thr Val Leu Val Glu Pro Leu Ser Val Ala Ile
            35                  40                  45

His Gly Ala Arg Val Ala Gly Ile Thr Pro Gly His Thr Val Leu Val
        50                  55                  60

Gln Ala Ser Gly Thr Ile Gly Leu Phe Cys Ala Ala Thr Ala Thr Ala
65                  70                  75                  80

Phe Gly Ala Lys Gln Val Ile Ile Ser Asp Ile Asn Gln Thr Lys Leu
                85                  90                  95

Asp Phe Ala Arg Asp Tyr Leu Gly Cys Pro Ile Phe Leu Pro Asn Ile
                100                 105                 110

Ser Ser Ser His Pro Glu Glu Ala Ser Arg Met Lys Glu Tyr Ile
            115                 120                 125

Glu Ser Gln Arg Arg Cys Arg Tyr Ser Ser Val Val Tyr Gly Ser Gly
        130                 135                 140

Ile Leu Val Ala Lys Ser Gly Pro Gly Gly Val Val Val Pro Asn Trp
145                 150                 155                 160

Thr Arg Phe Asn Arg Val Gln Ser Asn Gly Thr Tyr His Gln Tyr Val
                165                 170                 175

<210> SEQ ID NO 179
<211> LENGTH: 86
<212> TYPE: PRT
<213> ORGANISM: Unknown
<220> FEATURE:
<223> OTHER INFORMATION: metagenomes purified from environmentally
      challenged niches

<400> SEQUENCE: 179

Met Pro Arg Gly Ala Glu Tyr Ala Asn Gly Pro Leu Gln Ser Asp Asn
1               5                   10                  15

Ala Ile Glu Ala Gly Glu Asn Lys Ala His Gly Thr Ser Gly Asn Thr
                20                  25                  30

Gly Leu Asn Arg Val Asn Lys Val Ala Glu Phe Pro Glu Gly Ala Arg
            35                  40                  45

Gly Thr Gly Thr Ala Ala Asn Pro Leu Ser Gly Gln Gly Ser Ala Gly
        50                  55                  60

His Gln Asp Gly Lys Gly Gly His Asp Pro Lys Thr Leu Gly Glu Asn
65                  70                  75                  80

Lys Gly Leu Gly Thr Gln
                85

<210> SEQ ID NO 180
<211> LENGTH: 78
<212> TYPE: PRT
<213> ORGANISM: Unknown
<220> FEATURE:
<223> OTHER INFORMATION: metagenomes purified from environmentally
      challenged niches -continued

<400> SEQUENCE: 180

Met Pro Ser Lys Leu Ala Lys Ile Arg Pro Thr Glu Pro Val Thr
1               5                   10                  15

Pro Ala Ser Thr Ala Ser Thr Arg Ser Pro Asn Ser Pro Lys Ala Pro
            20                  25                  30

Glu Glu Pro Val Pro Leu Leu Thr Arg Ser Val Ala Arg Val Ala Pro
        35                  40                  45

Ala Ile Arg Met Glu Arg Val Ala Met Thr Arg Arg Pro Leu Glu Arg
    50                  55                  60

Thr Arg Asp Trp Val Leu Asn Asp Leu Met Ile Gln Lys Thr
65                  70                  75

<210> SEQ ID NO 181
<211> LENGTH: 166
<212> TYPE: PRT
<213> ORGANISM: Unknown
<220> FEATURE:
<223> OTHER INFORMATION: metagenomes purified from environmentally
      challenged niches

<400> SEQUENCE: 181

Met Thr Thr Ile Thr Glu Phe Pro Pro Phe Tyr Thr Gln Gln Pro Asn
1               5                   10                  15

Ala Ser Ala Leu Thr Gln Gln Leu Gly Leu Trp Gln Lys His Ile Leu
            20                  25                  30

Ser Thr Cys Lys Gln Arg Arg Gln Phe Lys Leu Ser Val Ser Asp Asp
        35                  40                  45

Ile Trp Ala Asn Glu Arg Ile Lys Arg Ala Ala Ser Arg Glu Phe Ile
    50                  55                  60

Ser Val Ile Ile Ser Ser Leu Val Thr Glu Gly Leu Ala Ser Tyr Thr
65                  70                  75                  80

Asp Ala Thr Lys Glu Ala Val Trp Val Tyr Trp Arg Ser Leu Ser Asp
                85                  90                  95

Trp Ala Gln Ala Ala Tyr Ala Tyr Ala Glu Ser Thr Ala Gln Leu Asn
            100                 105                 110

Thr Pro Leu Thr Tyr Tyr Glu Leu Val Gln Gly Glu Tyr Ser His Leu
        115                 120                 125

Ser Glu Leu His Glu Met Pro Val Glu Leu Leu Lys Leu Ala Val Ser
    130                 135                 140

Leu Leu Val Lys Gln Asn Lys Ala Val Ile Ile Lys Thr Ser Gln Gly
145                 150                 155                 160

Glu Gly Val Lys Phe Val
                165

<210> SEQ ID NO 182
<211> LENGTH: 130
<212> TYPE: PRT
<213> ORGANISM: Unknown
<220> FEATURE:
<223> OTHER INFORMATION: metagenomes purified from environmentally
      challenged niches

<400> SEQUENCE: 182

Met Ser Ile Pro Lys Ala Ala His Thr Asp Lys Ala Pro Gln Pro
1               5                   10                  15

Phe Lys Asp Leu Tyr Ser Gln Ala Val Ile Ala Gly Gly Val Val Tyr
            20                  25                  30

Cys Ser Gly Ile Val Ala Ile Asp Pro Glu Thr Gly Ser Leu Ile Glu
            35                  40                  45

Gly Asp Val Lys Ala His Thr Glu Arg Ile Leu Gln Ser Leu Ser Ser
 50                  55                  60

Thr Leu Gln Ala Ala Gly Thr Ser Leu Asp Arg Ala Val Lys Ile Asn
 65                  70                  75                  80

Val Tyr Leu Ala Asn Met Glu Asp Phe Thr Ser Met Asn Ser Val Tyr
                 85                  90                  95

Glu Lys Tyr Phe Val Asp Gly Val Lys Pro Cys Arg Thr Cys Val Ala
            100                 105                 110

Val Lys Ser Leu Pro Phe Gly Thr Asp Val Glu Met Glu Cys Ile Ala
            115                 120                 125

Val Leu
    130

<210> SEQ ID NO 183
<211> LENGTH: 113
<212> TYPE: PRT
<213> ORGANISM: Unknown
<220> FEATURE:
<223> OTHER INFORMATION: metagenomes purified from environmentally
      challenged niches

<400> SEQUENCE: 183

Met Leu Arg Ser Gln Phe Gly Val Ile Ser Asn Ala Ala Lys Thr Ala
 1               5                  10                  15

Ala Phe Leu Lys Pro Val Gln Thr Arg Leu Tyr Ala Ser Gly Ala Leu
             20                  25                  30

Ser Lys Gly Asp Ile Gln Thr Arg Ile Phe Asp Val Leu Lys Ser Phe
         35                  40                  45

Asp Lys Val Lys Ala Asp Asn Leu Thr Glu Ser Ala Ser Phe Thr Asn
 50                  55                  60

Asp Leu Gly Leu Asp Ser Leu Asp Ala Val Glu Val Val Met Ala Ile
 65                  70                  75                  80

Glu Glu Glu Phe Ala Ile Glu Ile Pro Asp Ala Glu Ala Asp Ala Ile
                 85                  90                  95

Gln Asn Val Asn Gln Ala Ile Glu Tyr Ile Ala Lys Thr Pro Glu Ala
            100                 105                 110

His

<210> SEQ ID NO 184
<211> LENGTH: 200
<212> TYPE: PRT
<213> ORGANISM: Unknown
<220> FEATURE:
<223> OTHER INFORMATION: metagenomes purified from environmentally
      challenged niches

<400> SEQUENCE: 184

Val Val Ser Thr Gln Ser Gly Ala Pro Gly Thr Lys Lys Val Ser Ser
 1               5                  10                  15

Thr Tyr Leu Ser Lys Ile Cys Lys Glu Gln His Lys Ser Ile Phe Phe
             20                  25                  30

Tyr Leu Ile Asp Leu His Ser Ser Ala Ser Leu Arg Ser Val Thr Thr
         35                  40                  45

Leu Pro Ala Arg Met Glu Arg Ile Arg Leu Ser Glu Gln Ala Ala Thr
 50                  55                  60

Ile Cys Asn Gln Ile Arg Glu Met Ile Pro Glu Thr Ala Thr Leu Pro

```
                65                  70                  75                  80
Asn Gln Pro Gly Lys Asp Gln Ala Glu Leu Met His Glu Asp Glu Asn
                    85                  90                  95

Gly Asn Lys Ile Tyr Gly Gly Lys Leu Leu Thr Glu Arg Ala Ala Arg
                100                 105                 110

Leu Lys Glu His Met Lys Ile Asp Gln Val Ser Ala Arg Phe Ile Ser
                115                 120                 125

Gln Tyr Phe Thr Asn Gly Ile Gln Asp Trp Thr Glu Arg Leu Val Tyr
            130                 135                 140

Trp Thr Lys Pro Thr Lys Leu Leu Asn Gln Arg Lys Gln Gly Tyr Ile
145                 150                 155                 160

Ile Pro Leu Ser Lys Asp Ile Val Leu Gln Pro Gly Gly Pro Leu Glu
                165                 170                 175

Ala Asn Asn Gly Phe Arg Val Thr Asn Glu Arg Ile Leu Ser Ser Gly
                180                 185                 190

Ala Ala Leu Phe Ile Met Pro Gln
                195                 200

<210> SEQ ID NO 185
<211> LENGTH: 524
<212> TYPE: PRT
<213> ORGANISM: Unknown
<220> FEATURE:
<223> OTHER INFORMATION: metagenomes purified from environmentally
      challenged niches

<400> SEQUENCE: 185

Met Leu Ala Arg Ser Leu Gln Gln Ile Arg Arg Ser Ser Arg Leu Ser
1               5                   10                  15

Leu Gln Leu Arg Ala Tyr Ala Ser Ser Pro Asp Arg Ser Ala Ser Phe
                20                  25                  30

Ser Lys Leu Ser Glu Gln Asp Leu Pro Ser Leu Ala Ser Ile Phe Ser
            35                  40                  45

Ser Pro Asp Thr Ser Leu Leu Thr Thr Leu Gly Asp Lys Pro Thr Ala
        50                  55                  60

Thr Ser Asp Asp Leu Glu Pro Phe Asn Val Asp Trp Met Gly Lys Tyr
65                  70                  75                  80

Lys Gly His Ser Ser Ile Ile Val Lys Pro Lys Thr Thr Gln Glu Val
                85                  90                  95

Ser Lys Val Leu Gln Trp Cys Asn Glu Arg Asn Val Ala Val Val Pro
                100                 105                 110

Gln Gly Gly Asn Thr Gly Leu Val Gly Gly Ser Val Pro Leu His Asp
            115                 120                 125

Glu Val Val Leu Ser Leu Ser Ser Met Asn Ser Ile Arg His Phe Asp
        130                 135                 140

Pro Leu Ser Gly Tyr Val Ser Val Asp Ser Gly Ile Val Leu Glu Asn
145                 150                 155                 160

Leu Asp Asn Tyr Leu Ala Gln Gln Gly His Ile Val Pro Leu Asp Leu
                165                 170                 175

Gly Ala Lys Gly Ser Cys Gln Ile Gly Gly Asn Val Ala Thr Asn Ala
                180                 185                 190

Gly Gly Leu Arg Met Leu Arg Tyr Gly Ser Leu His Gly Asn Val Leu
            195                 200                 205

Gly Leu Glu Val Val Leu Pro Asp Gly Arg Val Ile Asn Gly Met Lys
        210                 215                 220
```

Gly Leu Lys Lys Asp Asn Thr Gly Ile Asp Leu Lys Gln Leu Phe Ile
225                 230                 235                 240

Gly Ser Glu Gly Val Leu Gly Val Ile Thr Gly Val Thr Leu Ala Thr
            245                 250                 255

Pro Val Arg Pro Ser Ala Thr Asn Val Ala Val Phe Ala Leu Pro Asp
            260                 265                 270

Tyr Glu Ser Val Gln Thr Ala Phe Ser Ser Ala Arg Arg Asp Leu Gly
        275                 280                 285

Glu Ile Leu Ser Ala Phe Glu Phe Phe Asp Ala Ala Ser Tyr Lys Leu
        290                 295                 300

Val Arg Ser His Gly His Ala Ala Glu Arg Lys Thr Phe Glu Asp Gly
305                 310                 315                 320

Glu Asp Ala Pro Phe Phe Cys Leu Val Glu Thr Ser Gly Ser Asn Lys
            325                 330                 335

Asp His Asp Asp Glu Lys Leu Gly Ala Phe Leu Glu Gln Leu Met Glu
            340                 345                 350

Ser Gly Ile Val Asn Asp Gly Val Leu Ala Gln Asp Glu Thr Gln Ile
        355                 360                 365

Gly Gln Leu Trp Ser Leu Arg Glu Gly Ile Pro Glu Ala Ala Gly Lys
370                 375                 380

Ala Gly Arg Val Tyr Lys Tyr Asp Leu Ser Leu Pro Val Glu Lys Met
385                 390                 395                 400

Tyr Ser Leu Val Pro Glu Leu Arg Gln Lys Leu Ala Glu Lys Gly Leu
            405                 410                 415

Leu Ala Ala Glu Ser Glu Gly Gly Asn Gly Asp Gly Pro Val Lys Thr
            420                 425                 430

Val Phe Gly Phe Gly His Leu Gly Asp Gly Asn Leu His Ile Asn Ile
        435                 440                 445

Val Ala Asp Ala Tyr Arg Lys Glu Val Glu Val Val Glu Pro Tyr
450                 455                 460

Ile Tyr Glu Leu Val Ala Lys Tyr Asn Gly Ser Ile Ser Ala Glu His
465                 470                 475                 480

Gly Leu Gly Leu Met Lys Ala Pro Tyr Val Ala Tyr Ser Gln Asp Ala
            485                 490                 495

Pro Ser Leu Asp Leu Met Arg Thr Leu Lys Lys Thr Leu Asp Pro Lys
            500                 505                 510

Gly Ile Leu Asn Pro Tyr Lys Cys Val Thr Ala Glu
        515                 520

<210> SEQ ID NO 186
<211> LENGTH: 185
<212> TYPE: PRT
<213> ORGANISM: Unknown
<220> FEATURE:
<223> OTHER INFORMATION: metagenomes purified from environmentally
      challenged niches

<400> SEQUENCE: 186

Met Ala Leu Tyr Tyr Gly Ile Val Phe Gly Ile Leu Thr Phe Glu Ile
1               5                   10                  15

Ile Leu Phe Phe Leu Phe Leu Leu Pro Ile Pro Thr Trp Gln Lys
            20                  25                  30

Pro Val Phe Arg Trp Leu Ala Thr Ser Pro Thr Ile Ala His Ala Gln
        35                  40                  45

Tyr Ile Met Lys Ile Val Phe Val Phe Ile Phe Val Leu Phe Leu Asp
    50                  55                  60

Ser Val Asn Thr Leu Arg Ala Phe Tyr Glu Val Val Asn Thr Glu Asp
 65                  70                  75                  80

Glu Asn Gly Gly Ile Pro Ala Ala Gly Asn Ser Asp Phe Arg Ala Gln
                 85                  90                  95

Val Gly Gln Ala Ala Lys Lys Phe Tyr Ala Gln Arg Asn Leu Tyr Leu
            100                 105                 110

Thr Gly Phe Thr Ile Leu Leu Leu Ile Leu Asn Lys Ile Lys Asn
        115                 120                 125

Met Ala Met Asp Tyr Ile Arg Leu Glu Asp Gln Phe Ile Glu Leu Glu
130                 135                 140

Gly Ser Val Ser Lys Asp Pro Ala Ile Arg Lys Ala Ser Lys Glu Ile
145                 150                 155                 160

Asp Thr Thr Pro Ile Glu Asp His Val Thr Arg Leu Glu Pro Val Glu
                165                 170                 175

Gln Glu Gln Glu Asn Lys Lys Asp Ile
            180                 185

<210> SEQ ID NO 187
<211> LENGTH: 138
<212> TYPE: PRT
<213> ORGANISM: Unknown
<220> FEATURE:
<223> OTHER INFORMATION: metagenomes purified from environmentally
      challenged niches

<400> SEQUENCE: 187

Val Ala Arg Arg Glu Ala Pro Asn Gly His Glu Leu Pro Pro Arg Gly
1               5                   10                  15

Tyr Asp Pro Gly Glu Asn Thr Tyr Gln Ala Pro Pro Asp Glu Arg Ser
            20                  25                  30

Gln Val Asp Val Ala Ile Asp Pro Lys Ser Asn Arg Leu Gln Leu Leu
        35                  40                  45

Lys Pro Phe Gln Lys Trp Asp Gly Lys Asp Ile Thr Asn Val Pro Ile
 50                 55                  60

Leu Ile Lys Val Gln Gly Lys Cys Thr Thr Asp His Ile Ser Met Ala
 65                 70                  75                  80

Gly Pro Trp Leu Lys Tyr Arg Gly His Leu Asp Asn Ile Ser Asn Asn
                85                  90                  95

Phe Leu Ile Gly Ala Lys Ser Ser Glu Gly Lys Val Asn Ser Ile Lys
            100                 105                 110

Asn Ala Phe Thr Gly Glu Tyr Lys Gly Val Gln Lys Gln Leu Val Ile
        115                 120                 125

Thr Arg Arg Lys Val Phe Val Gly Ser Trp
130                 135

<210> SEQ ID NO 188
<211> LENGTH: 144
<212> TYPE: PRT
<213> ORGANISM: Unknown
<220> FEATURE:
<223> OTHER INFORMATION: metagenomes purified from environmentally
      challenged niches

<400> SEQUENCE: 188

Gly Cys Pro Glu Thr Ala Arg Asp Tyr Lys Lys Glu Gly Val Arg Trp
1               5                   10                  15

Val Val Val Gly Asp Glu Asn Tyr Gly Glu Gly Ser Ser Arg Glu His
            20                  25                  30

```
Ala Ala Leu Glu Pro Arg Phe Leu Asn Gly Ala Ala Ile Ile Thr Lys
            35                  40                  45

Ser Phe Ala Arg Ile His Glu Thr Asn Leu Lys Lys Gln Gly Met Leu
 50                  55                  60

Pro Leu Thr Phe Ala Asp Pro Lys Asp Tyr Asp Lys Val Asp Ala Ser
 65                  70                  75                  80

Asp Lys Val Asp Ile Leu Gly Leu Thr Asp Phe Gln Glu Gly Lys Pro
                 85                  90                  95

Leu Thr Leu Arg Leu His Lys Lys Asp Gly Ser Thr Val Asp Val Pro
            100                 105                 110

Leu Asn His Thr Phe Asn Gly Gln Gln Ile Glu Trp Phe Lys His Gly
            115                 120                 125

Ser Ala Leu Asn Leu Met Lys Glu Asn Thr Ala Lys Asn Gly Ser Leu
130                 135                 140
```

<210> SEQ ID NO 189
<211> LENGTH: 264
<212> TYPE: PRT
<213> ORGANISM: Unknown
<220> FEATURE:
<223> OTHER INFORMATION: metagenomes purified from environmentally
      challenged niches

<400> SEQUENCE: 189

```
Val Ala Arg Arg Glu Ala Pro Asn Gly His Glu Leu Pro Pro Arg Gly
 1               5                  10                  15

Tyr Asp Pro Gly Glu Asn Thr Tyr Gln Ala Pro Pro Asp Glu Arg Ser
            20                  25                  30

Gln Val Asp Val Ala Ile Asp Pro Lys Ser Asn Arg Leu Gln Leu Leu
            35                  40                  45

Lys Pro Phe Gln Lys Trp Asp Gly Lys Asp Ile Thr Asn Val Pro Ile
 50                  55                  60

Leu Ile Lys Val Gln Gly Lys Cys Thr Thr Asp His Ile Ser Met Ala
 65                  70                  75                  80

Gly Pro Trp Leu Lys Tyr Arg Gly His Leu Asp Asn Ile Ser Asn Asn
                 85                  90                  95

Phe Leu Ile Gly Ala Lys Ser Ser Glu Gly Lys Val Asn Ser Ile Lys
            100                 105                 110

Asn Ala Phe Thr Gly Glu Tyr Lys Gly Val Pro Glu Thr Ala Arg Asp
            115                 120                 125

Tyr Lys Lys Glu Gly Val Arg Trp Val Val Gly Asp Glu Asn Tyr
130                 135                 140

Gly Glu Gly Ser Ser Arg Glu His Ala Ala Leu Glu Pro Arg Phe Leu
145                 150                 155                 160

Asn Gly Ala Ala Ile Ile Thr Lys Ser Phe Ala Arg Ile His Glu Thr
                165                 170                 175

Asn Leu Lys Lys Gln Gly Met Leu Pro Leu Thr Phe Ala Asp Pro Lys
            180                 185                 190

Asp Tyr Asp Lys Val Asp Ala Ser Asp Lys Val Asp Ile Leu Gly Leu
            195                 200                 205

Thr Asp Phe Gln Glu Gly Lys Pro Leu Thr Leu Arg Leu His Lys Lys
        210                 215                 220

Asp Gly Ser Thr Val Asp Val Pro Leu Asn His Thr Phe Asn Gly Gln
225                 230                 235                 240

Gln Ile Glu Trp Phe Lys His Gly Ser Ala Leu Asn Leu Met Lys Glu
```

-continued

```
                245                 250                 255

Asn Thr Ala Lys Asn Gly Ser Leu
            260

<210> SEQ ID NO 190
<211> LENGTH: 195
<212> TYPE: PRT
<213> ORGANISM: Unknown
<220> FEATURE:
<223> OTHER INFORMATION: metagenomes purified from environmentally
      challenged niches

<400> SEQUENCE: 190

Gly Ala Pro Leu Thr Gln Glu His Gly Phe Pro Val Arg Val Ile Val
1               5                   10                  15

Pro Gly Val Ala Gly Ala Arg Ala Val Lys Trp Leu Asp His Ile Thr
            20                  25                  30

Val Gln Arg Glu Met Ser Ser Asn His Tyr Met His Phe Asp Tyr Lys
        35                  40                  45

Val Leu Pro Pro Glu Ala Val Asp Ala Glu Arg Ala Arg Thr Phe Trp
    50                  55                  60

His Lys Val Pro Pro Val Ile Asp Met Pro Ala Asn Ser Ala Ile Thr
65                  70                  75                  80

Ser Pro Arg Asn Glu Asp Thr Val Glu Val Asp Ala Glu Gly Phe Ile
                85                  90                  95

Thr Val Asp Gly Tyr Ala Leu Pro Gly Gly Glu Asp Gly Pro Val Lys
            100                 105                 110

Arg Val Glu Val Ser Ile Asp Lys Glu Arg Trp Val Asp Ala Glu Leu
        115                 120                 125

Phe Thr His Pro Met Glu Ser Lys Trp Thr Trp Lys Ile Trp Lys Ala
    130                 135                 140

Lys Val Gln Val Glu Pro Gly Glu Arg Arg Cys Leu Tyr Ser Arg Thr
145                 150                 155                 160

Thr Asp Glu Ala Gly Asn Ser Gln Pro Gln Arg Ser Gln Trp Asn Leu
                165                 170                 175

Arg Gly Val Cys Tyr Asn Gly Tyr Gly Glu Val Arg Asn Leu Lys Val
            180                 185                 190

Val Lys Gly
        195

<210> SEQ ID NO 191
<211> LENGTH: 50
<212> TYPE: PRT
<213> ORGANISM: Unknown
<220> FEATURE:
<223> OTHER INFORMATION: metagenomes purified from environmentally
      challenged niches

<400> SEQUENCE: 191

Met Pro Ala Asn Thr Met Ser Thr Leu Arg Ser Leu His Val Pro
1               5                   10                  15

Gly Lys Pro Val Ile Phe Ala Asn Val Trp Asp Thr Val Ser Ala Lys
            20                  25                  30

Ser Ile Ala Pro Leu Asp Ser Cys Lys Ala Leu Ala Thr Ala Ser Tyr
        35                  40                  45

Ala Ile
    50
```

```
<210> SEQ ID NO 192
<211> LENGTH: 373
<212> TYPE: PRT
<213> ORGANISM: Unknown
<220> FEATURE:
<223> OTHER INFORMATION: metagenomes purified from environmentally
      challenged niches

<400> SEQUENCE: 192
```

| | | | | | | | | | | | | | | | |
|---|---|---|---|---|---|---|---|---|---|---|---|---|---|---|---|
| Ala | Leu | Pro | Met | Leu | Ile | Asn | Pro | Pro | Arg | Asn | Leu | Ile | Gly | Gln | |
| 1 | | | | 5 | | | | | 10 | | | | | 15 | |
| Ser | Gln | Ser | Gly | Thr | Gly | Lys | Thr | Ala | Ala | Phe | Thr | Leu | Asn | Met | Leu |
| | | | 20 | | | | | 25 | | | | | 30 | | |
| Ser | Arg | Val | Asp | Pro | Asn | Ile | Met | Thr | Pro | Gln | Ala | Ile | Cys | Leu | Ala |
| | | 35 | | | | | 40 | | | | | 45 | | | |
| Pro | Ser | Arg | Glu | Leu | Ala | Arg | Gln | Ile | Gln | Glu | Val | Val | Asp | Lys | Ile |
| | 50 | | | | | 55 | | | | | 60 | | | | |
| Gly | Gln | Phe | Thr | Gln | Ile | Lys | Ser | Phe | Leu | Ala | Val | Pro | Gly | Ser | Trp |
| 65 | | | | | 70 | | | | | 75 | | | | | 80 |
| Ser | Arg | Asn | Val | Lys | Ile | Asp | Lys | His | Ile | Leu | Val | Gly | Thr | Pro | Gly |
| | | | | 85 | | | | | 90 | | | | | 95 | |
| Thr | Leu | Val | Asp | Met | Leu | Ser | Arg | Gly | Gly | Arg | Ile | Phe | Asp | Pro | Lys |
| | | | 100 | | | | | 105 | | | | | 110 | | |
| Gln | Ile | Arg | Val | Phe | Val | Leu | Asp | Glu | Ala | Asp | Glu | Met | Ile | Ala | Leu |
| | | 115 | | | | | 120 | | | | | 125 | | | |
| Gln | Gly | Leu | Gly | Asp | Gln | Thr | Lys | Arg | Ile | Lys | Arg | Met | Leu | Pro | Pro |
| | 130 | | | | | 135 | | | | | 140 | | | | |
| Gly | Val | Gln | Asn | Val | Leu | Phe | Ser | Ala | Thr | Phe | Pro | Asp | Asn | Val | Arg |
| 145 | | | | | 150 | | | | | 155 | | | | | 160 |
| Asp | Phe | Ala | Gly | Asp | Phe | Ala | Pro | Glu | Ala | Asn | Gln | Ile | Phe | Leu | Lys |
| | | | | 165 | | | | | 170 | | | | | 175 | |
| Lys | Glu | Glu | Ile | Thr | Val | Asp | Ala | Ile | Lys | Gln | Leu | Tyr | Leu | Glu | Cys |
| | | | 180 | | | | | 185 | | | | | 190 | | |
| Asp | Gly | Glu | Glu | Gln | Lys | Tyr | Asn | Ala | Leu | Ser | Ala | Leu | Tyr | Asp | Ile |
| | | 195 | | | | | 200 | | | | | 205 | | | |
| Met | Ser | Ile | Gly | Gln | Ser | Ile | Val | Phe | Cys | Lys | Arg | Lys | Asp | Thr | Ala |
| | 210 | | | | | 215 | | | | | 220 | | | | |
| Asp | Arg | Ile | Ala | Ala | Arg | Leu | Thr | Asp | Glu | Gly | His | Ser | Val | Ala | Ser |
| 225 | | | | | 230 | | | | | 235 | | | | | 240 |
| Leu | His | Gly | Asp | Lys | Gln | Thr | Arg | Asp | Arg | Asp | Ile | Leu | Asp | Ala | |
| | | | | 245 | | | | | 250 | | | | | 255 | |
| Phe | Arg | Asp | Gly | Lys | Thr | Lys | Val | Leu | Ile | Thr | Thr | Asn | Val | Val | Ala |
| | | | 260 | | | | | 265 | | | | | 270 | | |
| Arg | Gly | Ile | Asp | Ile | Gln | Gln | Val | Asn | Met | Val | Val | Asn | Tyr | Asp | Val |
| | | 275 | | | | | 280 | | | | | 285 | | | |
| Pro | Asp | Leu | Gly | Pro | Glu | Gly | Asp | Trp | Lys | Pro | Asp | Ile | Glu | Thr | Tyr |
| | 290 | | | | | 295 | | | | | 300 | | | | |
| Ile | His | Arg | Ile | Gly | Arg | Thr | Gly | Arg | Phe | Arg | Lys | Gly | Cys | Ser | |
| 305 | | | | | 310 | | | | | 315 | | | | | 320 |
| Val | Ile | Phe | Ala | His | Asp | Gln | Arg | Ser | Met | Gln | Asp | Val | Gln | Phe | Ile |
| | | | | 325 | | | | | 330 | | | | | 335 | |
| Ala | Asp | Thr | Leu | Gly | Lys | Lys | Met | Ser | Arg | Ile | Asn | Ala | Thr | Arg | Gln |
| | | | 340 | | | | | 345 | | | | | 350 | | |
| Thr | Asp | Leu | Asp | Gln | Leu | Glu | Ala | Ala | Leu | Lys | Ala | Ala | Ile | Lys | Gly |
| | | 355 | | | | | 360 | | | | | 365 | | | |

Asn Gln Pro Lys Glu
    370

<210> SEQ ID NO 193
<211> LENGTH: 274
<212> TYPE: PRT
<213> ORGANISM: Unknown
<220> FEATURE:
<223> OTHER INFORMATION: metagenomes purified from environmentally
    challenged niches

<400> SEQUENCE: 193

Met Ala Thr Phe Ser Thr Arg Ile Asn Leu Val Pro Thr Ser Arg Thr
1               5                      10               15

Leu Ala Ser Gly Val Pro Phe Ala Pro Arg Ile Ala Leu Val His Pro
                  20                   25                   30

Pro Ala Ser His Gly His Gly Thr Ser Gly Pro Arg Ser Asp Val Pro
            35                    40                   45

Pro Arg Trp Ala Gly Val Gln Gly Gly Phe Ala Ser Asn Ser Arg Val
    50                      55                   60

Asn Val Leu Pro Thr Gly Asn Phe Gln Gln Arg Phe Met Ser Thr Thr
65                70                   75                   80

Pro Ala Arg Lys Ile Glu Ala Gln Pro His Val Arg Gly Val Pro Asp
                  85                   90                   95

Trp Ser Ala Tyr Gln Ser Ser Gly Lys Gly Glu Asn Thr Arg Ser Leu
            100                   105                110

Ser Tyr Phe Met Val Gly Ser Leu Gly Val Leu Ala Ala Ser Gly Ala
            115                   120                125

Lys Ser Thr Val Ser Asp Ile Leu Ser Asn Met Ala Ala Ser Ala Asp
    130                     135                  140

Val Leu Ala Leu Ala Lys Ile Glu Val Glu Met Gly Ala Ile Pro Glu
145              150                  155                 160

Gly Lys Asn Leu Ile Val Lys Trp Arg Gly Lys Pro Val Phe Ile Arg
               165                   170                175

His Arg Thr Glu Asp Glu Ile Asn Glu Ala Arg Ala Val Asp Ile Lys
            180                   185                190

Ser Leu Arg Asp Pro Glu Ser Asp Glu Asp Arg Thr Gln Arg Gly Glu
            195                   200                205

Trp Leu Val Met Leu Gly Val Cys Thr His Leu Gly Cys Val Pro Ile
    210                     215                  220

Gly Glu Ala Gly Asp Tyr Gly Gly Trp Phe Cys Pro Cys His Gly Ser
225              230                  235                 240

His Tyr Asp Ile Ser Gly Arg Ile Arg Arg Gly Pro Ala Pro Leu Asn
               245                   250                255

Leu Glu Val Pro Glu Tyr Ala Phe Asn Asp Asp Glu Glu Lys Leu Val
            260                   265                270

Ile Gly

<210> SEQ ID NO 194
<211> LENGTH: 472
<212> TYPE: PRT
<213> ORGANISM: Unknown
<220> FEATURE:
<223> OTHER INFORMATION: metagenomes purified from environmentally
    challenged niches

<400> SEQUENCE: 194

Gly Glu His His His Ser Asp Arg Asp Cys Ser Ser Val Lys Arg Val

-continued

```
1               5                   10                  15
Phe Ala Leu Gly Arg Leu Asp Val Thr Leu Ala Val Glu Cys Gly Ser
                20                  25                  30

Val Arg Thr Met Ser Leu Arg Asp Leu Ala Cys Tyr Thr Leu Thr Leu
                35                  40                  45

Lys Pro Ser Thr Glu Asn Thr Leu Leu Thr Glu Leu Thr Ala Leu Glu
 50                  55                  60

Gly Pro Ser Glu Pro Arg Phe Ala Arg Val Arg Glu Lys Val Glu
 65                  70                  75                  80

Gly Glu Val Tyr Ser Ser Ala Ile Tyr Asp Ala Leu Thr Gly Ala Lys
                85                  90                  95

Leu Ala Ser Val Gly Phe Ala Ser Glu Lys Gln Lys Asn Arg Arg Leu
                100                 105                 110

Gln Leu His Asn Pro Asp Glu Ser Val Pro Phe Asp Asn Thr Ser Lys
                115                 120                 125

Leu Gly Phe Glu Trp Thr Phe Ile Phe Glu Gly Asn Lys Tyr Arg Trp
                130                 135                 140

Thr Arg Glu Leu Tyr Gly Lys Asp Tyr Ile Cys Ser Leu Asp Arg Lys
145                 150                 155                 160

Pro Asp Pro Arg Val Glu Ile Cys Leu Ala Arg Asp Ala Asp Ser Lys
                165                 170                 175

Ala Pro Gly Arg Leu Gln Ile Leu His Tyr Asn Ile Glu Arg Phe Pro
                180                 185                 190

Asn Glu Ile Lys Asp Leu Arg Gly Leu Glu Thr Leu Leu Ile Ala Thr
                195                 200                 205

Leu Met Cys Phe Val Asp Ala Ala Glu Asp Arg Ser Asn Ser Gly Pro
210                 215                 220

Thr Arg Thr Ser Pro Leu Pro Ala Lys Pro Val Ala Asn Ala Ala Ala
225                 230                 235                 240

Gly Gln Ser Gly Thr Ser Ala Ser Gly Ser Ser Asp Thr Arg Ala Lys
                245                 250                 255

Val Ala Pro Val Thr Val Pro Val Ile Thr Ala Glu Asp Phe Glu Asp
                260                 265                 270

Asp Cys Asp Pro Asn Glu Ile Leu Val Gly Thr Glu Thr Asp Val Gly
                275                 280                 285

Glu His Ile Ala Arg Ala Ile Ala Leu Leu Glu Asp Pro Thr Met Leu
                290                 295                 300

Phe Ile Val Ile Arg Thr Arg Thr Ala Ala Ala Ser Ser Arg Ala Leu
305                 310                 315                 320

Glu Val Ser Leu Gly Val Thr Arg Phe Arg His Arg Glu Gly Met Ser
                325                 330                 335

Glu Leu His Gln Tyr Val Val Glu Glu Asp Pro Val Arg Lys Pro Lys
                340                 345                 350

Pro Ile Met Pro Ala Gln Gly Leu Lys Leu Ile Asn Leu Asp Asp Arg
                355                 360                 365

Pro Ala Ala Gln Ser Pro Thr Lys Pro Glu Trp Ser Ala Pro Pro Asn
                370                 375                 380

Ile Ala Val Tyr Leu Ser Ser Ile Glu Leu Pro Asp Leu Thr Pro Lys
385                 390                 395                 400

Pro Lys Pro Val Gln Gly His Thr Arg Pro Thr Gln Ala Pro His
                405                 410                 415

Ala Arg Pro Pro Pro Ser Gln Leu Pro Gln Lys Pro Gln Pro Arg
                420                 425                 430
```

```
Pro Arg Pro Pro Ser Asp Gly Ser Gly Ser Ser Gln Thr Thr Leu
        435                 440                 445

Ala Ser Thr Arg Pro Pro Gln Asp Asp Gly Lys Asp Ser Arg Lys Ser
450                 455                 460

Ser Phe Gly Arg Leu Phe Gly Arg
465                 470

<210> SEQ ID NO 195
<211> LENGTH: 82
<212> TYPE: PRT
<213> ORGANISM: Unknown
<220> FEATURE:
<223> OTHER INFORMATION: metagenomes purified from environmentally
      challenged niches

<400> SEQUENCE: 195

Met Ala Ser Gln Leu Met Pro Leu Glu Leu Ile Asp Arg Cys Ile Gly
1               5                   10                  15

Ser Arg Met Arg Val Ile Met Lys Gly Asp Lys Glu Phe Ser Gly Thr
            20                  25                  30

Leu Leu Gly Phe Asp Asp Phe Val Asn Met Val Leu Glu Asp Val Thr
        35                  40                  45

Glu Tyr Asp Tyr Thr Gly Ala Thr Thr Lys Leu Pro Lys Ile Leu Leu
50                  55                  60

Asn Gly Asn Asn Ile Cys Met Leu Ile Pro Gly Gly Met Pro Glu Gly
65                  70                  75                  80

Glu Ser

<210> SEQ ID NO 196
<211> LENGTH: 116
<212> TYPE: PRT
<213> ORGANISM: Unknown
<220> FEATURE:
<223> OTHER INFORMATION: metagenomes purified from environmentally
      challenged niches

<400> SEQUENCE: 196

Gly Asp Asp Asn Lys Lys Thr Ile Pro His Leu Asn Ile Phe Asn Asn
1               5                   10                  15

Gly Val Pro Ile Asp Ala Pro Gly Ala Asp Arg Ser Leu His Arg Ile
            20                  25                  30

Lys Asn Ala Cys Asp His Glu Arg Arg Gln Arg Val Gln Arg His Thr
        35                  40                  45

Ser Arg Ile Arg Arg Leu Arg Gln Tyr Gly Ala Arg Gly Cys His Arg
    50                  55                  60

Val Arg Leu His Arg Arg Asn Asp Gln Ala Ser Gln Asp Pro Ser Glu
65                  70                  75                  80

Arg Gln Gln His Leu His Ala His Pro Arg Trp His Ala Arg Gly Arg
                85                  90                  95

Val Met Asn His Gly His Met Ile Ser Leu Leu Thr Ser Leu Glu Met
            100                 105                 110

Ala Lys Arg Val
        115

<210> SEQ ID NO 197
<211> LENGTH: 108
<212> TYPE: PRT
<213> ORGANISM: Unknown
<220> FEATURE:
```

<223> OTHER INFORMATION: metagenomes purified from environmentally
      challenged niches

<400> SEQUENCE: 197

Ala Lys Glu Leu Ser Pro Asp Val Lys Pro Glu Pro Thr Trp Ser Cys
1               5                   10                  15

Gly Glu Val Val Asn Val Val Asp Glu His Gly Asn Val Ile Lys Pro
            20                  25                  30

Ser Asp Leu Trp Val Lys Met Gly Met Gln Gln Asp Asn Val Asp
        35                  40                  45

Asn Leu Leu Ile Asp Asp Leu Cys Asp Gln Met Arg Ala Lys Ala Lys
50                  55                  60

Cys Thr Glu Asn Gly Ala Gln Leu Asn Val Asp Asp Leu Asn His Met
65                  70                  75                  80

Met Ser Tyr Asp Lys Ser Tyr Lys Gln Lys Arg Val Asp Leu Lys
            85                  90                  95

Asp Lys Tyr Gly Trp Gly Ala Val Phe Gly Pro Lys
            100                 105

<210> SEQ ID NO 198
<211> LENGTH: 38
<212> TYPE: PRT
<213> ORGANISM: Unknown
<220> FEATURE:
<223> OTHER INFORMATION: metagenomes purified from environmentally
      challenged niches

<400> SEQUENCE: 198

Gly Ser Leu Thr Arg Arg Ala Trp Phe Ile Gln Ser Thr Cys Ala Thr
1               5                   10                  15

Thr Gly Asp Gly Leu Tyr Glu Gly Leu Glu Trp Leu Ala Asp Thr Leu
            20                  25                  30

Arg Lys Thr Asn Arg Asp
        35

<210> SEQ ID NO 199
<211> LENGTH: 311
<212> TYPE: PRT
<213> ORGANISM: Unknown
<220> FEATURE:
<223> OTHER INFORMATION: metagenomes purified from environmentally
      challenged niches

<400> SEQUENCE: 199

Met Glu Asn Leu Leu Arg Gln Met Gln Gly Gly Gly Arg Met Gly
1               5                   10                  15

Ala Arg Pro Gly Pro Gly Gly Glu Thr Ile Leu Ala Asp Asn Gly Glu
            20                  25                  30

Thr Val His Ile Ser Ser Leu Ala Leu Leu Lys Met Leu Lys His Gly
        35                  40                  45

Arg Ala Gly Val Pro Met Glu Val Met Gly Leu Met Gly Glu Phe
50                  55                  60

Val Asp Asp Tyr Thr Ile Ser Cys Val Asp Val Phe Ala Met Pro Gln
65                  70                  75                  80

Ser Gly Thr Thr Val Thr Val Glu Ser Val Asp His Val Phe Gln Thr
            85                  90                  95

Lys Met Leu Asp Met Leu Lys Gln Thr Gly Arg Pro Glu Met Val Val
            100                 105                 110

Gly Trp Tyr His Ser His Pro Gly Phe Gly Cys Trp Leu Ser Ser Val

```
            115                 120                 125
Asp Val Asn Thr Gln Gln Ser Phe Glu Gln Leu His Pro Arg Ala Val
            130                 135                 140

Ala Val Val Ile Asp Pro Ile Gln Ser Val Arg Gly Lys Val Val Ile
145                 150                 155                 160

Asp Ala Phe Arg Ser Ile Asn Pro Gln Ser Leu Val Ala Gly Gln Glu
                165                 170                 175

Ser Arg Gln Thr Thr Ser Asn Ile Gly His Leu Asn Lys Pro Ser Ile
            180                 185                 190

Gln Ala Leu Ile His Gly Leu Asn Arg His Tyr Tyr Ser Leu Ala Ile
            195                 200                 205

Asp Tyr Arg Lys Thr Glu Gly Glu Gln Gly Met Leu Leu Asn Leu His
            210                 215                 220

Lys Arg Gly Trp Thr Glu Gly Leu Lys Met Arg Asp His Ser Glu Met
225                 230                 235                 240

Lys Glu Gly Asn Glu Lys Ala Ile Lys Glu Met Leu Ser Leu Ala Ser
                245                 250                 255

Ala Tyr Thr Lys Ser Val Gln Glu Glu Thr Thr Met Thr Ala Glu Gln
                260                 265                 270

Leu Lys Thr Arg His Val Gly Lys Leu Asp Pro Lys Arg His Leu Gly
            275                 280                 285

Glu Ala Ala Glu Lys Ala Met Gly Asp Gln Val Thr Gln Ser Leu Ala
290                 295                 300

Met Gly Val Leu Ala Glu Leu
305                 310

<210> SEQ ID NO 200
<211> LENGTH: 213
<212> TYPE: PRT
<213> ORGANISM: Unknown
<220> FEATURE:
<223> OTHER INFORMATION: metagenomes purified from environmentally
      challenged niches

<400> SEQUENCE: 200

Gly His Thr Gly Asp Val Leu Ser Val Ser Phe Ser Ala Asp Asn Arg
1               5                   10                  15

Gln Ile Val Ser Ala Ser Arg Asp Arg Thr Thr Lys Leu Trp Asn Thr
            20                  25                  30

Leu Gly Glu Cys Lys Phe Asn Ile Val Asp Asp Gly His Ser Glu Trp
        35                  40                  45

Val Ser Cys Val Arg Phe Ser Pro Asn Pro Val Ile Pro Val Ile Val
    50                  55                  60

Ser Ala Gly Trp Asp Lys Val Val Lys Val Trp Glu Leu Ser Lys Cys
65                  70                  75                  80

Lys Leu Lys Thr Asn His His Gly His Thr Gly Tyr Ile Asn Thr Leu
                85                  90                  95

Ala Val Ser Pro Asp Gly Ser Leu Ala Ala Ser Gly Gly Lys Tyr Gly
            100                 105                 110

Ile Thr Met Leu Trp Asp Leu Asn Asp Gly Lys His Leu Tyr Ser Leu
        115                 120                 125

Glu Ala Gly Asp Ile Val Asn Ser Leu Val Phe Ser Pro Asn Arg Tyr
    130                 135                 140

Trp Leu Cys Ala Ala Thr Ala Ser Ser Ile Lys Ile Leu Asp Leu Glu
145                 150                 155                 160
```

```
Ser Lys Ser Ile Val Asp Asp Leu Lys Pro Asp Phe Ser Ala Glu Tyr
            165                 170                 175

Pro Asp Lys Ala Gln Lys Pro Gln Cys Thr Ser Leu Ala Trp Ser Ala
            180                 185                 190

Asp Gly Gln Thr Leu Phe Ala Gly Phe Ser Asp Asn Leu Val Arg Val
            195                 200                 205

Trp Val Val Thr Ala
    210

<210> SEQ ID NO 201
<211> LENGTH: 76
<212> TYPE: PRT
<213> ORGANISM: Unknown
<220> FEATURE:
<223> OTHER INFORMATION: metagenomes purified from environmentally
      challenged niches

<400> SEQUENCE: 201

Met Val Thr Arg Ser Gly Ser Leu Ala Phe Asp Ser Leu Leu Thr Pro
1               5                   10                  15

Ser Phe Pro Ser Ser Leu Leu Val Gly Thr Arg Ser Ser Arg Ser
            20                  25                  30

Gly Asn Cys Pro Ser Ala Ser Ser Arg Pro Thr Thr Thr Val Thr Leu
            35                  40                  45

Val Thr Ser Thr Pro Ser Pro Phe Arg Pro Thr Asp Arg Ser Pro His
    50                  55                  60

Pro Val Glu Ser Met Ala Ser Pro Cys Phe Gly Ile
65                  70                  75

<210> SEQ ID NO 202
<211> LENGTH: 99
<212> TYPE: PRT
<213> ORGANISM: Unknown
<220> FEATURE:
<223> OTHER INFORMATION: metagenomes purified from environmentally
      challenged niches

<400> SEQUENCE: 202

Met Leu Trp Asp Leu Asn Asp Gly Lys His Leu Tyr Ser Leu Glu Ala
1               5                   10                  15

Gly Asp Ile Val Asn Ser Leu Val Phe Ser Pro Asn Arg Tyr Trp Leu
            20                  25                  30

Cys Ala Ala Thr Ala Ser Ser Ile Lys Ile Leu Asp Leu Glu Ser Lys
            35                  40                  45

Ser Ile Val Asp Asp Leu Lys Pro Asp Phe Ser Ala Glu Tyr Pro Asp
    50                  55                  60

Lys Ala Gln Lys Pro Gln Cys Thr Ser Leu Ala Trp Ser Ala Asp Gly
65                  70                  75                  80

Gln Thr Leu Phe Ala Gly Phe Ser Asp Asn Leu Val Arg Val Trp Val
                85                  90                  95

Val Thr Ala

<210> SEQ ID NO 203
<211> LENGTH: 124
<212> TYPE: PRT
<213> ORGANISM: Unknown
<220> FEATURE:
<223> OTHER INFORMATION: metagenomes purified from environmentally
      challenged niches

<400> SEQUENCE: 203
```

Val Phe Ala Ile Val Gln Ile Pro Lys His Gly Asp Ala Ile Leu Ser
1               5                   10                  15

Thr Gly Cys Gly Glu Arg Ser Val Gly Arg Asn Gly Glu Gly Val Asp
            20                  25                  30

Val Thr Ser Val Thr Val Val Gly Leu Glu Leu Ala Leu Gly Gln
        35                  40                  45

Phe Pro Asp Leu Asp Asp Leu Val Pro Thr Ser Arg Asp Asp Asp Gly
    50                  55                  60

Asn Asp Gly Val Arg Arg Glu Ser Asn Ala Arg Asp Pro Leu Arg Val
65                  70                  75                  80

Thr Ile Val Asn Asn Val Glu Leu Ala Leu Ser Glu Ser Val Pro Glu
                85                  90                  95

Leu Gly Ser Ser Val Ser Gly Ser Arg Asn Asp Leu Ser Val Val Gly
                100                 105                 110

Arg Glu Arg Asp Ala Gln Asp Val Thr Gly Val Ser
            115                 120

<210> SEQ ID NO 204
<211> LENGTH: 38
<212> TYPE: PRT
<213> ORGANISM: Unknown
<220> FEATURE:
<223> OTHER INFORMATION: metagenomes purified from environmentally
      challenged niches

<400> SEQUENCE: 204

Gly Ser Leu Thr Arg Arg Ala Trp Phe Ile Gln Ser Thr Cys Ala Thr
1               5                   10                  15

Thr Gly Asp Gly Leu Tyr Glu Gly Leu Glu Trp Leu Ala Asp Thr Leu
            20                  25                  30

Arg Lys Thr Asn Arg Asp
            35

<210> SEQ ID NO 205
<211> LENGTH: 393
<212> TYPE: PRT
<213> ORGANISM: Unknown
<220> FEATURE:
<223> OTHER INFORMATION: metagenomes purified from environmentally
      challenged niches

<400> SEQUENCE: 205

Gly Arg Tyr Asp Phe Lys Gln Pro Gln Arg Ile Arg Asp Ala Ser Val
1               5                   10                  15

Thr Ala Thr Pro Glu Trp Asn Leu Leu Glu Glu Ile Glu Phe Gly Arg
            20                  25                  30

Leu Gly Lys Leu Asn Leu Ser Val Glu Glu Pro Glu Asp Leu Glu Ser
            35                  40                  45

His Gly Thr Leu Gln Gly Tyr Asp Lys Thr Phe Asp Arg Ile Asn Thr
    50                  55                  60

Arg Thr Glu Arg Pro Leu Glu Ile Ile Asp Arg Ala Trp Tyr Asn Gln
65                  70                  75                  80

Thr Thr Ser Asp Asp Pro Val Ile Ala Gln Leu Ala Gln Thr Gln Ser
                85                  90                  95

Ala Gln Ile Phe Ala Thr Asp Ala Ile Leu Ala Val Leu Met Cys Thr
            100                 105                 110

Thr Arg Ser Val Asn Ser Trp Asp Ile Ile Leu Glu Arg Arg Gly Asn
            115                 120                 125

Gln Leu Phe Leu Asp Lys Arg Asp Ser Gly Pro Phe Asp Tyr Val Thr
            130                 135                 140

Val His Glu Asn Ala Ala Asp Pro Pro Ala Asp Ser Asp Pro Asn
145                 150                 155                 160

Asn Val Asn Ser Ala Ser Ser Leu Ser Leu Glu Ala Thr Tyr Ile Thr
                165                 170                 175

Arg Asn Phe Ser Ser Gln Val Ile Asp Ala Lys Ser Lys Pro Tyr Ser
            180                 185                 190

Pro Ser Pro Asn Pro Phe Tyr Ser Glu Asp Glu Pro Ser Pro Val Ala
        195                 200                 205

Ser Cys Leu Tyr Arg Tyr Arg Lys Phe Asp Leu Ser Val Gly Glu Glu
            210                 215                 220

Asp Thr Leu Asp Leu Ile Val Arg Thr Glu Val Asp Ala Tyr Gln Gly
225                 230                 235                 240

Lys Lys Asp Ser Leu Val Thr Val Lys Ala Leu Asn Glu Phe Asp Pro
                245                 250                 255

Arg Ala Ser Gly Gly Lys Ala Leu Asp Trp Arg Lys Tyr Leu Asp
            260                 265                 270

Thr Gln Lys Gly Ala Ile Val Ala Ser Glu Met Lys Asn Asn Ser Ala
        275                 280                 285

Lys Leu Ala Arg Trp Ala Ile Gln Ser Val Leu Ala Gly Ala Glu Val
290                 295                 300

Met Lys Met Gly Tyr Ile Ser Arg Ala Ser Pro Arg Asp Thr Thr His
305                 310                 315                 320

His Val Ile Val Gly Val Gln Asn Tyr Lys Pro Lys Asp Phe Ala Ala
                325                 330                 335

Gln Met Asn Val Ser Leu Asn Asn Gly Trp Gly Ile Val Arg Thr Ile
            340                 345                 350

Ala Asp Leu Val Leu Lys Gln Pro Glu Gly Lys Tyr Val Leu Val Lys
        355                 360                 365

Asp Pro Asn Ala Gly Ile Ile Arg Leu Tyr Ser Val Pro Glu Asn Ala
370                 375                 380

Phe Glu Ala Glu Glu Glu Glu Gln
385                 390

<210> SEQ ID NO 206
<211> LENGTH: 106
<212> TYPE: PRT
<213> ORGANISM: Unknown
<220> FEATURE:
<223> OTHER INFORMATION: metagenomes purified from environmentally
      challenged niches

<400> SEQUENCE: 206

Met Thr Ser Ser Ser Leu Ser Glu Phe Glu Thr Leu Leu Ser Arg Pro
1               5                   10                  15

Arg Gln Asn Gly Thr Cys Leu Lys Arg Ser Ser Leu Ala Asp Trp Ala
            20                  25                  30

Ser Ser Thr Phe Pro Ser Lys Ser Pro Lys Thr Ser Asn Arg Thr Val
        35                  40                  45

Pro Ser Lys Val Thr Thr Arg Arg Leu Thr Ala Ser Thr Leu Val Pro
    50                  55                  60

Lys Asp Leu Ser Arg Ser Leu Ile Glu His Gly Thr Ile Lys Pro Leu
65                  70                  75                  80

Leu Thr Ile Pro Leu Leu Leu Ser Ser Leu Lys Arg Ser Leu Pro Lys

```
                 85                  90                  95

Ser Ser Arg Gln Met Pro Phe Leu Arg Phe
            100                 105

<210> SEQ ID NO 207
<211> LENGTH: 245
<212> TYPE: PRT
<213> ORGANISM: Unknown
<220> FEATURE:
<223> OTHER INFORMATION: metagenomes purified from environmentally
      challenged niches

<400> SEQUENCE: 207

Glu Arg Ser Arg Ser Leu Ala Pro Glu Ala Asp Gln Gly Val Ala Thr
1               5                   10                  15

Gln Cys His Glu Val Arg Ser Ser Gly Ser Tyr Asp Thr Phe Glu Ile
            20                  25                  30

Gly His His Gln Pro Asp Ser Asp Thr Ser Gly Val Ala Asp Leu Arg
        35                  40                  45

Thr Ser Ser Arg Met Asp Thr Cys Asp Ala His Leu Leu Arg Arg Val
    50                  55                  60

Lys Ser Cys Pro Leu Phe Ser Tyr Arg Glu Asp Glu Val Ser Glu Thr
65                  70                  75                  80

Val Gln Leu Pro Thr Gly Glu Trp Thr Thr Ile Arg Asp Ile Thr Pro
                85                  90                  95

Ser Ala Pro Lys Ile Gly Phe Glu Val Arg Asp Ser Leu Ser Ala Phe
            100                 105                 110

Pro Thr Ala Lys Pro Val Glu Ala Lys His Glu Ser Ala Ser Ser Ile
        115                 120                 125

Ser Asn Asp Leu Pro Ser Gln Pro Ser Ser Arg Pro Leu Ile Glu Cys
    130                 135                 140

Pro Thr Leu Val Ala Asp Ser Arg Thr Thr Thr Gly Ser Asn Ser Val
145                 150                 155                 160

Arg Ser Phe Asp Ala Gln Thr Glu Arg Leu Ser Gly Leu Ser Asp Val
                165                 170                 175

His His Arg Tyr Met Gln Asp Lys Pro Ser Gln Arg Ser Asp Ser Trp
            180                 185                 190

Thr Asp Val Lys Ser Ser Ala Pro Ser Ser Gln Ser Met Ala Val Pro
        195                 200                 205

Asn Lys Ala Ala Tyr Leu Ala Pro Ile Pro Ala Gly Pro Asn Asp Ser
    210                 215                 220

Lys Thr Ser Ser Ser Gly Arg Ala Pro Ser Asp Ala Ala Thr Glu His
225                 230                 235                 240

Glu Cys Ser Leu Gln
                245

<210> SEQ ID NO 208
<211> LENGTH: 148
<212> TYPE: PRT
<213> ORGANISM: Unknown
<220> FEATURE:
<223> OTHER INFORMATION: metagenomes purified from environmentally
      challenged niches

<400> SEQUENCE: 208

Met Ala Pro Lys Ser Thr Asp Lys Pro Ala Ser Thr Ala Gly Lys Ala
1               5                   10                  15

Pro Ser Ala Gly Gly Lys Ala Pro Ala Ser Lys Thr Val Gly Ala Lys
```

```
            20                  25                  30
Lys Thr Ala Ala Lys Lys Ser Ala Lys Ser Thr Gly Glu Gly Gly Glu
            35                  40                  45

Lys Lys Lys Arg Val Lys Ser Arg Lys Glu Thr Tyr Ser Thr Tyr Ile
        50                  55                  60

Tyr Lys Val Leu Lys Gln Val His Pro Asp Thr Gly Ile Ser Asn Lys
65                  70                  75                  80

Ala Met Leu Ile Leu Asn Ser Phe Val Asn Asp Ile Phe Glu Arg Ile
                85                  90                  95

Ala Gly Glu Ala Ser Lys Leu Ala Thr Tyr Asn Lys Lys Ser Thr Ile
            100                 105                 110

Ser Ser Arg Glu Ile Gln Thr Ala Val Arg Leu Ile Leu Pro Gly Glu
        115                 120                 125

Leu Ser Lys His Ala Ile Ser Glu Gly Thr Lys Gly Val Thr Lys Tyr
        130                 135                 140

Ser Ser Ser Lys
145

<210> SEQ ID NO 209
<211> LENGTH: 369
<212> TYPE: PRT
<213> ORGANISM: Unknown
<220> FEATURE:
<223> OTHER INFORMATION: metagenomes purified from environmentally
      challenged niches

<400> SEQUENCE: 209

Asp Val Lys Arg Phe Thr Lys Asp Leu Leu Phe Asn Ser Glu Gly Asn
1               5                   10                  15

Leu Thr Phe Lys Pro His Leu Trp Asn Asp Ile Arg His Thr Leu Leu
            20                  25                  30

Pro Thr Phe Ile Arg Gln Ile Gly Tyr Val Pro Ile Pro Arg Ala Glu
        35                  40                  45

Phe Ser Ser Pro Asp Ile Asp Leu Val Ile Glu Asn Leu Val Leu Ser
    50                  55                  60

Gly Pro Asn Leu Phe Pro Asn Val Val Ser Leu Glu Ser His Asn Ser
65                  70                  75                  80

Phe Lys Phe Ser Pro Tyr Gln Gln Leu Asn Lys Gly Met Asp Thr His
                85                  90                  95

His His Lys Phe Arg Leu Gly Met Ser Gln Ile Gln Ala Asp Ile Arg
            100                 105                 110

Asp Val Arg Phe Ser Phe Arg Arg Lys Thr Gly Trp Pro Lys Leu Lys
        115                 120                 125

Asp His Gly Leu Ala Asp Val Ile Leu Ala Gly Lys Gly Met Ser Ile
    130                 135                 140

Asp Val Glu Leu Glu Ser Val Glu Gly Arg Arg Asp Ser Val Val Arg
145                 150                 155                 160

Val Asn His Val His Thr Thr Ile Asp Thr Leu Thr Phe Ser Ile Arg
                165                 170                 175

Asp Ser Lys His Asp Leu Leu Tyr Lys Phe Val Lys Ser Val Ala Thr
            180                 185                 190

Gly Thr Ile Lys Lys Ala Ile Gln Ala Ala Val Asp Asn Ala Ile Arg
        195                 200                 205

Thr Ala Val Gly His Leu Asp Asp Gln Leu Val Gln Val Arg Asn Thr
    210                 215                 220
```

```
Val Asp Asp Ala Lys Lys Ser Asp Glu Thr Thr Arg Thr Gln Ala Leu
225                 230                 235                 240

Lys Asp Leu Tyr Ser Lys Ala Asp Thr Ala Gln Lys Lys Gln Ala
            245                 250                 255

Glu Ser Lys Glu Gln Pro Gly Thr Phe Arg Ile Val Ala Asn Arg Asp
            260                 265                 270

Ser Val Leu Asn Pro Asp Met Gly Gly Gly Lys Gly Ala Met Thr Asn
            275                 280                 285

Lys Met Trp Lys Thr Glu Asp Leu Ala His Ser Gly Lys Glu Trp His
            290                 295                 300

Ser Pro Ala Phe Asp Leu Leu Asp Ser Lys His Pro Ala Arg Thr Gly
305                 310                 315                 320

Gln Thr His Pro Glu Ala Lys Glu Gly Ala Gly His Gly Asn Ser Leu
                325                 330                 335

Ser Ser Lys Ala Gln Pro Gly Ala Asn Ala Ala Asp Gln Leu Lys Ala
            340                 345                 350

Thr His Gly Gln Ser Glu Ala Glu Ala Ile Ala Gly Gln Lys Arg Gln
            355                 360                 365

Gln

<210> SEQ ID NO 210
<211> LENGTH: 173
<212> TYPE: PRT
<213> ORGANISM: Unknown
<220> FEATURE:
<223> OTHER INFORMATION: metagenomes purified from environmentally
      challenged niches

<400> SEQUENCE: 210

Met Ser Asp Ser Arg Ser Asp Glu Arg Leu Asp Gly Pro Ser Ser Arg
1               5                   10                  15

Thr Thr Val Ser Pro Met Ser Ser Leu Pro Val Arg Val Cys Arg Ser
            20                  25                  30

Thr Ser Ser Ser Leu Ser Arg Asp Asp Glu Thr Leu Leu Cys Glu
        35                  40                  45

Ser Thr Thr Ser Thr Pro Pro Ser Thr Pro Ser Pro Ser Pro Ser Glu
    50                  55                  60

Thr Pro Ser Thr Thr Cys Ser Thr Ser Ser Ser Arg Trp Pro Arg
65                  70                  75                  80

Val Arg Ser Arg Arg Gln Ser Arg Pro Pro Ser Thr Met Pro Ser Val
            85                  90                  95

Arg Leu Ser Val Thr Ser Thr Thr Ser Ser Ser Arg Ser Glu Thr Pro
            100                 105                 110

Ser Met Thr Pro Arg Ser Leu Thr Arg Pro Pro Glu Arg Lys Pro Ser
            115                 120                 125

Arg Thr Cys Thr Arg Arg Arg Thr Arg His Arg Arg Ser Arg Pro
    130                 135                 140

Ser Pro Arg Ser Ser Leu Val Leu Ser Glu Ser Ser Pro Thr Glu Thr
145                 150                 155                 160

Leu Phe Ser Thr Pro Thr Trp Ala Val Ala Arg Ala Pro
                165                 170

<210> SEQ ID NO 211
<211> LENGTH: 248
<212> TYPE: PRT
<213> ORGANISM: Unknown
<220> FEATURE:
```

-continued

<223> OTHER INFORMATION: metagenomes purified from environmentally
      challenged niches

<400> SEQUENCE: 211

```
Met Tyr Thr Ser Ala Val Thr Leu Leu Ser Leu Val Leu Leu Leu Ala
1               5                   10                  15

Thr Ser Val Ile Ala Gln Glu Gln Ala Gly Arg Pro Gly Thr Gln Arg
            20                  25                  30

Gly Gly Val Phe Phe Gly Cys Tyr Ala Asp Arg Pro Thr Gly Asn Ala
        35                  40                  45

Asn Gln Pro Ile Thr Arg Val Ala Asn Ser Asp Thr Phe Phe Glu Cys
    50                  55                  60

Met Glu Asn Cys Ala Ala Ile Thr Ser Pro Ser Leu Leu Gly Tyr Tyr
65                  70                  75                  80

Gln Pro Ser Ser Gly Gln Cys Phe Cys Gly Asn Leu Leu Phe Asn Pro
                85                  90                  95

Gln Ala Gln Leu Asn Gly Asn Gly Cys Gln Gly Ser Asp Trp Ser Phe
            100                 105                 110

Gly Arg Thr Ser Thr Thr Phe Arg Arg Phe Gly Asp Ala Cys Arg Pro
        115                 120                 125

Phe Gly Gly Val Gly Phe Ser Ala Asn Gln Tyr Thr Thr Val Thr Gly
    130                 135                 140

Pro Val Ala Cys His Val Gln Cys Ala Ser Asn Arg Phe Ala Tyr Val
145                 150                 155                 160

Trp Ser Asp Thr Gly Ser Asn Ser Trp Gln Cys Ala Cys Ser Asn Asn
                165                 170                 175

Val Arg Val Gln Glu Asp Phe Gln Tyr Thr Cys Gln Gly Gly Gly Val
            180                 185                 190

Phe Val Phe Glu His Ser Val Gln Ala Gln Ala Ser Ser Leu Asn Arg
        195                 200                 205

Lys Arg Thr Val Glu Glu Gln Trp Ala Val Pro Lys Asp Ala Leu Cys
    210                 215                 220

Pro Phe Gly Met Ser Ala Cys Lys Val Ser Gly Val Asp Asn Ala Tyr
225                 230                 235                 240

Glu Val Cys Phe Phe Ser Asp Arg
                245
```

<210> SEQ ID NO 212
<211> LENGTH: 116
<212> TYPE: PRT
<213> ORGANISM: Unknown
<220> FEATURE:
<223> OTHER INFORMATION: metagenomes purified from environmentally
      challenged niches

<400> SEQUENCE: 212

```
Met Phe Asn Ala His Gln Thr Asp Ser Pro Met Ser Gly Pro Ile Leu
1               5                   10                  15

Glu Ala Thr His Gly Asn Val Leu Ala Thr Met Ser Val Phe Arg
            20                  25                  30

Arg Thr Ser Ser Thr Leu Val Lys Val Ala Val Tyr Leu Cys Leu Asn
        35                  40                  45

Ile Gln Tyr Lys Leu Arg Leu Leu Arg Leu Thr Gly Ser Gly Arg Trp
    50                  55                  60

Arg Asn Asn Gly Leu Phe Arg Lys Thr Pro Ser Val His Ser Glu Cys
65                  70                  75                  80
```

Gln Arg Ala Arg Tyr Gln Val Ser Ile Met Leu Thr Arg Tyr Ala Ser
            85                  90                  95

Phe Gln Thr Ala Arg Pro Leu Val Pro Trp Pro Arg Gly Leu Lys His
        100                 105                 110

Ala Ile Asp Leu
        115

<210> SEQ ID NO 213
<211> LENGTH: 271
<212> TYPE: PRT
<213> ORGANISM: Unknown
<220> FEATURE:
<223> OTHER INFORMATION: metagenomes purified from environmentally
      challenged niches

<400> SEQUENCE: 213

Gly Gly Gly Thr Val Val Ser Asn Ala Leu Leu Glu Asn Ala Lys Leu
1               5                   10                  15

Cys Lys Thr Gln Gly Lys Glu Ser Ser Leu Arg Val Ile Val Cys Gly
            20                  25                  30

Arg Asn Arg Leu Glu Asn Gly Ser Ala Pro His Trp Ala Glu Ala Phe
        35                  40                  45

Ala Thr His Gly Lys Leu Val Glu Val Arg Met Pro Gln Asn Gly Ile
    50                  55                  60

Arg Met Glu Gly Ile Lys Ala Ile Ala Asp Gly Leu Ala Lys Cys Pro
65                  70                  75                  80

Thr Leu Glu Val Leu Asp Leu Gln Asp Asn Thr Ala Thr Lys Thr Gly
            85                  90                  95

Thr Arg Ser Ile Val Arg His Leu Ser Thr Trp Pro Lys Leu Arg Ile
        100                 105                 110

Leu Asn Leu Ser Asp Cys Leu Leu Gly Ser Val Gly Gly Ile Ala Leu
        115                 120                 125

Ala Thr Ala Leu Ser Thr Gly Ser Asn Lys His Leu Glu Gln Leu Lys
    130                 135                 140

Leu Gln Tyr Gly Glu Phe Asp Lys Arg Thr Val Glu Ile Leu Ser Thr
145                 150                 155                 160

Ala Ile Ser Gln His Leu Pro Lys Leu Thr Thr Leu Glu Leu Asn Gly
            165                 170                 175

Asn Arg Phe Asp Ala Glu Asp Glu Cys Val Glu Thr Leu Lys Lys Ala
        180                 185                 190

Leu Glu Leu His Gly Asn Glu Asp Ala Leu Asp Glu Leu Asp Asp Met
        195                 200                 205

Glu Glu Val Asp Glu Asp Glu Asp Asp Asp Glu Asp Glu Glu
    210                 215                 220

Asp Glu Asp Glu Asp Lys Asp Thr Ser Ala Asp Gly Ile Asp Ala
225                 230                 235                 240

Gly Ala Ala Gly Glu Asp Ala Leu Pro Pro Val Thr Lys Lys Asp Glu
            245                 250                 255

Asp Val Leu Ala Asp Leu Leu Ser Lys Val His Val Gln Pro Ser
        260                 265                 270

<210> SEQ ID NO 214
<211> LENGTH: 222
<212> TYPE: PRT
<213> ORGANISM: Unknown
<220> FEATURE:
<223> OTHER INFORMATION: metagenomes purified from environmentally
      challenged niches

<400> SEQUENCE: 214

```
Leu Asp Arg Arg Ser Ala Ser Thr Ser Ser Phe Phe Val Thr Gly
1               5                   10                  15

Gly Arg Ala Ser Ser Pro Ala Ala Pro Ala Ser Ile Pro Ser Ser Ala
            20                  25                  30

Leu Val Ser Leu Ser Ser Ser Ser Ser Ser Ser Ser Ser Ser Ser
                35                  40                  45

Ser Ser Ser Ser Ser Ser Thr Ser Ser Ile Ser Ser Ser Ser Ser Lys
    50                  55                  60

Ala Ser Ser Phe Pro Cys Ser Ser Ser Ala Phe Phe Arg Val Ser Thr
65                  70                  75                  80

His Ser Ser Ser Ala Ser Lys Arg Phe Pro Phe Ser Ser Ser Val Val
                85                  90                  95

Asn Phe Gly Lys Cys Trp Leu Ile Ala Val Asp Ser Ile Ser Thr Val
                100                 105                 110

Leu Leu Ser Asn Ser Pro Tyr Cys Ser Leu Ser Cys Ser Arg Cys Leu
                115                 120                 125

Phe Glu Pro Val Asp Asn Ala Val Ala Arg Ala Ile Pro Pro Thr Glu
130                 135                 140

Pro Lys Arg Gln Ser Glu Arg Leu Ser Ile Arg Ser Leu Gly Gln Val
145                 150                 155                 160

Glu Arg Cys Arg Thr Ile Leu Arg Val Pro Val Leu Val Ala Val Leu
                165                 170                 175

Ser Cys Lys Ser Ser Thr Ser Asn Val Gly His Leu Ala Ser Pro Ser
                180                 185                 190

Ala Ile Ala Leu Met Pro Ser Met Arg Met Pro Phe Cys Gly Ile Leu
                195                 200                 205

Thr Ser Thr Asn Leu Pro Cys Val Ala Asn Ala Ser Ala Gln
                210                 215                 220

<210> SEQ ID NO 215
<211> LENGTH: 176
<212> TYPE: PRT
<213> ORGANISM: Unknown
<220> FEATURE:
<223> OTHER INFORMATION: metagenomes purified from environmentally
      challenged niches

<400> SEQUENCE: 215

Met Val Lys Leu Ser Asn Ser Leu Val Arg Arg Leu Lys Trp Gln His
1               5                   10                  15

Val Arg Ser Leu Gly Val Val Ala Leu Thr Ala Gln Leu Arg Gly Pro
            20                  25                  30

Gln Pro Gln Ser Ala Glu Asp Glu Asp Ser Glu Ala Ala Gly Lys Lys
            35                  40                  45

Leu Lys Leu Ala Gly Asp Gln Ala Thr Ser Ala Val Ile Pro Lys Ser
        50                  55                  60

Ala Asp Lys Pro Asp Thr Phe Pro Leu Leu Asp Thr Leu Pro Ala Thr
65                  70                  75                  80

Met Ala Ala Gly Thr Arg Ser Met Thr Arg Pro Leu His Val Gly Asp
                85                  90                  95

Leu Arg Leu Ala Asp Leu Arg Lys Ile Met Gln Ala Ala Gly His Thr
                100                 105                 110

Ala Glu Phe Arg Gly Glu Gly Thr Leu Leu Ile Asp Lys Ser Val Ala
                115                 120                 125
```

Val Arg Lys Ser Gly Thr Gly Gln Ile Glu Ile Glu Ala Ser Ala Gln
            130                 135                 140

Ala Ala Ala Asn Gln Ala Thr Pro Gly Arg Gly Ala Ser Ser Phe Leu
145                 150                 155                 160

Ala Val Lys Arg Lys Ile Tyr Glu Gly Leu Ala Val Val Thr Gly Ser
            165                 170                 175

<210> SEQ ID NO 216
<211> LENGTH: 139
<212> TYPE: PRT
<213> ORGANISM: Unknown
<220> FEATURE:
<223> OTHER INFORMATION: metagenomes purified from environmentally
      challenged niches

<400> SEQUENCE: 216

Lys Met Lys Ile Asp Val Glu Lys Leu Asn Lys Asp Ile Ser Leu Phe
1               5                   10                  15

Pro Gln Val His Pro Ile Thr Glu Asp Met Lys Ile Thr His Lys Gly
            20                  25                  30

Val Ser Arg Leu Val Met Leu Asp Arg Tyr Ser Phe Lys Asp Thr Glu
        35                  40                  45

Lys Ile Thr Leu Ser Glu Gly Asp Phe Val Val Leu Thr Ile Lys Glu
    50                  55                  60

Asp Pro Lys Phe Pro Ala Arg Gly Leu Gly Tyr Ile Lys Glu Ile Asp
65                  70                  75                  80

Trp Glu Asn Lys Lys Ala Lys Val Gln Val Glu Glu Phe Arg His
                85                  90                  95

Thr Leu Glu Lys Pro Glu Glu Arg Glu Thr Gly Ile Ile Val Arg Ser
            100                 105                 110

Leu Asp Val Ile Glu Lys Pro Leu Glu Ile Phe Tyr Glu Gln Ile Ala
        115                 120                 125

Lys Arg Asn Ala Thr Gly Leu Ala Ala Val Glu
    130                 135

<210> SEQ ID NO 217
<211> LENGTH: 282
<212> TYPE: PRT
<213> ORGANISM: Unknown
<220> FEATURE:
<223> OTHER INFORMATION: metagenomes purified from environmentally
      challenged niches

<400> SEQUENCE: 217

Gly Asp Ala Thr Val Thr Gln Leu Arg Glu Ile Met Asp Asp Pro Ala
1               5                   10                  15

Gly Tyr Phe Leu Pro Asn Leu Lys His Gly Ala Asp Asn Met Phe Tyr
            20                  25                  30

Val Gly Pro Arg Gly Leu Ala Gln Glu Leu Glu Glu Leu Phe Thr Phe
        35                  40                  45

Pro Ser Thr Ile Leu Arg Lys Arg Gln Asp Thr Ser Gln His Asp Glu
    50                  55                  60

Arg Gln Ala Lys Lys Ala Arg Thr Gln Glu Asp Glu Ala Ala Gly Asp
65                  70                  75                  80

Ala Leu Glu Glu Pro Glu Thr Gly Arg Arg Asp Ser Val Leu Pro Thr
                85                  90                  95

Glu Arg Ala Ala Phe Gly Leu Glu Gly Asp Asp Ser Gly Phe Phe Leu
            100                 105                 110

Gly Asp Gln Thr Met Gly Asp Met Leu Pro Met Asp Asp Met Gly
            115                 120                 125

Ala Met Asp Thr Gly Val Asp Gln Arg Arg Met Arg Thr Pro Ser Val
130                 135                 140

Ala Pro Ser Val Thr Glu Ser Ile Ala Arg Gln Ile Gln Asn Asp Arg
145                 150                 155                 160

Ser Ala Gly Thr His Pro Leu Ala Ile Phe Glu Lys Glu Ala Arg Asp
                165                 170                 175

Asp Thr Gln Ser Gln Ser Gln Ala Thr Pro Asn Lys Ser Val Ala Ser
            180                 185                 190

Glu Ser Ile Ser Lys Thr Ser Ser Gly Gln Ser Lys Asn Thr Gly Met
            195                 200                 205

Ala Met Gly Leu Leu Arg Arg Glu Ile Glu Ala Ile Glu Glu Glu Asp
            210                 215                 220

Lys Met Val Gly Phe Asp His Leu Ala Asp Lys Ala Ser Lys Arg Ala
225                 230                 235                 240

Ala Ser Ala Phe Phe Phe Glu Leu Leu Val Leu Gly Thr Lys His Ala
                245                 250                 255

Val Lys Leu Glu Gln Ala Gln Ala Phe Gly Asp Ile His Ile Arg Gly
            260                 265                 270

Lys Asp Lys Leu Phe Ala Glu Val Val Ala
            275                 280

<210> SEQ ID NO 218
<211> LENGTH: 261
<212> TYPE: PRT
<213> ORGANISM: Unknown
<220> FEATURE:
<223> OTHER INFORMATION: metagenomes purified from environmentally
      challenged niches

<400> SEQUENCE: 218

Met Ala Pro Ile Thr Cys Ser Thr Ser Val His Ala Asp Leu His Lys
1               5                   10                  15

Ser Ser Arg Ser Phe Leu Pro Ser Gln Ala Gln Ser Ser Glu Ser Ala
            20                  25                  30

Arg Ile Pro Val Ser Met Thr Lys Gly Arg Gln Arg Arg Ala Arg
        35                  40                  45

Lys Arg Thr Lys Arg Leu Val Thr Arg Trp Arg Ser Pro Arg Leu Gly
50                  55                  60

Asp Ala Thr Val Cys Phe Arg Leu Asn Gly Pro Leu Leu Val Ser Arg
65                  70                  75                  80

Val Met Thr Arg Ala Phe Ser Leu Ala Thr Arg Arg Trp Glu Thr Thr
                85                  90                  95

Cys Cys Leu Trp Thr Thr Trp Glu Pro Trp Thr Pro Glu Trp Thr Ser
            100                 105                 110

Asp Ala Cys Glu His His Gln Ser His Arg Arg Ser Pro Asn Arg Ser
            115                 120                 125

His Val Arg Phe Arg Met Thr Glu Ala Leu Ala His Thr His Trp Leu
            130                 135                 140

Tyr Ser Arg Arg Arg Gln Gly Thr Thr Arg Ser Arg Asn Arg Arg Leu
145                 150                 155                 160

Arg Pro Thr Asn Arg Trp Pro Pro Ser Leu Ser Ala Arg Leu Leu Leu
                165                 170                 175

Ala Asn Gln Arg Ile Leu Ala Trp Pro Trp Val Cys Cys Glu Gly Arg

```
            180                 185                 190
Leu Arg Arg Ser Arg Arg Lys Thr Arg Trp Ser Gly Leu Ile Thr Trp
                195                 200                 205
Gln Thr Arg Arg Pro Ser Glu Gln Arg Leu His Ser Ser Ser Ser Cys
            210                 215                 220
Trp Cys Leu Val Pro Asn Met Arg Ser Ser Leu Asn Lys Leu Arg Leu
225                 230                 235                 240
Ser Ala Thr Ser Thr Tyr Ala Ala Lys Thr Ser Cys Leu Gln Arg Leu
                245                 250                 255
Leu His Arg Gln Thr
            260
```

<210> SEQ ID NO 219
<211> LENGTH: 108
<212> TYPE: PRT
<213> ORGANISM: Unknown
<220> FEATURE:
<223> OTHER INFORMATION: metagenomes purified from environmentally
      challenged niches

<400> SEQUENCE: 219

```
Met Gly Asp His Ala Thr Thr Asn Asp Pro Ser Asn Ala Thr Phe Glu
1               5                   10                  15
Glu Lys Gly Lys Gly Lys Asp Val Gln Asp Gln Ile Ala Glu Asp Ser
                20                  25                  30
Ser Asp Glu Glu Ser Asp Gln Glu Pro Glu Met Val Asp Glu Glu Glu
            35                  40                  45
Asp Asp Asn Asn Leu Glu Pro Ile Ser Gln Asp Asn Ile Ile Ser Gly
50                  55                  60
Gly Arg Arg Thr Arg Gly Lys Ile Ile Asp Tyr Ala Ala Glu Ala Glu
65                  70                  75                  80
Lys Asn Lys Asp Glu Met Glu Asp Ser Glu Asp Glu Asp Tyr Gln
                85                  90                  95
Gly Ala Asn Asp Asp Glu Asp Gln Met Arg Asp
            100                 105
```

<210> SEQ ID NO 220
<211> LENGTH: 78
<212> TYPE: PRT
<213> ORGANISM: Unknown
<220> FEATURE:
<223> OTHER INFORMATION: metagenomes purified from environmentally
      challenged niches

<400> SEQUENCE: 220

```
Glu Leu Lys Tyr Phe Lys Ala Val Ala Leu Tyr Asn Leu Ser Arg Tyr
1               5                   10                  15
Leu Asp Ala Arg Lys Ala Ile Asn Asp Leu Ile Gln Ser Tyr Pro Asp
                20                  25                  30
Phe Arg Gln Ala Glu Ala Leu Lys Ser Ala Ile Asp Asp Lys Val Val
            35                  40                  45
Arg Asp Gly Leu Ile Gly Val Ser Val Ala Gly Ala Val Val Ala Gly
        50                  55                  60
Val Val Gly Leu Ala Val Ala Leu Ala Arg Gly Asn Arg Gly
65                  70                  75
```

<210> SEQ ID NO 221
<211> LENGTH: 27
<212> TYPE: PRT

<213> ORGANISM: Unknown
<220> FEATURE:
<223> OTHER INFORMATION: metagenomes purified from environmentally
      challenged niches

<400> SEQUENCE: 221

Met Gly His Val Glu Ser Arg Val Asn Gln Arg Gly Pro Pro Arg Lys
1               5                   10                  15

Ala Lys Tyr Ser Trp Val Thr Asp Ser Glu Lys
            20                  25

<210> SEQ ID NO 222
<211> LENGTH: 27
<212> TYPE: PRT
<213> ORGANISM: Unknown
<220> FEATURE:
<223> OTHER INFORMATION: metagenomes purified from environmentally
      challenged niches

<400> SEQUENCE: 222

Met Leu Lys Ala Pro Phe Phe His Arg Pro Cys Gly Gly Lys Gly Val
1               5                   10                  15

Gln Leu Lys Trp Ala Thr Pro Asp Ser Ala Val
            20                  25

<210> SEQ ID NO 223
<211> LENGTH: 177
<212> TYPE: PRT
<213> ORGANISM: Unknown
<220> FEATURE:
<223> OTHER INFORMATION: metagenomes purified from environmentally
      challenged niches

<400> SEQUENCE: 223

Met Pro Val Arg Pro Tyr Leu Glu Glu Met Ala Asp Met Pro Val Pro
1               5                   10                  15

Leu Phe Ala Tyr Asp Ala Pro Pro Thr Leu Ala Asp His Pro His Ala
            20                  25                  30

Arg Glu His Gln His Thr Thr Phe Met Gln Tyr Leu Ala Arg Lys Gln
        35                  40                  45

Pro Asp Pro Lys Asn Tyr Pro Asn Tyr Pro Asp Val Asp Ile Arg Asp
    50                  55                  60

Ala Ile Asn His Tyr Leu Ile Glu Leu Glu Cys Pro Gly Ile Lys Asp
65                  70                  75                  80

Ala Ala Asp Ile His Cys Gln Trp Thr Ser Ser Arg His Leu Thr Val
                85                  90                  95

Thr Gly Asp Ile Ala Arg Pro Glu Glu Ser Gln Ile Glu Ala Gln Ile
            100                 105                 110

Glu Ser Arg Pro Val Tyr Leu Val Leu Gly Glu Arg Ile Gly Ser
        115                 120                 125

Phe Arg Arg Asn Phe Thr Phe Pro Val Glu Val Glu Gln Glu Asn Met
    130                 135                 140

Thr Ala Lys Leu Glu Ala Gly Leu Leu Lys Ile Val Leu Pro Lys His
145                 150                 155                 160

Lys His His Thr Pro Lys Gly Thr Gly Lys Val Asp Ile Asp Val Ile
                165                 170                 175

Glu

<210> SEQ ID NO 224
<211> LENGTH: 163

<212> TYPE: PRT
<213> ORGANISM: Unknown
<220> FEATURE:
<223> OTHER INFORMATION: metagenomes purified from environmentally
      challenged niches

<400> SEQUENCE: 224

Met Val Leu Val Leu Gly Gln Asp Asn Leu Gln Gln Ser Gly Leu Gln
1               5                   10                  15

Leu Gly Ser His Ile Phe Leu Leu Asp Leu His Arg Glu Gly Lys Val
                20                  25                  30

Ala Thr Glu Arg Ala Asn Ala Ser Leu Ser Gln Asn Gln Val Asp Gly
            35                  40                  45

Pro Ala Leu Asp Leu Arg Phe Asp Leu Ala Phe Leu Arg Thr Gly Asp
    50                  55                  60

Val Ala Gly Asp Gly Gln Val Pro Arg Ala Arg Pro Leu Ala Val Asp
65                  70                  75                  80

Val Gly Cys Val Phe Asp Pro Arg Ala Phe Glu Leu Asp Gln Val Val
                85                  90                  95

Ile Asp Gly Val Ala Asp Val His Val Arg Val Gly Val Val Leu
                100                 105                 110

Trp Val Arg Leu Leu Ala Arg Lys Val Leu His Glu Gly Arg Val Leu
                115                 120                 125

Val Leu Ala Gly Val Arg Val Val Gly Gln Gly Arg Cys Val Val
    130                 135                 140

Arg Glu Gln Gly His Gly His Val Gly His Phe Phe Gln Val Gly Ser
145                 150                 155                 160

Tyr Gly His

<210> SEQ ID NO 225
<211> LENGTH: 118
<212> TYPE: PRT
<213> ORGANISM: Unknown
<220> FEATURE:
<223> OTHER INFORMATION: metagenomes purified from environmentally
      challenged niches

<400> SEQUENCE: 225

Met Phe Gly Phe Asn Phe Asn Thr Thr Lys Leu Leu Lys Thr Ile Leu
1               5                   10                  15

Val Val Cys Tyr Leu Gln Ala Thr Val Leu Ala Asp Pro Tyr Thr Arg
                20                  25                  30

Val Ser Trp Glu Ala Tyr Met Asn His Val Asn Gly Ser Asp Asp Tyr
            35                  40                  45

Arg Thr Gln Gly Asp Asp Thr Arg Ala Thr Arg Phe Pro Glu Thr Lys
    50                  55                  60

Pro Pro Lys Gln Gly Lys Asp Phe Leu Trp Ser Ser Lys Pro Val Pro
65                  70                  75                  80

Ser Ser Asp Leu Phe Leu Glu Phe Met Tyr Glu Gly Glu Pro Asp
                85                  90                  95

Glu Phe Ser Arg Thr Thr Glu Ser Tyr Gln Ser Leu Pro Ser Asn Ala
                100                 105                 110

Leu Thr Ala Arg Gln Lys
        115

<210> SEQ ID NO 226
<211> LENGTH: 349
<212> TYPE: PRT

<213> ORGANISM: Unknown
<220> FEATURE:
<223> OTHER INFORMATION: metagenomes purified from environmentally challenged niches

<400> SEQUENCE: 226

Met Ser Pro Thr Pro Thr Ser Pro His Asn Lys Leu Ser Leu Pro Ala
1               5                   10                  15

Arg Ala Ser Ser His Asp Ser Thr Asp Gly Ile Arg Lys Arg Val Cys
            20                  25                  30

Lys Ala Cys Asp Arg Cys Arg Leu Lys Lys Ser Lys Cys Asp Gly Ser
        35                  40                  45

Ser Pro Cys Ser Arg Cys Lys Ala Asp Asn Ala Ile Cys Val Phe Gly
50                  55                  60

Glu Arg Lys Arg Ser His Asp Lys His Tyr Pro Lys Gly Tyr Val Glu
65                  70                  75                  80

Met Leu Glu Gln Gln Gly Gln Leu Val Ser Gly Leu Lys Glu Met
                85                  90                  95

Tyr His Arg Leu Gln Lys Ala Ser Ala Trp Asp Gly Pro Val Leu Asp
            100                 105                 110

Glu Ser Thr Gly Gln Pro Leu Thr His Asp Ile Leu Ser Ala Leu Asp
        115                 120                 125

Leu Leu Glu Pro Lys His Asp Asp Ser Asn Glu Pro Glu Val Phe Glu
130                 135                 140

Glu Asn Cys Glu Lys Leu Gln Ser Lys Leu Leu Ala Asp Gly Ala Gly
145                 150                 155                 160

Phe Ala His Arg Arg Gly Ser Ile Ser Ser Asp Ser Glu His Ser His
            165                 170                 175

His Asp Arg Pro Lys Thr Ser Ser Arg His Asp Thr Pro Val Gln Pro
        180                 185                 190

Lys Pro Ser Ile Phe Lys Glu Asn Leu Ser Phe Ala Ser Ala Ala Ser
        195                 200                 205

Ser Pro Leu Thr Gln Ser Pro Ile Pro Arg Ser Lys Pro Leu Asn Val
210                 215                 220

Met Pro Tyr Gln Thr Leu Gln Pro Ser Ser Arg Pro Ser Pro Leu Gln
225                 230                 235                 240

Met Pro Ser Ala Tyr Asn Asp Pro Gln Leu Tyr Ala Pro Glu Trp Ala
            245                 250                 255

Gln Ala Leu Ala Asp Met Ser Gly Asp Pro Asn Tyr Arg Gln Arg Phe
        260                 265                 270

Ser Met Gln Gln Gln Gln Asn Asp Phe Asp Asn Leu Leu Trp Asp
        275                 280                 285

Pro Ser Ala Gln Ala Pro Met Glu Ser Pro Phe Ser Gln Pro Ala Phe
290                 295                 300

Phe Asn Gln Ala Gln Leu Ile Gly Ser Gly Asn Val Phe Gly Leu Ser
305                 310                 315                 320

Asp Ile Asn Asp Leu Gly Pro Asn Pro Ala Asp Gly Gly Met Asp Phe
            325                 330                 335

Asp Phe Ser Lys Phe Val Gln Gln Thr Glu Val Met Thr
        340                 345

<210> SEQ ID NO 227
<211> LENGTH: 149
<212> TYPE: PRT
<213> ORGANISM: Unknown
<220> FEATURE:

<223> OTHER INFORMATION: metagenomes purified from environmentally
      challenged niches

<400> SEQUENCE: 227

Met Ser Ser Phe Arg Val Ala Ala Pro Lys Met Ala Ser Met Ala Ala
1               5                   10                  15

Gln Ser Ser Val Lys Val Ala Arg Pro Ala Phe Gln Ala Ala Gln Leu
            20                  25                  30

Gln Lys Phe Thr Arg Ala Tyr Ser Ala Val Pro Lys Asn Thr Val Phe
        35                  40                  45

Asn Thr Met Lys Arg Thr Gln Met Met Ala Arg Gln Ala Ser Pro Ile
50                  55                  60

Ala Lys Arg Ala Tyr Ser Ser Glu Met Ala Asn Ala Leu Val Gln Val
65                  70                  75                  80

Ser Gln Asn Ile Gly Met Gly Ser Ala Ala Ile Gly Leu Ala Gly Ala
                85                  90                  95

Gly Val Gly Ile Gly Leu Val Phe Ala Ala Leu Ile Gln Ala Val Ala
            100                 105                 110

Arg Asn Pro Ser Leu Arg Gly Gln Leu Phe Ser Tyr Ala Ile Leu Gly
        115                 120                 125

Phe Ala Phe Val Glu Ala Ile Gly Leu Phe Asp Leu Met Val Ala Met
130                 135                 140

Met Ala Lys Phe Leu
145

<210> SEQ ID NO 228
<211> LENGTH: 165
<212> TYPE: PRT
<213> ORGANISM: Unknown
<220> FEATURE:
<223> OTHER INFORMATION: metagenomes purified from environmentally
      challenged niches

<400> SEQUENCE: 228

Met Glu Cys Thr Phe Leu Gln Glu Leu Gly His His Gly Asn His Glu
1               5                   10                  15

Val Glu Glu Thr Asp Gly Leu Asp Glu Ser Thr Lys Asn Gly Val
            20                  25                  30

Arg Glu Lys Leu Ala Thr Glu Gly Val Ala Gly Asp Gly Leu Asp
        35                  40                  45

Glu Gly Gly Glu Asp Glu Thr Asp Thr Asp Thr Ser Thr Gly Lys Thr
    50                  55                  60

Asp Gly Gly Gly Thr His Thr Asp Val Leu Gly Asp Leu Asp Glu Gly
65                  70                  75                  80

Val Gly His Leu Arg Gly Val Gly Thr Leu Gly Asp Gly Gly Leu
            85                  90                  95

Ala Gly His His Leu Gly Ala Leu His Gly Val Glu Asp Gly Val Leu
            100                 105                 110

Gly Asp Arg Gly Val Gly Ala Gly Glu Leu Leu Glu Leu Ser Ser Leu
        115                 120                 125

Glu Gly Arg Ala Gly Asp Leu His Gly Leu Ser Gly His Gly Gly
        130                 135                 140

His Leu Gly Gly Gly Asp Ala Glu Gly Arg His Cys Asp Asp Gly Glu
145                 150                 155                 160

Val Val Arg Trp Ser
            165

<210> SEQ ID NO 229
<211> LENGTH: 425
<212> TYPE: PRT
<213> ORGANISM: Unknown
<220> FEATURE:
<223> OTHER INFORMATION: metagenomes purified from environmentally challenged niches

<400> SEQUENCE: 229

```
Gly Gly Phe Ser Val Lys Phe Arg Thr Ala Glu Gly Asn Trp Asp Phe
1               5                   10                  15

Val Ala Asn Asn Thr Pro Val Phe Phe Leu Arg Asp Pro Ala Lys Phe
            20                  25                  30

Pro His Phe Ile His Thr Gln Lys Arg Asp Pro Ala Thr His Leu Ser
        35                  40                  45

Gly Asp Asp Ser Thr Met Phe Trp Asp Tyr Leu Ser Gln Asn Pro
    50                  55                  60

Glu Ser Ile His Gln Val Met Ile Leu Met Gly Asp Arg Gly Ile Pro
65                  70                  75                  80

Lys Gly Trp Arg Phe Met His Gly Tyr Tyr Gly His Thr Leu Lys Ile
                85                  90                  95

Val Asn Asp Lys Gly Glu Trp Val Tyr Ala Gln Phe His Leu Ile Ser
            100                 105                 110

Asp Gln Gly Thr Gln Asn Phe Thr Gly Asp Glu Ala Ala Gln Gln Ser
        115                 120                 125

Asn Asp Tyr Gly Gln Lys Asp Leu Tyr Glu Ala Ile Glu Lys Gly Asp
    130                 135                 140

Phe Pro Ser Trp Thr Met Lys Val Gln Ile Met Thr Glu Lys Gln Ala
145                 150                 155                 160

Glu Glu Ala Trp Glu Gln Lys Arg Ile Asn Val Phe Asp Leu Thr His
                165                 170                 175

Val Trp Pro His Gly Asp Tyr Pro Leu Arg Thr Val Gly Lys Phe Thr
            180                 185                 190

Leu Asn Glu Asn Ala Lys Asn Tyr Phe Ala Glu Val Glu Gln Val Ala
        195                 200                 205

Phe Asn Pro Ser His Met Ile Pro Gly Val Glu Pro Ser Asn Asp Pro
    210                 215                 220

Val Leu Gln Ser Arg Leu Phe Ser Tyr Pro Asp Ala His Arg His Arg
225                 230                 235                 240

Ile Gly Ala Asn Tyr Gln Gln Leu Pro Val Asn Gln Asn Val Cys Pro
                245                 250                 255

Phe Ala Leu Gly Asn Phe Gln Arg Asp Gly Gln Met Ala Phe Tyr Asn
            260                 265                 270

Gln Gly Ser Arg Pro Asn Tyr Leu Ser Ser Ile Glu Pro Ile Ser Phe
        275                 280                 285

Lys Glu Arg Ala Tyr Asp Leu Asn Lys Val His Gly Lys Phe Val Gly
    290                 295                 300

Glu Ala Val Ala Phe Leu Ser Glu Ile Arg Pro Glu Asp Phe Asn Ala
305                 310                 315                 320

Pro Arg Ala Leu Trp Gln Lys Val Phe Ser Glu Ser Lys Gln Arg
                325                 330                 335

Phe Val Asp Thr Val Ser Gly His Met Ser Thr Val Arg Asp Lys Ala
            340                 345                 350

Ile Thr Ala Arg Met Met Thr Ile Phe Arg Glu Val Ser Pro Asp Leu
        355                 360                 365
```

Gly Asp Arg Leu Glu Lys Ala Thr Gly Val Lys Gly Glu Ser Thr Ile
    370                 375                 380

Ala Gly Met Lys Phe Asn Gly Thr His Asn Gly Phe Asp Lys Ala Asn
385                 390                 395                 400

Lys Ile Pro Ala Asn Gly Met Lys Lys Gly Gly Glu Val Ile Phe Asp
                405                 410                 415

Asn Gly Ala Pro Ala Thr Ala Ala Arg
            420                 425

<210> SEQ ID NO 230
<211> LENGTH: 239
<212> TYPE: PRT
<213> ORGANISM: Unknown
<220> FEATURE:
<223> OTHER INFORMATION: metagenomes purified from environmentally
      challenged niches

<400> SEQUENCE: 230

Val Ser Val Ser Ile Gly Val Arg Glu Gln Ser Arg Leu Gln His Trp
1               5                   10                  15

Val Val Gly Arg Leu Asp Thr Gly Asn His Val Arg Arg Val Glu Cys
            20                  25                  30

Asp Leu Phe His Leu Gly Glu Val Leu Gly Ile Leu Val Lys Gly
        35                  40                  45

Glu Phe Thr Asp Cys Ser Lys Trp Val Ile Thr Met Arg Pro Asp Val
    50                  55                  60

Gly Gln Ile Lys Asp Val Asp Pro Leu Leu Pro Cys Leu Leu Gly
65                  70                  75                  80

Leu Leu Leu Gly His Asp Leu Asn Leu His Arg Pro Arg Gly Glu Val
                85                  90                  95

Ser Leu Leu Asp Gly Phe Val Gln Ile Leu Leu Ser Val Ile Val Gly
            100                 105                 110

Leu Leu Ser Ser Leu Val Thr Arg Glu Val Leu Gly Ala Leu Ile Arg
        115                 120                 125

Asp Glu Val Glu Leu Gly Val Asp Pro Phe Ala Leu Val Ile Asp Asn
130                 135                 140

Leu Glu Gly Val Ala Val Ala Met His Glu Ser Pro Ala Leu Gly
145                 150                 155                 160

Asp Thr Ser Ile Thr His Glu Asp His Asp Leu Val Asp Arg Leu Gly
                165                 170                 175

Val Leu Arg Gln Val Val Pro Glu His Gly Arg Val Ile Val Thr Arg
            180                 185                 190

Gln Val Gly Gly Gly Ile Ser Leu Leu Gly Val Asp Glu Val Gly Glu
        195                 200                 205

Leu Gly Arg Val Ser Glu Glu Asp Gly Val Val Gly His Lys
210                 215                 220

Val Pro Ile Ser Phe Cys Gly Pro Glu Leu Asp Arg Glu Ser Ser
225                 230                 235

<210> SEQ ID NO 231
<211> LENGTH: 368
<212> TYPE: PRT
<213> ORGANISM: Unknown
<220> FEATURE:
<223> OTHER INFORMATION: metagenomes purified from environmentally
      challenged niches

<400> SEQUENCE: 231

```
Asp Thr Ile Asp Ala Glu Val Leu Asp Ser Leu Gly Val Thr Gln Glu
1               5                   10                  15

Asn Phe Gln Phe Ala Leu Gly Val Ser Asn Pro Ser Ala Leu Arg Glu
            20                  25                  30

Val Ala Val Val Glu Val Pro Asn Val Arg Trp Glu Asp Ile Gly Gly
        35                  40                  45

Leu Glu Glu Val Lys Arg Glu Leu Ile Glu Ser Val Gln Tyr Pro Val
50                  55                  60

Asp His Pro Glu Lys Phe Leu Lys Phe Gly Met Ser Pro Ser Lys Gly
65                  70                  75                  80

Val Leu Phe Tyr Gly Pro Pro Gly Thr Gly Lys Thr Leu Leu Ala Lys
                85                  90                  95

Ala Val Ala Asn Glu Cys Ala Ala Asn Phe Ile Ser Val Lys Gly Pro
            100                 105                 110

Glu Leu Leu Ser Met Trp Phe Gly Glu Ser Glu Ser Asn Ile Arg Asp
        115                 120                 125

Ile Phe Asp Lys Ala Arg Ala Ala Pro Cys Val Val Phe Leu Asp
130                 135                 140

Glu Leu Asp Ser Ile Ala Lys Ser Arg Gly Gly Ser Gln Gly Asp Ala
145                 150                 155                 160

Gly Gly Ala Ser Asp Arg Val Val Asn Gln Leu Leu Thr Glu Met Asp
                165                 170                 175

Gly Met Thr Ser Lys Lys Asn Val Phe Val Ile Gly Ala Thr Asn Arg
            180                 185                 190

Pro Glu Gln Leu Asp Asn Ala Leu Cys Arg Pro Gly Arg Leu Asp Thr
        195                 200                 205

Leu Val Tyr Val Pro Leu Pro Asp Gln Glu Gly Arg Glu Ser Ile Leu
210                 215                 220

Lys Ala Gln Leu Arg Lys Thr Pro Ile Ala Asp Asp Ile Asp Leu Ser
225                 230                 235                 240

Tyr Met Ala Ser Lys Thr His Gly Phe Ser Gly Ala Asp Leu Gly Phe
                245                 250                 255

Ile Thr Gln Arg Ala Val Lys Leu Ala Ile Lys Gln Ser Ile Asp Leu
            260                 265                 270

Ala Ile Gln Asn Gln Lys Ala Arg Glu Ala Glu Gly Asp Thr Ala Met
        275                 280                 285

Asp Glu Asp Ile Glu Glu Asp Pro Val Pro Glu Leu Thr Lys Ala
290                 295                 300

His Phe Glu Glu Ala Met Ser Met Ala Arg Arg Ser Val Thr Asp Thr
305                 310                 315                 320

Glu Ile Arg Arg Tyr Glu Ala Phe Ala Gln Ser Met Lys Ser Ser Gly
                325                 330                 335

Gly Gly Ser Ala Phe Phe Arg Phe Pro Glu Ser Gly Ala Asp Gly Asn
            340                 345                 350

Ala Ala Glu Gln Gln Gln Asn Gly Ala Gly Glu Glu Asp Leu Tyr Asp
        355                 360                 365

<210> SEQ ID NO 232
<211> LENGTH: 317
<212> TYPE: PRT
<213> ORGANISM: Unknown
<220> FEATURE:
<223> OTHER INFORMATION: metagenomes purified from environmentally
      challenged niches
```

<400> SEQUENCE: 232

Met His Asp Cys Ser Leu His Leu Glu Tyr Tyr Ser Asp Asn Ser Lys
1               5                   10                  15

Gly Leu Gly Arg Glu Val Arg Glu Thr Asn Leu Val Val Glu Val Leu
            20                  25                  30

Leu Ala Ser Thr Ile Leu Leu Leu Gly Cys Val Ala Ile Gly Thr
        35                  40                  45

Ala Leu Arg Glu Ala Glu Ser Ala Ala Thr Gly Ala Leu His
    50                  55                  60

Ala Leu Gly Glu Ser Leu Val Ala Pro Asp Leu Gly Val Gly Asp Gly
65                  70                  75                  80

Ala Thr Ser His Ala His Ser Leu Leu Lys Val Ser Leu Gly Gln Leu
                85                  90                  95

Gly His Gly Val Val Leu Leu Asp Val Leu Val His Gly Gly Val Thr
            100                 105                 110

Leu Gly Leu Ser Ser Leu Leu Val Leu Asp Gly Gln Val Asn Arg Leu
        115                 120                 125

Leu Asp Gly Gln Leu Asp Gly Thr Leu Gly Asp Glu Ala Lys Ile Gly
130                 135                 140

Thr Arg Glu Thr Val Ser Leu Gly Gly His Val Gly Lys Val Asp Val
145                 150                 155                 160

Val Gly Asp Arg Ser Leu Ala Glu Leu Gly Leu Glu Asn Ala Leu Thr
                165                 170                 175

Ala Leu Leu Val Arg Gln Gly Asn Val Asp Glu Ser Val Glu Thr Thr
            180                 185                 190

Arg Thr Ala Glu Ser Val Val Glu Leu Leu Arg Pro Val Gly Gly Thr
        195                 200                 205

Asp Asp Glu Asn Val Leu Leu Ala Gly His Thr Val His Leu Ser Glu
210                 215                 220

Lys Leu Val Asp His Thr Val Gly Ser Thr Ala Ser Ile Ala Leu Arg
225                 230                 235                 240

Thr Ala Thr Arg Leu Gly Asp Gly Val Gln Leu Val Glu Glu Asp Asn
                245                 250                 255

Ala Arg Arg Gly Ser Thr Ser Leu Val Glu Asp Val Thr Asn Val Ala
            260                 265                 270

Leu Arg Leu Thr Glu Pro His Gly Glu Lys Leu Gly Thr Leu Asp Gly
        275                 280                 285

Asn Lys Val Gly Arg Ala Leu Val Gly Asp Ser Leu Gly Gln Lys Ser
290                 295                 300

Leu Thr Ser Thr Arg Gly Thr Val Glu Lys His Thr Leu
305                 310                 315

<210> SEQ ID NO 233
<211> LENGTH: 166
<212> TYPE: PRT
<213> ORGANISM: Unknown
<220> FEATURE:
<223> OTHER INFORMATION: metagenomes purified from environmentally
      challenged niches

<400> SEQUENCE: 233

Val Ser Pro Lys Arg Thr Ser Ser Leu Pro Leu Ala Ser Ala Thr Pro
1               5                   10                  15

Leu Pro Phe Ala Arg Ser Gln Trp Ser Arg Phe Pro Thr Ser Asp Gly
            20                  25                  30

Arg Thr Leu Val Val Ser Arg Arg Ser Arg Gly Ser Ser Arg Ala
            35                  40                  45

Cys Asn Thr Pro Ser Thr Thr Pro Arg Ser Ser Ser Leu Ala Cys
 50                  55                  60

Pro His Gln Arg Val Cys Phe Ser Thr Val Pro Leu Val Leu Val Arg
 65                  70                  75                  80

Leu Phe Trp Pro Arg Leu Ser Pro Thr Ser Ala Arg Pro Thr Leu Phe
                 85                  90                  95

Pro Ser Arg Val Pro Ser Phe Ser Pro Cys Gly Ser Val Ser Leu Arg
                100                 105                 110

Ala Thr Phe Val Thr Ser Ser Thr Arg Leu Val Leu Pro Arg Leu Ala
            115                 120                 125

Leu Ser Ser Ser Thr Ser Trp Thr Pro Ser Pro Ser Leu Val Ala Val
130                 135                 140

Leu Arg Ala Met Leu Ala Val Leu Pro Thr Val Trp Ser Thr Ser Phe
145                 150                 155                 160

Ser Leu Arg Trp Thr Val
                165

<210> SEQ ID NO 234
<211> LENGTH: 160
<212> TYPE: PRT
<213> ORGANISM: Unknown
<220> FEATURE:
<223> OTHER INFORMATION: metagenomes purified from environmentally
      challenged niches

<400> SEQUENCE: 234

Met Gly His Ser Ala Gly Leu Arg Lys Gly Thr Arg Tyr Ala Phe Ser
1                5                  10                  15

Arg Asp Phe Lys Lys Arg Gly Met Ile Pro Leu Ser Thr Tyr Leu Lys
                20                  25                  30

Gln Tyr Lys Val Gly Asp Ile Val His Val Val Cys Asn Gly Ala Val
            35                  40                  45

Gln Lys Gly Met Pro His Lys Asp Phe His Gly Lys Thr Gly Val Val
 50                  55                  60

Tyr Asn Val Thr Lys Ser Ala Val Gly Val Ile Leu Tyr Lys Gln Val
65                  70                  75                  80

Gly Asn Arg Tyr Ile Glu Lys Arg Val Asn Leu Arg Ile Glu His Val
                85                  90                  95

Arg Leu Ser Arg Ser Arg Glu Glu Phe Ile Val Arg Val Lys Thr Asn
                100                 105                 110

Ala Glu Lys Lys Arg Lys Ala Lys Glu Glu Gly Thr Thr Val Phe Leu
            115                 120                 125

Lys Arg Gln Ala Asp Lys Pro Arg Glu Ala Arg Thr Ile Ser Ala Lys
        130                 135                 140

Asp Asn Lys Pro Glu Ser Ile Ala Pro Ile Ala Tyr Asp Thr His Ile
145                 150                 155                 160

<210> SEQ ID NO 235
<211> LENGTH: 526
<212> TYPE: PRT
<213> ORGANISM: Unknown
<220> FEATURE:
<223> OTHER INFORMATION: metagenomes purified from environmentally
      challenged niches

<400> SEQUENCE: 235

-continued

```
Asp Met Gly Ile Gly Gly Leu Asp Thr Glu Phe Ser Ala Ile Phe Arg
1               5                   10                  15

Arg Ala Phe Ala Ser Arg Ile Phe Pro Pro Gly Leu Val Glu Lys Leu
                20                  25                  30

Gly Ile Gln His Val Lys Gly Ile Leu Leu Phe Gly Pro Pro Gly Thr
            35                  40                  45

Gly Lys Thr Leu Met Ala Arg Gln Ile Gly Thr Met Leu Asn Ala Arg
        50                  55                  60

Glu Pro Lys Val Val Asn Gly Pro Glu Ile Leu Asn Lys Phe Val Gly
65                  70                  75                  80

Gln Ser Glu Glu Asn Ile Arg Lys Leu Phe Ala Asp Ala Glu Lys Glu
                85                  90                  95

Gln Lys Glu Lys Gly Asp Glu Ser Gly Leu His Ile Ile Ile Phe Asp
            100                 105                 110

Glu Leu Asp Ala Ile Cys Lys Gln Arg Gly Ser Thr Asn Ser Gly Thr
        115                 120                 125

Gly Val Gly Asp Ser Val Val Asn Gln Leu Leu Ser Lys Met Asp Gly
    130                 135                 140

Val Asp Gln Leu Asn Asn Val Leu Ile Ile Gly Met Thr Asn Arg Met
145                 150                 155                 160

Asp Met Ile Asp Glu Ala Leu Leu Arg Pro Gly Arg Leu Glu Val His
                165                 170                 175

Ile Glu Ile Ser Leu Pro Asp Glu Ala Gly Arg Phe Gln Ile Leu Asn
            180                 185                 190

Ile His Thr Asn Lys Met Arg Thr Asn Gly Val Met Asp Ser Asp Val
        195                 200                 205

Asp Leu Gly Glu Leu Ala Ala Leu Thr Lys Asn Phe Ser Gly Ala Glu
    210                 215                 220

Ile Gly Gly Leu Val Lys Ser Ala Thr Ser Phe Ala Phe Asn Arg His
225                 230                 235                 240

Val Lys Val Gly Ser Val Ala Ala Phe Asp Asp Ile Asp Asn Met Lys
                245                 250                 255

Ile Ser Arg Ala Asp Phe Leu His Ala Leu Asp Glu Val Thr Pro Ala
            260                 265                 270

Phe Gly Val Ser Glu Glu Leu Gln Gln Val Val Gln Asn Gly Ile
        275                 280                 285

Ile His Tyr Ser Gln His Val Asn Asp Thr Leu Asn Asp Gly Ser Leu
    290                 295                 300

Leu Val Glu Gln Val Arg Lys Ser Asp Arg Thr Pro Leu Val Ser Ala
305                 310                 315                 320

Leu Leu His Gly Pro Ser Gly Ala Gly Lys Thr Ala Leu Ala Ala Thr
                325                 330                 335

Ile Ala Met Ala Ser Glu Phe Pro Phe Ile Lys Leu Ile Ser Pro Glu
            340                 345                 350

Thr Met Val Gly Phe Ser Glu Pro Gln Lys Ile Ala Gln Leu Asn Lys
        355                 360                 365

Val Phe Thr Asp Ser Tyr Lys Ser Pro Met Ser Ile Ile Val Val Asp
    370                 375                 380

Ser Leu Glu Arg Leu Leu Asp Trp Asn Pro Ile Gly Pro Arg Phe Ser
385                 390                 395                 400

Asn Gly Val Leu Gln Ala Leu Val Val Leu Phe Gly Lys Arg Pro Pro
                405                 410                 415

Lys Gly Arg Arg Leu Leu Ile Leu Ala Thr Thr Ser Asn Arg Asn Ile
```

```
                    420                 425                 430
Leu Thr Asp Met Asp Val Leu Ser Ala Phe Asp Thr Asp Ile Pro Ile
                435                 440                 445

Asn Pro Ile Ser Ser Ile Asp Ala Val Val His Val Leu Asp Glu Val
            450                 455                 460

Lys Leu Phe Pro Asn Ser Lys Glu Lys Gln Arg Ala Thr Gln Met Leu
465                 470                 475                 480

Arg Glu Ala Arg Leu Gly Glu Gly Gly Arg Pro Asp Leu Leu Val Gly
                485                 490                 495

Val Lys Lys Leu Leu Ser Met Ala Glu Met Ala Arg Gln Asp Pro Asp
                500                 505                 510

Pro Thr Met Lys Ile Val Thr Ser Ile Leu Arg Glu Ala Ser
                515                 520                 525

<210> SEQ ID NO 236
<211> LENGTH: 425
<212> TYPE: PRT
<213> ORGANISM: Unknown
<220> FEATURE:
<223> OTHER INFORMATION: metagenomes purified from environmentally
      challenged niches

<400> SEQUENCE: 236

Gly Gly Phe Ser Val Lys Phe Arg Thr Ala Glu Gly Asn Trp Asp Phe
1               5                   10                  15

Val Ala Asn Asn Thr Pro Val Phe Phe Leu Arg Asp Pro Ala Lys Phe
                20                  25                  30

Pro His Phe Ile His Thr Gln Lys Arg Asp Pro Ala Thr His Leu Ser
            35                  40                  45

Gly Asp Asp Asp Ser Thr Met Phe Trp Asp Tyr Leu Ser Gln Asn Pro
        50                  55                  60

Glu Ser Ile His Gln Val Met Ile Leu Met Gly Asp Arg Gly Ile Pro
65                  70                  75                  80

Lys Gly Trp Arg Phe Met His Gly Tyr Tyr Gly His Thr Leu Lys Ile
                85                  90                  95

Val Asn Asp Lys Gly Glu Trp Val Tyr Ala Gln Phe His Leu Ile Ser
                100                 105                 110

Asp Gln Gly Thr Gln Asn Phe Thr Gly Asp Glu Ala Ala Gln Gln Ser
            115                 120                 125

Asn Asp Tyr Gly Gln Lys Asp Leu Tyr Glu Ala Ile Glu Lys Gly Asp
        130                 135                 140

Phe Pro Ser Trp Thr Met Lys Val Gln Ile Met Thr Glu Lys Gln Ala
145                 150                 155                 160

Glu Glu Ala Trp Glu Gln Lys Arg Ile Asn Val Phe Asp Leu Thr His
                165                 170                 175

Val Trp Pro His Gly Asp Tyr Pro Leu Arg Thr Val Gly Lys Phe Thr
                180                 185                 190

Leu Asn Glu Asn Ala Lys Asn Tyr Phe Ala Glu Val Glu Gln Val Ala
            195                 200                 205

Phe Asn Pro Ser His Met Ile Pro Gly Val Glu Pro Ser Asn Asp Pro
        210                 215                 220

Val Leu Gln Ser Arg Leu Phe Ser Tyr Pro Asp Ala His Arg His Arg
225                 230                 235                 240

Ile Gly Ala Asn Tyr Gln Gln Leu Pro Val Asn Gln Asn Val Cys Pro
                245                 250                 255
```

```
Phe Ala Leu Gly Asn Phe Gln Arg Asp Gly Gln Met Ala Phe Tyr Asn
                260                 265                 270

Gln Gly Ser Arg Pro Asn Tyr Leu Ser Ser Ile Glu Pro Ile Ser Phe
            275                 280                 285

Lys Glu Arg Ala Tyr Asp Leu Asn Lys Val His Gly Lys Phe Val Gly
        290                 295                 300

Glu Ala Val Ala Phe Leu Ser Glu Ile Arg Pro Glu Asp Phe Asn Ala
305                 310                 315                 320

Pro Arg Ala Leu Trp Gln Lys Val Phe Ser Glu Ser Lys Gln Arg
                325                 330                 335

Phe Val Asp Thr Val Ser Gly His Met Ser Thr Val Arg Asp Lys Ala
                340                 345                 350

Ile Thr Ala Arg Met Met Thr Ile Phe Arg Glu Val Ser Pro Asp Leu
                355                 360                 365

Gly Asp Arg Leu Glu Lys Ala Thr Gly Val Lys Gly Glu Ser Thr Ile
            370                 375                 380

Ala Gly Met Lys Phe Asn Gly Thr His Asn Gly Phe Asp Lys Ala Asn
385                 390                 395                 400

Lys Ile Pro Ala Asn Gly Met Lys Lys Gly Gly Glu Val Ile Phe Asp
                405                 410                 415

Asn Gly Ala Pro Ala Thr Ala Ala Arg
                420                 425

<210> SEQ ID NO 237
<211> LENGTH: 122
<212> TYPE: PRT
<213> ORGANISM: Unknown
<220> FEATURE:
<223> OTHER INFORMATION: metagenomes purified from environmentally
      challenged niches

<400> SEQUENCE: 237

Met Leu Thr Asp Thr Glu Ser Glu Pro Thr Ile Ser Asn Cys Pro Leu
1               5                   10                  15

Thr Arg Met Cys Ala Pro Ser Pro Trp Ala Thr Ser Ser Glu Thr Ala
                20                  25                  30

Arg Trp His Ser Thr Ile Lys Val Val Asp Pro Thr Thr Phe Leu Arg
            35                  40                  45

Leu Ser Gln Ser His Ser Arg Arg Gly Arg Met Ile Ser Thr Arg Ser
        50                  55                  60

Thr Ala Asn Ser Ser Glu Lys Pro Ser Pro Ser Cys Leu Lys Ser Gly
65                  70                  75                  80

Gln Arg Thr Ser Met Pro Gln Gly His Cys Gly Arg Lys Ser Leu Ala
                85                  90                  95

Arg Lys Ala Ser Ser Asp Ser Ser Thr Pro Ser Leu Val Thr Cys Arg
            100                 105                 110

Gln Ser Glu Thr Lys Pro Ser Pro Leu Glu
        115                 120

<210> SEQ ID NO 238
<211> LENGTH: 309
<212> TYPE: PRT
<213> ORGANISM: Unknown
<220> FEATURE:
<223> OTHER INFORMATION: metagenomes purified from environmentally
      challenged niches

<400> SEQUENCE: 238
```

```
Met Pro Pro Arg Gln Pro Ala Thr Arg Leu Phe Ala Leu Pro Pro Arg
1               5                   10                  15

Phe Leu Cys Pro Ser Leu Pro Thr Thr Gln Thr Arg Thr Ile Arg Ser
            20                  25                  30

Ile Asp Lys Pro Ala Pro Lys Pro Ser Arg Phe Asn Ala Ser Leu Asn
            35                  40                  45

Leu Pro Val Leu Gly Ser Ser Thr Ala Ala Phe Ala Arg Lys Glu
    50                  55                  60

His Ser Leu Pro Leu Arg Thr Gly Ala Leu Ala Ile Lys Lys Gly Met
65                  70                  75                  80

Thr Ala Leu Phe Asp Pro Val Thr Ala Lys Arg Thr Pro Cys Thr Val
                85                  90                  95

Leu Gln Leu Asp Arg Cys Gln Val Val Ser His Lys Arg Arg Asp Ile
                100                 105                 110

His Gly Tyr Trp Ala Val Gln Val Gly Ala Gly Ala Lys Glu Ala Arg
                115                 120                 125

Asn Val Thr Arg Pro Glu Arg Gly His Phe Ala Ala Tyr Asn Val Pro
130                 135                 140

Leu Ser Arg His Leu Ala Glu Phe Arg Val Lys Asn Ala Glu Gly Leu
145                 150                 155                 160

Pro Pro Val Gly Ser Ala Ile Thr Ala Asp Leu Phe Ile Glu Gly Gln
                165                 170                 175

Phe Ile Asp Ala Lys Ala Asp Arg Arg Gly Met Gly Phe Glu Gly Gly
                180                 185                 190

Met Lys Arg Trp Asn Phe Gly Gly Gln Pro Ala Ser His Gly Asn Ser
                195                 200                 205

Leu Ala His Arg Leu Met Gly Ser Ser Gly Gly Gln Gly Ser Gly
210                 215                 220

Ser Arg Val Leu Pro Gly Lys Lys Met Pro Gly Arg Met Gly Gly Glu
225                 230                 235                 240

Gln Ala Thr Val Ala Asn Leu Arg Val Met Gln Val Asp Lys Glu Asn
                245                 250                 255

Gly Ile Val Val Val Ser Gly Ala Val Pro Gly Pro Lys Asn Cys Met
                260                 265                 270

Val Lys Leu Gln Asp Ala Leu Lys Lys Pro Trp Pro Asp Ala Thr Trp
                275                 280                 285

Pro Pro Ser Ile Glu Gly Ala Thr Glu Val Leu Arg Glu Ala Thr Glu
                290                 295                 300

Lys Ala Pro Ala Ala
305

<210> SEQ ID NO 239
<211> LENGTH: 130
<212> TYPE: PRT
<213> ORGANISM: Unknown
<220> FEATURE:
<223> OTHER INFORMATION: metagenomes purified from environmentally
      challenged niches

<400> SEQUENCE: 239

Met Gly Ile Trp Asp Ala Phe Thr Asp Ile Val Glu Ala Val Thr Pro
1               5                   10                  15

Trp Ser Val Val Glu Ala Glu Ala Pro Ala Glu Glu Pro Gln Glu Glu
                20                  25                  30

Asn Glu Ser Lys Thr Glu Ser Lys Asp Glu Pro Glu Glu Glu Glu Glu
                35                  40                  45
```

```
Asp Glu Glu Glu Glu Asp Glu Asp Asp Glu Glu Leu Val Asp
    50                  55                  60

Pro Lys Glu Thr Leu Glu Glu Cys Lys Asn Ser Pro Gln Cys Ala
65                  70                  75                  80

Pro Ala Lys His His Phe Asp Cys Val Glu Arg Val Gln Gln Gln
                85                  90                  95

Glu Ser Glu Gly Gly Ala Lys Glu Asp Cys Val Glu Glu Phe Phe His
            100                 105                 110

Leu Ala His Cys Ala Thr Ala Cys Ala Ala Pro Lys Leu Trp Ser Gln
            115                 120                 125

Leu Lys
    130
```

<210> SEQ ID NO 240
<211> LENGTH: 136
<212> TYPE: PRT
<213> ORGANISM: Unknown
<220> FEATURE:
<223> OTHER INFORMATION: metagenomes purified from environmentally
      challenged niches

<400> SEQUENCE: 240

```
Met Arg Lys Lys Arg Met Arg Met Met Arg Arg Ser Ser Ser Thr
1                   5                   10                  15

Pro Arg Arg Leu Ser Arg Lys Ser Ala Arg Thr Leu Leu Asn Val Pro
                20                  25                  30

Pro Pro Ser Thr Thr Ser Thr Ser Val Leu Ser Ala Phe Ser Ser Arg
            35                  40                  45

Arg Ala Arg Val Val Leu Arg Arg Thr Val Ser Arg Ser Ser Ser Thr
50                  55                  60

Leu Pro Thr Val Arg Pro Leu Ala Pro Leu Pro Ser Phe Gly Leu Ser
65                  70                  75                  80

Ser Ser Lys Leu Thr Thr Leu Gly Tyr Arg Leu Leu Arg Arg Arg Asn
                85                  90                  95

Gly Tyr Ile His Val Glu Lys Met Pro Gly Ala Gly Thr Arg Gln Cys
            100                 105                 110

Cys Pro Leu Arg Lys Ala Val Pro Leu Tyr Glu Cys Ser Ser Ala Gly
            115                 120                 125

Tyr Gln Val Gly Gln Arg Leu Leu
    130                 135
```

<210> SEQ ID NO 241
<211> LENGTH: 194
<212> TYPE: PRT
<213> ORGANISM: Unknown
<220> FEATURE:
<223> OTHER INFORMATION: metagenomes purified from environmentally
      challenged niches

<400> SEQUENCE: 241

```
Gly Arg Tyr Tyr Arg Ala Pro Glu Ile Met Leu Thr Trp Gln Lys Tyr
1                   5                   10                  15

Asp Val Ala Val Asp Ile Trp Ser Thr Gly Cys Ile Phe Ala Glu Met
                20                  25                  30

Leu Glu Gly Lys Pro Leu Phe Pro Gly Lys Asp His Val Asn Gln Phe
            35                  40                  45

Ser Ile Ile Thr Glu Leu Leu Gly Thr Pro Pro Asp Asp Val Ile Gln
50                  55                  60
```

```
Thr Ile Ala Ser Glu Asn Thr Leu Arg Phe Val Gln Ser Leu Pro Lys
 65                  70                  75                  80

Arg Glu Lys Val Pro Phe Thr Thr Lys Phe Ala Asn Ala Asp Pro Leu
                 85                  90                  95

Ser Leu Asp Leu Leu Glu Lys Met Leu Val Phe Asp Pro Arg Thr Arg
            100                 105                 110

Ile Ser Ala Ser Glu Gly Leu Ser His Glu Tyr Leu Ala Pro Tyr His
            115                 120                 125

Asp Pro Thr Asp Glu Pro Val Ala Ala Glu Val Phe Asp Trp Ser Phe
            130                 135                 140

Asn Asp Ala Asp Leu Pro Val Asp Thr Trp Lys Val Met Met Tyr Ser
145                 150                 155                 160

Glu Ile Leu Asp Phe His Asn Leu Gly Asp Ile Gln Gln Asp Gln Ala
                165                 170                 175

Ala Glu Gly Pro Val Thr Gly Asp Leu Ala Pro Pro Ser Ala Thr Thr
            180                 185                 190

Ser Ala

<210> SEQ ID NO 242
<211> LENGTH: 134
<212> TYPE: PRT
<213> ORGANISM: Unknown
<220> FEATURE:
<223> OTHER INFORMATION: metagenomes purified from environmentally
      challenged niches

<400> SEQUENCE: 242

Met Ser Pro Ser Thr Phe Gly Ala Gln Asp Val Ser Ser Pro Arg Cys
1               5                   10                  15

Ser Arg Glu Ser Pro Cys Ser Arg Ala Arg Thr Thr Leu Ile Ser Ser
            20                  25                  30

Arg Ser Ser Gln Asn Cys Ser Ala His Leu Leu Thr Met Ser Ser Arg
        35                  40                  45

Pro Ser His Leu Arg Thr Pro Ser Asp Ser Ser Arg Cys Pro Ser
 50                  55                  60

Val Arg Arg Ser His Ser Leu Arg Asn Ser Pro Met Pro Thr Arg Phe
 65                  70                  75                  80

Arg Leu Thr Cys Trp Arg Arg Cys Leu Ser Ser Ile His Val Pro Val
                 85                  90                  95

Ser Arg His Gln Lys Gly Cys Arg Thr Ser Thr Leu Arg His Thr Met
            100                 105                 110

Thr Arg Arg Met Ser Pro Ser Leu Pro Arg Cys Leu Thr Gly Val Ser
            115                 120                 125

Thr Met Arg Ile Tyr Gln
            130

<210> SEQ ID NO 243
<211> LENGTH: 111
<212> TYPE: PRT
<213> ORGANISM: Unknown
<220> FEATURE:
<223> OTHER INFORMATION: metagenomes purified from environmentally
      challenged niches

<400> SEQUENCE: 243

Gly Tyr Pro Leu Asn Leu Ser Ile Ser Ile Ser Gly Gly Lys Glu Thr
1               5                   10                  15
```

```
Asn Arg Asp Cys Pro Ser Asn Gly Glu Arg Ser Gly Lys Ser Asn
            20                  25                  30

Leu Lys Ala Gly Pro Leu Gly Val Arg Ile Val Cys Arg Gly Cys
        35                  40                  45

Phe Gly Asn Gly Pro His Leu Ser Ala Leu Glu Arg Ala Val Ile Glu
    50                  55                  60

Gly Glu Asn Pro Val Trp Asp Gly Val Ala Ala Pro Val Ser Ser Ser
65                  70                  75                  80

Phe Asp Glu Ser Ser Cys Leu Gly Met Gln Leu Lys Leu Gly Gly Lys
                85                  90                  95

Phe His Leu Lys Leu Asn Ile Gly Arg Arg Pro Ile Ala His Lys
            100                 105                 110

<210> SEQ ID NO 244
<211> LENGTH: 41
<212> TYPE: PRT
<213> ORGANISM: Unknown
<220> FEATURE:
<223> OTHER INFORMATION: metagenomes purified from environmentally
      challenged niches

<400> SEQUENCE: 244

Gly Leu Val Ala Ile Ala Arg Arg Pro His Pro Phe Pro Cys Gln Thr
1               5                   10                  15

Arg Lys Leu Ser Val Ser Ala Pro Lys Val Val Gly Ser Pro Pro
            20                  25                  30

Val Arg Ile Gly Arg Cys Gln Ala Lys
            35                  40

<210> SEQ ID NO 245
<211> LENGTH: 218
<212> TYPE: PRT
<213> ORGANISM: Unknown
<220> FEATURE:
<223> OTHER INFORMATION: metagenomes purified from environmentally
      challenged niches

<400> SEQUENCE: 245

Met Glu Pro Asp Gln Glu Glu Ser Glu Glu Glu Glu Glu Glu Glu Asp
1               5                   10                  15

Asp Glu Met Asp Glu Asp Glu Asp Gly Gln Gln Gln Asp Ala Ser
            20                  25                  30

Gly Met Gln Thr Pro Ser Gly Leu Ala Thr Pro Ser Gly Tyr Ala Ser
        35                  40                  45

Thr Thr Ser Thr Met Pro Gly Gly Met Glu Thr Pro Asp Phe Met Asp
50                  55                  60

Leu Arg Lys Gln Arg Gln Thr Arg Asp Glu Thr Ala Asp Gln Glu Asp
65                  70                  75                  80

Gln Gly Ala Pro Arg Asp Leu Tyr Thr Val Val Pro Glu Arg Arg Ala
                85                  90                  95

Thr Ala Ser Gly Phe Leu Gly Ser Asp Arg Ala Tyr Asp Leu Ser Asn
            100                 105                 110

Ala Pro Gln Ser Ser Asn Met Pro Val Leu Gly Gln Glu Asp Ser Arg
        115                 120                 125

Lys Lys Lys Gly Gly Arg Ser Gly Ala Asp Asp Val Asp Leu Ala Leu
    130                 135                 140

Asp Pro Ala Glu Leu Glu Gly Met Ser Glu Gln Glu Leu Arg Gln Lys
145                 150                 155                 160
```

```
Tyr Asp Ser His Arg Arg Ser Ser Ser Gln Gly Ala Gly Gly Gln
            165                 170                 175

Gln Asp Lys Glu Asp Phe Ser Asp Phe Val Ala Gln Glu Val Ala Lys
        180                 185                 190

Lys Arg Gln Arg Ala Gln Gln Arg Gly Gly Ser Gly Arg Asp Arg Glu
    195                 200                 205

Ser Ser Arg Ser Lys Glu Lys Phe Lys Phe
210                 215

<210> SEQ ID NO 246
<211> LENGTH: 210
<212> TYPE: PRT
<213> ORGANISM: Unknown
<220> FEATURE:
<223> OTHER INFORMATION: metagenomes purified from environmentally
      challenged niches

<400> SEQUENCE: 246

Met Thr Arg Trp Met Lys Met Arg Met Arg Ala Ser Ser Arg Thr Pro
1               5                   10                  15

Val Ala Cys Arg His Pro Leu Gly Ser Pro Arg Pro Gln Ala Met Pro
            20                  25                  30

Leu Leu His Leu Gln Cys Leu Val Ala Trp Arg Arg Leu Thr Leu Trp
        35                  40                  45

Thr Cys Ala Ser Ser Asp Arg Arg Ala Thr Arg Pro Leu Ile Lys Arg
50                  55                  60

Thr Arg Val His Arg Glu Thr Ser Ile Arg Ser Cys Pro Ser Ala Glu
65                  70                  75                  80

Pro Pro Leu Leu Ala Ser Ser Val Leu Thr Ala Pro Met Thr Cys Pro
                85                  90                  95

Met Arg His Ser Leu Pro Thr Cys Leu Cys Trp Val Lys Lys Thr Arg
            100                 105                 110

Ala Arg Arg Lys Ala Ala Asp Leu Val Gln Thr Thr Ser Thr Trp Pro
        115                 120                 125

Trp Ile Gln Leu Ser Ser Arg Ala Cys Leu Ser Lys Ser Leu Gly Arg
130                 135                 140

Ser Thr Thr Arg Thr Gly Ala Pro Arg Pro Val Lys Ala Pro Ala Asp
145                 150                 155                 160

Ser Arg Thr Lys Lys Ile Ser Gln Ile Ser Ser Arg Lys Arg Ser Gln
                165                 170                 175

Arg Arg Gly Arg Gly Leu Ser Ser Ala Ala Val Asp Ala Thr Ala
            180                 185                 190

Lys Ala Leu Gly Ala Arg Lys Ser Ser Ser Phe Arg Val Tyr Val Cys
        195                 200                 205

Ile Val
    210

<210> SEQ ID NO 247
<211> LENGTH: 164
<212> TYPE: PRT
<213> ORGANISM: Unknown
<220> FEATURE:
<223> OTHER INFORMATION: metagenomes purified from environmentally
      challenged niches

<400> SEQUENCE: 247

Gly Val Ile Gln Val Asp Glu Pro Ala Leu Arg Glu Gly Leu Pro Leu
1               5                   10                  15
```

```
Arg Thr Gly Ala Ala Arg Asp Ala Tyr Val Lys Trp Ala Val Asn Ala
            20                  25                  30

Phe Lys Leu Ser Thr Ala Gly Val Thr Asp Ser Thr Gln Val His Ser
        35                  40                  45

His Phe Cys Tyr Ser Glu Phe Gln Asp Phe Phe His Ala Ile Ala Ala
    50                  55                  60

Leu Asp Thr Asp Val Leu Ser Ile Glu Asn Ser Lys Ser Asp Ala Lys
65                  70                  75                  80

Leu Leu Gln Val Phe Val Asp Gln Ser Phe Pro Ala His Ile Gly Pro
                85                  90                  95

Gly Val Tyr Asp Ile His Ser Pro Arg Val Pro Ser Val Asp Glu Ile
            100                 105                 110

Lys Glu Arg Ile Glu Gln Met Leu Gln Tyr Leu Lys Pro Glu Gln Leu
        115                 120                 125

Trp Ile Asn Pro Asp Cys Gly Leu Lys Thr Arg Thr Thr Glu Gln Thr
    130                 135                 140

Ile Gly Gln Leu Thr Ser Leu Val Glu Ala Ala Lys Phe Tyr Arg Gln
145                 150                 155                 160

Lys Tyr Thr Gln

<210> SEQ ID NO 248
<211> LENGTH: 125
<212> TYPE: PRT
<213> ORGANISM: Unknown
<220> FEATURE:
<223> OTHER INFORMATION: metagenomes purified from environmentally
      challenged niches

<400> SEQUENCE: 248

Val Arg Val Phe Leu Cys Val Leu Ala Leu Pro Val Met Leu Met Leu
1               5                   10                  15

Ser Gly Leu Ser Met Leu Ser Ser Cys Leu Leu Leu Val Ser Pro Thr
            20                  25                  30

Ala Pro Arg Ser Thr Pro Thr Ser Ala Thr Val Asn Ser Arg Thr Ser
        35                  40                  45

Ser Thr Leu Leu Leu Pro Leu Ile Pro Met Phe Cys Pro Ser Arg Thr
    50                  55                  60

Ala Ser Pro Met Pro Ser Ser Ser Arg Ser Ser Leu Ile Arg Val Ser
65                  70                  75                  80

Pro Pro Thr Leu Asp Leu Val Ser Thr Ile Ser Thr Leu Leu Val Phe
                85                  90                  95

Pro Pro Trp Met Arg Ser Arg Ser Val Ser Ser Arg Cys Ser Ser Thr
            100                 105                 110

Ser Ser Leu Ser Ser Ser Gly Ser Thr Leu Thr Ala Val
        115                 120                 125

<210> SEQ ID NO 249
<211> LENGTH: 171
<212> TYPE: PRT
<213> ORGANISM: Unknown
<220> FEATURE:
<223> OTHER INFORMATION: metagenomes purified from environmentally
      challenged niches

<400> SEQUENCE: 249

Met Leu Met Arg Thr Glu Leu Leu Ser Val Leu Leu Ala Val Glu Leu
1               5                   10                  15

Ser Ser Leu Asp Gln Arg Gly Gln Leu Ala Asp Ser Leu Leu Ser Gly
```

```
            20                  25                  30
Thr Gly Leu Gln Thr Ala Val Arg Val Asp Pro Glu Leu Leu Arg Leu
            35                  40                  45
Glu Val Leu Glu His Leu Leu Asp Thr Leu Leu Asp Leu Ile His Gly
        50                  55                  60
Gly Asn Thr Arg Arg Val Asp Ile Val Asp Thr Arg Ser Asn Val Gly
65                  70                  75                  80
Gly Glu Thr Leu Ile Asn Glu Asp Leu Glu Glu Leu Gly Ile Gly Leu
                85                  90                  95
Ala Val Leu Asp Gly Gln Asn Ile Gly Ile Lys Gly Ser Asn Ser Val
            100                 105                 110
Glu Glu Val Leu Glu Phe Thr Val Ala Glu Val Gly Val Asp Leu Gly
            115                 120                 125
Ala Val Gly Asp Thr Ser Ser Arg Gln Leu Glu Ser Ile Asp Ser Pro
        130                 135                 140
Leu Asn Ile Ser Ile Thr Gly Ser Ala Ser Thr Gln Arg Lys Thr Leu
145                 150                 155                 160
Thr Gln Gly Arg Leu Val Asp Leu Asp Asp Pro
                165                 170

<210> SEQ ID NO 250
<211> LENGTH: 66
<212> TYPE: PRT
<213> ORGANISM: Unknown
<220> FEATURE:
<223> OTHER INFORMATION: metagenomes purified from environmentally
      challenged niches

<400> SEQUENCE: 250

Leu Lys Ser Gly Val Phe Gly Val Arg Val Ile Cys Arg Gly Cys
1               5                   10                  15

Phe Trp Ala Ala Thr Asp Leu Ser Ser Leu Glu Gln Asp Val Ile Glu
            20                  25                  30

Gly Glu Asn Pro Val Cys Gly Arg Lys Gly Thr Leu His Val Ala Pro
        35                  40                  45

Ser Thr Ser Arg Val Val Trp Glu Cys Ser Ser Lys Trp Glu Val Asn
    50                  55                  60

Phe Phe
65

<210> SEQ ID NO 251
<211> LENGTH: 189
<212> TYPE: PRT
<213> ORGANISM: Unknown
<220> FEATURE:
<223> OTHER INFORMATION: metagenomes purified from environmentally
      challenged niches

<400> SEQUENCE: 251

Met Lys Leu Ser Asn Ser Ala His Tyr Ser Leu Phe Leu Leu Ser Ser
1               5                   10                  15

Ile Leu Gly Phe Ser Ser Ala Ser Ala Asn Ser His Leu Ser Asp Asp
            20                  25                  30

Ser Pro Cys Val Ala Arg Ser Pro Thr Ser Gly Leu Tyr Tyr Asp Leu
        35                  40                  45

Asn Ala Ile Ser Leu Ala Pro Pro Glu Trp Lys Asn Gly Lys Lys Val
    50                  55                  60

Asp Gln Glu Ala Arg Asp Glu Ser Trp His Ala Lys Gly His Asp Tyr
```

```
                65                  70                  75                  80

Pro Ala Asn Phe Thr Ile Asn Val Cys Ala Pro Val Leu Glu Asn Val
                    85                  90                  95

Thr Asn Val Val Gly Val Asp Ala Ser Arg Trp Ala Asn Val Ser Ala
                100                 105                 110

Phe Tyr Glu Gln Ala Gly Lys Ile Tyr Ser Met Gly Glu Gln Ala Ser
                115                 120                 125

Glu Pro Phe Phe Arg Gly Arg Lys Leu Val Leu Asn Tyr Thr Asp Gly
130                 135                 140

Ser Pro Cys Pro Gly Asp Ser Asn Thr Ala Ser Gly Asn Ser Ser Ile
145                 150                 155                 160

Arg Thr Lys Ser Thr Leu Met Ser Phe Leu Cys Asp Arg Ala Ala Glu
                165                 170                 175

Phe Pro Gly Leu Glu Lys Leu Gly Ser Thr Gly Ser Arg
                180                 185

<210> SEQ ID NO 252
<211> LENGTH: 393
<212> TYPE: PRT
<213> ORGANISM: Unknown
<220> FEATURE:
<223> OTHER INFORMATION: metagenomes purified from environmentally
      challenged niches

<400> SEQUENCE: 252

Met Asn Gly Phe Asn Glu Lys Gly Leu Asp Gly Asp Ala Phe Gly Glu
1               5                   10                  15

Lys Ser Asn Leu Ser Gly Leu Lys Thr Phe Asp Ala Phe Pro Lys Thr
                20                  25                  30

Lys Thr Ser Tyr Thr Thr Pro Thr Arg Arg Gly Gly Gln Trp Thr Val
            35                  40                  45

Leu Ile Leu Ala Val Cys Thr Leu Phe Ser Leu His Glu Leu Arg Thr
        50                  55                  60

Trp Arg Gly Thr Glu Ala His His Phe Ser Val Glu Lys Gly Val
65                  70                  75                  80

Ser His Asp Leu Gln Leu Asn Leu Asp Met Val Val His Met Pro Cys
                85                  90                  95

Asp Thr Leu Arg Ile Asn Ile Gln Asp Ala Ser Gly Asp Arg Val Leu
                100                 105                 110

Ala Gly Glu Leu Leu Thr Arg Glu Asp Thr Asn Trp Asp Leu Trp Met
                115                 120                 125

Lys Lys Arg Asn Phe Glu Ser His Gly Glu His Glu Tyr Gln Thr Leu
130                 135                 140

Asn His Glu Ala Ala Asp Arg Leu Ser Ala Gln Asp Glu Asp Ala His
145                 150                 155                 160

Val His His Val Leu Gly Glu Val Arg Arg Asn Pro Arg Arg Lys Phe
                165                 170                 175

Ser Lys Gly Pro Arg Leu Arg Trp Gly Asp Asn Lys Asp Ser Cys Arg
                180                 185                 190

Ile Tyr Gly Ser Leu Glu Gly Asn Lys Val Gln Gly Asp Phe His Ile
            195                 200                 205

Thr Ala Arg Gly His Gly Tyr Met Glu Leu Ala Pro His Leu Asp His
        210                 215                 220

Glu Val Phe Asn Phe Ser His Met Ile Thr Glu Leu Ser Phe Gly Pro
225                 230                 235                 240
```

His Tyr Pro Ser Leu Leu Asn Pro Leu Asp Lys Thr Ile Ala Glu Ser
                245                 250                 255

Glu Thr His Tyr Gln Lys Phe Gln Tyr Phe Leu Ser Val Val Pro Thr
        260                 265                 270

Leu Tyr Ser Lys Gly His Asn Ala Leu Asp Leu Val Thr Thr Asn Lys
            275                 280                 285

Asp Asn Ser Val Arg Tyr Gly Arg Asn Thr Ile Phe Thr Asn Gln Tyr
290                 295                 300

Ala Ala Thr Ser Gln Ser Thr Ala Leu Pro Glu Ile Pro Thr Leu Ile
305                 310                 315                 320

Pro Gly Ile Phe Phe Lys Tyr Asn Ile Glu Pro Ile Leu Leu Val
                325                 330                 335

Ser Glu Glu Arg Thr Gly Phe Leu Ala Leu Val Ile Arg Val Ile Asn
                340                 345                 350

Thr Val Ser Gly Val Leu Val Thr Gly Gly Trp Ile Tyr Gln Ile Ser
            355                 360                 365

Gly Trp Ile Val Glu Ile Leu Gly Lys Arg Lys Arg Gln Ser Glu Gly
        370                 375                 380

Val Leu Thr Gly Lys His Tyr Ser Asp
385                 390

<210> SEQ ID NO 253
<211> LENGTH: 292
<212> TYPE: PRT
<213> ORGANISM: Unknown
<220> FEATURE:
<223> OTHER INFORMATION: metagenomes purified from environmentally
      challenged niches

<400> SEQUENCE: 253

Met Phe Thr Arg Thr Leu Arg Pro Ala Val Ala Val Ala Arg Thr Gln
1               5                   10                  15

Ala Val Gln Gln Gln Gln Ala Gly Met Ala Thr Leu Lys Glu Ile Asp
                20                  25                  30

Gln Arg Leu Lys Ser Val Lys Asn Ile Gly Lys Ile Thr Lys Ser Met
            35                  40                  45

Lys Val Val Ala Ser Thr Lys Leu Thr Arg Ala Glu Lys Ala Met Arg
        50                  55                  60

Glu Ala Lys Lys Tyr Gly Ala Ala Asn Asn Val Leu Phe Glu Gln Thr
65                  70                  75                  80

Lys Ala Gly Glu Glu Glu Pro Lys Glu Arg Lys Ile Leu Tyr Leu Ala
                85                  90                  95

Met Thr Ser Asp Gly Gly Leu Cys Gly Gly Ile His Ser Asn Ile Thr
            100                 105                 110

Arg Tyr Met Lys Lys Ala Val Ala Lys Glu Pro Gly Met Leu Ala Val
        115                 120                 125

Val Gly Asp Lys Pro Lys Ala Gln Leu Ser Arg Ala Met Pro Lys Ala
    130                 135                 140

Leu Thr Met Ser Phe Asn Gly Val Gly Lys Asp Val Pro Thr Phe Val
145                 150                 155                 160

Glu Ala Ser Ala Ile Ala Asp Glu Ile Met Lys Ser Ala Gly Asp Phe
                165                 170                 175

Asp Glu Ile Arg Ile Val Ser Asn Lys Tyr Leu Ser Ala Ile Ala Tyr
            180                 185                 190

Glu Pro His Thr Asn Ala Val Ile Ser Ala Glu Ala Leu Arg Gln Ala
        195                 200                 205

```
Ala Gly Phe Gln Gln Tyr Glu Met Glu Glu Asp Val Ser Lys Asp Leu
        210                 215                 220

Ala Glu Phe Ala Leu Ala Asn Ala Ile Tyr Thr Ala Leu Val Glu Gly
225                 230                 235                 240

His Ala Ala Glu Ile Ser Ala Arg Arg Gln Ala Met Glu Asn Ala Ser
                245                 250                 255

Asn Asn Ala Asn Asp Met Ile Asn Ser Leu Gln Leu Gln Tyr Asn Arg
        260                 265                 270

Gly Arg Gln Ala Val Ile Thr Thr Glu Leu Ile Asp Ile Ile Thr Gly
        275                 280                 285

Ala Ser Ala Leu
        290

<210> SEQ ID NO 254
<211> LENGTH: 317
<212> TYPE: PRT
<213> ORGANISM: Unknown
<220> FEATURE:
<223> OTHER INFORMATION: metagenomes purified from environmentally
      challenged niches

<400> SEQUENCE: 254

Met Ser Phe Ala Ala Cys His Phe Cys Cys Phe Val His Leu Val Tyr
1               5                   10                  15

Thr Arg Leu Gln Ser Arg Gly Thr Gly Asn Asp Ile Asp Gln Leu Gly
            20                  25                  30

Gly Asn Asp Ser Leu Ser Thr Thr Val Val Leu Gln Leu Glu Arg Val
        35                  40                  45

Asp His Val Val Gly Val Val Gly Ser Val Leu His Ser Leu Pro Pro
50                  55                  60

Cys Arg Asp Leu Gly Gly Val Ser Leu Asp Gln Gly Ser Val Asp Gly
65                  70                  75                  80

Val Gly Lys Ser Glu Leu Gly Gln Val Leu Gly Asp Ile Leu Leu His
                85                  90                  95

Leu Val Leu Leu Glu Thr Gly Gly Leu Ser Glu Cys Leu Ser Gly Asp
            100                 105                 110

Asp Gly Val Gly Val Arg Phe Val Gly Asp Ser Gly Lys Val Leu Val
        115                 120                 125

Arg Asp Asp Ser Asp Leu Val Lys Val Thr Gly Arg Phe His Asn Leu
130                 135                 140

Ile Gly Asp Ser Ala Gly Leu Asp Glu Ser Gly Asp Ile Leu Ala Asp
145                 150                 155                 160

Ala Val Glu Arg His Gly Gln Ser Leu Gly His Arg Ser Arg Glu Leu
                165                 170                 175

Ser Leu Gly Leu Val Thr Asp Asn Ser Gln His Ser Gly Phe Leu Gly
            180                 185                 190

His Ser Leu Leu His Val Ser Arg Asn Val Gly Val Asp Thr Thr Ala
        195                 200                 205

Gln Thr Thr Val Gly Cys His Gly Glu Val Glu Asp Leu Ala Leu Leu
    210                 215                 220

Gly Leu Leu Leu Thr Ser Leu Gly Leu Leu Glu Gln Asn Val Val Gly
225                 230                 235                 240

Gly Thr Val Leu Leu Gly Phe Thr His Gly Leu Leu Ser Ser Arg Gln
                245                 250                 255

Leu Gly Arg Gly Asn Asp Leu His Arg Leu Gly Asp Leu Pro Asn Val
```

```
                    260                 265                 270
Leu Asp Gly Phe Gln Thr Leu Val Asp Phe Leu Gln Cys Gly His Thr
            275                 280                 285
Gly Leu Leu Leu Asp Ser Leu Ser Pro Gly Asp Arg His Gly Arg
        290                 295                 300
Ser Glu Ser Thr Arg Glu His Gly Val Glu Arg Gly Glu
305                 310                 315

<210> SEQ ID NO 255
<211> LENGTH: 311
<212> TYPE: PRT
<213> ORGANISM: Unknown
<220> FEATURE:
<223> OTHER INFORMATION: metagenomes purified from environmentally
      challenged niches

<400> SEQUENCE: 255

Met Glu Asn Leu Leu Arg Gln Met Gln Gly Gly Gly Arg Met Gly
1               5                   10                  15

Ala Arg Pro Gly Pro Gly Gly Glu Thr Ile Leu Ala Asp Asn Gly Glu
            20                  25                  30

Thr Val His Ile Ser Ser Leu Ala Leu Leu Lys Met Leu Lys His Gly
        35                  40                  45

Arg Ala Gly Val Pro Met Glu Val Met Gly Leu Met Leu Gly Glu Phe
    50                  55                  60

Val Asp Asp Tyr Thr Ile Ser Cys Val Asp Val Phe Ala Met Pro Gln
65                  70                  75                  80

Ser Gly Thr Thr Val Thr Val Glu Ser Val Asp His Val Phe Gln Thr
                85                  90                  95

Lys Met Leu Asp Met Leu Lys Gln Thr Gly Arg Pro Glu Met Val Val
            100                 105                 110

Gly Trp Tyr His Ser His Pro Gly Phe Gly Cys Trp Leu Ser Ser Val
        115                 120                 125

Asp Val Asn Thr Gln Gln Ser Phe Glu Gln Leu His Pro Arg Ala Val
    130                 135                 140

Ala Val Val Ile Asp Pro Ile Gln Ser Val Arg Gly Lys Val Val Ile
145                 150                 155                 160

Asp Ala Phe Arg Ser Ile Asn Pro Gln Ser Leu Val Ala Gly Gln Glu
                165                 170                 175

Ser Arg Gln Thr Thr Ser Asn Ile Gly His Leu Asn Lys Pro Ser Ile
            180                 185                 190

Gln Ala Leu Ile His Gly Leu Asn Arg His Tyr Tyr Ser Leu Ala Ile
        195                 200                 205

Asp Tyr Arg Lys Thr Glu Gly Glu Gln Gly Met Leu Leu Asn Leu His
    210                 215                 220

Lys Arg Gly Trp Thr Glu Gly Leu Lys Met Arg Asp His Ser Glu Met
225                 230                 235                 240

Lys Glu Gly Asn Glu Lys Ala Ile Lys Glu Met Leu Ser Leu Ala Ser
                245                 250                 255

Ala Tyr Thr Lys Ser Val Gln Glu Glu Thr Thr Met Thr Ala Glu Gln
            260                 265                 270

Leu Lys Thr Arg His Val Gly Lys Leu Asp Pro Lys Arg His Leu Gly
        275                 280                 285

Glu Ala Ala Glu Lys Ala Met Gly Asp Gln Val Thr Gln Ser Leu Ala
    290                 295                 300
```

Met Gly Val Leu Ala Glu Leu
305                 310

<210> SEQ ID NO 256
<211> LENGTH: 93
<212> TYPE: PRT
<213> ORGANISM: Unknown
<220> FEATURE:
<223> OTHER INFORMATION: metagenomes purified from environmentally
      challenged niches

<400> SEQUENCE: 256

Met Gly Ala Ile Pro Glu Tyr Asp Pro Glu Pro Leu Glu Thr Lys
1               5                   10                  15

Pro Phe Lys Phe Val Thr Ala Gly Tyr Asp Ala Arg Phe Pro Gln Gln
                20                  25                  30

Asn Gln Thr Lys His Cys Trp Gln Asn Tyr Val Asp Tyr Tyr Lys Cys
            35                  40                  45

Val Glu Ala Lys Gly Glu Asp Phe Arg Pro Cys Lys Gln Phe Tyr His
    50                  55                  60

Ala Phe Arg Ser Leu Cys Pro Lys Ala Trp Thr Asp Arg Trp Asp Thr
65                  70                  75                  80

Gln Arg Glu Gly Gly Asn Phe Pro Ala Ile Leu Asn Lys
                85                  90

<210> SEQ ID NO 257
<211> LENGTH: 252
<212> TYPE: PRT
<213> ORGANISM: Unknown
<220> FEATURE:
<223> OTHER INFORMATION: metagenomes purified from environmentally
      challenged niches

<400> SEQUENCE: 257

Gly Pro Leu Leu Glu Glu Leu Asp Val Glu Ala Tyr Ala Lys Lys Tyr
1               5                   10                  15

Arg Tyr Leu Arg Phe Met Cys Gln Glu Thr Leu Asp His Leu Ala Phe
                20                  25                  30

Leu Lys Asp Lys Val Lys Asp Val Glu Gly Phe Trp Ala Ser Thr Leu
            35                  40                  45

Leu Lys His Arg Asp Leu Arg Gly Tyr Ile Thr Ser Arg Ser Asp Lys
    50                  55                  60

Asp Ala Leu Lys Tyr Leu Thr His Ile Glu Leu Val Gln Asp Pro Lys
65                  70                  75                  80

Asp Pro Arg Pro Phe Ala Leu Lys Phe Tyr Lys Glu Asn Pro Tyr
                85                  90                  95

Phe Ser Asp Leu Val Leu Glu Lys Lys Tyr Asp Met Ser Glu Gly Ser
                100                 105                 110

Glu Pro Ala Pro Ala Asp Gly Ser Ile Thr Glu Gly Met Arg Asn Phe
            115                 120                 125

Lys Glu Asp Glu Leu Val Thr Lys Ala Thr Ile Asn Trp Lys Ser
    130                 135                 140

Asp Asp Lys Asn Leu Val Ala Lys Gln Pro Arg Ser Lys Ile Pro Asp
145                 150                 155                 160

Asn Asp Asp Asp Glu Asp Phe Asp Gly Asp Val Gly Ser Phe Phe Asn
                165                 170                 175

Tyr Phe Thr Asp Asp Thr Asp Ile Phe Gln Ile Gly Ala Leu Leu Gln
                180                 185                 190

```
Ser Glu Leu Leu Pro Asp Ala Ile Asp Tyr Phe Val Gly Arg Gly Glu
            195                 200                 205

Gln Val Asp Ser Glu Gly Glu Glu Leu Asp Glu Leu Glu Glu Asp Asp
        210                 215                 220

Glu Asp Asp Asp Glu Asp Asp Glu Gly Ser Ile Asp Leu Glu Asp Glu
225                 230                 235                 240

Glu Glu Gln Pro Ser Lys Lys Pro Lys Arg Ala
                245                 250

<210> SEQ ID NO 258
<211> LENGTH: 165
<212> TYPE: PRT
<213> ORGANISM: Unknown
<220> FEATURE:
<223> OTHER INFORMATION: metagenomes purified from environmentally
      challenged niches

<400> SEQUENCE: 258

Gly Ser Phe Leu Thr Pro Gln His Thr His Thr Pro Phe Gly Arg Ala
1               5                   10                  15

Met His Asn Ala Leu Thr Val Ser Arg Leu Asn Asp Lys Phe Gln Glu
            20                  25                  30

Pro Leu Val Val Leu Val Glu Leu Leu Arg Ala Arg Val Leu His Asp
        35                  40                  45

Arg Asn Phe Ser Asn Arg Gln Phe Ser Gly Gly Pro Ser Phe Gly Thr
    50                  55                  60

Asp Asn Gln Lys Arg Ser Met Leu Leu Ile Phe Arg Thr Leu Ser Ile
65                  70                  75                  80

Ile Pro Leu Gln Phe Lys Ala Glu His Trp Ser Gly Pro Leu Ser Arg
                85                  90                  95

Glu Leu Leu Val Phe Asn Ser Phe His Lys Thr Leu Ser Arg Ser Leu
            100                 105                 110

Arg Thr Leu Val Glu Ser Ile Thr Met Asn Ala Phe Leu Lys Asn Asn
        115                 120                 125

Ala Arg Arg Ala Arg Asp Asp Tyr Leu Asp Ile Ala Leu Ser Leu Pro
    130                 135                 140

Phe Gln Asn Asp Thr Asn Thr Gly Phe Gly Ile Phe Lys Val Gly
145                 150                 155                 160

Gly Leu Ala Gly Val
                165

<210> SEQ ID NO 259
<211> LENGTH: 94
<212> TYPE: PRT
<213> ORGANISM: Unknown
<220> FEATURE:
<223> OTHER INFORMATION: metagenomes purified from environmentally
      challenged niches

<400> SEQUENCE: 259

Gln Ile Tyr Leu Asp Ala Leu Thr Thr Phe Ala Glu Gly Asn Ile Thr
1               5                   10                  15

Glu Glu Asn Lys Asp Ser Glu Ser Val Lys Glu Ala Lys Gln Ser Ala
            20                  25                  30

Met Glu Ile Leu Gly Asp Ala Ile Pro Asn Val Lys Asp Pro Glu Ala
        35                  40                  45

Glu Leu Leu Arg Gly Phe Arg Phe Trp Asp Ala Val Leu Val Cys Val
    50                  55                  60
```

```
Arg Thr Leu Lys Ala Asp Arg Ala Ile Asp Leu Lys Leu Ala Glu Ser
 65                  70                  75                  80

Phe Glu Ala Ala Asn Ser Tyr Leu Asn Met Met Arg Pro Asn
                 85                  90
```

```
<210> SEQ ID NO 260
<211> LENGTH: 251
<212> TYPE: PRT
<213> ORGANISM: Unknown
<220> FEATURE:
<223> OTHER INFORMATION: metagenomes purified from environmentally
      challenged niches

<400> SEQUENCE: 260
```

```
Gly Ser Phe Leu Thr Pro Gln His Thr His Thr Pro Phe Gly Arg Ala
  1               5                  10                  15

Met His Asn Ala Leu Thr Val Ser Arg Leu Asn Asp Lys Phe Gln Glu
                 20                  25                  30

Pro Leu Val Val Leu Val Glu Leu Leu Arg Ala Arg Val Leu His Asp
             35                  40                  45

Arg Asn Phe Ser Asn Arg Gln Phe Ser Gly Gly Pro Ser Phe Gly Thr
 50                  55                  60

Asp Asn Gln Lys Arg Ser Met Leu Leu Ile Phe Arg Thr Leu Ser Ile
 65                  70                  75                  80

Ile Pro Leu Gln Phe Lys Ala Glu His Trp Ser Gly Pro Leu Ser Arg
                 85                  90                  95

Glu Leu Leu Val Phe Asn Ser Phe His Lys Thr Leu Ser Arg Ser Leu
            100                 105                 110

Arg Thr Leu Val Glu Ser Ile Thr Met Asn Ala Phe Leu Lys Asn Asn
            115                 120                 125

Ala Arg Arg Ala Arg Asp Asp Tyr Leu Asp Ile Ala Leu Ser Leu Pro
        130                 135                 140

Phe Gln Asn Asp Thr Asn Thr Gly Phe Gly Ile Phe Phe Lys Ile Tyr
145                 150                 155                 160

Leu Asp Ala Leu Thr Thr Phe Ala Glu Gly Asn Ile Thr Glu Glu Asn
                165                 170                 175

Lys Asp Ser Glu Ser Val Lys Glu Ala Lys Gln Ser Ala Met Glu Ile
            180                 185                 190

Leu Gly Asp Ala Ile Pro Asn Val Lys Asp Pro Glu Ala Glu Leu Leu
        195                 200                 205

Arg Gly Phe Arg Phe Trp Asp Ala Val Leu Val Cys Val Arg Thr Leu
    210                 215                 220

Lys Ala Asp Arg Ala Ile Asp Leu Lys Leu Ala Glu Ser Phe Glu Ala
225                 230                 235                 240

Ala Asn Ser Tyr Leu Asn Met Met Arg Pro Asn
                245                 250
```

```
<210> SEQ ID NO 261
<211> LENGTH: 148
<212> TYPE: PRT
<213> ORGANISM: Unknown
<220> FEATURE:
<223> OTHER INFORMATION: metagenomes purified from environmentally
      challenged niches

<400> SEQUENCE: 261
```

```
Gly Ile Tyr Leu Asp Gly Asn Asn Asp Leu Val Thr Met Lys Gly Asn
  1               5                  10                  15
```

```
Tyr Ile Tyr His Thr Ser Gly Arg Ser Pro Lys Val Gln Gly Asn Thr
                20                  25                  30

Leu Leu His Ala Val Asn Asn Tyr Trp His Asp Asn Ser Gly His Ala
            35                  40                  45

Phe Glu Ile Gly Glu Gly Gly Tyr Val Leu Ala Glu Gly Asn Val Phe
        50                  55                  60

Gln Asp Val Thr Thr Pro Val Glu Asp Pro Val Asp Gly Gln Leu Leu
65                  70                  75                  80

Thr Ser Pro Asp Pro Ser Thr Asn Ala Gln Cys Ser Ser Tyr Leu Gly
                85                  90                  95

Arg Ala Cys Glu Ile Asn Gly Phe Gly Asn Ser Gly Thr Phe Asn Gln
            100                 105                 110

Ala Asp Thr Ser Leu Leu Ser Lys Phe Lys Gly Gln Asn Ile Ala Ser
        115                 120                 125

Ala Asp Ala Tyr Ser Lys Val Ala Ser Ser Val Ala Ser Asn Ala Gly
    130                 135                 140

Gln Gly His Leu
145
```

<210> SEQ ID NO 262
<211> LENGTH: 120
<212> TYPE: PRT
<213> ORGANISM: Unknown
<220> FEATURE:
<223> OTHER INFORMATION: metagenomes purified from environmentally
      challenged niches

<400> SEQUENCE: 262

```
Val Arg Val Val Thr Phe Trp Pro Arg Val Thr Ser Ser Arg Met Leu
1               5                   10                  15

Leu Pro Pro Leu Arg Thr Pro Leu Thr Ala Ser Ser Leu Pro Leu
                20                  25                  30

Thr Pro Ala Pro Thr Leu Ser Ala Arg His Thr Leu Ala Gly Pro Ala
            35                  40                  45

Lys Ser Thr Ala Ser Val Thr Leu Val Pro Ser Thr Arg Leu Thr Leu
        50                  55                  60

Ala Cys Cys Leu Asn Leu Arg Val Arg Thr Leu Leu Leu Met Leu
65                  70                  75                  80

Thr Leu Arg Leu Pro Arg Ala Leu Pro Ala Thr Pro Val Arg Asp Thr
                85                  90                  95

Cys Lys Met Glu Arg Gly Gly Ser Glu Leu Asn Leu Leu Met Ser Asp
            100                 105                 110

Asp Ile Ala Leu Ala Ala Cys Trp
        115                 120
```

<210> SEQ ID NO 263
<211> LENGTH: 160
<212> TYPE: PRT
<213> ORGANISM: Unknown
<220> FEATURE:
<223> OTHER INFORMATION: metagenomes purified from environmentally
      challenged niches

<400> SEQUENCE: 263

```
Met Ser Ala Gln Pro Leu Arg Ile Val Met Ala Cys Asp Glu Ala Gly
1               5                   10                  15

Val Pro Tyr Lys Asp Ala Ile Lys Ala Val Leu Glu Lys Ser Pro Leu
                20                  25                  30
```

Val Ala Ser Val Ser Asp Val Gly Val Asn Asp Ala Ser Asp Lys Thr
           35                  40                  45

Ala Tyr Pro His Pro Ala Val Glu Gly Ala Gln Gln Ile Lys Ala Gly
 50                  55                  60

Lys Ala Asp Arg Gly Leu Phe Ile Cys Gly Thr Gly Leu Gly Val Ala
 65                  70                  75                  80

Ile Ala Ala Asn Lys Val Pro Gly Ile Arg Ala Val Thr Ala His Asp
                 85                  90                  95

Pro Phe Ser Val Glu Arg Ser Ile Leu Ser Asn Asp Ala Gln Val Leu
                100                 105                 110

Cys Met Gly Gln Arg Val Ile Gly Val Glu Leu Ala Lys Lys Leu Ala
            115                 120                 125

Leu Asp Trp Leu Asn Tyr Arg Phe Asp Pro Lys Ser Ala Ser Ala Ala
130                 135                 140

Lys Val Gln Ala Ile Ser Asp Tyr Glu Thr Lys Phe Ala Gly Ser Ser
145                 150                 155                 160

<210> SEQ ID NO 264
<211> LENGTH: 150
<212> TYPE: PRT
<213> ORGANISM: Unknown
<220> FEATURE:
<223> OTHER INFORMATION: metagenomes purified from environmentally
      challenged niches

<400> SEQUENCE: 264

Met Ser Val Thr Thr Ser Ser Ala Ala Ala Ser Cys Thr Pro
 1               5                  10                  15

Ser Trp Gln Ile Pro Val Asp Asp Val Ala Cys Ala Gly Gln Ile Ser
                20                  25                  30

Gly Asn Ile Thr Lys Val Phe Asp Thr Cys Cys Lys Gly Asn Ser Pro
            35                  40                  45

Val Lys Tyr Asn Asp Asp Cys Asn Ile Tyr Cys Leu Ala Gln Gly Gln
 50                  55                  60

Thr Lys Gln Glu Leu Thr Asp Cys Leu Thr Glu Lys Ser Gly Asn Asn
 65                  70                  75                  80

Gln Ile Phe Cys Gly His Gly Lys Gln Asn Ala Thr Ala Thr Ala Glu
                 85                  90                  95

Ala Thr Thr Thr Lys Glu Thr Gly Thr Ser Thr Gly Thr Ser Thr Ser
                100                 105                 110

Ser Thr Gly Thr Ser Thr Glu Thr Asn Ala Ala Val Leu Asn Gln Pro
            115                 120                 125

Ile Ser Lys Thr Gly Leu Gly Leu Val Ala Met Leu Phe Cys Ser Ala
130                 135                 140

Leu Val Gly Val Val Ala
145                 150

<210> SEQ ID NO 265
<211> LENGTH: 197
<212> TYPE: PRT
<213> ORGANISM: Unknown
<220> FEATURE:
<223> OTHER INFORMATION: metagenomes purified from environmentally
      challenged niches

<400> SEQUENCE: 265

Ala Gly Val Asp Arg Gly Val Ile Thr Lys Asp Glu Lys Asp Ser Ser
 1               5                  10                  15

Ile Asn Arg Leu Leu Val Thr Gly Tyr Gly Leu Ala Glu Val Met Gly
            20                  25                  30

Thr Asp Gly Val Asn Gly Ile Lys Thr Arg Thr Asn His Val Met Glu
        35                  40                  45

Thr Cys Glu Val Leu Gly Ile Glu Ala Ala Arg Gln Thr Ile Tyr Asn
    50                  55                  60

Glu Ile Gln His Thr Met Thr Ser His Gly Met Ser Ile Asp Pro Arg
65                  70                  75                  80

His Val Met Leu Leu Gly Asp Val Met Thr Tyr Lys Gly Glu Val Leu
                85                  90                  95

Gly Ile Thr Arg Phe Gly Val Gln Lys Met Lys Asp Ser Val Leu Met
            100                 105                 110

Leu Ala Ser Phe Glu Lys Thr Thr Asp His Leu Phe Asp Ala Ser Leu
        115                 120                 125

Phe Ser Lys Lys Asp Glu Ile Gln Gly Val Ser Glu Cys Ile Ile Met
    130                 135                 140

Gly Thr Pro Ala Pro Gly Cys Gly Thr Ser Leu Ala Ser Ile Val Thr
145                 150                 155                 160

Pro Ala Pro Leu Leu Pro Arg Lys Lys Pro Leu Leu Phe Glu Thr Ala
                165                 170                 175

Phe Lys Ala Gly Gln Asp Arg Leu Ser Tyr His Glu Asn Asn Gly Gly
            180                 185                 190

Met Glu Val Asp Met
            195

<210> SEQ ID NO 266
<211> LENGTH: 249
<212> TYPE: PRT
<213> ORGANISM: Unknown
<220> FEATURE:
<223> OTHER INFORMATION: metagenomes purified from environmentally
      challenged niches

<400> SEQUENCE: 266

Ala Gly Ser Gly Gly Ala Tyr Ser Phe Ser Leu Thr Thr Phe Ser Pro
1               5                   10                  15

Ser Gly Lys Leu Val Gln Ile Glu His Ala Leu Ala Ala Val Ala Gly
            20                  25                  30

Gly Thr Thr Ser Leu Gly Ile Lys Ala Thr Asn Gly Val Val Leu Ala
        35                  40                  45

Thr Glu Lys Lys Ser Pro Ser Leu Leu Leu Asp Thr Ser Val Leu Glu
    50                  55                  60

Lys Val Ala Pro Ile Cys Pro Asn Ile Gly Phe Val Tyr Ser Gly Met
65                  70                  75                  80

Gly Pro Asp Phe Arg Val Leu Val Ala Lys Ala Arg Lys Ile Ala Gln
                85                  90                  95

Ala Tyr Tyr Lys Val Tyr Gly Glu Tyr Pro Pro Thr Lys Val Leu Val
            100                 105                 110

Gln Glu Val Ala Gly Val Met Gln Lys Ala Thr Gln Ser Gly Gly Val
        115                 120                 125

Arg Pro Tyr Gly Ile Ser Leu Leu Ile Ala Gly Trp Asp Ser His Arg
    130                 135                 140

Gly Gln Ser Leu Tyr Gln Val Asp Pro Ser Gly Ser Tyr Trp Ala Trp
145                 150                 155                 160

Lys Ala Ser Ala Ile Gly Lys Asn Met Val Asn Gly Lys Thr Phe Leu
                165                 170                 175

-continued

Glu Lys Arg Tyr Asn Asp Asp Leu Ser Leu Glu Asp Ala Ile His Thr
              180                 185                 190

Ala Leu Leu Thr Leu Lys Glu Gly Phe Glu Gly Gln Met Thr Glu Asn
          195                 200                 205

Thr Ile Glu Ile Gly Val Val Thr Val Pro Thr Ala Glu Gln Met Gln
    210                 215                 220

Glu Lys Pro Gly Glu Arg Leu Pro Pro Thr Phe Arg Lys Leu Thr Glu
225                 230                 235                 240

Gln Glu Val Arg Asp Tyr Leu Ala Leu
                245

<210> SEQ ID NO 267
<211> LENGTH: 346
<212> TYPE: PRT
<213> ORGANISM: Unknown
<220> FEATURE:
<223> OTHER INFORMATION: metagenomes purified from environmentally
      challenged niches

<400> SEQUENCE: 267

Met Leu Thr Ser Ala Phe Ser Thr Ser Ala Ser Lys Met Leu Gly Lys
1               5                   10                  15

Arg Ala Val Ser Ser Ser Ala Leu Asn Gly Lys Val Ala Val Leu
            20                  25                  30

Gly Ala Ala Gly Gly Ile Gly Gln Pro Leu Ser Leu Leu Val Lys Gln
        35                  40                  45

Asn Pro Ala Val Ser Ser Leu Ser Leu Tyr Asp Val Arg Gly Ser Pro
50                  55                  60

Gly Val Ala Ala Asp Ile Ser His Ile Asn Thr Pro Ala Val Thr Glu
65                  70                  75                  80

Gly Phe Leu Pro Asp Asn Asp Gly Leu Lys Gln Ala Leu Glu Gly Ala
                85                  90                  95

Glu Val Val Leu Ile Pro Ala Gly Val Pro Arg Lys Pro Gly Met Thr
            100                 105                 110

Arg Asp Asp Leu Phe Asn Thr Asn Ala Ser Ile Val Lys Met Leu Ala
        115                 120                 125

Glu Ala Ser Ala Lys Tyr Cys Pro Lys Ala Met Met Leu Ile Ile Ala
    130                 135                 140

Asn Pro Val Asn Ser Thr Val Pro Ile Val Ala Glu Thr Phe Lys Arg
145                 150                 155                 160

Ala Gly Val Tyr Asp Pro Ala Arg Leu Phe Gly Val Thr Thr Leu Asp
                165                 170                 175

Val Val Arg Ser Ser Thr Phe Val Ser Gly Ile Thr Gly Ala Lys Pro
            180                 185                 190

Ser Asp Thr Val Val Gln Val Ile Gly Gly His Ser Gly Ala Thr Ile
        195                 200                 205

Val Pro Leu Leu Ser Gln Ile Pro Gln Gly Asp Lys Ile Val Lys Ala
    210                 215                 220

Gly Gly Gln Gln Tyr Ala Asp Leu Val Lys Arg Ile Gln Phe Gly Gly
225                 230                 235                 240

Asp Glu Val Val Lys Ala Lys Asp Gly Thr Gly Ser Ala Thr Leu Ser
                245                 250                 255

Met Ala Tyr Ala Ala Ala Val Phe Asn Asp Ala Leu Leu Lys Ala Met
            260                 265                 270

Asp Gly Gln Lys Gly Leu Val Gln Pro Ala Tyr Val Glu Ser Pro His

```
                275                 280                 285
Phe Ala Lys Glu Gly Ala Lys Tyr Phe Ala Ser Asn Val Glu Leu Gly
            290                 295                 300
Pro Asn Gly Val Glu Lys Ile Leu Asp Ile Gly Asn Met Ser Ser Glu
305                 310                 315                 320
Glu Gln Glu Leu Leu Lys Glu Cys Leu Pro Gln Leu Ala Lys Asn Ile
                325                 330                 335
Ala Ala Gly Glu Lys Phe Val Ala Asp Asn
            340                 345

<210> SEQ ID NO 268
<211> LENGTH: 373
<212> TYPE: PRT
<213> ORGANISM: Unknown
<220> FEATURE:
<223> OTHER INFORMATION: metagenomes purified from environmentally
      challenged niches

<400> SEQUENCE: 268

Met Ser Leu Phe Leu Leu Phe Ser Leu Ala Leu Ile Ile Ile Gly Ser
1               5                   10                  15
Asn Val Val Gly Tyr Pro Leu Val Val Ser Asp Glu Leu Leu Thr Ser
            20                  25                  30
Ser Asn Val Leu Gly Glu Leu Gly Lys Ala Leu Leu Lys Glu Leu Leu
        35                  40                  45
Leu Leu Arg Gly His Val Ala Asp Val Glu Asp Leu Leu Asn Thr Val
    50                  55                  60
Gly Ala Glu Leu Asp Val Gly Glu Val Leu Ser Thr Leu Leu Gly
65                  70                  75                  80
Glu Val Gly Ala Leu Asp Val Ser Gly Leu Asn Glu Thr Leu Leu Ala
                85                  90                  95
Val His Ser Leu Glu Glu Ser Val Val Glu Asp Gly Ser Gly Val Ser
            100                 105                 110
His Gly Glu Gly Ser Gly Ala Ser Ala Val Leu Gly Leu Asp Asp Phe
        115                 120                 125
Val Thr Ala Lys Leu Asp Ala Leu Asp Glu Val Ser Val Leu Leu Ala
    130                 135                 140
Ala Ser Leu Asp Asn Leu Val Ala Leu Arg Asp Leu Gly Glu Gln Gly
145                 150                 155                 160
His Asp Gly Gly Ala Arg Val Thr Thr Asp Leu Asp His Gly Val
                165                 170                 175
Gly Gly Leu Gly Thr Gly Asp Ala Asp Glu Ser Gly Arg Ala Asp
            180                 185                 190
Asn Val Glu Gly Gly Asp Thr Glu Glu Thr Gly Arg Val Val Asp Thr
        195                 200                 205
Ser Thr Leu Glu Gly Leu Ser Asp Asp Arg His Gly Gly Val Asp Gly
    210                 215                 220
Val Gly Asn Asp Glu His His Ser Leu Gly Ala Val Leu Gly Arg Ser
225                 230                 235                 240
Leu Ser Lys His Leu Asp Asp Gly Ser Val Gly Val Glu Lys Val Val
                245                 250                 255
Thr Gly His Ala Gly Leu Ala Arg Asn Thr Ser Arg Asn Glu Asp His
            260                 265                 270
Leu Ser Thr Leu Glu Gly Leu Leu Glu Ala Ile Val Val Gly Glu Glu
        275                 280                 285
```

```
Ala Leu Gly Asp Ser Arg Gly Val Asp Val Ala Asn Val Ser Ser Asn
    290             295                 300

Thr Arg Gly Ala Ala Asn Ile Val Lys Gly Glu Ala Gly Asp Ser Arg
305             310                 315                 320

Val Leu Leu Asp Gln Gln Gly Glu Gly Leu Ala Asn Thr Ala Ser Ser
                325                 330                 335

Thr Glu Asp Gly Asn Leu Ser Val Gln Gly Ala Gly Arg Arg Asp Cys
                340                 345                 350

Ser Leu Ala Glu His Leu Gly Ser Arg Cys Arg Lys Gly Ala Gly Gln
                355                 360                 365

His Phe Gly Ser Lys
    370

<210> SEQ ID NO 269
<211> LENGTH: 435
<212> TYPE: PRT
<213> ORGANISM: Unknown
<220> FEATURE:
<223> OTHER INFORMATION: metagenomes purified from environmentally
      challenged niches

<400> SEQUENCE: 269

Gly Ala Ser Val Leu Leu Pro Ala Leu His Phe Asp Glu Arg Glu Gln
1               5                   10                  15

Arg Pro Gly Arg Thr Ser Thr Ala Ser Leu Leu Gln Arg His Asp
                20                  25                  30

Arg Asn Glu Pro Leu Ser Leu Asn Ser His Ser Pro Thr Ser Val Asp
                35                  40                  45

His Thr Pro Thr Thr Ala His Phe Thr Gly Ala Glu Glu Leu Leu Ala
    50                  55                  60

Ser Asp Val Gly Pro Thr Ala Thr Ala Gly Leu Pro Gly Asp Ala Glu
65                  70                  75                  80

Leu Glu Ser Lys Leu Lys Leu Leu Glu Glu Val Lys Arg Ala Arg Glu
                85                  90                  95

Ser Val His Ser Ser Leu Glu Arg Ile Arg Ala Gly Thr Pro Thr Pro
                100                 105                 110

Ser Ile Ser Gln Gly Met Pro Ser Pro Thr Pro Ser Gly Ala Pro Gly
            115                 120                 125

Tyr Ala Arg Thr Pro Ser Ser Val Gly Leu Ser Asp Asp Val Arg Ser
            130                 135                 140

Arg Arg Gly Ser Thr Thr Ser Ser Lys Val Leu Asp Ala Ile Asp Lys
145                 150                 155                 160

Pro Arg Val Ala Thr Gln Ser Glu Trp Asp Glu Tyr Val Arg Asn Arg
                165                 170                 175

His Val Ile Ser Pro Pro Thr Gln Phe Ala Val Leu Pro Thr Ser
                180                 185                 190

Ala Ala Met Val Asp Arg Gly Thr Ser Arg His Ser Gln Tyr Ala Leu
            195                 200                 205

Val Ser Asp Gly Val Ala Lys Ala Leu Asp Arg Arg Glu Arg Thr Ile
    210                 215                 220

Ser Met Met Glu Pro Gln Val Ala Glu Asp Trp Gly Pro Arg Glu Thr
225                 230                 235                 240

Leu Asp Ser Thr Pro Ala His Val Ser Met Gly Arg Arg Ala Met Ser
                245                 250                 255

Phe His Glu Ile Pro Leu Ala Ser Pro Val Ala Ala Ser Arg Pro Gln
                260                 265                 270
```

-continued

```
Asp Arg Ser Ser Tyr Ser Ala Gly Pro Arg Gln Val Ile Gly Ser Ala
            275                 280                 285

Ala Gly His Thr Gln Arg Pro Gly Ile Ser Gln Ser Arg Ser Ala His
        290                 295                 300

Gly Arg Thr Met Thr Tyr Asp Glu Leu Thr Glu Arg His Arg Gln Arg
305                 310                 315                 320

Leu Ser Ala Leu Gln Ala Pro Val Ser Ala Lys Ile Arg Glu Pro Met
                325                 330                 335

Asp Ile Ala Ser Ala Lys Ala Ser Trp Asp Lys Gln Lys Arg Val Glu
            340                 345                 350

Arg Asp Glu Met Lys Arg Glu Ala Glu Lys Leu Ala Gln Ala His
        355                 360                 365

Ala Arg Glu Arg Gly Pro Ala Val Asp Lys Lys Glu Val Leu Lys
    370                 375                 380

Ser Thr Asp Glu Trp Arg Arg Ser Val His Gly Gly Leu Asp Gly Phe
385                 390                 395                 400

Ala Val Pro His Leu Pro Ala His Ala Arg Gly Ser Thr Gln Pro Gly
                405                 410                 415

Gly Ser Gly Ala Lys Arg Ser Ser Leu Ser Gln Arg Pro Ser Asn Tyr
            420                 425                 430

Phe Ala Asn
        435
```

<210> SEQ ID NO 270
<211> LENGTH: 225
<212> TYPE: PRT
<213> ORGANISM: Unknown
<220> FEATURE:
<223> OTHER INFORMATION: metagenomes purified from environmentally challenged niches

<400> SEQUENCE: 270

```
Gly Gln Ala Cys Cys Phe Arg His Cys Ile Ser Thr Ser Gly Ser Asn
1               5                   10                  15

Asp Leu Asp Val Arg Leu Arg Leu Gln Val Cys Cys Ser Val Thr Ile
            20                  25                  30

Ala Met Asn Leu Tyr Arg Ser Thr Arg Thr Arg Arg His Leu Trp Thr
        35                  40                  45

Thr Leu Pro Leu Leu Arg Ile Ser Leu Val Leu Lys Ser Cys Ser Pro
    50                  55                  60

Pro Thr Ser Asp Arg Pro Arg Gln Leu Gly Tyr Pro Val Met Arg Ser
65                  70                  75                  80

Leu Arg Ala Ser Ser Ser Cys Leu Lys Arg Ser Asn Val His Gly Asn
                85                  90                  95

Arg Tyr Ile Ala Arg Ser Arg Gly Ser Glu Pro Ala Arg Leu Pro Arg
            100                 105                 110

Leu Ser Ala Arg Glu Cys Pro Ala Arg His Pro Leu Val Pro Leu Val
        115                 120                 125

Thr Leu Glu Leu Arg Arg Leu Ser Ala Cys Arg Thr Thr Cys Ala Arg
    130                 135                 140

Asp Glu Ala Gln Arg Pro Ala Pro Arg Phe Leu Thr Leu Ser Thr Ser
145                 150                 155                 160

Leu Glu Ser Leu Pro Asn Pro Asn Gly Thr Ser Thr Phe Ala Thr Gly
                165                 170                 175

Met Ser Ser His Leu His Pro Leu Ser Leu Pro Tyr Cys Pro His Leu
```

```
                180             185             190
Leu Arg Trp Ser Ile Val Val Pro Val Asp Thr Ala Ser Met Pro Leu
        195                 200                 205

Phe Pro Thr Ala Leu Pro Lys Arg Leu Thr Gly Gly Ser Glu Leu Phe
        210                 215                 220

Gln
225

<210> SEQ ID NO 271
<211> LENGTH: 168
<212> TYPE: PRT
<213> ORGANISM: Unknown
<220> FEATURE:
<223> OTHER INFORMATION: metagenomes purified from environmentally
      challenged niches

<400> SEQUENCE: 271

Met Gly Ser Pro Ala Pro His His Arg His Gln Ser Ser Leu Glu Gly
1               5                   10                  15

Val Ile Asp Phe Ser Thr Gly Arg Gly His Pro Leu Asn Pro Tyr Gln
            20                  25                  30

Arg Asp Lys Ala Glu Ser Val Phe Thr Gly Ile Ile Asn Arg Phe Glu
        35                  40                  45

Asp Ser Ser Thr Val Glu Lys Pro Tyr Asn Arg Ala Lys Leu Val Arg
    50                  55                  60

Leu Thr Tyr Glu Tyr Ala Arg Ser Glu Asp Ser Arg Cys Asn Phe Leu
65                  70                  75                  80

Gln Ala Phe Phe Gly Ser Val Asn Val Thr Met Asp Asp Ser Ile Asp
                85                  90                  95

Phe Asp Asp Glu Ala Val Glu Glu Gly Ile Arg Ser Ser Leu Asn Ser
            100                 105                 110

Phe Ala Asp Phe Leu Val Glu Asn Phe Phe Leu Pro Leu Lys Ala Ser
        115                 120                 125

Ala Ser Arg Thr Pro Pro Ala Pro Gln Pro Lys Phe Arg Ala Asp Val
    130                 135                 140

Leu Leu Trp Gly Leu Trp Lys Glu Trp Pro Arg Ser Asp Ala Thr Ala
145                 150                 155                 160

Ser Ser Ala Ile Asp Ile Val Ala
                165

<210> SEQ ID NO 272
<211> LENGTH: 253
<212> TYPE: PRT
<213> ORGANISM: Unknown
<220> FEATURE:
<223> OTHER INFORMATION: metagenomes purified from environmentally
      challenged niches

<400> SEQUENCE: 272

Gln Asp Ala Pro Ser Pro Ala Gln Val Pro Ser Arg Arg Pro Ala
1               5                   10                  15

Val Gly Ser Val Glu Arg Val Ala Ser Leu Arg Arg Asp Cys Leu Ile
            20                  25                  30

Arg Asp Arg His Arg Cys Val Ile Ser Arg Asn Phe Met Lys Glu
        35                  40                  45

Ala Glu Arg Arg Leu Asp Asp Ser Gly Tyr Asp His Ala Ser Asp Asp
    50                  55                  60

Glu Gly His Leu Leu Lys Asp Gln Glu His Gly Ser Phe Ala Glu Leu
```

```
                65                  70                  75                  80
Glu Val Ala His Ile Leu Pro His Ser Leu Met Thr Thr Thr Ala Asn
                    85                  90                  95
Ser Glu Leu Asn Lys Ser Lys Glu Thr Ala Leu Thr Ile Leu Asn Met
                    100                 105                 110
Phe Asp Ser Gly Ile Val His Leu Ile Asp Gly Pro Asp Ile Asp Arg
                    115                 120                 125
Pro Arg Asn Ala Leu Thr Leu Ser Ile Asp Leu His Arg Gln Phe Gly
            130                 135                 140
Asn Phe Lys Val Phe Phe Glu Pro Met Pro Glu Pro His Thr Tyr Arg
145                 150                 155                 160
Ile Asp Ser Thr Leu Arg Gln Pro Phe Arg Asn Pro Ile Phe Pro Val
                    165                 170                 175
Thr Arg Ala Leu Tyr Leu Thr Pro Glu Arg Thr Ile Asp Pro Pro Ser
                    180                 185                 190
Gly Arg Leu Leu Ala Val His Arg Ala Ile Cys His Ile Leu His Leu
                    195                 200                 205
Ser Ala Ala Gly Asn Tyr Ile Asp Ser Ile Leu Arg Asp Met Asp Asp
            210                 215                 220
Gly Thr Val Gln Ala Asn Gly Ser Thr Arg Leu Ala Ser Ile Val Arg
225                 230                 235                 240
Leu Lys Leu Gly Gly Trp Trp Asp Gly Thr Val Val Gly
                    245                 250
```

<210> SEQ ID NO 273
<211> LENGTH: 106
<212> TYPE: PRT
<213> ORGANISM: Unknown
<220> FEATURE:
<223> OTHER INFORMATION: metagenomes purified from environmentally challenged niches

<400> SEQUENCE: 273

```
Met Val Asn Ile Pro Lys Thr Arg Arg Thr Tyr Cys Lys Gly Lys Glu
1               5                   10                  15
Cys Lys Lys His Thr Gln His Lys Val Thr Gln Tyr Lys Ala Gly Lys
                    20                  25                  30
Ala Ser Leu Phe Ala Gln Gly Lys Arg Arg Tyr Asp Arg Lys Gln Ser
                35                  40                  45
Gly Tyr Gly Gly Gln Thr Lys Pro Val Phe His Lys Lys Ala Lys Thr
            50                  55                  60
Thr Lys Lys Val Val Leu Arg Leu Glu Cys Thr Ser Cys Lys Thr Lys
65                  70                  75                  80
Ala Gln Leu Ala Leu Lys Arg Cys Lys His Phe Glu Leu Gly Gly Asp
                    85                  90                  95
Lys Lys Thr Lys Gly Ala Ala Leu Val Phe
                    100                 105
```

<210> SEQ ID NO 274
<211> LENGTH: 84
<212> TYPE: PRT
<213> ORGANISM: Unknown
<220> FEATURE:
<223> OTHER INFORMATION: metagenomes purified from environmentally challenged niches

<400> SEQUENCE: 274

Met Ile Leu Glu Gly Ser Glu Ser Lys Leu Arg Phe Ser Tyr Asp Arg

-continued

```
                 1               5                  10                 15
Pro Thr Arg Lys Asp Met Ser Arg His Ile Met Ala Cys Ala Gln His
                        20                 25                 30

Ser Ser Arg Val His Gln Arg Cys Pro Thr Leu Pro Leu Arg Cys Val
            35                 40                 45

Gly Cys Asp Ser Ser Thr Thr Ala Phe Gln Tyr His Leu Phe Ala Cys
        50                 55                 60

Arg Ser Glu Asp Asp Phe Thr Thr Val His Ile Thr Asn Arg Lys Cys
65                  70                 75                 80

Gln Gln Asp Gln

<210> SEQ ID NO 275
<211> LENGTH: 41
<212> TYPE: PRT
<213> ORGANISM: Unknown
<220> FEATURE:
<223> OTHER INFORMATION: metagenomes purified from environmentally
      challenged niches

<400> SEQUENCE: 275

Met Lys Leu Thr Phe Lys Asp Leu Lys Gln Glu Lys Phe Val Ile Glu
1               5                  10                 15

Val Glu Pro Ser Glu Thr Val Arg Glu Val Lys Gln Lys Leu Leu Lys
            20                 25                 30

Lys Lys Ala Asn Met Arg Arg Asn Glu
        35                 40

<210> SEQ ID NO 276
<211> LENGTH: 369
<212> TYPE: PRT
<213> ORGANISM: Unknown
<220> FEATURE:
<223> OTHER INFORMATION: metagenomes purified from environmentally
      challenged niches

<400> SEQUENCE: 276

Gly Pro Glu Ala Gly Glu Val Arg Asn Arg Gly Arg Ala Leu Arg Asp
1               5                  10                 15

Cys Ser Arg Ser Gln Ala Lys Ile Ala Gln Glu Lys Gly Glu Tyr Glu
            20                 25                 30

Ala Glu Arg Met Lys Val Ile Tyr Ser Gly Lys Ile Leu Gln Asp Asp
        35                 40                 45

Lys Thr Val Glu Ser Tyr Asn Ile Gln Glu Lys Asp Phe Leu Val Cys
    50                 55                 60

Leu Pro Ser Lys Gly Pro Lys Pro Ala Ser Ser Ala Ser Gln
65                  70                 75                 80

Ala Pro Ala Thr Pro Ala Pro Arg Ala Pro Val Ala Thr Pro Ala Ala
                85                 90                 95

Pro Ala Pro Ala Ala Pro Ala Pro Ala Ser Ser Thr Pro Ala Val Pro
            100                105                110

Ala Thr Pro Ser Pro Ala Gly Ala Gln Thr Gly Pro Ser Phe Gly Asp
        115                120                125

Pro Ser Ala Leu Thr Met Gly Ser Ala Ala Glu Gly Ala Val Thr Gln
    130                135                140

Met Glu Ala Met Gly Phe Ala Arg Ser Asp Ile Asp Arg Ala Met Arg
145                 150                155                160

Ala Ala Phe Phe Asn Pro Asp Arg Ala Val Asp Tyr Leu Leu Asn Gly
                165                170                175
```

```
Ile Pro Ala Asp Val Gln Gln Glu Gln Gln Arg Gln Gln Glu Gln
            180                 185                 190

Gln Ala Asp Arg Ala Ala Glu Gln Ala Pro Val Pro Ser Ala Glu Asp
        195                 200                 205

Ala Ala Ala Ala Ala Leu Gly Gly Asp Glu Gly Phe Asn Met Phe
210                 215                 220

Glu Ala Ala Gln Ala Gly Asp Arg Gly Gly Ala Arg Ser
225                 230                 235                 240

Gly Gly Ser Glu Ala Leu Ala Asn Leu Asp Phe Leu Arg Ser Asn Pro
                245                 250                 255

His Phe Gln Gln Leu Arg Gln Leu Val Gln Gln Pro His Met Leu
            260                 265                 270

Glu Pro Ile Leu Gln Gln Val Ala Ala Gly Asn Pro Gln Ile Ser Gln
        275                 280                 285

Ile Ile Gly Gln Asn Ser Glu Gln Phe Leu Gln Leu Ser Glu Glu
290                 295                 300

Gly Asp Glu Glu Asp Ala Ala Leu Pro Pro Gly Thr Gln Ala Ile Ser
305                 310                 315                 320

Val Thr Glu Glu Glu Arg Asp Ala Ile Glu Arg Leu Cys Arg Leu Gly
                325                 330                 335

Phe Pro Arg Asp Ser Val Ile Gln Ala Tyr Phe Ala Cys Asp Lys Asn
            340                 345                 350

Glu Glu Leu Ala Ala Asn Phe Leu Phe Asp Gln Pro Asp Asp Asp Glu
        355                 360                 365

Glu

<210> SEQ ID NO 277
<211> LENGTH: 375
<212> TYPE: PRT
<213> ORGANISM: Unknown
<220> FEATURE:
<223> OTHER INFORMATION: metagenomes purified from environmentally
      challenged niches

<400> SEQUENCE: 277

Met Lys Leu Thr Phe Lys Asp Leu Lys Gln Glu Lys Phe Val Ile Glu
1               5                   10                  15

Val Glu Pro Ser Glu Thr Val Arg Glu Val Lys Gln Lys Ile Ala Gln
            20                  25                  30

Glu Lys Gly Glu Tyr Glu Ala Glu Arg Met Lys Val Ile Tyr Ser Gly
        35                  40                  45

Lys Ile Leu Gln Asp Asp Lys Thr Val Glu Ser Tyr Asn Ile Gln Glu
50                  55                  60

Lys Asp Phe Leu Val Cys Leu Pro Ser Lys Gly Pro Lys Pro Ala Ala
65                  70                  75                  80

Ser Ser Ser Ala Ser Gln Ala Pro Ala Thr Pro Ala Pro Arg Ala Pro
                85                  90                  95

Val Ala Thr Pro Ala Ala Pro Ala Pro Ala Ala Pro Ala Pro Ala Ser
            100                 105                 110

Ser Thr Pro Ala Val Pro Ala Thr Pro Ser Pro Ala Gly Ala Gln Thr
        115                 120                 125

Gly Pro Ser Phe Gly Asp Pro Ser Ala Leu Thr Met Gly Ser Ala Ala
    130                 135                 140

Glu Gly Ala Val Thr Gln Met Glu Ala Met Gly Phe Ala Arg Ser Asp
145                 150                 155                 160
```

-continued

```
Ile Asp Arg Ala Met Arg Ala Ala Phe Phe Asn Pro Asp Arg Ala Val
                165                 170                 175

Asp Tyr Leu Leu Asn Gly Ile Pro Ala Asp Val Gln Gln Glu Gln Gln
            180                 185                 190

Gln Arg Gln Gln Glu Gln Gln Ala Asp Arg Ala Ala Glu Gln Ala Pro
        195                 200                 205

Val Pro Ser Ala Glu Asp Ala Ala Ala Ala Ala Leu Gly Gly Asp
    210                 215                 220

Glu Gly Phe Asn Met Phe Glu Ala Ala Ala Gln Ala Gly Asp Gly Arg
225                 230                 235                 240

Gly Gly Gly Ala Arg Ser Gly Gly Ser Glu Ala Leu Ala Asn Leu Asp
                245                 250                 255

Phe Leu Arg Ser Asn Pro His Phe Gln Gln Leu Arg Gln Leu Val Gln
                260                 265                 270

Gln Gln Pro His Met Leu Glu Pro Ile Leu Gln Gln Val Ala Ala Gly
            275                 280                 285

Asn Pro Gln Ile Ser Gln Ile Ile Gly Gln Asn Ser Glu Gln Phe Leu
        290                 295                 300

Gln Leu Leu Ser Glu Glu Gly Asp Glu Glu Asp Ala Ala Leu Pro Pro
305                 310                 315                 320

Gly Thr Gln Ala Ile Ser Val Thr Glu Glu Arg Asp Ala Ile Glu
                325                 330                 335

Arg Leu Cys Arg Leu Gly Phe Pro Arg Asp Ser Val Ile Gln Ala Tyr
                340                 345                 350

Phe Ala Cys Asp Lys Asn Glu Glu Leu Ala Ala Asn Phe Leu Phe Asp
            355                 360                 365

Gln Pro Asp Asp Glu Glu
        370                 375
```

<210> SEQ ID NO 278
<211> LENGTH: 342
<212> TYPE: PRT
<213> ORGANISM: Unknown
<220> FEATURE:
<223> OTHER INFORMATION: metagenomes purified from environmentally
      challenged niches

<400> SEQUENCE: 278

```
Ala Pro Gly Asp Met Glu Thr Ala Asp Ala Lys Asn Arg Ala Met Arg
1               5                   10                  15

Ala Ala Gly Phe Ile Val Pro Ser Thr Phe Glu Asp Leu Pro Glu Val
                20                  25                  30

Leu Lys Thr Thr Tyr Thr Gly Leu Val Gln Lys Gly Val Ile Val Pro
            35                  40                  45

Lys Ala Glu Ile Asp Pro Pro Asn Ile Pro Met Asp Tyr Gln Trp Ala
    50                  55                  60

Ser Lys Leu Gly Leu Ile Arg Lys Pro Ala Ala Phe Ile Ser Thr Ile
65                  70                  75                  80

Ser Asp Glu Arg Gly Gln Glu Leu Met Tyr Ala Gly Met Arg Ile Ser
                85                  90                  95

Asp Val Phe Lys Glu Glu Ile Gly Ile Gly Gly Val Ile Ser Leu Leu
                100                 105                 110

Trp Phe Lys Arg Arg Leu Pro Pro Phe Ala Cys Lys Phe Ile Glu Met
            115                 120                 125

Val Leu Gln Leu Thr Ala Asp His Gly Pro Ala Val Ser Gly Ala Met
```

```
                130                 135                 140
Asn Thr Ile Ile Thr Ala Arg Ala Gly Lys Asp Leu Ile Ser Ser Leu
145                 150                 155                 160

Ala Ala Gly Leu Leu Thr Ile Gly Asp Arg Phe Gly Ala Leu Asp
                165                 170                 175

Gly Ala Ala Ala Glu Phe Ser Arg Gly Leu Asn Ser Gly Ala Thr Pro
                180                 185                 190

Arg Glu Phe Val Asp Ser Met Arg Lys Ala Asn Arg Leu Ile Pro Gly
                195                 200                 205

Ile Gly His Lys Ile Lys Ser Lys Thr Asn Pro Asp Leu Arg Val Val
                210                 215                 220

Leu Val Val Asp Tyr Val Lys Lys His Phe Pro Ser His Lys Thr Leu
225                 230                 235                 240

Asp Phe Ala Leu Ala Val Glu Asp Val Thr Thr Gln Lys Ser Asn Thr
                245                 250                 255

Leu Ile Leu Asn Val Asp Gly Ala Ile Ala Ala Ser Phe Cys Asp Leu
                260                 265                 270

Leu Ser Gly Cys Gly Ala Phe Thr Glu Asp Glu Ala Ala Asp Tyr Leu
                275                 280                 285

Lys Asn Gly Thr Leu Asn Gly Leu Phe Val Leu Gly Arg Ser Ile Gly
                290                 295                 300

Phe Ile Gly His Tyr Leu Asp Gln Arg Leu Leu Lys Gln Pro Leu Tyr
305                 310                 315                 320

Arg His Pro Ala Asp Asp Ile Phe Ile Asn Met Gln Glu Arg Val Val
                325                 330                 335

Phe Gln Pro Gly Ser Asn
                340

<210> SEQ ID NO 279
<211> LENGTH: 182
<212> TYPE: PRT
<213> ORGANISM: Unknown
<220> FEATURE:
<223> OTHER INFORMATION: metagenomes purified from environmentally
      challenged niches

<400> SEQUENCE: 279

Gly Ala Tyr Lys Glu Gly Lys Phe Thr Ser Glu Ser Ile Gln Lys Ser
1               5                   10                  15

Lys Leu Arg Phe Gln Asp Ile Leu Val Glu Leu Pro Leu Arg Val His
                20                  25                  30

Asn Ser His Leu Leu Thr Ser Phe Leu His Gln Val Pro Gln Ala Pro
                35                  40                  45

Pro Ala Lys Asn Pro Leu Asp Phe Pro Ser Ser Leu Ala Glu Leu Ser
                50                  55                  60

Arg Asp Ser Asp Val Ser Ser Asn Pro Phe Ala Pro Asn Leu Asp Thr
65                  70                  75                  80

Leu Asp Leu Ser Ile Asp Pro Phe Gln Tyr Trp Gln Arg Ala Leu Gly
                85                  90                  95

Arg Glu Gln Gln Lys Ile Thr Ala Trp Gln Lys Arg Lys Ala Glu
                100                 105                 110

Asn Ala Ala Arg Ala Ala Ser Lys Gln Pro Pro Leu Asp Glu Asn Glu
                115                 120                 125

Trp Gln Lys Leu Phe Lys Leu Pro Thr Glu Pro Ser Arg Leu Glu Ala
                130                 135                 140
```

```
Leu Leu Val Gly Arg Gln Val Glu Gln Tyr Ala Arg Gln Val Asp Gly
145                 150                 155                 160

Phe Ser Ala Thr Val Ser Ala Lys Met Phe Gly Val Arg Gly Asn Leu
                165                 170                 175

Leu Pro Asn Glu Ile Glu
            180
```

<210> SEQ ID NO 280
<211> LENGTH: 171
<212> TYPE: PRT
<213> ORGANISM: Unknown
<220> FEATURE:
<223> OTHER INFORMATION: metagenomes purified from environmentally
      challenged niches

<400> SEQUENCE: 280

```
Met Ser Ala Pro Thr Pro Ser His Pro Thr Leu Thr Pro Trp Thr Ser
1               5                   10                  15

Ala Ser Thr Pro Ser Ser Thr Gly Ser Ala Pro Ser Ala Ala Ser Ser
                20                  25                  30

Arg Arg Ser Pro His Gly Asn Arg Ser Ala Arg Leu Arg Met Leu His
            35                  40                  45

Ala Pro Arg Ala Ser Ser Arg Pro Leu Thr Arg Met Ser Gly Arg Ser
        50                  55                  60

Cys Ser Ser Cys Pro Arg Ser Pro Ala Gly Ser Arg Leu Cys Leu Ser
65                  70                  75                  80

Ala Gly Arg Ser Ser Thr Pro Ala Arg Ser Thr Asp Ser Pro Pro
                85                  90                  95

Pro Phe Pro Pro Arg Cys Leu Ala Ser Gly Ala Thr Ser Ser Leu Thr
            100                 105                 110

Arg Ser Ser Arg Gly Arg Ile Leu Arg Arg Arg Asp Arg Leu Cys
        115                 120                 125

Ile Ala Arg Arg Ser Arg Leu Gly Gly Val Glu Tyr Met Arg His Gly
130                 135                 140

Tyr Lys Lys Lys Asp Asp Val Val Pro Pro Ser Thr Ser Ser Gly Gln
145                 150                 155                 160

Arg Cys Ile Glu Ser Gln Lys Lys Lys Gly Phe
                165                 170
```

<210> SEQ ID NO 281
<211> LENGTH: 217
<212> TYPE: PRT
<213> ORGANISM: Unknown
<220> FEATURE:
<223> OTHER INFORMATION: metagenomes purified from environmentally
      challenged niches

<400> SEQUENCE: 281

```
Met Arg Arg Ser Ser Lys Phe Lys Asn Val Lys Ile Leu Ser Ser Phe
1               5                   10                  15

Gly Ile Leu Cys Ser Val Ala Leu Asn Ser Ser Met Ala Glu Pro His
                20                  25                  30

His Pro Phe Phe Cys Ser His Ala Ala Cys Thr Leu Pro His Pro Ala
            35                  40                  45

Glu Asn Ala Ser Leu Cys Ile Asn Ala Gly Pro Val Ser Val Ile Phe
        50                  55                  60

Val Leu Tyr Ser Ile Ser Leu Gly Arg Arg Leu Pro Leu Thr Pro Asn
65                  70                  75                  80
```

```
Ile Leu Ala Glu Thr Val Ala Glu Asn Pro Ser Thr Trp Arg Ala Tyr
             85                  90                  95

Cys Ser Thr Cys Leu Pro Thr Ser Arg Ala Ser Ser Leu Leu Gly Ser
            100                 105                 110

Val Gly Ser Leu Asn Ser Phe Cys His Ser Phe Ser Arg Gly Gly
            115                 120                 125

Cys Leu Leu Ala Ala Arg Ala Ala Phe Ser Ala Leu Arg Phe Cys Cys
130                 135                 140

His Ala Val Ile Phe Cys Cys Ser Arg Pro Arg Ala Arg Cys Gln Tyr
145                 150                 155                 160

Trp Lys Gly Ser Met Leu Arg Ser Arg Val Ser Arg Leu Gly Ala Lys
                165                 170                 175

Gly Leu Glu Leu Thr Ser Glu Ser Arg Glu Ser Ser Ala Arg Asp Glu
            180                 185                 190

Gly Lys Ser Arg Gly Phe Phe Ala Gly Gly Ala Cys Gly Thr Trp Cys
        195                 200                 205

Arg Lys Leu Val Arg Arg Trp Glu Leu
210                 215

<210> SEQ ID NO 282
<211> LENGTH: 150
<212> TYPE: PRT
<213> ORGANISM: Unknown
<220> FEATURE:
<223> OTHER INFORMATION: metagenomes purified from environmentally
      challenged niches

<400> SEQUENCE: 282

Met Tyr Ser Thr Pro Pro Ser Arg Glu Arg Leu Ala Met His Lys Arg
1               5                   10                  15

Arg Ser Arg Leu Arg Asn Ile Arg Pro Leu Leu Asp Leu Val Arg Glu
            20                  25                  30

Glu Val Ala Pro Asp Ala Lys His Leu Gly Gly Asn Gly Gly Gly Glu
        35                  40                  45

Ser Val Asp Leu Ala Gly Val Leu Leu Asp Leu Pro Ala Asp Lys Gln
50                  55                  60

Ser Leu Glu Pro Ala Gly Leu Arg Gly Gln Leu Glu Gln Leu Leu Pro
65                  70                  75                  80

Leu Ile Leu Val Lys Gly Arg Leu Leu Ala Arg Gly Ala Cys Ser Ile
                85                  90                  95

Leu Ser Leu Ala Leu Leu Leu Pro Cys Gly Asp Leu Leu Leu Leu Ala
            100                 105                 110

Ala Glu Gly Ala Leu Pro Val Leu Glu Gly Val Asp Ala Glu Val Gln
        115                 120                 125

Gly Val Lys Val Gly Cys Glu Val Gly Ala Asp Ile Gly Val Ala
    130                 135                 140

Arg Lys Leu Cys Lys Gly
145                 150

<210> SEQ ID NO 283
<211> LENGTH: 269
<212> TYPE: PRT
<213> ORGANISM: Unknown
<220> FEATURE:
<223> OTHER INFORMATION: metagenomes purified from environmentally
      challenged niches

<400> SEQUENCE: 283
```

```
Met Ser Asn Ser Phe Ile Arg His Leu Pro Ser Thr Leu Arg Ala Phe
1               5                   10                  15

Arg Ser Ser Thr Ala Phe Ser Leu Thr Arg Ser Phe Ser Ser Thr Met
            20                  25                  30

Ala Ser Asn Gly Thr Ser Thr Asn Gly Val Gln His Asp Ala Arg Lys
            35                  40                  45

Val Phe Phe Phe Asp Ile Asp Asn Cys Leu Tyr Pro Lys Ser Tyr Gln
        50                  55                  60

Ile His Asp Lys Met Ala Val Leu Ile Asp Asn Tyr Phe Gln Asn His
65                  70                  75                  80

Leu Ser Leu Ser Gln Glu Asp Ala Thr Thr Leu His Gln Arg Tyr Tyr
                85                  90                  95

Lys Asp Tyr Gly Leu Ala Ile Glu Gly Leu Val Arg His His Lys Val
            100                 105                 110

Asp Pro Leu Glu Tyr Asn Glu Lys Val Asp Asp Ala Leu Pro Leu Asp
            115                 120                 125

Asp Ile Ile Lys Pro Asp Pro Lys Leu Arg Lys Leu Leu Gln Asp Ile
    130                 135                 140

Asp Thr Asp Lys Val Lys Leu Trp Leu Phe Thr Asn Ala Tyr Val Asn
145                 150                 155                 160

His Ala Lys Arg Val Thr Arg Leu Leu Gly Val Asp Asp Leu Phe Glu
                165                 170                 175

Gly Met Thr Phe Cys Asp Tyr Ala Ala Glu Arg Leu Leu Cys Lys Pro
            180                 185                 190

Thr Thr Glu Met Tyr Asn Lys Ala Met Gln Glu Ala Asn Ala Thr Asp
            195                 200                 205

Ile Asp Gln Cys Tyr Phe Val Asp Asp Ser Ala Leu Asn Ala Ala Ala
    210                 215                 220

Ala Met Lys Tyr Gly Trp Lys Thr Ala His Leu Val Glu Pro Thr Ala
225                 230                 235                 240

Lys Pro Pro Pro Gln Pro Val Ser Gln His Gln Ile Ser Asn Leu Glu
                245                 250                 255

Glu Leu Arg Lys Val Phe Pro Glu Val Phe Lys Thr Ser
            260                 265

<210> SEQ ID NO 284
<211> LENGTH: 256
<212> TYPE: PRT
<213> ORGANISM: Unknown
<220> FEATURE:
<223> OTHER INFORMATION: metagenomes purified from environmentally
      challenged niches

<400> SEQUENCE: 284

Met Ala Arg Ile Phe Ile Thr Gly Ser Thr Asp Gly Leu Gly Leu Leu
1               5                   10                  15

Ser Ala Lys Leu Leu Ser Glu Gln Gly His Ser Val Phe Leu His Ala
            20                  25                  30

Arg Asn Ala Glu Arg Ala Ser Gln Ala Lys Ala Ala Val Pro Lys Ala
            35                  40                  45

Gln Gly Val Ile Ile Gly Asp Leu Ser Asn Val Ser Asp Val Lys Gln
        50                  55                  60

Leu Ala Ala Asp Ala Asn Lys Ala Gly Pro Phe Asp Ala Val Val His
65                  70                  75                  80

Asn Ala Gly Leu Gly Leu Thr Thr Asn Gly Gln Lys Thr Ala Glu Gly
                85                  90                  95
```

Val Ala Gln Ile Phe Ala Val Asn Ser Met Ala Pro Tyr Ile Leu Thr
            100                 105                 110

Ala Leu Met Asp Lys Pro Lys Arg Leu Leu Tyr Val Ser Ser Gly Leu
            115                 120                 125

His Phe Gly Gly Asp Pro Ser Leu Glu Asp Val Thr Trp Ala Thr Arg
            130                 135                 140

Glu Phe Arg Pro Ser Asp Ala Tyr Asn Asp Thr Lys Met Gln Asn Val
145                 150                 155                 160

Met Leu Ser Lys Ala Val Ala Lys Arg Trp Pro Asp Val Gln Ser Gly
            165                 170                 175

Ser Leu Asp Pro Gly Trp Val Lys Thr Lys Leu Gly Gly Ser Ala Ala
            180                 185                 190

Pro Gly Thr Thr Asp Ala Pro Ala Glu Met Ile Ala Glu Tyr Ala Ala
            195                 200                 205

Gly Lys Ser Cys Ala Gly Asp Gln Thr Gly Ala Tyr Leu Thr Pro Arg
            210                 215                 220

Gly Val Glu Glu Pro His Asp Ala Thr Lys Leu Ala Glu Lys Gln Asp
225                 230                 235                 240

Arg Leu Met Gln Ile Tyr Lys Glu Val Ser Gly Val Ser Phe Pro Gln
            245                 250                 255

<210> SEQ ID NO 285
<211> LENGTH: 201
<212> TYPE: PRT
<213> ORGANISM: Unknown
<220> FEATURE:
<223> OTHER INFORMATION: metagenomes purified from environmentally
      challenged niches

<400> SEQUENCE: 285

Met Lys Leu Cys Leu Leu Gly Glu Arg Asn Thr Arg Tyr Leu Leu Val
1               5                   10                  15

Asn Leu His Gln Thr Ile Leu Leu Gly Gln Leu Ser Arg Ile Met
            20                  25                  30

Arg Leu Phe His Ala Thr Arg Ser Gln Val Gly Thr Cys Leu Ile Ala
            35                  40                  45

Cys Ala Arg Phe Ala Gly Ser Val Leu Ser Asn His Leu Cys Trp Ser
            50                  55                  60

Val Gly Gly Ala Arg Arg Gly Arg Pro Ala Glu Leu Ser Leu His Pro
65                  70                  75                  80

Ala Trp Val Lys Arg Ala Ala Leu His Ile Arg Pro Ala Phe Gly Asp
            85                  90                  95

Cys Phe Arg Glu His Asp Val Leu His Leu Cys Ile Val Val Cys Ile
            100                 105                 110

Arg Trp Ser Glu Leu Pro Cys Gly Pro Ser Asp Val Leu Glu Ala Gly
            115                 120                 125

Val Ala Thr Glu Val Gln Ser Gly Ala Asp Val Gln Glu Pro Leu Arg
            130                 135                 140

Leu Val His Glu Ser Gly Gln Asn Val Arg Cys His Ala Val Asn Gly
145                 150                 155                 160

Lys Asn Leu Gly Tyr Ala Leu Ser Ser Leu Ala Ile Gly Gly Glu
            165                 170                 175

Ser Glu Ala Ser Ile Val Asn Asn Gly Val Lys Arg Ser Ser Leu Val
            180                 185                 190

Gly Ile Gly Gly Glu Leu Leu His Val

```
                195                 200

<210> SEQ ID NO 286
<211> LENGTH: 192
<212> TYPE: PRT
<213> ORGANISM: Unknown
<220> FEATURE:
<223> OTHER INFORMATION: metagenomes purified from environmentally
      challenged niches

<400> SEQUENCE: 286

Met Ala Ile Gly Gln Ser Ser Gln Gln Ala Asp Gly Gln Asn Val
1               5                   10                  15

Val Thr Gln Gly Asn Ser Asp Lys Ala Ala Asn Pro Met Arg Glu Leu
                20                  25                  30

Arg Ile Gln Lys Leu Val Leu Asn Ile Ser Val Gly Glu Ser Gly Asp
            35                  40                  45

Arg Leu Thr Arg Ala Ala Lys Val Leu Glu Gln Leu Ser Gly Gln Thr
        50                  55                  60

Pro Val Tyr Ser Lys Ala Arg Tyr Thr Val Arg Thr Phe Gly Ile Arg
65                  70                  75                  80

Arg Asn Glu Lys Ile Ser Val His Val Thr Val Arg Gly Ala Lys Ala
                85                  90                  95

Glu Glu Ile Leu Glu Arg Gly Leu Lys Val Lys Glu Tyr Glu Leu Arg
            100                 105                 110

Lys Arg Asn Phe Ser Ala Thr Gly Asn Phe Gly Phe Gly Ile Ser Glu
        115                 120                 125

His Ile Asp Leu Gly Ile Lys Tyr Asp Pro Ala Ile Gly Ile Tyr Gly
    130                 135                 140

Met Asp Phe Tyr Val Val Met Ser Arg Pro Gly Glu Arg Val Ala Arg
145                 150                 155                 160

Arg Arg Arg Ala Lys Thr Arg Val Gly Ala Ser His Lys Val Asn Ala
                165                 170                 175

Pro Glu Val Ile Lys Trp Tyr Lys Asn Arg Phe Glu Gly Ile Val Arg
            180                 185                 190

<210> SEQ ID NO 287
<211> LENGTH: 213
<212> TYPE: PRT
<213> ORGANISM: Unknown
<220> FEATURE:
<223> OTHER INFORMATION: metagenomes purified from environmentally
      challenged niches

<400> SEQUENCE: 287

Gly His Thr Gly Asp Val Leu Ser Val Ser Phe Ser Ala Asp Asn Arg
1               5                   10                  15

Gln Ile Val Ser Ala Ser Arg Asp Arg Thr Ile Lys Leu Trp Asn Thr
                20                  25                  30

Leu Gly Glu Cys Lys Phe Asn Ile Val Asp Gly His Ser Glu Trp
            35                  40                  45

Val Ser Cys Val Arg Phe Ser Pro Asn Pro Ile Pro Val Ile Val
        50                  55                  60

Ser Ala Gly Trp Asp Lys Val Val Lys Val Trp Glu Leu Ser Lys Cys
65                  70                  75                  80

Lys Leu Lys Thr Asn His His Gly His Thr Gly Tyr Ile Asn Thr Leu
                85                  90                  95

Ala Val Ser Pro Asp Gly Ser Leu Ala Ala Ser Gly Gly Lys Asp Gly
```

```
            100                 105                 110
Ile Thr Met Leu Trp Asp Leu Asn Asp Gly Lys His Leu Tyr Ser Leu
        115                 120                 125

Glu Ala Gly Asp Ile Val Asn Ser Leu Val Phe Ser Pro Asn Arg Tyr
        130                 135                 140

Trp Leu Cys Ala Ala Thr Ala Ser Ser Ile Lys Ile Phe Asp Leu Glu
145                 150                 155                 160

Ser Lys Ser Ile Val Asp Asp Leu Lys Pro Asp Phe Ser Ala Glu Tyr
                165                 170                 175

Ser Asp Lys Ala Gln Lys Pro Gln Cys Thr Ser Leu Ala Trp Ser Ala
            180                 185                 190

Asp Gly Gln Thr Leu Phe Ala Gly Phe Ser Asp Asn Leu Val Arg Val
        195                 200                 205

Trp Val Val Thr Ala
        210

<210> SEQ ID NO 288
<211> LENGTH: 347
<212> TYPE: PRT
<213> ORGANISM: Unknown
<220> FEATURE:
<223> OTHER INFORMATION: metagenomes purified from environmentally
      challenged niches

<400> SEQUENCE: 288

Met Ala Pro Ser Thr Gln Lys Gln Trp Thr Val Lys Asn Gly Glu Gln
1               5                   10                  15

Asp Phe Asp Gly Leu Val Tyr Gly Asp Ala Pro Val Pro Thr Ala Gly
            20                  25                  30

Asp Ser Glu Val Val Val Lys Leu His Gly Ala Ser Leu Asn Tyr Arg
        35                  40                  45

Asp Leu Ile Ile Pro Lys Gly Lys Tyr Pro Phe Pro Leu Ser Phe Pro
    50                  55                  60

Val Val Pro Gly Ser Asp Gly Ala Gly Glu Val Val Glu Val Gly Ser
65                  70                  75                  80

Lys Val Lys Gln Phe Lys Lys Gly Asp Lys Val Val Thr Leu Phe Asn
                85                  90                  95

Gln Leu His Gln Tyr Gly Pro Val Asp Ala Ala Ala Ser Ser Gly
            100                 105                 110

Leu Gly Gly Ala Val Asp Gly Thr Leu Arg Gln Tyr Gly Val Phe Asn
        115                 120                 125

Glu Asn Gly Val Val Arg Ala Pro Thr Asn Leu Asn Phe Leu Glu Ser
    130                 135                 140

Ser Thr Leu Thr Cys Ala Gly Leu Thr Ser Trp Asn Ala Leu Tyr Gly
145                 150                 155                 160

Leu Lys Pro Leu Leu Pro Gly Gln Thr Val Leu Val Gln Gly Thr Gly
                165                 170                 175

Gly Val Ser Ile Phe Ala Leu Gln Phe Ala Lys Ala Ala Gly Ala Thr
            180                 185                 190

Val Ile Ala Thr Thr Ser Ser Glu Glu Lys Gly Lys Arg Leu Lys Asp
        195                 200                 205

Leu Gly Ala Asp His Val Ile Asn Tyr Lys Thr Gln Thr Asn Trp Gly
    210                 215                 220

Glu Ile Ala Arg Gly Leu Thr Arg Asp Asn Ile Gly Val Asp His Ile
225                 230                 235                 240
```

```
Ile Glu Val Gly Gly Ala Gly Thr Leu Glu Gln Ser Phe Lys Cys Ile
            245                 250                 255

Lys Phe Glu Gly Val Ile Ser Ile Ile Gly Phe Leu Gly Gly Met Asn
        260                 265                 270

Pro Ser Thr Ile Pro Asn Val Leu Gln Thr Leu Ser Asn Ile Cys Thr
            275                 280                 285

Val Arg Gly Val Tyr Val Gly Ser Lys Ala Leu Met Asn Asp Met Ile
        290                 295                 300

Asn Ala Ile Glu Ala Asn Ile His Pro Val Asp Gly Thr Val
305                 310                 315                 320

Phe Thr Leu Glu Lys Thr Arg Glu Ala Tyr Glu Tyr Met Trp Ala Gln
                325                 330                 335

Lys His Phe Gly Lys Leu Thr Ile Gln Ile Ala
            340                 345
```

<210> SEQ ID NO 289
<211> LENGTH: 518
<212> TYPE: PRT
<213> ORGANISM: Unknown
<220> FEATURE:
<223> OTHER INFORMATION: metagenomes purified from environmentally
      challenged niches

<400> SEQUENCE: 289

```
Met Leu Glu Gln Gln Tyr Gln Met Arg Lys Glu Gln Gln Val Gln Phe
1               5                   10                  15

Thr Pro Met Ala Ser Pro Ser Ser Thr Pro Tyr His Met His Gln Asp
            20                  25                  30

Phe Thr Val Pro Gly Asp Phe Phe Ser Pro Leu Thr Ser Pro Ala Leu
        35                  40                  45

His Ala Gln Asn Gln Pro Gln Ser Arg Gln Gln Phe Thr Ala His Gln
    50                  55                  60

Gln Gly Tyr Tyr Thr Asn Pro Ser Thr Ala Ala Ser Ser Ala Ala Pro
65                  70                  75                  80

Ser Pro Ile Asp Ala Asn Gly Asp Val Glu Met Gly Gly Asp Gly Val
                85                  90                  95

Ala Leu Pro Glu Ser Ala Ser Gln Pro Lys Lys Pro Ser Arg Arg Lys
            100                 105                 110

Pro Ala Thr Pro Arg Thr Phe Ala Met Asn Lys Val Lys Gln Ser Pro
        115                 120                 125

Ile Gln Lys Pro Gln Lys Arg Lys Ser Val Ala Leu Ala His Lys Asp
    130                 135                 140

Ala Asp Ala Val Val Gln Asp Ala Gln Arg Ser Gly His Ile Ala Pro
145                 150                 155                 160

Lys Ser Ala Gly Leu Gln Met Pro Pro Phe Glu Ser Ser Glu Asn
                165                 170                 175

Asp Ser Val Ser Pro Glu Ala Leu Asn Asp Leu Pro Met Gly Pro Pro
            180                 185                 190

Pro Arg Pro Gly Ser Val Ser Gln Ser Pro Ala Ile Ala Pro Gln Asn
        195                 200                 205

Gln Ser Val Ser Gly Pro Ala Thr Pro Lys Ser Leu Leu Ser Met
    210                 215                 220

Lys Gly Ala Gln Asp Met Asn Ala Pro Ala Ser Thr Gly Ile Ser Gly
225                 230                 235                 240

Gln Met Gly Gln Ala Ser Leu Glu Asp Leu Glu Leu Pro Glu Ala Ala
                245                 250                 255
```

```
Glu Asn Pro Gly Ser Thr Ala Thr His Ser Gln Val Leu Asn Ser Gln
            260                 265                 270

Glu Pro Thr Pro Arg Leu Met Pro Ser Arg Lys Thr Pro Lys Leu Gly
            275                 280                 285

Pro Leu Ser Thr Pro Ser Ser Gly Lys Pro Thr Ser Ala Ser Asn Ser
290                 295                 300

Pro Ala His Ala Leu Ser Pro Met Thr Ala Ser Thr Pro Ala Gly Leu
305                 310                 315                 320

Leu Lys Asp Lys Lys Asp Asn Lys Gly Gly Arg Ala Thr Ser Lys Lys
                325                 330                 335

Arg Gly Ser Val Ser Thr Thr Asn Ser Ala Met Val Ser Pro Ala Leu
            340                 345                 350

Arg Pro Lys Val Ser Pro Ser Ile Lys Pro Leu Leu Pro Glu Gly Thr
            355                 360                 365

Ser Leu Asn Ser Pro Thr His Ala Leu Leu Leu Ala Ser Lys Ser Asn
370                 375                 380

Tyr Gln Asn Leu Leu Glu Gly Asn His Leu Pro Gly Ile Ser Tyr Pro
385                 390                 395                 400

Asp Ser Leu Ser Thr Gly Leu Thr Ser Lys Arg Thr Ser His Lys Val
                405                 410                 415

Ala Glu Gln Gly Arg Arg Asn Arg Ile Asn Asp Ala Leu Lys Glu Met
            420                 425                 430

Gln Ala Leu Ile Pro Ala Ser Ser Gly Ala Arg Ala Glu Glu Leu Met
            435                 440                 445

Thr Ala Asp Ala Gly Asp Asp Ser Gln Glu Thr Lys Glu Lys Asp
            450                 455                 460

Arg Asp Ala Ala Val Lys Ser Asn Ser Ser Lys Ala Ala Thr Val Glu
465                 470                 475                 480

Ser Ala Asn Arg Tyr Ile Arg Val Leu Lys Glu Ser Asp Ala Ala Gln
                485                 490                 495

Lys Asp Ala Ile Ala Arg Pro Asn Ser Pro Gly Ser Arg Ser Leu Asp
            500                 505                 510

Pro Pro Asp Leu Asp Asn
            515

<210> SEQ ID NO 290
<211> LENGTH: 126
<212> TYPE: PRT
<213> ORGANISM: Unknown
<220> FEATURE:
<223> OTHER INFORMATION: metagenomes purified from environmentally
      challenged niches

<400> SEQUENCE: 290

Met Arg Asn Ile Leu Leu Val Leu Ala Ser Ala Ala Leu Ala Val Val
1               5                   10                  15

Ala Gln Lys Pro Asp Leu Asp Val Lys Gly Thr Phe Gly Asp Ala Asn
            20                  25                  30

Pro Phe Ser Lys Val Val Asn Gly Gln Ser Asn Lys Leu Tyr Leu Thr
        35                  40                  45

Leu Asp Asn His Ser Pro Glu Ser Leu Val Val Lys Ser Ile Ser Gly
    50                  55                  60

Ser Trp Ser Glu Lys Thr Ser Ala Ser Ser Gly Gln Glu Lys Phe Leu
65                  70                  75                  80

Lys Asn Ser Thr Thr Gln Glu Lys Leu Thr Val Pro Ile Pro Pro Lys
```

```
                85                  90                  95
Ser Glu Gly Ala Phe Gln Pro Pro Thr Val Leu Thr Tyr Gln Phe Trp
            100                 105                 110
Ser Glu Phe Lys Pro Arg Glu Leu Leu Leu Thr Val Leu Gly
            115                 120                 125

<210> SEQ ID NO 291
<211> LENGTH: 91
<212> TYPE: PRT
<213> ORGANISM: Unknown
<220> FEATURE:
<223> OTHER INFORMATION: metagenomes purified from environmentally
      challenged niches

<400> SEQUENCE: 291

Met Val Leu Ala Leu Val Gly Gly Ala Gly Tyr Leu Ala Tyr Asn Ile
1               5                   10                  15
Tyr Phe Pro Pro Ala Arg Lys Pro Arg Arg Ser Ala Asn Thr Ala Pro
                20                  25                  30
Thr Asp Ala Pro Ala Ala Pro Ala Asp Pro Asp Glu Trp Ile Pro Val
            35                  40                  45
His His Lys Arg Ala Lys Lys Thr Ser Gly Gly Gly Ala Thr Ser Gly
        50                  55                  60
Glu Glu Ser Glu Ala Thr Glu Gly Tyr Ala Ser Glu Lys Ser Ala Ser
65                  70                  75                  80
Gly Ala Lys Lys Arg Gly Lys Gly Gly Arg Lys
                85                  90

<210> SEQ ID NO 292
<211> LENGTH: 252
<212> TYPE: PRT
<213> ORGANISM: Unknown
<220> FEATURE:
<223> OTHER INFORMATION: metagenomes purified from environmentally
      challenged niches

<400> SEQUENCE: 292

Met Ser Asp Asn Asn Asp Gly Asn His Gly Gly Gly Val Gly Ala Ser
1               5                   10                  15
Tyr Tyr Tyr Gly Gly Ile Ala Ile Ala Leu Cys Leu Val Ile Val Leu
                20                  25                  30
Thr Leu Val Ser Arg Ile Leu Tyr Arg Arg Val Arg Asn Arg Leu
            35                  40                  45
Leu Arg Ala Asn Arg Gln Glu Arg Ile Thr Leu Arg Asp Arg Gly Glu
    50                  55                  60
Ala Pro Gly Leu Pro Thr Tyr Arg Glu Ser Arg Asn Gln Pro Ser Leu
65                  70                  75                  80
Pro Arg Tyr Thr Ala Glu Ala Asp Tyr Ala Pro Pro Gly Pro Pro
                85                  90                  95
Pro Ser Asn Ser Pro Asp Asn Glu Gly His His Phe His Phe His Phe
            100                 105                 110
Pro Ser Leu His Val Pro Gln Ala Leu His Leu Arg Pro Arg Gln Ala
        115                 120                 125
Asp Asp Pro Ala Asp Gln Ile Pro Thr Val Pro Pro Ser Tyr Glu
    130                 135                 140
Pro Pro Lys Tyr Glu Pro Pro Ser Gly Ala Pro Pro Glu Gln Gln Gln
145                 150                 155                 160
Glu Pro Val Ala Ser Gly Ser Ser Glu His His His Gln Gln Ser Ala
```

```
                    165                 170                 175

Leu Gly Glu His Thr Ala Ala Thr Ala Ala Thr Thr Pro Ala
                180                 185                 190

Glu His Ser Gly Glu Ser Thr Glu Leu Arg Ser Ala Ser Pro Ser Gln
            195                 200                 205

Pro Gln Ser Gln Ser Gln Pro Gln Ala Pro Ala Gln Pro Gln Glu Gln
        210                 215                 220

Asp Tyr Gly Tyr Asp Asp Ala Asp Phe Ile His Pro Glu Glu Arg Arg
225                 230                 235                 240

Arg Ile Glu Ala Ala Gln Arg Asn Asp Pro Gln Thr
                245                 250

<210> SEQ ID NO 293
<211> LENGTH: 161
<212> TYPE: PRT
<213> ORGANISM: Unknown
<220> FEATURE:
<223> OTHER INFORMATION: metagenomes purified from environmentally
      challenged niches

<400> SEQUENCE: 293

Met Ser Arg Ile Gly Asp Pro Thr Asn Asn Pro Ala Thr Gln Gln Leu
1               5                   10                  15

Tyr Ser Asp Arg Pro Leu His Leu Pro Gly Pro Gly Leu Lys Pro Ser
            20                  25                  30

Arg Gln Leu Thr Ile Ser Ser Ala Val Ala Phe Arg Glu Asp Ser Gly
        35                  40                  45

Gln Thr Arg Phe Asn Leu Ile Ser Ser Asp His Arg Glu Val Leu His
    50                  55                  60

Ile Ser Ile Arg Ala Arg Asp Asn Val Leu Val Leu Asn Thr Lys Ala
65                  70                  75                  80

Pro Asp Gly Asp Trp Gly Lys Glu Glu Arg His Asp Leu Lys Pro Leu
                85                  90                  95

Phe Asp Thr Pro Leu Leu Pro Tyr Ile Thr Val Met Ala Thr Lys Asn
            100                 105                 110

Ser Tyr Ile Leu Ser Val Pro Gly Lys Arg Glu Ile Ile Phe Asn Lys
        115                 120                 125

Arg Lys Gly Phe Met Glu Pro Ala Val Arg Ile Glu Tyr Asp Tyr Asp
    130                 135                 140

Glu Met Ser Ala Phe Ser Asp Pro Cys Tyr Ile Thr Val Pro Ser Ser
145                 150                 155                 160

Ser

<210> SEQ ID NO 294
<211> LENGTH: 84
<212> TYPE: PRT
<213> ORGANISM: Unknown
<220> FEATURE:
<223> OTHER INFORMATION: metagenomes purified from environmentally
      challenged niches

<400> SEQUENCE: 294

Met Pro Gln Glu Ile Lys Asp Ile Lys Asn Leu Leu Glu Ile Ala Arg
1               5                   10                  15

Arg Lys Asp Ala Arg Ser Ala Arg Ile Lys Lys Thr Lys Thr Val Gly
            20                  25                  30

Ala Lys Gly Glu Pro Ala Gln Leu Thr Lys Phe Lys Ile Arg Cys Ser
        35                  40                  45
```

```
Arg Tyr Leu Tyr Thr Leu Val Val Ser Asp Gly Glu Lys Ala Glu Lys
         50                  55                  60

Leu Lys Gln Ser Leu Pro Pro Thr Leu Asn Val Glu Glu Ile Gly Lys
 65                  70                  75                  80

Val Ser Lys Lys

<210> SEQ ID NO 295
<211> LENGTH: 173
<212> TYPE: PRT
<213> ORGANISM: Unknown
<220> FEATURE:
<223> OTHER INFORMATION: metagenomes purified from environmentally
      challenged niches

<400> SEQUENCE: 295

Met Ser His Thr Phe Tyr Asp Gly Thr Ile Val Val Leu Gln Gly Ile
 1               5                  10                  15

Leu Glu Thr Phe Ser His Ile Leu His Lys Ala Glu Glu Ser Pro Asn
                20                  25                  30

Ser Ser Ala Phe Pro Ala Ala Arg Leu His Glu Asp Met Tyr Pro Leu
            35                  40                  45

Thr Asp Gln Ile Arg Leu Ala Thr Gln Phe Ser Glu Tyr Ile Leu Ala
 50                  55                  60

Lys Val Thr Gly Arg Glu Pro Arg Lys Phe Gly Asn Pro Leu Thr
 65                  70                  75                  80

Phe Ala Glu Phe Tyr Glu Arg Ile Asp Thr Met Leu Lys Ser Leu Lys
                85                  90                  95

Glu Ala Asp Lys Asp Val Val Asn Ala Asn Ala Asp Lys Glu Glu Leu
            100                 105                 110

Thr Gln Val Gly Pro Thr Ala Lys Ile Glu Leu Ser Asn Ala Ile Tyr
        115                 120                 125

Ala His Arg Ile Ala Leu Pro Asn Ile Tyr Phe His Leu Asn Ile Ala
    130                 135                 140

Tyr Gly Ile Leu Arg Lys Glu Gly Val Pro Leu Gly Lys Leu Asp Tyr
145                 150                 155                 160

Phe Ala Gly Phe Phe Pro Pro Ser Met Ala Gln Gly Lys
                165                 170

<210> SEQ ID NO 296
<211> LENGTH: 162
<212> TYPE: PRT
<213> ORGANISM: Unknown
<220> FEATURE:
<223> OTHER INFORMATION: metagenomes purified from environmentally
      challenged niches

<400> SEQUENCE: 296

Met Ser Arg Ile Gly Asp Phe Ala Asn Asn Asn Gln Ala Thr Gln Gln
 1               5                  10                  15

Leu Phe Ser Asp Arg Pro Met Gln Leu Pro Gly Pro Gly Leu Lys Pro
                20                  25                  30

Ser Arg Gln Leu Thr Val Ser Ser Ala Met Ala Phe Arg Trp Asp Ser
            35                  40                  45

Gly Gln Thr Arg Phe Asn Leu Ile Ser Ser Arg Arg Glu Val Leu
 50                  55                  60

His Ile Ser Ile Arg Ala Lys Asp Asp Val Leu Val Leu Asn Thr Lys
 65                  70                  75                  80
```

Ala Pro Asp Gly Asn Trp Gly Lys Glu Glu Arg His Glu Leu Lys Pro
            85                  90                  95

Leu Phe Asp Thr Pro Met Leu Pro Tyr Ile Thr Val Thr Ala Thr Lys
            100                 105                 110

Thr Ser Tyr Ile Leu Ser Val Pro Gly Asn Gln Glu Ile Ile Phe Asn
            115                 120                 125

Lys Arg Lys Gly Phe Met Glu Pro Ala Val Lys Ile Glu Tyr Asp Tyr
            130                 135                 140

Asp Glu Asn Pro Ala Phe Ser Asp Pro Cys Tyr Val Thr Val Pro His
145                 150                 155                 160

Leu Ser

<210> SEQ ID NO 297
<211> LENGTH: 313
<212> TYPE: PRT
<213> ORGANISM: Unknown
<220> FEATURE:
<223> OTHER INFORMATION: metagenomes purified from environmentally
      challenged niches

<400> SEQUENCE: 297

Met Ser Glu Gln Leu His Tyr Lys Gly Ser Leu Ala Gly His Gly Asn
1               5                   10                  15

Trp Val Thr Ala Ile Ala Thr Ser Ala Glu Asn Pro Asp Met Ile Leu
            20                  25                  30

Thr Ala Ser Arg Asp Lys Ser Val Ile Val Trp Gln Leu Thr Arg Asp
            35                  40                  45

Asp Ala Gln Tyr Gly Tyr Pro Lys Arg Ile Leu Lys Gly His Asn His
            50                  55                  60

Phe Val Ser Asp Val Ser Ile Ser Tyr Asp Gly Gln Phe Ala Leu Ser
65              70                  75                  80

Ser Ser Trp Asp Lys Thr Leu Arg Leu Trp Asp Leu Asn Thr Gly Leu
            85                  90                  95

Thr Thr Arg Arg Phe Val Gly His Glu Ala Asp Val Leu Ser Val Ser
            100                 105                 110

Phe Ser Ala Asp Asn Arg Gln Ile Val Ser Gly Ser Arg Asp Arg Thr
            115                 120                 125

Ile Lys Leu Trp Asn Thr Leu Gly Glu Cys Lys Phe Asp Ile Lys Asp
            130                 135                 140

Glu Gly His Ser Glu Trp Val Ser Cys Val Arg Phe Ser Pro Asn Pro
145                 150                 155                 160

Met Asn Pro Val Ile Val Ser Ala Gly Trp Asp Lys Val Val Lys Val
            165                 170                 175

Trp Glu Leu Ser Asn Cys Lys Leu Lys Thr Asn His Tyr Gly His Thr
            180                 185                 190

Gly Tyr Ile Asn Thr Val Ser Val Ser Pro Asp Gly Ser Leu Ala Ala
            195                 200                 205

Ser Gly Gly Lys Asp Gly Ile Thr Met Leu Trp Asp Leu Asn Glu Gly
            210                 215                 220

Lys His Leu Tyr Ser Leu Glu Ala Gly Asp Ile Val Asn Ala Leu Val
225                 230                 235                 240

Phe Ser Pro Asn Arg Tyr Trp Leu Cys Ala Ala Thr Ala Ser Cys Ile
            245                 250                 255

Lys Ile Phe Asp Leu Glu Ser Lys Ser Ile Val Asp Gly Leu Lys Pro
            260                 265                 270

```
Asp Phe Val Asp Val Gly Lys Asn Ser Arg Glu Pro Glu Ala Val Ser
            275                 280                 285

Leu Ser Trp Ser Ala Asp Gly Gln Thr Leu Phe Ala Gly Phe Thr Asp
    290                 295                 300

Asn Ala Val Arg Val Trp Thr Val Ala
305                 310

<210> SEQ ID NO 298
<211> LENGTH: 107
<212> TYPE: PRT
<213> ORGANISM: Unknown
<220> FEATURE:
<223> OTHER INFORMATION: metagenomes purified from environmentally
      challenged niches

<400> SEQUENCE: 298

Gly Glu Gly Gly Gly Ile His Gly Thr Thr Phe Asn Ser Ile Met Lys
1               5                   10                  15

Cys Asp Val Asp Val Arg Lys Asp Leu Tyr Gly Asn Ile Val Met Ser
            20                  25                  30

Gly Gly Thr Thr Met Tyr Pro Gly Ile Ala Asp Arg Met Gln Lys Glu
        35                  40                  45

Ile Thr Ala Leu Ala Pro Ser Ser Met Lys Val Lys Ile Ala Pro
    50                  55                  60

Pro Glu Arg Lys Tyr Ser Val Trp Ile Gly Gly Ser Ile Leu Ala Ser
65                  70                  75                  80

Leu Ser Thr Phe Gln Gln Met Trp Ile Ser Lys Gln Glu Tyr Asp Glu
                85                  90                  95

Ser Gly Pro Ser Ile Val His Arg Lys Cys Phe
            100                 105

<210> SEQ ID NO 299
<211> LENGTH: 111
<212> TYPE: PRT
<213> ORGANISM: Unknown
<220> FEATURE:
<223> OTHER INFORMATION: metagenomes purified from environmentally
      challenged niches

<400> SEQUENCE: 299

Met Arg Leu Ser Leu Glu Ala Leu Ala Val Asp Asp Arg Arg Ala Ala
1               5                   10                  15

Leu Val Val Leu Leu Leu Arg Asp Pro His Leu Leu Glu Gly Gly Gln
            20                  25                  30

Arg Ser Gln Asp Gly Thr Thr Asn Pro His Arg Val Phe Thr Leu Arg
        35                  40                  45

Arg Ser Asn Asp Leu Asp Leu His Arg Arg Ser Lys Ser Gly Asp
    50                  55                  60

Phe Leu Leu His Thr Val Gly Asn Thr Arg Val His Ser Ser Thr Thr
65                  70                  75                  80

Arg His Asp Asn Val Ala Ile Glu Ile Leu Thr Asp Val Asn Ile Thr
                85                  90                  95

Leu His Asp Gly Val Glu Gly Gly Ser Val Asp Thr Thr Thr Phe
            100                 105                 110

<210> SEQ ID NO 300
<211> LENGTH: 213
<212> TYPE: PRT
<213> ORGANISM: Unknown
<220> FEATURE:
```

<223> OTHER INFORMATION: metagenomes purified from environmentally
      challenged niches

<400> SEQUENCE: 300

Met Ala Phe Phe Pro His Tyr Thr Thr Asn Leu Ser Pro Leu Leu Tyr
1               5                   10                  15

Leu Leu Asp Asp Asp Tyr Ala Val Tyr Arg Ser Thr Cys Pro Lys Ser
            20                  25                  30

Asn Tyr His His Lys Gln His His Ser Arg Arg Gln Pro Ser Pro Val
        35                  40                  45

Arg Tyr Phe Ser Pro Asn Phe Asp Met Arg Glu Gly Asn Asp Ser Tyr
    50                  55                  60

Tyr Leu Asp Gly Glu Leu Pro Gly Val Asn Gln Asn Asp Val Asp Ile
65                  70                  75                  80

Glu Phe Ser Asp Pro Gln Thr Leu Val Ile Lys Gly Arg Val Glu Arg
                85                  90                  95

Asn Tyr Asn Asn Leu Asp Gly Met Asn Glu Glu Asn Gln Gln Asp Glu
            100                 105                 110

Glu Gln Phe Ser Glu Thr Leu Ser Ser Lys Ser Tyr Gln Pro Thr Val
        115                 120                 125

Glu Asp Glu Asp Glu Ala Asn His Ser Pro Pro Val Ala Thr Pro Thr
    130                 135                 140

Tyr Ser Glu Lys Ser Val Thr Glu Lys Thr Gln Lys Pro Ala Tyr Lys
145                 150                 155                 160

Tyr Arg Asn Ser Glu Arg Ala Ile Gly Glu Phe His Arg Ala Phe Asn
                165                 170                 175

Leu Pro Thr Arg Val Asp Gln Asp Ala Val Arg Ala Thr Leu Arg Asn
            180                 185                 190

Gly Ile Leu Ser Leu Glu Leu Pro Lys Glu Pro Ala Pro Lys Met Lys
        195                 200                 205

Lys Ile Arg Ile Glu
    210

<210> SEQ ID NO 301
<211> LENGTH: 161
<212> TYPE: PRT
<213> ORGANISM: Unknown
<220> FEATURE:
<223> OTHER INFORMATION: metagenomes purified from environmentally
      challenged niches

<400> SEQUENCE: 301

Met Ser Arg Ile Gly Asp Pro Thr Asn Asn Pro Ala Thr Gln Gln Leu
1               5                   10                  15

Tyr Ser Asp Arg Pro Leu His Leu Pro Gly Pro Gly Leu Lys Pro Ser
            20                  25                  30

Arg Gln Leu Thr Ile Ser Ser Ala Val Ala Phe Arg Glu Asp Ser Gly
        35                  40                  45

Gln Thr Arg Phe Asn Leu Ile Ser Ser Asp His Arg Glu Val Leu His
    50                  55                  60

Ile Ser Ile Arg Ala Arg Asp Asn Val Leu Val Leu Asn Thr Lys Ala
65                  70                  75                  80

Pro Asp Gly Asp Trp Gly Lys Glu Glu Arg His Asp Leu Lys Pro Leu
                85                  90                  95

Phe Asp Thr Pro Leu Leu Pro Tyr Ile Thr Val Met Ala Thr Lys Asn
            100                 105                 110

```
Ser Tyr Ile Leu Ser Val Pro Gly Lys Arg Glu Ile Phe Asn Lys
            115                 120                 125

Arg Lys Gly Phe Met Glu Pro Ala Val Arg Ile Glu Tyr Asp Tyr Asp
130                 135                 140

Glu Met Ser Ala Phe Ser Asp Pro Cys Tyr Ile Thr Val Pro Ser Ser
145                 150                 155                 160

Ser

<210> SEQ ID NO 302
<211> LENGTH: 178
<212> TYPE: PRT
<213> ORGANISM: Unknown
<220> FEATURE:
<223> OTHER INFORMATION: metagenomes purified from environmentally
      challenged niches

<400> SEQUENCE: 302

Met Lys Ala Tyr Trp Tyr Asp Asn Gln Pro Gly Asp Gln Arg Leu Pro
1               5                   10                  15

His Asp Ser Gly Arg Pro Val Thr Glu Ser Tyr Leu Glu Ser Ile Gly
            20                  25                  30

Val Phe Tyr Arg His Cys Pro Thr Ile Asp Leu Val Asp Ser Leu Ala
        35                  40                  45

Ala Glu Arg Gly Tyr Lys Asn Arg Asp Glu Val Cys Val Ser Pro Gln
50                  55                  60

Thr Met Gly Asp Val Tyr Glu Glu Lys Val Lys Thr Phe Phe Ser Glu
65                  70                  75                  80

His Leu His Glu Asp Glu Ile Arg Tyr Ile Arg Asp Gly Glu Gly
                85                  90                  95

Tyr Phe Asp Val Arg Gly Gln Leu Asp Glu Trp Val Arg Ile Arg Leu
                100                 105                 110

Ser Lys Asp Asp Leu Ile Ile Leu Pro Ala Gly Ile Tyr His Arg Phe
            115                 120                 125

Thr Thr Asp Asp Lys Asn Tyr Val Lys Ala Met Arg Leu Phe Gln Glu
130                 135                 140

Glu Pro Lys Trp Thr Pro Leu Asn Arg Gly Pro Glu Val Asp Val Asn
145                 150                 155                 160

Pro His Arg Lys Thr Tyr Leu Glu Thr Val Pro Ser Pro Ala Val Ala
                165                 170                 175

Ala Asn

<210> SEQ ID NO 303
<211> LENGTH: 216
<212> TYPE: PRT
<213> ORGANISM: Unknown
<220> FEATURE:
<223> OTHER INFORMATION: metagenomes purified from environmentally
      challenged niches

<400> SEQUENCE: 303

Val Ala Ala Gly Tyr Thr Pro Glu Ala Leu Glu Ile Leu Ser Lys Lys
1               5                   10                  15

Lys Gly Gly Lys Tyr Leu Val Leu Glu Met Asp Glu Tyr Asn Pro
            20                  25                  30

Pro Ala Glu Glu Thr Arg Thr Leu Tyr Gly Val Gln Leu Thr Gln Ala
        35                  40                  45

Arg Asn Asp Ala Val Ile Ser Pro Gln Lys Thr Phe Asn Thr Ile Ile
50                  55                  60
```

```
Thr Pro Lys Asn Thr Glu Ser Leu Pro Glu Ser Ala Leu Arg Asp Leu
 65                  70                  75                  80

Thr Val Ala Thr Leu Ala Leu Lys Tyr Thr Gln Ser Asn Ser Val Cys
             85                  90                  95

Tyr Ala Leu Asn Gly Gln Val Val Gly Leu Gly Ala Gly Gln Gln Ser
            100                 105                 110

Arg Ile His Cys Thr Arg Leu Ala Gly Asp Lys Thr Asp Asn Trp Trp
            115                 120                 125

Met Arg Phe His Glu Arg Val Leu Asn Ile Lys Trp Lys Gln Gly Thr
130                 135                 140

Lys Arg Ala Asp Lys Ser Asn Ala Ile Asp Leu Leu Cys Ser Gly Gln
145                 150                 155                 160

Thr Pro Arg Asn Asp Ala Glu Lys Val Glu Tyr Glu Arg Val Phe Ala
                165                 170                 175

Glu Val Pro Ala Pro Phe Thr Gln Glu Arg Asp Ala Trp Leu Ser
            180                 185                 190

Gln Leu Thr Asn Val Ala Ile Ser Ser Asp Ala Phe Val Cys Leu Ser
            195                 200                 205

Pro Leu Leu Glu His Ser Lys Phe
            210                 215

<210> SEQ ID NO 304
<211> LENGTH: 51
<212> TYPE: PRT
<213> ORGANISM: Unknown
<220> FEATURE:
<223> OTHER INFORMATION: metagenomes purified from environmentally
      challenged niches

<400> SEQUENCE: 304

Phe Pro Phe Ile Asp Asn Val Phe Arg Ala Ala Arg Ser Gly Val Lys
1               5                   10                  15

Tyr Ile Ala Ala Pro Ser Gly Ser Gln Asn Asp Gly Pro Val Phe Glu
            20                  25                  30

Thr Ala Glu Lys Leu Gly Ile Ser Phe Val Glu Gln Gly Thr Arg Leu
        35                  40                  45

Phe His His
    50

<210> SEQ ID NO 305
<211> LENGTH: 255
<212> TYPE: PRT
<213> ORGANISM: Unknown
<220> FEATURE:
<223> OTHER INFORMATION: metagenomes purified from environmentally
      challenged niches

<400> SEQUENCE: 305

Val Ala Ala Gly Tyr Thr Pro Glu Ala Leu Glu Ile Leu Ser Lys Lys
1               5                   10                  15

Lys Gly Gly Lys Tyr Leu Val Leu Glu Met Asp Glu Thr Tyr Asn Pro
            20                  25                  30

Pro Ala Glu Glu Thr Arg Thr Leu Tyr Gly Val Gln Leu Thr Gln Ala
        35                  40                  45

Arg Asn Asp Ala Val Ile Ser Pro Gln Lys Thr Phe Asn Thr Ile Ile
    50                  55                  60

Thr Pro Lys Asn Thr Glu Ser Leu Pro Glu Ser Ala Leu Arg Asp Leu
 65                  70                  75                  80
```

```
Thr Val Ala Thr Leu Ala Leu Lys Tyr Thr Gln Ser Asn Ser Val Cys
                85                  90                  95

Tyr Ala Leu Asn Gly Gln Val Val Gly Leu Gly Ala Gly Gln Gln Ser
            100                 105                 110

Arg Ile His Cys Thr Arg Leu Ala Gly Asp Lys Thr Asp Asn Trp Trp
        115                 120                 125

Met Arg Phe His Glu Arg Val Leu Asn Ile Lys Trp Lys Gln Gly Thr
130                 135                 140

Lys Arg Ala Asp Lys Ser Asn Ala Ile Asp Leu Leu Cys Ser Gly Gln
145                 150                 155                 160

Thr Pro Arg Asn Asp Ala Glu Lys Val Glu Tyr Glu Arg Val Phe Ala
                165                 170                 175

Glu Val Pro Ala Pro Phe Thr Gln Glu Glu Arg Asp Ala Trp Leu Ser
            180                 185                 190

Gln Leu Thr Asn Val Ala Ile Ser Ser Asp Ala Phe Phe Pro Phe Ile
        195                 200                 205

Asp Asn Val Phe Arg Ala Ala Arg Ser Gly Val Lys Tyr Ile Ala Ala
    210                 215                 220

Pro Ser Gly Ser Gln Asn Asp Gly Pro Val Phe Glu Thr Ala Glu Lys
225                 230                 235                 240

Leu Gly Ile Ser Phe Val Glu Gln Gly Thr Arg Leu Phe His His
                245                 250                 255

<210> SEQ ID NO 306
<211> LENGTH: 316
<212> TYPE: PRT
<213> ORGANISM: Unknown
<220> FEATURE:
<223> OTHER INFORMATION: metagenomes purified from environmentally
      challenged niches

<400> SEQUENCE: 306

Met Cys Asp Arg Ser Arg Ile Gly Pro Lys Gly Trp Glu Ala Val Val
1               5                   10                  15

Ser Thr Gln Ala Val Val Ser Thr Gln Ala Val Val Ser Thr Gln Ala
                20                  25                  30

Val Val Ser Thr Gln Ala Val Val Ser Thr Gln Ala Val Val Ser Thr
            35                  40                  45

Gln Ser Ala Gln Pro Gly Ala Ile Ser Ala Pro Val Ala Ala Gly Lys
        50                  55                  60

Asp Val Glu Leu Gln Trp Thr Glu Trp Pro Glu Ser His His Gly Pro
65                  70                  75                  80

Val Ile Thr Tyr Leu Ala Asn Cys Asn Gly Asp Cys Ser Glu Val Asp
                85                  90                  95

Lys Ser Ser Leu Glu Phe Phe Lys Ile Asp Gln Lys Gly Leu Ile Asp
            100                 105                 110

Asp Ser Asn Val Pro Gly Thr Trp Ala Thr Asp Lys Leu Ile Ser Asn
        115                 120                 125

Asn Asn Ser Tyr Thr Val Thr Ile Pro Ser Asp Ile Ala Ala Gly Asn
    130                 135                 140

Tyr Val Leu Arg His Glu Ile Ile Ala Leu His Ser Ala Gly Asn Glu
145                 150                 155                 160

Asp Gly Ala Gln Asn Tyr Pro Gln Cys Leu Asn Leu Lys Val Thr Gly
                165                 170                 175

Gly Gly Asn Ala Ser Pro Ser Gly Thr Leu Gly Thr Lys Leu Tyr Asn
```

```
                 180                 185                 190
Glu Asp Asp Ser Gly Ile Leu Val Ser Ile Tyr Gln Gln Leu Asp Ser
            195                 200                 205

Tyr Asp Ile Pro Gly Pro Ala Leu Tyr Ser Gly Ala Ser Ser Ser Ser
        210                 215                 220

Asn Ser Gly Ser Ser Ser Val Ala Ser Ala Thr Ala Ser Ala Thr
225                 230                 235                 240

Ser Ala Ala Ala Ser Ser Pro Ser Ser Ser Gln Ala Ser Gly Thr Pro
            245                 250                 255

Ala Ser Gln Val Lys Ala Gln Thr Ala Ser Ser Thr Pro Ser Ala Ser
        260                 265                 270

Ser Gly Ala Thr Ser Gly Ser Leu Ser Asp Tyr Phe Ser Ser Leu Ser
    275                 280                 285

Ala Glu Glu Phe Leu Asn Val Ile Ser Glu Thr Leu Ser Trp Leu Val
        290                 295                 300

Thr Asp Lys Ile His Ala Arg Asp Leu Ser Thr Ala
305                 310                 315

<210> SEQ ID NO 307
<211> LENGTH: 138
<212> TYPE: PRT
<213> ORGANISM: Unknown
<220> FEATURE:
<223> OTHER INFORMATION: metagenomes purified from environmentally
      challenged niches

<400> SEQUENCE: 307

Met Lys Ser Leu Leu Cys Thr Pro Leu Ala Thr Arg Met Val Pro Arg
1               5                  10                  15

Thr Thr Pro Ser Val Ser Thr Ser Arg Leu Leu Val Val Ala Thr Leu
            20                  25                  30

Leu Pro Gln Val Leu Leu Val Pro Ser Ser Thr Thr Arg Thr Thr Arg
        35                  40                  45

Val Ser Leu Ser Val Ser Thr Ser Ser Leu Thr Pro Thr Thr Ser Pro
50                  55                  60

Ala Leu Leu Cys Thr Leu Ala Leu Pro Arg Pro Pro Thr Leu Val Leu
65                  70                  75                  80

Leu Pro Ala Leu Leu Arg Pro Leu Leu Leu Pro Leu Leu Pro Leu Leu
            85                  90                  95

Pro Leu Pro Arg Pro Leu Arg Leu Pro Val Pro Pro Leu Pro Arg Ser
        100                 105                 110

Arg Leu Arg Pro Leu Ala Leu Leu Leu Ala Leu Arg Pro Val Pro Leu
    115                 120                 125

Pro Ala Val Cys Pro Thr Thr Ser Ala Leu
        130                 135

<210> SEQ ID NO 308
<211> LENGTH: 272
<212> TYPE: PRT
<213> ORGANISM: Unknown
<220> FEATURE:
<223> OTHER INFORMATION: metagenomes purified from environmentally
      challenged niches

<400> SEQUENCE: 308

Val Val Ser Thr Gln Ser Ala Gln Pro Gly Ala Ile Ser Ala Pro Val
1               5                  10                  15

Ala Ala Gly Lys Asp Val Glu Leu Gln Trp Thr Glu Trp Pro Glu Ser
```

20                  25                  30

His His Gly Pro Val Ile Thr Tyr Leu Ala Asn Cys Asn Gly Asp Cys
            35                  40                  45

Ser Glu Val Asp Lys Ser Ser Leu Glu Phe Phe Lys Ile Asp Gln Lys
        50                  55                  60

Gly Leu Ile Asp Asp Ser Asn Val Pro Gly Thr Trp Ala Thr Asp Lys
 65                  70                  75                  80

Leu Ile Ser Asn Asn Ser Tyr Thr Val Thr Ile Pro Ser Asp Ile
                    85                  90                  95

Ala Ala Gly Asn Tyr Val Leu Arg His Glu Ile Ile Ala Leu His Ser
                100                 105                 110

Ala Gly Asn Glu Asp Gly Ala Gln Asn Tyr Pro Gln Cys Leu Asn Leu
            115                 120                 125

Lys Val Thr Gly Gly Gly Asn Ala Ser Pro Ser Gly Thr Leu Gly Thr
        130                 135                 140

Lys Leu Tyr Asn Glu Asp Asp Ser Gly Ile Leu Val Ser Ile Tyr Gln
145                 150                 155                 160

Gln Leu Asp Ser Tyr Asp Ile Pro Gly Pro Ala Leu Tyr Ser Gly Ala
                165                 170                 175

Ser Ser Ser Ser Asn Ser Gly Ser Ser Ser Val Ala Ser Ala Thr
                180                 185                 190

Ala Ser Ala Thr Ser Ala Ala Ser Ser Pro Ser Ser Gln Ala
            195                 200                 205

Ser Gly Thr Pro Ala Ser Gln Val Lys Ala Gln Thr Ala Ser Ser Thr
        210                 215                 220

Pro Ser Ala Ser Ser Gly Ala Thr Ser Gly Ser Leu Ser Asp Tyr Phe
225                 230                 235                 240

Ser Ser Leu Ser Ala Glu Glu Phe Leu Asn Val Ile Ser Glu Thr Leu
                245                 250                 255

Ser Trp Leu Val Thr Asp Lys Ile His Ala Arg Asp Leu Ser Thr Ala
                260                 265                 270

<210> SEQ ID NO 309
<211> LENGTH: 138
<212> TYPE: PRT
<213> ORGANISM: Unknown
<220> FEATURE:
<223> OTHER INFORMATION: metagenomes purified from environmentally
      challenged niches

<400> SEQUENCE: 309

Met Lys Ser Leu Leu Cys Thr Pro Leu Ala Thr Arg Met Val Pro Arg
1               5                   10                  15

Thr Thr Pro Ser Val Ser Thr Ser Arg Leu Leu Val Val Ala Thr Leu
            20                  25                  30

Leu Pro Gln Val Leu Leu Val Pro Ser Ser Thr Thr Arg Thr Thr Arg
        35                  40                  45

Val Ser Leu Ser Val Ser Thr Ser Ser Leu Thr Pro Thr Thr Ser Pro
    50                  55                  60

Ala Leu Leu Cys Thr Leu Ala Leu Pro Arg Pro Thr Leu Val Leu
65                  70                  75                  80

Leu Pro Ala Leu Leu Arg Pro Leu Leu Pro Leu Leu Pro Leu Leu
                85                  90                  95

Pro Leu Pro Arg Pro Leu Arg Leu Pro Val Pro Leu Pro Arg Ser
                100                 105                 110

Arg Leu Arg Pro Leu Ala Leu Leu Ala Leu Arg Pro Val Pro Leu
            115                 120                 125

Pro Ala Val Cys Pro Thr Thr Ser Ala Leu
        130                 135

<210> SEQ ID NO 310
<211> LENGTH: 305
<212> TYPE: PRT
<213> ORGANISM: Unknown
<220> FEATURE:
<223> OTHER INFORMATION: metagenomes purified from environmentally
      challenged niches

<400> SEQUENCE: 310

Met Leu Ser Met Phe Thr Arg Val Ala Arg Gly Gln Ala Lys Val Phe
1               5                   10                  15

Thr Arg Asn Ala Ser Thr Ala Ser Ser Lys Pro Thr Asn Gln Ser Ser
            20                  25                  30

Asn Lys Ala Ala Thr Ile Ala Ala Ser Ile Ser Gly Val Thr Ala Ala
        35                  40                  45

Leu Tyr Ala His Gln Tyr Gly Leu Ile Asp Ser Val Phe Ala Ser Gly
    50                  55                  60

Leu Glu Glu Gly Leu His Ala Pro His Phe Pro Trp Ser His Asn Gly
65                  70                  75                  80

Trp Leu Asp Ser Phe Asp His Asn Ser Ile Arg Arg Gly Tyr Gln Val
                85                  90                  95

Tyr Arg Glu Val Cys Ser Ser Cys His Ser Leu Asp Arg Ile Ala Trp
            100                 105                 110

Arg Asn Leu Val Ala Val Ser His Thr Ser Asp Glu Ala Arg Ala Met
        115                 120                 125

Ala Glu Glu Gln Glu Tyr Thr Asp Gly Pro Asn Asp Gln Gly Glu Ser
    130                 135                 140

Phe Gln Arg Pro Gly Lys Leu Ala Asp Tyr Met Pro Ala Pro Tyr Pro
145                 150                 155                 160

Asn Glu Glu Ala Ser Arg Ala Ala Asn Gly Gly Ala Leu Pro Pro Asp
                165                 170                 175

Leu Ser Leu Ile Val Lys Ala Arg His Gly Gly Ala Asp Tyr Ile Met
            180                 185                 190

Ala Leu Leu Thr Gly Tyr Gln Asp Pro Pro Ala Gly Ile Gln Val Gln
        195                 200                 205

Glu Gly Met Asn Phe Asn Pro Tyr Phe Pro Gly Gly Gly Ile Ala Met
    210                 215                 220

Gly Arg Val Leu Phe Asp Gly Leu Val Glu Tyr Asp Asp Gly Thr Pro
225                 230                 235                 240

Ala Thr Thr Thr Gln Met Ala Lys Asp Val Ala Thr Phe Leu Ser Trp
                245                 250                 255

Ala Ser Glu Pro Glu His Asp Asp Arg Lys Lys Met Gly Phe Gln Ala
            260                 265                 270

Val Ile Ile Leu Ser Ala Met Thr Ala Ile Ser Leu Tyr Val Lys Arg
        275                 280                 285

Leu Lys Trp Ser Pro Ile Lys Thr Arg Lys Leu Thr Tyr Asn Pro Pro
    290                 295                 300

Lys
305

<210> SEQ ID NO 311

<211> LENGTH: 165
<212> TYPE: PRT
<213> ORGANISM: Unknown
<220> FEATURE:
<223> OTHER INFORMATION: metagenomes purified from environmentally
      challenged niches

<400> SEQUENCE: 311

Gly Gly Ser Pro Ala Lys Lys Ser Leu Ile Gly Ala Met Glu Ala Gln
1               5                   10                  15

Asn Leu Lys Thr Phe Pro Lys Gln Pro Ile Phe Gln Asn Ser Lys Thr
            20                  25                  30

Arg Gly Asn Lys Lys Val Thr Lys Asp Arg Arg Trp Tyr Lys Asp Val
        35                  40                  45

Gly Leu Gly Phe Lys Thr Pro Gln Glu Ala Ile Thr Gly Thr Tyr Ile
    50                  55                  60

Asp Lys Lys Cys Pro Trp Thr Gly Glu Val Ser Ile Arg Gly Arg Ile
65                  70                  75                  80

Leu Ser Gly Lys Val Val Ser Thr Lys Met Thr Arg Thr Ile Val Ile
                85                  90                  95

Arg Arg Glu Tyr Leu His Tyr Val Pro Lys Tyr Asn Arg Tyr Glu Lys
            100                 105                 110

Arg His Lys Asn Leu Pro Val His Ala Ser Pro Ala Phe Arg Ile Glu
        115                 120                 125

Asn Gly Asp Gln Val Val Gly Gln Cys Arg Pro Leu Ser Lys Thr
    130                 135                 140

Val Arg Phe Asn Val Leu Arg Val Ile Lys Asn Lys Ala Ala Ala Lys
145                 150                 155                 160

Ala Phe Ala Lys Phe
                165

<210> SEQ ID NO 312
<211> LENGTH: 72
<212> TYPE: PRT
<213> ORGANISM: Unknown
<220> FEATURE:
<223> OTHER INFORMATION: metagenomes purified from environmentally
      challenged niches

<400> SEQUENCE: 312

Met Pro Pro Arg Lys Pro Arg Cys Ser Phe Glu Cys Lys Glu Gln
1               5                   10                  15

Ala Gln Arg Ile Val Gly Asp Cys Ser Phe Cys Ser Gly His Phe Cys
            20                  25                  30

Ser Lys His Arg Met Leu Glu Ala His Ser Cys Ser Gly Leu Glu Asp
        35                  40                  45

Cys Lys Lys Glu Ser His Ala Arg Asn Ala Asp Lys Leu Asn Ser Glu
    50                  55                  60

Arg Thr Gln Val Ile Lys Gly Val
65                  70

<210> SEQ ID NO 313
<211> LENGTH: 161
<212> TYPE: PRT
<213> ORGANISM: Unknown
<220> FEATURE:
<223> OTHER INFORMATION: metagenomes purified from environmentally
      challenged niches

<400> SEQUENCE: 313

Met Ser Arg Asn Phe Gly Asp Phe Ser Thr Asn Gln Ala Thr Gln Gln
1               5                   10                  15

Leu Tyr Ser Asp Arg Pro Leu His Leu Pro Gly Asn Gly Leu Lys Pro
            20                  25                  30

Ala Arg Gln Leu Thr Ile Ser Ser Ala Val Ala Phe Arg Trp Asp Ser
        35                  40                  45

Asp Gln Thr Arg Phe Asn Leu Ile Ser Ser Asp Arg Arg Glu Val Leu
    50                  55                  60

His Ile Ser Ile Arg Ala Lys Asp Asn Val Leu Val Leu Asn Thr Lys
65                  70                  75                  80

Ala Pro Asp Gly Asp Trp Gly Arg Glu Glu Arg His Glu Leu Lys Lys
                85                  90                  95

Leu Phe Asp Thr Pro Met Leu Pro Tyr Ile Thr Val Thr Ala Thr Lys
            100                 105                 110

Met Thr Tyr Asn Ile Thr Val Pro Ser Gly Gln Glu Ile Ile Phe Asn
        115                 120                 125

Lys Arg Lys Gly Phe Met Glu Pro Ala Val Lys Ile Glu Tyr Asp Tyr
    130                 135                 140

Asp Glu His Ser Ala Phe Ser Asp Pro Cys Tyr Ile Thr Val Pro Ser
145                 150                 155                 160

Ser

<210> SEQ ID NO 314
<211> LENGTH: 119
<212> TYPE: PRT
<213> ORGANISM: Unknown
<220> FEATURE:
<223> OTHER INFORMATION: metagenomes purified from environmentally
      challenged niches

<400> SEQUENCE: 314

Leu Leu Ala Ser Asn Ser Arg Ser Asn Glu Leu Ser Ser Pro Pro Ser
1               5                   10                  15

Thr His Leu His Ile Ser Gln Ser Thr Met Val Ser Lys Ile Leu Phe
            20                  25                  30

Trp Ser Gly Phe Gly Ile Ala Val Arg Leu Trp Gln Leu Gly Ile Glu
        35                  40                  45

Met Arg Pro Ile Leu Ala Lys Gln Gly Leu Trp Ala Tyr Pro Val Phe
    50                  55                  60

Ala Gly Val Gly Gly Ser Phe Gly Tyr Trp Leu Gln Gly Val Glu Asp
65                  70                  75                  80

Arg Gln Leu Lys Ile Leu Ala Gln Arg Arg Glu Ala Ile Leu Asp Lys
                85                  90                  95

Arg Arg Arg Arg Asp Glu Arg Glu Gly Leu Ser Asn Ile Glu Lys Glu
            100                 105                 110

Gly Thr Leu Ala Ala Thr Pro
        115

<210> SEQ ID NO 315
<211> LENGTH: 91
<212> TYPE: PRT
<213> ORGANISM: Unknown
<220> FEATURE:
<223> OTHER INFORMATION: metagenomes purified from environmentally
      challenged niches

<400> SEQUENCE: 315

Leu Asn Trp Ser Cys Asn Phe Ala Asp Cys Trp Pro Arg Thr Pro Asp

```
                1               5                  10                 15
        Arg Thr Asn Ser Pro Leu Leu Arg Gln Arg Thr Phe Thr Tyr Arg Lys
                            20                 25                 30

Ala Gln Trp Phe Pro Arg Phe Ser Ser Gly Val Ala Ser Ala Ser Pro
                        35                 40                 45

Ser Val Ser Gly Asn Ser Val Ser Lys Cys Val Pro Phe Leu Pro Ser
                    50                 55                 60

Arg Val Ser Gly Pro Thr Pro Ser Ser Gln Val Ser Val Glu Ala Ser
        65                 70                 75                 80

Val Thr Gly Ser Arg Val Ser Arg Thr Val Ser
                        85                 90
```

<210> SEQ ID NO 316
<211> LENGTH: 182
<212> TYPE: PRT
<213> ORGANISM: Unknown
<220> FEATURE:
<223> OTHER INFORMATION: metagenomes purified from environmentally
      challenged niches

<400> SEQUENCE: 316

```
        Met Ile His Ala Gln Gln Cys Asn Cys Arg Ser Phe Ser Glu Gly Ser
        1               5                  10                 15

Glu Asn Lys Gln Gln Pro Thr Gln Gln Ile Met Gly Ser Gln Pro Lys
                            20                 25                 30

Tyr Pro Pro Ser Gln Cys Cys Ser Asp Pro His Ala Arg Pro Val Ser
                        35                 40                 45

Gly Ala Cys Arg Gly Trp Leu Arg Gly Ala Ala Gln Glu Ser Ser Ala
                    50                 55                 60

Asp Gly Pro Arg His Pro Gly Ala Ser Asn Arg Ser Phe His Arg His
        65                 70                 75                 80

Leu Arg Arg Arg Gly Arg Pro Arg Asp Pro Ala Trp Gln Glu Trp Asp
                            85                 90                 95

Ala Phe Arg Tyr Arg Val Ala Arg Asp Gly Arg Arg Cys Arg Ser His
                        100                105                110

Ser Arg Arg Glu Ser Trp Lys Pro Leu Cys Phe Ala Ile Cys Glu Gly
                    115                120                125

Ala Leu Thr Glu Glu Arg Arg Val Arg Ser Ile Gly Ser Ser Arg Pro
        130                135                140

Ala Ile Ser Glu Ile Ala Gly Pro Ile Gln Thr Pro Ala Thr Lys Ala
        145                150                155                160

Asn Thr Ala Gly Asp Asn Arg Glu Ser Gly Ser Thr Pro Ala Asn
                            165                170                175

Lys Lys Phe Ser Ala Arg
                        180
```

<210> SEQ ID NO 317
<211> LENGTH: 127
<212> TYPE: PRT
<213> ORGANISM: Unknown
<220> FEATURE:
<223> OTHER INFORMATION: metagenomes purified from environmentally
      challenged niches

<400> SEQUENCE: 317

```
        Met Pro Ser Asn Ala Ile Ala Gly Leu Ser Pro Lys Ala Val Lys Ile
        1               5                  10                 15

Asn Asn Ser Gln Arg Asn Lys Ser Trp Gly Arg Ser Gln Ser Thr Leu
```

```
                20                  25                  30
Leu Leu Asn Val Ala Gln Thr Leu Thr Leu Val Pro Ser Pro Ala Leu
             35                  40                  45

Val Glu Asp Gly Phe Ala Ala Leu Arg Lys Asn Leu Gln Leu Thr Val
 50                  55                  60

Leu Asp Thr Leu Glu Pro Val Thr Glu Ala Ser Thr Asp Thr Cys Glu
 65                  70                  75                  80

Asp Gly Val Gly Pro Glu Thr Leu Leu Gly Lys Asn Gly Thr His Phe
                 85                  90                  95

Asp Thr Glu Leu Pro Glu Thr Asp Gly Asp Ala Glu Ala Thr Pro Glu
            100                 105                 110

Glu Asn Leu Gly Asn His Cys Ala Leu Arg Tyr Val Lys Val Arg
            115                 120                 125

<210> SEQ ID NO 318
<211> LENGTH: 300
<212> TYPE: PRT
<213> ORGANISM: Unknown
<220> FEATURE:
<223> OTHER INFORMATION: metagenomes purified from environmentally
      challenged niches

<400> SEQUENCE: 318

Met Pro Phe Ile Lys Glu Ala Lys Ser Asn Ser Tyr Phe Ser Arg Tyr
  1               5                  10                  15

Gln Val Lys Tyr Arg Arg Arg Glu Gly Lys Thr Asp Phe Tyr Ala
                 20                  25                  30

Arg Lys Arg Leu Val Thr Gln Ala Lys Asn Lys Tyr Asn Ala Pro Lys
             35                  40                  45

Tyr Arg Leu Val Val Arg Phe Thr Asn Lys Asp Ile Ile Cys Gln Ile
 50                  55                  60

Val Ser Ser Lys Leu Gln Gly Asp Val Val Leu Thr His Ala Arg Ala
 65                  70                  75                  80

Arg Glu Leu Pro Arg Tyr Gly Ile Lys His Gly Leu Thr Ser Trp Ser
                 85                  90                  95

Ser Ala Tyr Ala Val Gly Leu Leu Val Ala Arg Arg Ala Leu Thr Lys
            100                 105                 110

Leu Gly Leu Ala Asp Lys Tyr Glu Gly Asp Val Glu Ala Thr Gly Glu
            115                 120                 125

Tyr Asn Leu Thr Glu Pro Leu Gly Asp Asp Glu Pro Arg Pro Phe Lys
            130                 135                 140

Val Phe Leu Asp Val Gly Leu Lys Arg Thr Ser Thr Gly Ser Arg Val
145                 150                 155                 160

Phe Gly Ala Leu Lys Gly Ala Ser Asp Gly Leu Tyr Ile Pro His
                165                 170                 175

Ser Glu Asn Arg Phe Pro Gly Tyr Asp Ile Glu Ser Lys Glu Leu Asp
            180                 185                 190

Ala Glu Ile Leu Asn Lys Tyr Ile Leu Gly Gly His Ile Ala Glu Tyr
            195                 200                 205

Met Glu Ala Leu Glu Glu Glu Asp Glu Glu Arg Phe Lys Ala Gln Phe
            210                 215                 220

Ser Thr Tyr Leu Glu Asp Gly Ile Gly Ser Glu Asp Ile Glu Glu Ile
225                 230                 235                 240

Phe Ser Gly Ala His Glu Ala Ile Arg Ala Asp Pro Thr Phe Lys Pro
                245                 250                 255
```

Ser Glu Ala Ala Lys Gly Thr Asp Trp Lys Ser Glu Ser Lys Lys His
            260                 265                 270

Arg Ala Val Arg Leu Thr Lys Gln Gln Arg Glu Asp Ala Ile Gln Gln
        275                 280                 285

Arg Ile Lys Tyr Tyr Gln Gln Ala Gly Asp Leu Glu
    290                 295                 300

<210> SEQ ID NO 319
<211> LENGTH: 212
<212> TYPE: PRT
<213> ORGANISM: Unknown
<220> FEATURE:
<223> OTHER INFORMATION: metagenomes purified from environmentally
      challenged niches

<400> SEQUENCE: 319

Met Ala Phe Met Asn Leu Pro Trp Pro Thr Glu Cys Leu His Ala Ala
1               5                   10                  15

Leu Lys Asn Gly Ser Leu Pro Phe Trp Gly Phe Val Ile Tyr Arg Thr
            20                  25                  30

Thr Tyr Thr Ala Gln Ser Asp Ala Ala Trp Pro Gln Ile Ile Glu Leu
        35                  40                  45

Ile Ala Ser Tyr Met Lys Ala Leu Leu Tyr His Glu Tyr Asn Asp Lys
    50                  55                  60

Lys Lys Asp Gly Asp Glu Pro Thr Val Tyr Asp Glu Ile Trp Ala Arg
65                  70                  75                  80

His Gln Leu Thr Ile Met Asp Asp Arg Gln Phe Asn Gly Ala Ser Val
                85                  90                  95

Phe Asp Ile Gln Leu His Phe Glu Lys Trp Val Glu Ala Gln Gly Lys
            100                 105                 110

Arg Asp Glu Ser Thr Met Tyr Arg Met Cys Met Val Ile Asp Asp Glu
        115                 120                 125

Ser Ile Gln Thr Leu Leu Glu Ala Pro Pro Gly Glu Asn Arg Lys Leu
    130                 135                 140

Gly Arg Arg Ile Gly Gly Pro Val Arg Phe Val Lys Val Val Glu Ala
145                 150                 155                 160

Phe Pro Glu Leu Asp Ser Leu Asp Glu Phe Gln Gly Trp Met Lys Cys
                165                 170                 175

Glu Ile Asn Ala Leu Trp Pro Leu Trp Lys Met Met Ser Asp Gly Asp
            180                 185                 190

Glu Met Arg Met Ser Tyr Asp Glu Met Lys Gly Asn Gly Lys Gln Val
        195                 200                 205

Tyr Gly Ala Ile
    210

<210> SEQ ID NO 320
<211> LENGTH: 192
<212> TYPE: PRT
<213> ORGANISM: Unknown
<220> FEATURE:
<223> OTHER INFORMATION: metagenomes purified from environmentally
      challenged niches

<400> SEQUENCE: 320

Met Thr Glu Lys Leu Tyr Thr Glu Gln Val Asn Ala Phe Gly Asn Glu
1               5                   10                  15

Leu Pro Pro Leu Ser Tyr Lys Asp Leu Asp Lys Leu Pro Leu His Gln
            20                  25                  30

Asn Val Ile Lys Glu Thr Leu Arg Ile His Asn Ser Ile His Thr Leu
 35                  40                  45

Met Arg Lys Val Lys Asn Pro Leu Pro Val Pro Gly Thr Arg Phe Val
 50                  55                  60

Ile Pro Thr Ser His Thr Leu Leu Ala Ser Pro Gly Val Thr Thr Arg
 65                  70                  75                  80

Asp Asp Ser His Phe Arg Asn Ala Met Thr Trp Asp Pro His Arg Trp
                 85                  90                  95

Glu Thr Arg Ser Glu Val Glu Asp Gly Thr Ile Asp Tyr Gly
                100                 105                 110

Tyr Gly Val Val Ser Lys Gly Thr Lys Ser Pro Tyr Leu Pro Phe Gly
                115                 120                 125

Ala Gly Arg His Arg Cys Ile Gly Glu Lys Phe Ala Tyr Leu Asn Leu
130                 135                 140

Thr Val Ile Val Ala Thr Leu Val Arg Asn Phe Arg Phe Ser Glu Pro
145                 150                 155                 160

Asp Asp Arg Glu Gly Val Pro Glu Thr Asp Tyr Ser Ser Leu Phe Ser
                165                 170                 175

Arg Pro Met Arg Pro Ala Thr Ala Arg Trp Glu Arg Arg Gly Glu Tyr
                180                 185                 190

<210> SEQ ID NO 321
<211> LENGTH: 210
<212> TYPE: PRT
<213> ORGANISM: Unknown
<220> FEATURE:
<223> OTHER INFORMATION: metagenomes purified from environmentally
      challenged niches

<400> SEQUENCE: 321

Met Ala His Trp Arg Glu Glu Tyr Leu Thr Ala Leu Ala Val Arg Asp
 1                   5                  10                  15

Gln Arg Glu Lys Ala Asn Leu Ser Ile Tyr Asp Ala Tyr Thr Arg Leu
                 20                  25                  30

Ala Asp Ser Thr Ala Lys Leu Pro Ala Thr Ile Asp Thr Ser Gly Ser
                 35                  40                  45

Pro Ser Gly Asp Lys Gly Pro Ser Gly Thr Tyr Glu Ser Glu Lys Thr
 50                  55                  60

Ala Phe Ser Gln Ser Arg Thr Ala Lys Lys Gln Gln Thr Glu Val Glu
 65                  70                  75                  80

Pro Ser Val Thr Glu Leu Leu Asn Thr Thr Arg Ala Glu Leu Ala Glu
                 85                  90                  95

Ala Gln Arg Ser Arg Ala Glu Leu Arg Asp Arg Leu Glu Arg Ala Thr
                100                 105                 110

Asn Glu Ala Glu Lys Leu Arg Lys Gln Ile Gly Lys Asp Gly Arg Arg
                115                 120                 125

Ile His Gly Leu Glu Asn Glu Val Ala Gln Gln Lys Arg Arg Lys
130                 135                 140

Asp Val Glu Glu Glu Leu Arg Gly Lys Ala Lys Leu Leu Asn Glu Phe
145                 150                 155                 160

Gln Asp Glu Ile Ala Ala Leu Thr Leu Gln Val Asn Met Ala Glu Arg
                165                 170                 175

Lys Ala Lys Lys Leu Gly Glu Glu Asn Asp Asp Leu Val Asn Arg Trp
                180                 185                 190

Met Lys Arg Met Gly Gln Glu Ala Asp Ala Met Asn Asp Ala Ser Lys
                195                 200                 205

Phe Ser
    210

<210> SEQ ID NO 322
<211> LENGTH: 53
<212> TYPE: DNA
<213> ORGANISM: Artificial Sequence
<220> FEATURE:
<223> OTHER INFORMATION: poly-A mRNA primer
<220> FEATURE:
<221> NAME/KEY: misc_feature
<222> LOCATION: (52)..(52)
<223> OTHER INFORMATION: n= a, c or g
<220> FEATURE:
<221> NAME/KEY: misc_feature
<222> LOCATION: (52)..(52)
<223> OTHER INFORMATION: v= a, c or g
<220> FEATURE:
<221> NAME/KEY: misc_feature
<222> LOCATION: (53)..(53)
<223> OTHER INFORMATION: n= a, c, g or t

<400> SEQUENCE: 322
attctagagc gatcgcacat gttttttttt tttttttttt tttttttttt tvn           53

<210> SEQ ID NO 323
<211> LENGTH: 34
<212> TYPE: DNA
<213> ORGANISM: Artificial Sequence
<220> FEATURE:
<223> OTHER INFORMATION: poly-A mRNA primer
<220> FEATURE:
<221> NAME/KEY: modified_base
<222> LOCATION: (34)..(34)
<223> OTHER INFORMATION: LNA Modification

<400> SEQUENCE: 323
aagcagtggt atcaacgcag agtggcgcgc cggg                                34

<210> SEQ ID NO 324
<211> LENGTH: 34
<212> TYPE: DNA
<213> ORGANISM: Artificial Sequence
<220> FEATURE:
<223> OTHER INFORMATION: oligo-capping rapid amplification of cDNA ends
      primers
<220> FEATURE:
<221> NAME/KEY: 5' Inverted Dideoxy-T
<222> LOCATION: (1)..(1)
<223> OTHER INFORMATION: 5' Inverted Dideoxy-T
<220> FEATURE:
<221> NAME/KEY: Ribonuclotide
<222> LOCATION: (2)..(33)
<223> OTHER INFORMATION: Ribonuclotide

<400> SEQUENCE: 324
aagcagtggt atcaacgcag agtggcgcgc cggg                                34

<210> SEQ ID NO 325
<211> LENGTH: 33
<212> TYPE: DNA
<213> ORGANISM: Artificial Sequence
<220> FEATURE:
<223> OTHER INFORMATION: primer for amplification of prokaryote cDNA
      library
<220> FEATURE:
<221> NAME/KEY: 5' Inverted Dideoxy-T
<222> LOCATION: (1)..(1)
<223> OTHER INFORMATION: 5' Inverted Dideoxy-T
<220> FEATURE:
<221> NAME/KEY: Ribonucleotide

```
<222> LOCATION: (2)..(33)
<223> OTHER INFORMATION: Ribonucleotide

<400> SEQUENCE: 325
taagcagugg uaucaacgca gaguggcgcg ccg                                 33

<210> SEQ ID NO 326
<211> LENGTH: 20
<212> TYPE: DNA
<213> ORGANISM: Artificial Sequence
<220> FEATURE:
<223> OTHER INFORMATION: primer for CBF3 promoter

<400> SEQUENCE: 326
cagcatgctc tcactccaac                                               20

<210> SEQ ID NO 327
<211> LENGTH: 20
<212> TYPE: DNA
<213> ORGANISM: Artificial Sequence
<220> FEATURE:
<223> OTHER INFORMATION: primer for Erd10 promoter

<400> SEQUENCE: 327
cgtgagaatg acacaaccac                                               20

<210> SEQ ID NO 328
<211> LENGTH: 18
<212> TYPE: DNA
<213> ORGANISM: Artificial Sequence
<220> FEATURE:
<223> OTHER INFORMATION: primer for Kin1 promoter

<400> SEQUENCE: 328
ctcgtggcac cacactcc                                                 18

<210> SEQ ID NO 329
<211> LENGTH: 19
<212> TYPE: DNA
<213> ORGANISM: Artificial Sequence
<220> FEATURE:
<223> OTHER INFORMATION: primer for NOS/HSP terminator

<400> SEQUENCE: 329
ggaaattcgc ctcgagatc                                                19

<210> SEQ ID NO 330
<211> LENGTH: 1391
<212> TYPE: DNA
<213> ORGANISM: Arabidopsis thaliana

<400> SEQUENCE: 330
ataccggagc tcagagaatc atatgactaa ggacgtggtg gttgaaggaa atgagagaat    60
acatgaagaa gagaaacttc tttgagtgag aaggaagtgc gctggctgga gagaaaagag   120
agaaaagagt ttcgagtgag agagagggcg ttgagattgt gatcaactta atgtaatatg   180
ttcttttatt acattttctt tttgtcatat actcaaacct tttactattt tgtctcataa   240
atctaacaca ccccaccatt tgttaatgca tgatggtaga aaatattaaa tataattaac   300 tactttatg tgatcaaaat taggtttcag actcgtttcg cgatccgatc tacaattaca   360
actgcatgct tctaattgat ctaaattcta aattttttat acatattaaa aaacaacttt   420
tttgttaaat tctcaatcat cattttttgtg attaacaatt ttttataact ctaaaccaat   480
```

| | |
|---|---|
| aatatttgat tatttatttt atatgtataa tgatgattga gaattttaat tagcagtcta | 540 |
| tttagggttt tcctaaagtt acaatatgtt gttacccttc tagttaaatt ttccaaaata | 600 |
| ccatatttca taacttttca aactgtttat taattcaacc gtaaaaagca ctaaaatgtt | 660 |
| acatttgatc attcacccaa attaaattca aaagtttttc cgccaaaact acttggtgac | 720 |
| ttacgtgctt atatacggac gactattatt atgttctata cttttttata ctttgttgca | 780 |
| caaatatcta ctctcccaat tcatattcta gaaggatgtg ctataagaat gggagaaatt | 840 |
| acacaagaag agcatcttta aatatcctct cacaatcttt atgtctaata cacgggtgaa | 900 |
| caattaacga caatttcttt attcaggaat ataataatga ataacggtta ccctacacct | 960 |
| agtacactaa atccttaaca gccacacatt catacgcaaa gagtttataa aactcataaa | 1020 |
| ggtataataa taacgagtga ataagtcaaa aaaagtcttc tctggacaca tggcagatct | 1080 |
| taatgagtga atccttaaac tactcatttt acaattgctt cgctgtgtat agtttacgtg | 1140 |
| gcattaccag agacacaaac tccgtcttcg ccttttcttt tgcctctaaa atatcttccg | 1200 |
| ccattataaa acagcatgct ctcactccaa ctttttattta tctacaaaca ttaaatccac | 1260 |
| ctgaactaga acagaaagag agagaaacta ttatttcagc aaaccatacc aacaaaaaag | 1320 |
| acagagatct tttagttacc ttatccagtt tcttgaaaca gagtactctt ctgatcaggc | 1380 |
| gcgccgccat a | 1391 |

<210> SEQ ID NO 331
<211> LENGTH: 1215
<212> TYPE: DNA
<213> ORGANISM: Arabidopsis thaliana

<400> SEQUENCE: 331

| | |
|---|---|
| ataccggagc tcgactaggt ggacaaaata atttgttaat taaataaaaa ttagttcaat | 60 |
| atagaaatga aaacgattgc tttgtttggt atgtgtcggt acagtgacca tcctaatgcc | 120 |
| taatataaaa gattcgatcg gtatgttaca agttgcgtgt atatgaaaac gtcacatttt | 180 |
| attaagtggc acgtcgttgt gatgaatctt tcaaccgaac acgattcata atctataagc | 240 |
| aaaatccgaa aatggtgcct tctcaatgcc ccctatctgt tcaatctttt ttttttttt | 300 |
| tttttttgta tatctgttca atcttattta aatgtaatga caaattaaat gaagtttacg | 360 |
| ttagtaatat aagctgacaa acaacaccac attacataca taaaattaaa ttcttttaag | 420 |
| tatttcaata acgtttcttt atcttaaaaa ttaaatttac ttcgagagct tcctacttcg | 480 |
| tcaaaaataa aattttactt tgctgcatgt ttttactttc tttttgtaac gtcttaaaaa | 540 |
| ggtgattaac gtcaacttaa ttcaccgaaa gtctctgcaa ttgatatttt ctgccgacgt | 600 |
| ggcataagaa gtccgattgg cccacatgac cgacatccac gcttaaacca atcaaaaccg | 660 |
| gccattcagt tccatctgtg ggctcctgaa acgttctctt gacacgtgtt taccatatat | 720 |
| tggcttaatc catccatagt ctttctattt actgacaggt agtattttc ctatcaatta | 780 |
| tttatttca cgtggcatga tggctatggc tagttgaacc tgtgaataac ttggtcatat | 840 |
| ctactctcta tttatttaga tgattcattt tcttgaagga cttgcaattt tatccccctta | 900 |
| cttttatttc tttgagagat aacctaaaat tctcaaaatg agttggaaac atcccttttga | 960 |
| agttcctcta caggctttct atgtgcataa gaatctgctt aacattggaa ataatatatg | 1020 |
| cattcttctc caattctcct agttggatac atatatgaag tctataaatt acacatattt | 1080 |
| cccacaaaaa ttattgtaag agtttatatt tcaacatata gtatgcaaac ttaaatcgtg | 1140 |
| agaatgacac aaccactaat tcaaaccact acattatata ttctaatcca ttcaaattca | 1200 |

```
tggcgcgccg ccata                                                    1215

<210> SEQ ID NO 332
<211> LENGTH: 960
<212> TYPE: DNA
<213> ORGANISM: Arabidopsis thaliana

<400> SEQUENCE: 332
ataccggagc tcggtaactt gaattcaacc atgaactgtt tggattggca aacataaact      60
caaataaaat atctaggtat aattgtggtt catacaagaa ttacttcata ctgttgggcc     120
aaaggacgta tccttccccg cacctccaaa ccatgggctt actactgatc cgacatcaaa     180
accgtgttag ttgcaaccaa cgaatgataa gtcaataaga ttcaacttgt caacaaatat     240
acagcttata tgacatgtct ggctccaaac tgaattttag tagaaagtta ctaattcata     300
aaattaattt atatacaatt tttcaatttt tattttataa attaaagaaa aaaacatgaa     360
aaatacggga ggttcggcaa acacaacatt taacttgcca aacgtatcat ctaactttcc     420
caccttatac aaggaaccat tttttcaata ataaagtttt tttttttttg tcttcgcaaa     480
taagagcacg aaatgtttgc caaacgcata tgcaacaaac ccacgttaca taattctgtt     540
tacagccata gagcaagcta tattgttaaa gacctaaaaa aaactttact ataacatata     600
gaggcttcga gatatttcga aagactcaac ttatatataa ataaactcaa aaagaaaaca     660
cggaggcgag aggatcatac tctcacacag aaagagtcac attattatat cctctaaaaa     720
accaaactaa aacgacacgt gaagtcttga tcagccgata aatagctacc gacataaggc     780
aaaactgatc gtaccatcaa atgtaatcca cgtggtttta gattactcgt ggcaccacac     840 tcccttagc ctataaatat aaaccattaa gcccacatct cttctcatca tcactaacca     900
aaacacactt caaaaacgat tttacaagaa ataaatatct gaaaaggcg cgccgccata     960
```